(12) United States Patent
Wang et al.

(10) Patent No.: US 12,319,728 B2
(45) Date of Patent: *Jun. 3, 2025

(54) ANTI-VEGF PROTEIN COMPOSITIONS AND METHODS FOR PRODUCING THE SAME

(71) Applicant: Regeneron Pharmaceuticals, Inc., Tarrytown, NY (US)

(72) Inventors: Shunhai Wang, Scarsdale, NY (US); Ning Li, Greenwich, CT (US); Hunter Chen, New York, NY (US); Amardeep Singh Bhupender Bhalla, Montvale, NJ (US); Shawn M. Lawrence, Nyack, NY (US); Amy S. Johnson, Briarcliff Manor, NY (US); Meghan Casey, Ringwood, NJ (US); Jaimie Grapel, Waldwick, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/637,124

(22) Filed: Apr. 16, 2024

(65) Prior Publication Data
US 2024/0309064 A1    Sep. 19, 2024

Related U.S. Application Data

(60) Continuation of application No. 18/213,779, filed on Jun. 23, 2023, now Pat. No. 11,958,894, which is a continuation of application No. 18/116,166, filed on Mar. 1, 2023, now Pat. No. 12,012,444, which is a continuation of application No. 17/858,724, filed on Jul. 6, 2022, now Pat. No. 11,753,459, which is a continuation of application No. 17/842,286, filed on Jun. 16, 2022, now Pat. No. 11,542,317, which is a continuation of application No. 17/667,298, filed on Feb. 8, 2022, now Pat. No. 11,505,593, which is a continuation of application No. 17/575,425, filed on Jan. 13, 2022, now Pat. No. 11,485,770, which is a division of application No. 17/460,578, filed on Aug. 30, 2021, now Pat. No. 11,306,135, application No. 18/637,124 is a continuation of application No. 17/458,519, filed on Aug. 26, 2021, now Pat. No. 12,054,532, which is a continuation of application No. 16/996,293, filed on Aug. 18, 2020, now Pat. No. 11,186,625.

(60) Provisional application No. 63/065,012, filed on Aug. 13, 2020, provisional application No. 62/944,635, filed on Dec. 6, 2019.

(51) Int. Cl.
| | | |
|---|---|---|
| C07K 14/71 | (2006.01) | |
| A61K 38/18 | (2006.01) | |
| C07K 1/06 | (2006.01) | |
| C07K 1/113 | (2006.01) | |
| C07K 1/16 | (2006.01) | |
| C07K 1/18 | (2006.01) | |
| C07K 1/22 | (2006.01) | |
| C07K 1/36 | (2006.01) | |
| C07K 16/22 | (2006.01) | |
| C07K 16/28 | (2006.01) | |
| C12N 5/00 | (2006.01) | |
| C12N 15/66 | (2006.01) | |
| C12P 21/02 | (2006.01) | |
| C12P 21/06 | (2006.01) | |
| G01N 30/80 | (2006.01) | |
| G01N 30/02 | (2006.01) | |

(52) U.S. Cl.
CPC .......... *C07K 14/71* (2013.01); *A61K 38/1866* (2013.01); *C07K 1/06* (2013.01); *C07K 1/113* (2013.01); *C07K 1/16* (2013.01); *C07K 1/18* (2013.01); *C07K 1/22* (2013.01); *C07K 1/36* (2013.01); *C07K 16/22* (2013.01); *C07K 16/283* (2013.01); *C12N 5/0018* (2013.01); *C12N 5/0031* (2013.01); *C12N 15/66* (2013.01); *C12P 21/02* (2013.01); *C12P 21/06* (2013.01); *G01N 30/80* (2013.01); *C07K 2317/622* (2013.01); *C07K 2319/30* (2013.01); *C07K 2319/33* (2013.01); *C12N 2800/10* (2013.01); *G01N 2030/027* (2013.01)

(58) Field of Classification Search
None
See application file for complete search history.

(56) References Cited

U.S. PATENT DOCUMENTS

| | | | | |
|---|---|---|---|---|
| 7,807,164 | B2 * | 10/2010 | Furfine | A61K 9/0019 |
| | | | | 424/134.1 |
| 11,104,715 | B2 * | 8/2021 | Lawrence | A61P 19/02 |
| 11,306,135 | B2 * | 4/2022 | Wang | C12N 5/0018 |
| 11,472,861 | B2 * | 10/2022 | Lawrence | C07K 16/22 |

(Continued)

FOREIGN PATENT DOCUMENTS

WO    WO-2020229584 A1 *  11/2020 ........... C12N 5/0031

OTHER PUBLICATIONS

Chun et al. "Usability of size-excluded fractions of soy protein hydrolysates for growth and viability of Chinese hamster ovary cells in protein-free suspension culture" Bioresource Technology 98:1000-1005. (Year: 2007).*

(Continued)

*Primary Examiner* — Sudhakar Katakam
*Assistant Examiner* — Zachary J Miknis
(74) *Attorney, Agent, or Firm* — Kramer Levin Naftalis & Frankel LLP

(57) ABSTRACT

The present disclosure pertains to compositions comprising anti-VEGF proteins and methods for producing such compositions.

30 Claims, 60 Drawing Sheets

Specification includes a Sequence Listing.

(56) References Cited

U.S. PATENT DOCUMENTS

| | | | | |
|---|---|---|---|---|
| 11,485,770 | B2* | 11/2022 | Wang | C12P 21/06 |
| 11,505,593 | B2* | 11/2022 | Wang | A61P 35/00 |
| 11,535,663 | B2* | 12/2022 | Lawrence | C07K 1/22 |
| 11,542,317 | B1* | 1/2023 | Wang | C07K 1/18 |
| 11,548,932 | B2* | 1/2023 | Wang | A61K 38/179 |
| 11,732,025 | B2* | 8/2023 | Wang | A61K 38/1866 530/387.3 |
| 11,753,459 | B2* | 9/2023 | Wang | C12P 21/06 530/387.3 |
| 11,958,894 | B2* | 4/2024 | Wang | C12N 15/66 |
| 12,012,444 | B2* | 6/2024 | Wang | A61K 38/1866 |
| 12,012,445 | B2* | 6/2024 | Wang | C07K 1/18 |
| 2012/0010025 | A1* | 1/2012 | Chou | A63B 37/0074 473/378 |
| 2018/0326126 | A1* | 11/2018 | Fiedler | A61M 5/3129 |
| 2024/0294606 | A1* | 9/2024 | Wang | A61P 17/06 |

OTHER PUBLICATIONS

Byun, Juyoung et al., Journal of Microbiology and Biotechnology, Jan. 28, 2019, vol. 29, No. 1, pp. 55-58, DOI: 10.4014/jmb.1809.09018.

HyCell CHO medium, Thermo Fisher Scientific, Jun. 2013.

Rathore Anurag et al.: "Impact of Media Components on CQAs of Monoclonal Antibodies—Bioprocess Development Forum", Sep. 21, 2017 (Sep. 21, 2017), pp. 1-7, XP055818253, Retrieved from the Internet: URL:http://www.processdevelopmentforum.com/articles/impact-of-medi•• components-on-cqas-of-monoclonal-antibodies/ [retrieved on Jun. 25, 2021].

Gronemeyer Petra et al.: "Trends in Upstream and Downstream Process Development for Antibody Manufacturing", Bioengineering, vol. 1, No. 4, Oct. 1, 2014 (Oct. 1, 2014), pp. 188-212, XP093209642, ISSN: 2306-5354, DOI: 10.3390/bioengineering1040188.

Herzer Sibylle et al.: "Development and Scale-Up of the Recovery and Purification of a Domain Antibody Fc Fusion Protein-Comparison of a Two and Three-Step Approach", Mar. 13, 2015 (Mar. 13, 2015), XP093087146, DOI: 10.1002/bit.25561 /abstract) Retrieved from the Internet: URL:https://onlinelibrary.wiley.com/doi/10.1002/bit.25561 [retrieved on Sep. 29, 2023].

Angela et al.: "Design and Manufacture of therapeutic Fc. fusion proteins", Oct. 16, 2014 (Oct. 16, 2014), XP093209586, Retrieved from the Internet: URL:https://www.bioprocessintl.com/monoclonal-antibodies/immunoglobulin-fc-fusion-proteins-part-1-their-design-and-manufacture.

* cited by examiner

Scheme 1.

| PTM | Site | Peptide Sequence | Modification | Aflibercept AEX Load | Aflibercept AEX Pool | | | | |
|---|---|---|---|---|---|---|---|---|---|
| | | | | | POROS 50 HQ pH 8.4 2.0 mS/cm AEX Separation 1 | QsFF pH 8.0 2.5 mS/cm AEX Separation 2 | POROS 50 HQ pH 8.0 2.5 mS/cm AEX Separation 3 | QsFF pH 7.8 4.0 mS/cm AEX Separation 4 | POROS 50 HQ pH 7.8 4.0 mS/cm AEX Separation 5 |
| | | | | 3.06 | 1.05 | 0.96 | 1.33 | 1.35 | 1.55 |
| His Oxidation | H19 | SDTGRPFVEMYSEIPEIIHMTEGR | +14 | <0.01% | <0.01% | <0.01% | <0.01% | <0.01% | <0.01% |
| | H86 | EIGLLTC*EATVNGHLYK | +14 | 0.013% | 0.006% | 0.007% | 0.008% | 0.009% | 0.010% |
| | H95 | TNYLTHR | +14 | <0.01% | <0.01% | <0.01% | <0.01% | <0.01% | <0.01% |
| | H110 | QTNTIIDVVLSPSHGIELSVGEK | +14 | <0.01% | <0.01% | <0.01% | <0.01% | <0.01% | <0.01% |
| | H145 | TELNVGIDFNWEYPSSKHQHK | +14 | 0.067% | 0.039% | 0.033% | 0.035% | 0.038% | 0.042% |
| | H209 | THTC*PPC*PAPELLGGPSVFLFPPKPK | +14 | 0.056% | 0.027% | 0.037% | 0.040% | 0.045% | 0.040% |
| | H295 | VVSVLTVLHQDWLNGK | +14 | <0.01% | <0.01% | <0.01% | <0.01% | <0.01% | <0.01% |
| Trp Oxidation | W58 | IIWDSR | +4 | 0.012% | 0.008% | 0.007% | 0.009% | 0.009% | 0.011% |
| | | | +16 | 0.027% | 0.017 | 0.022% | 0.021% | 0.021% | 0.023% |
| | | | +32 | 0.114% | 0.102% | 0.111% | 0.121% | 0.114% | 0.135% |
| | | | +48 | <0.01% | <0.01% | <0.01% | <0.01% | <0.01% | <0.01% |
| | W138 | TELNVGIDFNWEYPSSK | +4 | 0.069% | 0.055% | 0.040% | 0.036 | 0.039% | 0.038% |
| | | | +16 | 0.131% | 0.078% | 0.070% | 0.089 | 0.077% | 0.081% |
| | | | +32 | 0.086% | 0.057% | 0.040% | 0.059% | 0.046% | 0.068% |

*: ALKYLATED CYSTEINE

FIG. 11

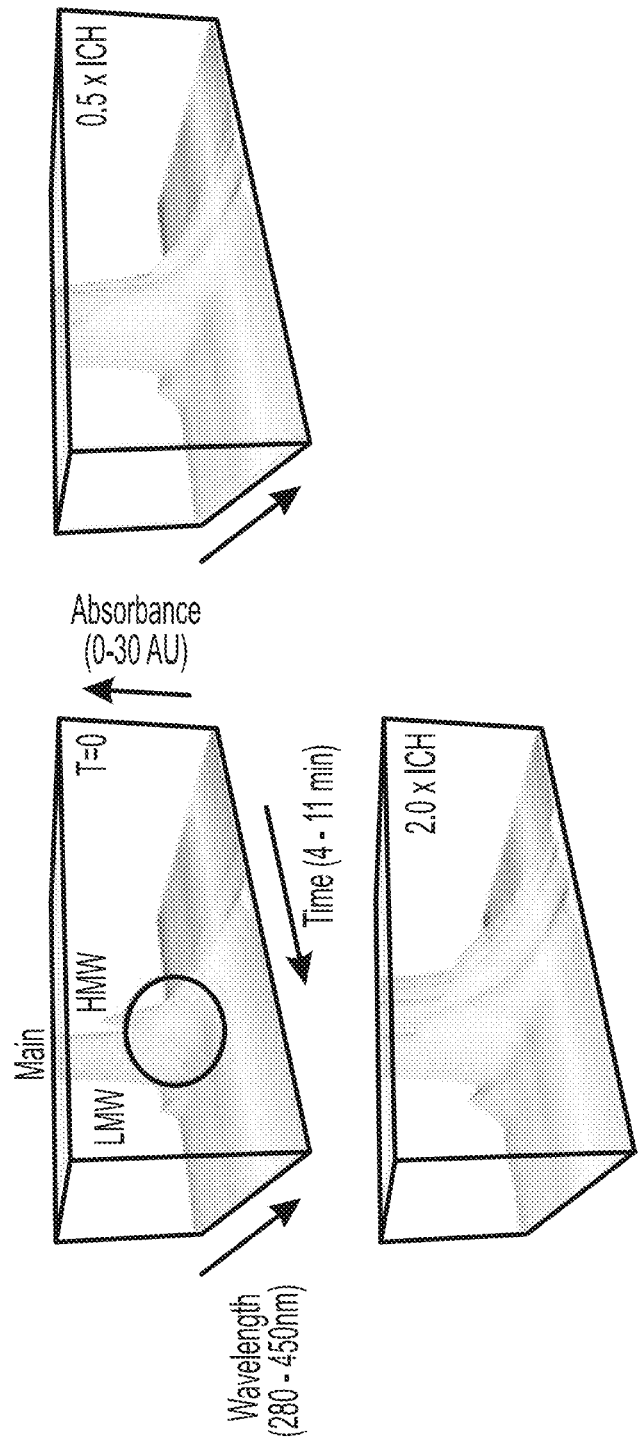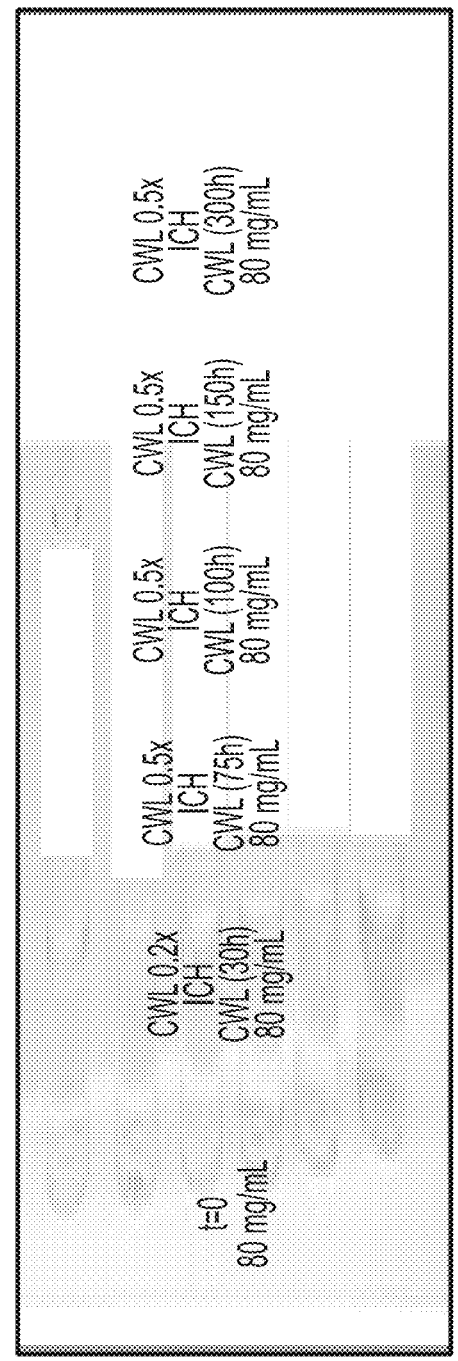
FIG. 21

| Term | Scaled Estimate | | Std Error | t Ratio | Prob>\|t\| |
|---|---|---|---|---|---|
| Intercept | 0.4682071 | | 0.009776 | 47.89 | <.0001* |
| Cysteine(0,1) | 0.3470799 | | 0.009806 | 35.40 | <.0001* |
| B-Vits Group(0,1) | 0.0373611 | | 0.009897 | 3.78 | 0.0008* |
| Iron(0,1) | 0.0698208 | | 0.010074 | 6.93 | <.0001* |
| Zinc(0,1) | 0.0538585 | | 0.010255 | 5.25 | <.0001* |
| Folic Acid(0,1) | 0.037899 | | 0.010172 | 3.73 | 0.0009* |
| Cysteine*B-Vits Group | 0.0253685 | | 0.009837 | 2.58 | 0.0155* |
| Cysteine*Iron | 0.07244 | | 0.01011 | 7.17 | <.0001* |
| Cysteine*Zinc | 0.0339284 | | 0.009973 | 3.40 | 0.0020* |
| Cysteine*Folic Acid | 0.0298402 | | 0.010218 | 2.92 | 0.0068* |
| B-Vits Group*Iron | 0.0229271 | | 0.009945 | 2.31 | 0.0288* |
| B-Vits Group*Folic Acid | -0.022614 | | 0.010243 | -2.21 | 0.0356* |

Control b-value = 1.67

| Term | Scaled Estimate | | Std Error | t Ratio | Prob>\|t\| |
|---|---|---|---|---|---|
| Intercept | 1.079804 | | 0.126434 | 8.54 | 0.0010* |
| Taurine (0,1) | -0.030846 | | 0.040585 | -0.76 | 0.4896 |
| Hypotaurine (0,1) | -0.085952 | | 0.044048 | -1.95 | 0.1228 |
| Glycine (0,1) | -0.181863 | | 0.047269 | -3.85 | 0.0183* |
| Thioctic Acid (0,1) | 0.0575148 | | 0.0465 | 1.24 | 0.2838 |
| Vitamin C (0,1) | -0.093266 | | 0.0392 | -2.38 | 0.0761 |
| Taurine*Hypotaurine | 0.1943093 | | 0.042535 | 4.57 | 0.0103* |
| Taurine*Thioctic Acid | -0.031889 | | 0.044591 | -0.72 | 0.5140 |
| Taurine*Vitamin C | 0.0948234 | | 0.046063 | 2.06 | 0.1086 |
| Hypotaurine*Trioctic Acid | -0.009982 | | 0.045049 | -0.22 | 0.8355 |
| Hypotaurine*Vitamin C | 0.1509187 | | 0.043708 | 3.45 | 0.0260* |
| Thioctic Acid*Vitamin C | -0.176346 | | 0.043781 | -4.03 | 0.0158* |
| Taurine*Taurine | 0.3679087 | | 0.117837 | 3.12 | 0.0355* |
| Hypotaurine*Hypotaurine | 0.192703 | | 0.110017 | 1.75 | 0.1547 |
| Glycine*Glycine | -0.270392 | | 0.11851 | -2.28 | 0.0846 |

FIG. 28C

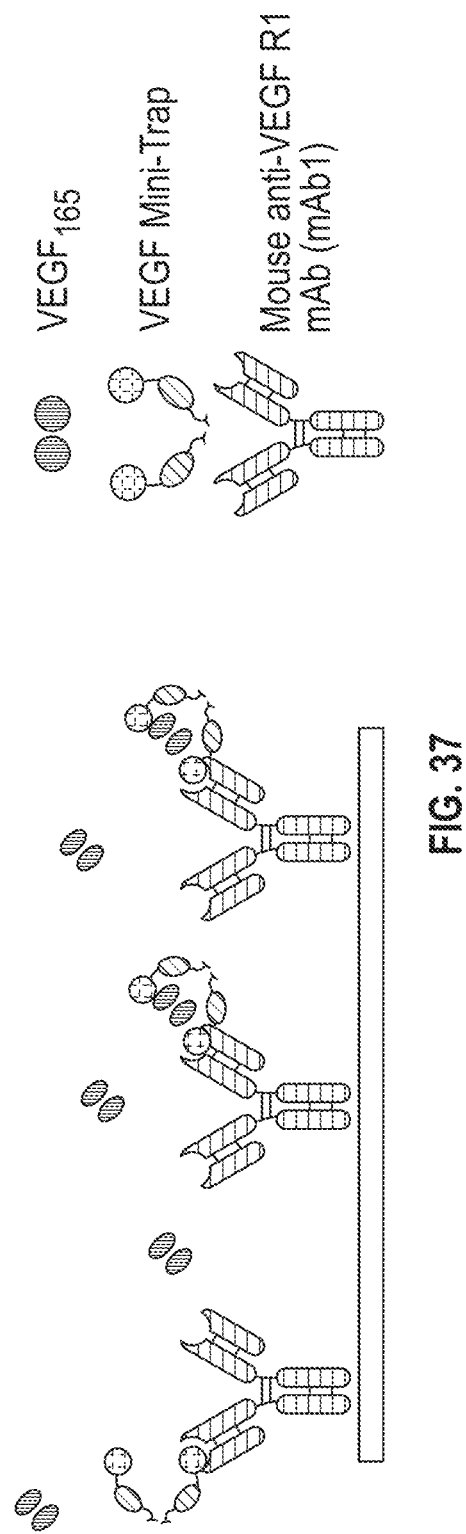

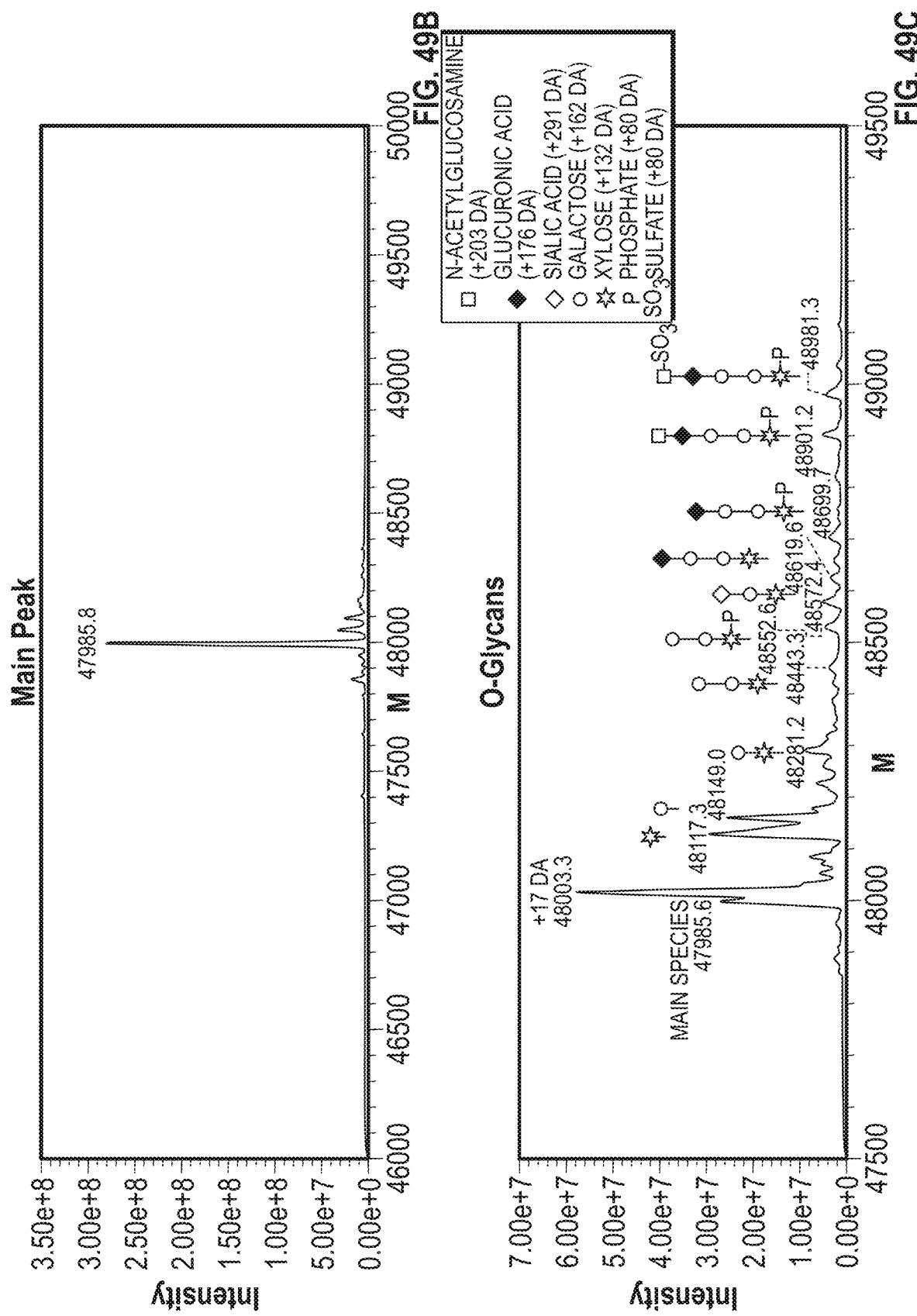

| Peak No. | Abbreviation | Glycan Structure | % Peak Area | | | Theoretical Mass (Da) |
|---|---|---|---|---|---|---|
| | | | MT6 | MT5 | MT1 | |
| 1 | G0-2GlcNAc | | 0.11 | 0.19 | 0.96 | 1221.50 |
| 2 | G0-GlcNAc | | 0.09 | 0.11 | 0.34 | 1424.58 |
| 3 | Man4 | | 0.51 | 0.56 | 0.62 | 1383.56 |
| 4 | G0 | | 0.07 | 0.05 | 0.26 | 1627.66 |
| 5 | G1-GlcNAc (1-6) | | 0.26 | 0.31 | 0.14 | 1586.63 |
| 6 | G1-GlcNAc (1-3) | | 0.55 | 0.61 | 1.76 | 1586.63 |
| 7 | G1F-GlcNAc (1-6) | | 0.34 | 0.37 | 0.92 | 1732.69 |
| 8 | Man5 | | 1.32 | 1.63 | 16.11 | 1545.61 |
| 9 | G1F-GlcNAc (1-3) | | 0.35 | 0.26 | 0.45 | 1732.69 |
| | G1 (1-6) | | | | | 1789.71 |
| 10 | G1 (1-3) | | 0.89 | 0.88 | 1.34 | 1789.71 |
| 11 | bG1 | | | | | 1992.79 |
| | G1S1-GlcNAc | | 0.26 | 0.22 | 0.78 | 1877.73 |
| | G1F (1-6) | | | | | 1935.77 |
| 12 | Man4_G1 | | 0.51 | 0.46 | 1.53 | 1748.69 |
| 13 | G1F (1-3) | | 0.67 | 0.64 | 1.11 | 1935.77 |
| 14 | G1S1-GlcNAc | | 0.73 | 1.20 | 1.86 | 1877.73 |
| 15 | bG1F | | 0.00 | 0.00 | 0.32 | 2138.85 |

FIG. 58A

| Peak No. | Abbreviation | Glycan Structure | % Peak Area | | | Theoretical Mass (Da) |
|---|---|---|---|---|---|---|
| | | | MT6 | MT5 | MT1 | |
| 16 | bG1F | | 0.00 | 0.00 | 0.40 | 2138.85 |
| 17 | Man6 | | 0.51 | 0.41 | 0.85 | 1707.66 |
| 18 | G2 | | 9.95 | 8.85 | 7.96 | 1951.77 |
| 19 | G1S1-GlcNAc | | 0.84 | 0.89 | 1.04 | 2080.81 |
| 20 | G2+GlcNAc | | 0.28 | 0.28 | 0.57 | 2154.85 |
| 21 | G2F | | 11.24 | 9.13 | 7.47 | 2097.82 |
| 22 | Man5_G1 | | 1.61 | 1.82 | 4.13 | 1910.74 |
| | Man4_G1S1 | | | | | 2039.78 |
| | G1FS1 | | | | | 2226.87 |
| 23 | bG2F | | 0.27 | 0.32 | 0.66 | 2300.90 |
| 24 | G2S1+Fuc | | 2.63 | 2.13 | 1.75 | 2242.86 |
| 25 | | | 13.42 | 14.46 | 9.50 | |
| 26 | Man6_G0+Phos | | 0.00 | 0.00 | 0.53 | 1787.63 |
| 27 | G2FS1 | | 4.00 | 2.43 | 1.67 | 2388.92 |
| 28 | | | 18.85 | 21.19 | 15.94 | 2388.92 |
| 29 | Man5_G1S1 | | 0.51 | 0.62 | 1.70 | 2201.84 |
| 30 | bG2FS1 | | 0.00 | 0.00 | 0.27 | 2592.00 |
| 31 | G2+NGNA | | 0.44 | 0.35 | 0.35 | 2258.86 |
| | G3 | | | | | 2316.90 |

FIG. 58B

| Peak No. | Abbreviation | Glycan Structure | % Peak Area | | | Theoretical Mass (Da) |
|---|---|---|---|---|---|---|
| | | | MT6 | MT5 | MT1 | |
| 32 | G2S1+Fuc | | 0.85 | 0.59 | 0.38 | 2388.92 |
| 33 | G2S2 | | 4.56 | 4.36 | 2.57 | 2533.96 |
| 34 | | | 1.31 | 0.99 | 0.71 | 2533.96 |
| 35 | G2FS2 | | 10.76 | 13.67 | 8.33 | 2680.02 |
| 36 | G3S1 | | 0.20 | 0.14 | 0.11 | 2607.99 |
| 37 | G2S1+NGNA | | 0.87 | 0.59 | 0.35 | 2549.95 |
| | G3FS1 | | | | | 2754.05 |
| 38 | G2S2+Fuc | | 0.23 | 0.13 | 0.07 | 2680.02 |
| 39 | G3FS1 | | 1.61 | 1.22 | 0.67 | 2754.05 |
| 40 | | | 1.77 | 1.77 | 0.95 | 2754.05 |
| | G2FS2+Fuc | | | | | 2826.07 |
| 41 | | | 0.24 | 0.24 | 0.15 | |
| 42 | G3FS2 | | 1.85 | 1.59 | 0.77 | 3045.15 |
| 43 | | | 0.78 | 0.77 | 0.32 | |
| 44 | G2FS2+2Fuc | | 0.34 | 0.31 | 0.14 | 2972.13 |
| 45 | G4FS1 | | 0.57 | 0.29 | 0.12 | 3119.18 |
| 46 | G3FS3 | | 1.14 | 1.43 | 0.58 | 3336.24 |
| 47 | G4FS2 | | 0.89 | 0.72 | 0.24 | 3410.28 |
| 48 | G4FS3 | | 0.63 | 0.60 | 0.18 | 3701.38 |
| 49 | G4FS4 | | 0.22 | 0.23 | 0.07 | 3992.47 |

FIG. 58C

ANTI-VEGF PROTEIN COMPOSITIONS AND METHODS FOR PRODUCING THE SAME

CROSS-REFERENCE TO RELATED APPLICATIONS

This application is a continuation of Ser. No. 18/213,779, filed on Jun. 23, 2023, which is a continuation of Ser. No. 18/116,166, filed on Mar. 1, 2023, which is a continuation of U.S. patent application Ser. No. 17/858,724, filed on Jul. 6, 2022, which is now U.S. Pat. No. 11,753,459, which is a continuation of U.S. patent application Ser. No. 17/842,286, filed on Jun. 16, 2022, which is now U.S. Pat. No. 11,542,317, which is a continuation of U.S. patent application Ser. No. 17/667,298, filed on Feb. 8, 2022, which is now U.S. Pat. No. 11,505,593, which is a continuation of U.S. patent application Ser. No. 17/575,425, filed on Jan. 13, 2022, which is now U.S. Pat. No. 11,485,770, which is a divisional of Ser. No. 17/460,578, filed on Aug. 30, 2021, which is now U.S. Pat. No. 11,306,135, which is a continuation of U.S. patent application Ser. No. 16/996,293, filed on Aug. 18, 2020, which is now U.S. Pat. No. 11,186,625, which claims priority to and the benefit of U.S. Provisional Patent Application No. 63/065,012, filed on Aug. 13, 2020, the content of which is incorporated herein by reference in its entirety. This application also claims priority to and the benefit of Provisional Patent Application No. 62/944,635, filed on Dec. 6, 2019. Also, this application is a continuation of Ser. No. 17/458,519 filed on Aug. 26, 2021, which is a continuation of U.S. patent application Ser. No. 16/996,293, filed on Aug. 18, 2020, which is now U.S. Pat. No. 11,186,625, which claims priority to and the benefit of U.S. Provisional Patent Application No. 63/065,012, filed on Aug. 13, 2020 and U.S. Provisional Patent Application No. 62/944,635, filed on Dec. 6, 2019, the content of which is incorporated herein by reference in its entirety.

SEQUENCE LISTING

The instant application contains a Sequence Listing which has been filed electronically in XML format and is hereby incorporated by reference in its entirety. Said XML copy, created on Mar. 1, 2023, is named 070816-02498_SL.xml and is 177,952 bytes in size.

FIELD

The present invention generally pertains to anti-VEGF compositions and methods for producing the same.

BACKGROUND

Protein-based biopharmaceutical compositions have emerged as important products for research, the treatment of ophthalmological diseases, cancer, autoimmune disease, and infection, as well as other diseases and disorders. Biopharmaceuticals represent one of the fastest growing product segments of the pharmaceutical industry.

A class of cell-derived dimeric mitogens with selectivity for vascular endothelial cells has been identified and designated vascular endothelial cell growth factor (VEGF).

Persistent angiogenesis may cause or exacerbate certain diseases such as psoriasis, rheumatoid arthritis, hemangiomas, angiofibromas, diabetic retinopathy and neovascular glaucoma. An inhibitor of VEGF activity would be useful as a treatment for such diseases and other VEGF-induced pathological angiogenesis and vascular permeability conditions, such as tumor vascularization. The angiopoietins and members of the vascular endothelial growth factor (VEGF) family are the only growth factors thought to be largely specific for vascular endothelial cells.

Several eye disorders are associated with pathological angiogenesis. For example, the development of age-related macular degeneration (AMD) is associated with a process called choroidal neovascularization (CNV). Leakage from the CNV causes macular edema and collection of fluid beneath the macula resulting in vision loss. Diabetic macular edema (DME) is another eye disorder with an angiogenic component. DME is the most prevalent cause of moderate vision loss in patients with diabetes and is a common complication of diabetic retinopathy, a disease affecting the blood vessels of the retina. Clinically significant DME occurs when fluid leaks into the center of the macula, the light-sensitive part of the retina responsible for sharp, direct vision. Fluid in the macula can cause severe vision loss or blindness.

Various VEGF inhibitors, such as the VEGF trap EYLEA® (aflibercept), have been approved to treat such eye disorders.

SUMMARY

The present invention relates to anti-VEGF proteins including the VEGF trap protein aflibercept, which is a fusion protein. The instant invention also pertains to a new anti-VEGF protein, the aflibercept MiniTrap or VEGF MiniTrap (collectively referred to as MiniTrap unless otherwise noted). Disclosed herein are methods of making these anti-VEGF proteins, including production modalities that provide efficient and effective means to produce the proteins of interest. In one aspect, the instant invention is directed towards the use of chemically defined media (CDM) to produce anti-VEGF proteins. In a particular aspect, the CDMs of interest are those that, when used, produce a protein sample wherein the sample has a yellow-brown color and may comprise oxidized species. Still further in the present application, protein variants of aflibercept and VEGF MiniTrap are disclosed together with attendant production methods.

Production of Aflibercept

The present disclosure describes the production of aflibercept using a cell culture medium. In one embodiment, the cell culture medium is a chemically defined medium ("CDM"). CDM is often used because it is a protein-free, chemically-defined formula using no animal-derived components and there is certainty as to the composition of the medium. In another embodiment, the cell culture medium is a soy hydrolysate medium.

In one embodiment, a method of producing a recombinant protein comprises: (a) providing a host cell genetically engineered to express a recombinant protein of interest; (b) culturing the host cell in a CDM under suitable conditions in which the cell expresses the recombinant protein of interest; and (c) harvesting a preparation of the recombinant protein of interest produced by the cell. In one aspect, the recombinant protein of interest is an anti-VEGF protein. In a particular aspect, the anti-VEGF protein is selected from the group consisting of aflibercept and recombinant MiniTrap (examples of which are disclosed in U.S. Pat. No. 7,279,159), an aflibercept scFv and other anti-VEGF proteins. In a preferred aspect, the recombinant protein of interest is aflibercept.

In one aspect of the present embodiment, aflibercept is expressed in a suitable host cell. Non-limiting examples of such host cells include, but are not limited to, CHO, CHO K1, EESYR®, NICE®, NS0, Sp2/0, embryonic kidney cells and BHK.

Suitable CDMs include Dulbecco's Modified Eagle's (DME) medium, Ham's Nutrient Mixture, Excell medium, and IS CHO-CD medium. Other CDMs known to those skilled in the art are also contemplated to be within the scope of the present invention. In a particular aspect, a suitable CDM is CDM1B (Regeneron) or Excell Advanced Medium (SAFC).

In one embodiment, a clarified harvest sample from a CDM culture comprising aflibercept is subjected to a capture chromatography procedure. In one aspect, the capture step is an affinity chromatography procedure using, for example, Protein A. In a further aspect, the eluate of the affinity procedure exhibits a certain color, for example, the eluate can exhibit a yellow-brown color. As described in more detail infra, color can be assessed using (i) the European Color Standard "BY" in which a qualitative visual inspection is made or (ii) a colorimetric assay, CIE L*, a*, b* (or CIELAB), which is more quantitative than the BY system. However, in either case, color assessment between multiple samples should be normalized against protein concentration in order to assure a meaningful assessment. For example, referring to Example 9 below, the Protein A eluate has a "b*" value of around 2.52 which corresponds to a BY value of approximately BY5 (when measured at a concentration of 5 g/L protein in the protein A eluate). If the color of the Protein A eluate is to be compared to another sample, then the comparison should be made against the same protein concentration. The b* value in the CIELAB color space is used to expresses coloration of the samples and covers blue (−) to yellow (+). A higher b* value of a sample compared to another indicates a more intense yellow-brown coloration in the sample compared to the other.

In one embodiment, aflibercept is produced from a host cell genetically engineered to express aflibercept using CDM. In one aspect, other species or variants of aflibercept are also produced. These variants include aflibercept isoforms that comprise one or more oxidized amino acid residues collectively referred to as oxo-variants. A clarified harvest sample produced using CDM comprising aflibercept as well as its oxo-variants can be subjected to a capture chromatography procedure. In one aspect, the capture step is an affinity chromatography procedure using, for example, a Protein A column. When a sample extracted from an affinity eluate, which may or may not manifest a yellow-brown color, is analyzed using, for example, liquid chromatography-mass spectrometry (LC-MS), one or more oxidized variants of aflibercept may be detected. Certain amino acid residues of a modified aflibercept are shown to be oxidized including, but not limited to, histidine and/or tryptophan residues. In one aspect, the variants can include oxidation of one or more methionine residues as well as other residues, see infra.

In another aspect, the variants can include oxidation of one or more tryptophan residues to form N-formylkynurenine. In a further aspect, the variants can include oxidation of one or more tryptophan residues to form mono-hydroxyl tryptophan. In a particular aspect, the protein variants can include oxidation of one or more tryptophan residues to form di-hydroxyl tryptophan. In a particular aspect, the protein variants can include oxidation of one or more tryptophan residues to form tri-hydroxyl tryptophan.

In another aspect, the variants can include one or more modifications selected from the group consisting of: deamidation of, for example, one or more asparagines; one or more aspartic acids converted to iso-aspartate and/or Asn; oxidation of one or more methionines; oxidation of one or more tryptophans to N-formylkynurenine; oxidation of one or more tryptophans to mono-hydroxyl tryptophan; oxidation of one or more tryptophans to di-hydroxyl tryptophan; oxidation of one or more tryptophans to tri-hydroxyl tryptophan; Arg 3-deoxyglucosonation of one or more arginines; removal of C-terminal glycine; and presence of one or more non-glycosylated glycosites.

In another embodiment, the invention is directed to methods for producing aflibercept. In one aspect, a clarified harvest sample comprising aflibercept and its variants are subjected to a capture step such as Protein A affinity chromatography. Subsequent to the affinity step, an affinity eluate can be subjected to ion exchange chromatography. The ion exchange chromatography can be either cation or anion exchange chromatography. Also contemplated to be within the scope of the present embodiment is mixed-mode or multimodal chromatography as well as other chromatographic procedures which are discussed further below. In a particular aspect, the ion exchange chromatography is anion exchange chromatography (AEX). Suitable conditions for employing AEX include, but are not limited to, Tris hydrochloride at a pH of about 8.3 to about 8.6. Following equilibration using, for example, Tris hydrochloride at a pH of about 8.3 to about 8.6, the AEX column is loaded with sample. Following the loading of the column, the column can be washed one or multiple times using, for example, the equilibrating buffer. In a particular aspect, the conditions used can facilitate the differential chromatographic behavior of aflibercept and its oxidized variants such that a fraction comprising aflibercept absent significant amounts of oxo-variants can be collected in a flowthrough fraction while a significant portion of oxo-variants are retained on the solid-phase of the AEX column and can be obtained upon stripping the column-see Example 2 below, FIG. 11. Referring to FIG. 11 and Example 2, changes in oxo-variants can be observed between the different production steps. For example, this change can be illustrated by data in the "Tryptophan Oxidation Level (%)" section, specifically, the "W138(+16)" column. There it can be observed that the oxo-variants (specifically, oxo-tryptophan) went from about 0.131% in a load sample to about 0.070% in a flowthrough sample following AEX chromatography (AEX separation 2), indicating that there was a reduction in oxo-variants of aflibercept using AEX.

Use of ion exchange can be used to mitigate or minimize color. In one aspect of the present embodiment, a clarified harvest sample is subjected to capture chromatography, for example, using Protein A affinity chromatography. The affinity column is eluted and has a first color with a particular BY and/or b* value assigned thereto. This Protein A eluate is then subjected to ion exchange chromatography such as anion exchange chromatography (AEX). The ion exchange column is washed and the flowthrough is collected and has a second color having a particular BY and/or b* value assigned thereto. In a particular aspect, the color value (either "BY" or "b*") of the first color differs from the second color. In a further aspect, the first color of the Protein A eluate has a more yellow-brown color as compared to the second color of the AEX flowthrough as reflected by the respective BY and/or b* value. Typically, there is a reduction in yellow-brown color of the second color following AEX when compared to the first color of the Protein A eluate. For example, the use of anion exchange reduced the yellow-brown color observed in a Protein A eluate sample from a b* value of about 3.06 (first color) to about 0.96 (second color) following AEX-see Example 2, Table 2-3 below.

In one aspect of the embodiment, the pH of both the equilibration and wash buffers for the AEX column can be from about 8.30 to about 8.60. In another aspect, the conductivity of both the equilibration and wash buffers for the AEX column can be from about 1.50 to about 3.00 mS/cm.

In one aspect of the embodiment, the equilibration and wash buffers can be about 50 mM Tris hydrochloride. In one aspect, the strip buffer comprises 2 M sodium chloride or 1N sodium hydroxide or both (see Table 2-2).

The present embodiment can include the addition of one or more steps, in no particular order, such as hydrophobic interaction chromatography (HIC), affinity chromatography, multimodal chromatography, viral inactivation (e.g., using low pH), viral filtration, and/or ultra/diafiltration as well as other well-known chromatographic steps.

In one embodiment, the anti-VEGF protein is glycosylated at one or more asparagines as follows: G0-GlcNAc glycosylation; G1-GlcNAc glycosylation; G1S-GlcNAc glycosylation; G0 glycosylation; G1 glycosylation; G1S glycosylation; G2 glycosylation; G2S glycosylation; G2S2 glycosylation; G0F glycosylation; G2F2S glycosylation; G2F2S2 glycosylation; GIF glycosylation; G1FS glycosylation; G2F glycosylation; G2FS glycosylation; G2FS2 glycosylation; G3FS glycosylation; G3FS3 glycosylation; G0-2GlcNAc glycosylation; Man4 glycosylation; Man4_A1G1 glycosylation; Man4_A1G1S1 glycosylation; Man5 glycosylation; Man5_A1G1 glycosylation; Man5_A1G1S1 glycosylation; Man6 glycosylation; Man6_G0+Phosphate glycosylation; Man6+Phosphate glycosylation; and/or Man7 glycosylation. In one aspect, the anti-VEGF protein can be aflibercept, anti-VEGF antibody or VEGF MiniTrap.

In one aspect, glycosylation profile of a composition of an anti-VEGF protein is as follows: about 40% to about 50% total fucosylated glycans, about 30% to about 55% total sialylated glycans, about 6% to about 15% mannose-5, and about 60% to about 79% galactosylated glycans (see Example 6). In one aspect, the anti-VEGF protein has Man5 glycosylation at about 32.4% of asparagine 123 residues and/or about 27.1% of asparagine 196 residues.

In one embodiment, the process can further comprise formulating a drug substance using a pharmaceutically acceptable excipient. In one aspect of the embodiment, the pharmaceutically acceptable excipient can be selected from the following: water, buffering agents, sugar, salt, surfactant, amino acid, polyol, chelating agent, emulsifier and preservative. Other well-known excipients to the skilled artisan are within the purview of this embodiment.

In one aspect of the embodiment, the formulation can be suitable for administration to a human subject. In particular, administration can be affected by intravitreal injection. In one aspect, the formulation can have about 40 to about 200 mg/mL of the protein of interest.

The formulation can be used as a method of treating or preventing angiogenic eye disorders which can include: age-related macular degeneration (e.g., wet or dry), macular edema, macular edema following retinal vein occlusion, retinal vein occlusion (RVO), central retinal vein occlusion (CRVO), branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy in a subject with diabetic macular edema; or diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME).

Production of VEGF MiniTrap

The present disclosure describes the production of a modified version of aflibercept wherein the Fc portion is removed or absent and is referred to as aflibercept MiniTrap or VEGF MiniTrap. This MiniTrap can be produced in cell culture medium including a chemically defined medium (CDM) or soy hydrolysate medium.

In one embodiment, the MiniTrap is produced using CDM. In one aspect of MiniTrap production, full length aflibercept is produced using a suitable host and under suitable conditions and is further processed whereby the Fc portion is enzymatically removed thus yielding MiniTrap. Alternatively, a gene encoding MiniTrap (e.g., a nucleotide sequence encoding aflibercept absent its Fc portion) can be produced under suitable conditions using a suitable host cell.

In one embodiment, a method for manufacturing Mini-Trap includes producing a full-length aflibercept fusion protein followed by cleavage of the Fc region. In one aspect, the method involves producing a recombinant protein, namely a full-length aflibercept fusion protein (see, U.S. Pat. No. 7,279,159, the entire teaching of which is incorporated herein by reference), comprising: (a) providing a host cell genetically engineered to express full length aflibercept; (b) culturing the host cell in CDM under suitable conditions in which the cell expresses the full length aflibercept; (c) harvesting a preparation of the full length aflibercept produced by the cell; and (d) subjecting the full length aflibercept to enzymatic cleavage specific for removing the Fc portion of the fusion protein. In another aspect, a nucleotide sequence encoding aflibercept minus its Fc portion is expressed from a suitable host cell under suitable conditions well known to those skilled in the art (see U.S. Pat. No. 7,279,159).

In one aspect of the present embodiment, the aflibercept is expressed in a suitable host cell. Non-limiting examples of such host cells include, but are not limited to, CHO, CHO K1, EESYR®, NICE®, NS0, Sp2/0, embryonic kidney cells and BHK.

Suitable CDMs include Dulbecco's Modified Eagle's (DME) medium, Ham's Nutrient Mixture, EX-CELL medium (SAFC), and IS CHO-CD medium (Irvine). Other CDMs known to those skilled in the art are also contemplated to be within the scope of the present invention. In a particular aspect, a suitable CDM is CDM1B (Regeneron) or Excell medium (SAFC).

In one aspect, during the production of MiniTrap, a sample comprising a protein of interest (i.e., aflibercept fusion protein and/or MiniTrap) along with its variants (including oxo-variants) can exhibit certain color properties—a yellow-brown color. For example, an eluate sample from an affinity chromatography step can exhibit a certain yellow-brown color measured using the BY and/or b* system (see Examples 2 and 9 below). Exemplary sources for a "sample" may include an affinity chromatography, such as Protein A, eluate; the sample may be obtained from a flowthrough fraction of ion exchange chromatography procedure; it may also be obtained from the strip of an ion exchange column—there are other sources during a production process well known to those skilled in the art from which a sample may be analyzed. As mentioned above and described further below, color can be assessed using (i) the European Color Standard "BY" in which a qualitative visual inspection is made or (ii) a colorimetric assay, CIELAB, which is more quantitative than the BY system. However, in either case, color assessment between multiple samples should be normalized, for example, using protein concentration, in order to assure a meaningful assessment between samples.

In one aspect of the present embodiment, a full-length aflibercept fusion protein can be subjected to enzymatic processing ("cleavage activity") in order to generate a VEGF MiniTrap, for example, using proteolytic digestion employing a protease or enzymatically active variant thereof. In one aspect of this embodiment, the protease can be an immunoglobulin-degrading enzyme of *Streptococcus pyogenes* (IdeS). In another aspect, the protease can be thrombin trypsin, endoproteinase Arg-C, endoproteinase Asp-N, endoproteinase Glu-C, outer membrane protease T (OmpT), IdeS, chymotrypsin, pepsin, thermolysin, papain, pronase, or protease from *Aspergillus saitoi*. In one aspect, the protease can be a cysteine protease. In a particular aspect of the embodiment, the protease can be IdeS. In another aspect, the protease can be a variant of IdeS. Non-limiting examples of variants of IdeS are described infra and include a polypeptide having an amino acid sequence as set forth in the group consisting of SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15 and SEQ ID NO.: 16. In one aspect, the protease can be immobilized on agarose or another suitable matrix.

In one aspect, a protein of interest (together with its variants) is produced using CDM. In a particular aspect, the protein of interest includes aflibercept or MiniTrap. The variants comprise one or more oxidized amino acid residues, collectively oxo-variants. Examples of oxidized residues include, but are not limited to, one or more histidine and/or tryptophan residues. Other oxidized residues have also been detected using LC-MS and are described below, such as oxidized methionine. Subsequent chromatography such as AEX can be used to isolate these oxo-variants from the protein of interest in a given sample and are described herein.

In one aspect, the variants can include oxidation of one or more tryptophan residues to form N-formylkynurenines. In a further aspect, the variants can include oxidation of one or more tryptophan residues to form mono-hydroxyl tryptophan. In a particular aspect, the protein variants can include oxidation of one or more tryptophan residues to form di-hydroxyl tryptophan. In a particular aspect, the protein variants can include oxidation of one or more tryptophan residues to form tri-hydroxyl tryptophan.

In another aspect, the oxo-variants can include one or more modifications selected from the group consisting of: deamidation of one or more asparagine residues; one or more aspartic acids converted to iso-aspartate and/or asparagine; oxidation of one or more methionine residues; oxidation of one or more tryptophan residues to form N-formylkynurenine; oxidation of one or more tryptophan residues to form mono-hydroxyl tryptophan; oxidation of one or more tryptophan residues to form di-hydroxyl tryptophan; oxidation of one or more tryptophan residues to form tri-hydroxyl tryptophan; Arg 3-deoxyglucosonation of one or more arginine residues; removal of C-terminal glycine; and presence of one or more non-glycosylated glycosites.

In one embodiment, the method of manufacturing a MiniTrap protein comprises (a) capturing a full-length aflibercept fusion protein on a first chromatographic platform and (b) cleaving the aflibercept thereby forming a MiniTrap protein, i.e., aflibercept absent its Fc domain. In one aspect, the first chromatographic support comprises an affinity chromatography media, an ion-exchange chromatography media, or a hydrophobic interaction chromatography media. In a particular aspect, the first chromatographic platform comprises an affinity chromatography platform such as a Protein A. In a further aspect, the protein of capture step (a) is eluted from the first chromatography platform prior to cleavage step (b). In a still further aspect, a second capture step follows cleavage step (b). In a particular aspect, this second capture step can be facilitated by affinity chromatography such as Protein A affinity chromatography. The flowthrough of this second capture step (comprising MiniTrap) has a first color, for example, a yellow-brown color and measured having a particular BY and/or b* value—see, e.g., Example 9 below. Additionally, LC-MS analysis of this second capture flowthrough may demonstrate the presence of oxo-variants wherein one or more residues of MiniTrap are oxidized (see Example 9 below).

In a further aspect, the second capture flowthrough can be subjected to ion exchange chromatography such as AEX. This AEX column can be washed using a suitable buffer and an AEX flowthrough fraction can be collected comprising essentially MiniTrap. This AEX flowthrough fraction can have a second color that is of a yellow-brown coloration having a particular BY and/or b* value. In a further aspect, the first color (flowthrough from second capture step) and second color (flowthrough of the ion exchange procedure) have different colors as measured either by the BY and/or b* system. In one aspect, the second color demonstrates a diminished yellow-brown color when compared to the first color using either a BY and/or b* value following AEX.

In another embodiment, the cleavage activity of step (b) can be performed using a chromatographic column wherein the cleavage activity, for example, an enzyme activity, is affixed or immobilized to a column matrix. The column used in step (b) can comprise one or more of the proteases already alluded to and more fully described below.

In one embodiment, the ion-exchange chromatography procedure can comprise an anion-exchange (AEX) chromatography media. In another aspect, the ion-exchange chromatography media comprises a cation exchange (CEX) chromatography media. Suitable conditions for employing AEX include, but are not limited to, Tris hydrochloride at a pH of about 8.3 to about 8.6. Following equilibration using, for example, Tris hydrochloride at a pH of about 8.3 to about 8.6, the AEX column is loaded with sample. Following the loading of the column, the column can be washed one or multiple times using, for example, the equilibrating buffer. In a particular aspect, the conditions used can facilitate the differential chromatographic behavior of MiniTrap and its oxo-variants using AEX such that the MiniTrap is substantially in the flowthrough fraction while the oxo-variants are substantially retained on the AEX column and can be collected by stripping the column (see Example 9 below).

In one example, samples from different stages of production were analyzed for color and presence of oxo-variants. Referring to Example 9, the affinity flowthrough pool (flowthrough from a second Protein A affinity step) had a first b* value of about 1.58 (see Table 9-3). This second affinity flowthrough was subjected to AEX. The AEX flowthrough had a second b* value of about 0.50, indicating a significant reduction in yellow-brown color following the use of AEX.

Stripping of the AEX column yielded a strip sample and a third b* value of about 6.10 was observed, indicating that this strip sample had a more yellow-brown color when compared to either the load or flowthrough.

Referring again to Example 9, oxo-variant analysis was also performed. Samples analyzed were the affinity flowthrough pool (second Protein A affinity eluate), AEX flowthrough, and AEX strip. Referring to Table 9-5 and Table 9-6, changes in oxo-variants can be observed between the different production steps. For example, this change can be illustrated by data in the "Tryptophan Oxidation Level (%)" section, specifically, the "W58(+16)" column. There it can be observed that the oxo-variants (specifically, oxo-tryptophan) went from about 0.055% in a load sample to about 0.038% in a flowthrough sample following AEX chromatography, indicating that there was a reduction in oxo-variants following AEX. The AEX strip was analyzed and the percent oxo-tryptophan species was found to be about 0.089%. When this strip value was compared to the load (as well as the flowthrough), it appeared that a significant portion of this oxo-variant was retained on the AEX column.

The present embodiment can include the addition of one or more steps, in no particular order, such as hydrophobic interaction chromatography, affinity chromatography, multimodal chromatography, viral inactivation (e.g., using low pH), viral filtration, and/or ultra/diafiltration.

One embodiment of the present invention is directed to a method for regenerating a chromatography column comprising a resin. In one aspect of the embodiment, the resin has an immobilized hydrolyzing agent. In yet another aspect of the embodiment, the resin comprises an immobilized protease enzyme. In still another aspect of the embodiment, the resin is a FabRICATOR® resin or a mutant of the resin. In one aspect of the embodiment, the method of regenerating a column comprising a resin improves reaction efficiency of the resin.

In one aspect of the embodiment, a method of regenerating a column comprising a resin includes incubating the column resin with acetic acid. In one aspect, the concentration of acetic acid used is from about 0.1 M to about 2 M. In one aspect, the concentration of acetic acid is about 0.5 M. In one aspect, the resin is incubated for at least about 10 minutes. In another aspect, the resin is incubated for at least about 30 minutes. In yet another aspect of this embodiment, the resin is incubated for at least about 50 minutes. In yet another aspect of this embodiment, the resin is incubated for at least about 100 minutes. In yet another aspect of this embodiment, the resin is incubated for at least about 200 minutes. In yet another aspect of this embodiment, the resin is incubated for at least about 300 minutes.

Optionally, the column resin is further incubated with guanidine hydrochloride (Gu-HCl). In one aspect, Gu-HCl absent acetic acid is used to regenerate the column resin. The concentration of Gu-HCl employed is from about 1N to about 10N. In another aspect, the concentration of Gu-HCl is about 6N. In a further aspect, the column resin can be incubated for at least about 10 minutes with the regenerative agents (acetic acid, Gu-HCl). In yet another aspect, the resin is incubated for at least about 30 minutes. In still another aspect, the resin is incubated for at least about 50 minutes. In yet another aspect, said resin is incubated for at least about 100 minutes.

In one embodiment, the column comprising a resin is stored in ethanol. In one aspect, the column is stored in ethanol, wherein the ethanol percentage is from about 5% v/v to about 20% v/v. In a particular aspect, the column is stored using 20% v/v ethanol.

In one embodiment, the process can further comprise formulating the VEGF MiniTrap using a pharmaceutically acceptable excipient. In one aspect, the pharmaceutically acceptable excipient can be selected from the following: water, buffering agents, sugar, salt, surfactant, amino acid, polyol, chelating agent, emulsifier and preservative. Other well-known excipients to the skilled artisan are within the purview of this embodiment.

The formulation of the present invention is suitable for administration to a human subject. In one aspect of the present embodiment, administration can be effected by intravitreal injection. In one aspect, the formulation can have about 40 to about 200 mg/mL of the protein of interest. In a particular aspect, the protein of interest is either aflibercept or aflibercept MiniTrap.

The formulation can be used in a method of treating or preventing angiogenic eye disorders which can include: age-related macular degeneration (e.g., wet or dry), macular edema, macular edema following retinal vein occlusion, retinal vein occlusion (RVO), central retinal vein occlusion (CRVO), branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy in a subject with diabetic macular edema; or diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME).

Variants of IdeS

The present disclosure describes the use of IdeS (FabRICATOR) (SEQ ID NO.: 1) or other polypeptides which are IdeS variants (SEQ ID NO.: 2 to 16) to produce a VEGF MiniTrap. IdeS (SEQ ID NO.: 1) includes asparagine residues at position 87, 130, 182 and/or 274 (shown as "N*" bolded and italicized in SEQ ID NO.: 1 below). The asparagine at these positions may be mutated to an amino acid other than asparagine to form IdeS variants (and the mutated amino acid(s) are shown as italicized and underscored amino acid(s)):

```
                                                    SEQ ID NO.: 1
MRKRCYSTSAAVLAAVTLFVLSVDRGVIADSFSANQEIRYSEVTPYHVTSVWTKGVTPP

ANFTQGEDVFHAPYVANQGWYDITKTFN*GKDDLLCGAATAGNMLHWWFDQNKDQI

KRYLEEHPEKQKINFN*GEQMFDVKEAIDTKNHQLDSKLFEYFKEKAFPYLSTKHLGVF

PDHVIDMFIN*GYRLSLTNHGPTPVKEGSKDPRGGIFDAVFTRGDQSKLLTSRHDFKEKN
```

LKEISDLIKKELTEGKALGLSHTYANVRINHVINLWGADFDS*N*\*GNLKAIYVTDSDSNAS
IGMKKYFVGVNSAGKVAISAKEIKEDNIGAQVLGLFTLSTGQDSWNQTN

SEQ ID NO.: 2
MRKRCYSTSAAVLAAVTLFVLSVDRGVIADSFSANQEIRYSEVTPYHVTSVWTKGVTPP
ANFTQGEDVFHAPYVANQGWYDITKTF*D*GKDDLLCGAATAGNMLHWWFDQNKDQIK
RYLEEHPEKQKINF*N*\*GEQMFDVKEAIDTKNHQLDSKLFEYFKEKAFPYLSTKHLGVFP
DHVIDMFI*N*\*GYRLSLTNHGPTPVKEGSKDPRGGIFDAVFTRGDQSKLLTSRHDFKEKNL
KEISDLIKKELTEGKALGLSHTYANVRINHVINLWGADFDS*N*\*GNLKAIYVTDSDSNASI
GMKKYFVGVNSAGKVAISAKEIKEDNIGAQVLGLFTLSTGQDSWNQTN

SEQ ID NO.: 3
MRKRCYSTSAAVLAAVTLFVLSVDRGVIADSFSANQEIRYSEVTPYHVTSVWTKGVTPP
ANFTQGEDVFHAPYVANQGWYDITKTF*N*\*GKDDLLCGAATAGNMLHWWFDQNKDQI
KRYLEEHPEKQKINFR*G*EQMFDVKEAIDTKNHQLDSKLFEYFKEKAFPYLSTKHLGVFP
DHVIDMFI*N*\*GYRLSLTNHGPTPVKEGSKDPRGGIFDAVFTRGDQSKLLTSRHDFKEKNL
KEISDLIKKELTEGKALGLSHTYANVRINHVINLWGADFDS*N*\*GNLKAIYVTDSDSNASI
GMKKYFVGVNSAGKVAISAKEIKEDNIGAQVLGLFTLSTGQDSWNQTN

SEQ ID NO.: 4
MRKRCYSTSAAVLAAVTLFVLSVDRGVIADSFSANQEIRYSEVTPYHVTSVWTKGVTPP
ANFTQGEDVFHAPYVANQGWYDITKTF*N*\*GKDDLLCGAATAGNMLHWWFDQNKDQI
KRYLEEHPEKQKINF*N*\*GEQMFDVKEAIDTKNHQLDSKLFEYFKEKAFPYLSTKHLGVF
PDHVIDMFI*L*GYRLSLTNHGPTPVKEGSKDPRGGIFDAVFTRGDQSKLLTSRHDFKEKNL
KEISDLIKKELTEGKALGLSHTYANVRINHVINLWGADFDS*N*\*GNLKAIYVTDSDSNASI
GMKKYFVGVNSAGKVAISAKEIKEDNIGAQVLGLFTLSTGQDSWNQTN

SEQ ID NO.: 5
MRKRCYSTSAAVLAAVTLFVLSVDRGVIADSFSANQEIRYSEVTPYHVTSVWTKGVTPP
ANFTQGEDVFHAPYVANQGWYDITKTF*N*\*GKDDLLCGAATAGNMLHWWFDQNKDQI
KRYLEEHPEKQKINF*N*\*GEQMFDVKEAIDTKNHQLDSKLFEYFKEKAFPYLSTKHLGVF
PDHVIDMFI*N*\*GYRLSLTNHGPTPVKEGSKDPRGGIFDAVFTRGDQSKLLTSRHDFKEKN
LKEISDLIKKELTEGKALGLSHTYANVRINHVINLWGADFDS*D*GNLKAIYVTDSDSNASI
GMKKYFVGVNSAGKVAISAKEIKEDNIGAQVLGLFTLSTGQDSWNQTN

SEQ ID NO.: 6
MRKRCYSTSAAVLAAVTLFVLSVDRGVIADSFSANQEIRYSEVTPYHVTSVWTKGVTPP
ANFTQGEDVFHAPYVANQGWYDITKTF*D*GKDDLLCGAATAGNMLHWWFDQNKDQIK
RYLEEHPEKQKINF*R*GEQMFDVKEAIDTKNHQLDSKLFEYFKEKAFPYLSTKHLGVFPD
HVIDMFI*N*\*GYRLSLTNHGPTPVKEGSKDPRGGIFDAVFTRGDQSKLLTSRHDFKEKNLK
EISDLIKKELTEGKALGLSHTYANVRINHVINLWGADFDS*N*\*GNLKAIYVTDSDSNASIG
MKKYFVGVNSAGKVAISAKEIKEDNIGAQVLGLFTLSTGQDSWNQTN

SEQ ID NO.: 7
MRKRCYSTSAAVLAAVTLFVLSVDRGVIADSFSANQEIRYSEVTPYHVTSVWTKGVTPP
ANFTQGEDVFHAPYVANQGWYDITKTF*D*GKDDLLCGAATAGNMLHWWFDQNKDQIK
RYLEEHPEKQKINF*N*\*GEQMFDVKEAIDTKNHQLDSKLFEYFKEKAFPYLSTKHLGVFP
DHVIDMFI*L*GYRLSLTNHGPTPVKEGSKDPRGGIFDAVFTRGDQSKLLTSRHDFKEKNLK

EISDLIKKELTEGKALGLSHTYANVRINHVINLWGADFDS*N*GNLKAIYVTDSDSNASIG

MKKYFVGVNSAGKVAISAKEIKEDNIGAQVLGLFTLSTGQDSWNQTN

SEQ ID NO.: 8

MRKRCYSTSAAVLAAVTLFVLSVDRGVIADSFSANQEIRYSEVTPYHVTSVWTKGVTPP

ANFTQGEDVFHAPYVANQGWYDITKTF*D*GKDDLLCGAATAGNMLHWWFDQNKDQIK

RYLEEHPEKQKINF*N\**GEQMFDVKEAIDTKNHQLDSKLFEYFKEKAFPYLSTKHLGVFP

DHVIDMFI*N\**GYRLSLTNHGPTPVKEGSKDPRGGIFDAVFTRGDQSKLLTSRHDFKEKNL

KEISDLIKKELTEGKALGLSHTYANVRINHVINLWGADFDS*D*GNLKAIYVTDSDSNASIG

MKKYFVGVNSAGKVAISAKEIKEDNIGAQVLGLFTLSTGQDSWNQTN

SEQ ID NO.: 9

MRKRCYSTSAAVLAAVTLFVLSVDRGVIADSFSANQEIRYSEVTPYHVTSVWTKGVTPP

ANFTQGEDVFHAPYVANQGWYDITKTF*N\**GKDDLLCGAATAGNMLHWWFDQNKDQI

KRYLEEHPEKQKINF*R*GEQMFDVKEAIDTKNHQLDSKLFEYFKEKAFPYLSTKHLGVFP

DHVIDMFI*L*GYRLSLTNHGPTPVKEGSKDPRGGIFDAVFTRGDQSKLLTSRHDFKEKNLK

EISDLIKKELTEGKALGLSHTYANVRINHVINLWGADFDS*N\**GNLKAIYVTDSDSNASIG

MKKYFVGVNSAGKVAISAKEIKEDNIGAQVLGLFTLSTGQDSWNQTN

SEQ ID NO.: 10

MRKRCYSTSAAVLAAVTLFVLSVDRGVIADSFSANQEIRYSEVTPYHVTSVWTKGVTPP

ANFTQGEDVFHAPYVANQGWYDITKTF*N\**GKDDLLCGAATAGNMLHWWFDQNKDQI

KRYLEEHPEKQKINF*R*GEQMFDVKEAIDTKNHQLDSKLFEYFKEKAFPYLSTKHLGVFP

DHVIDMFI*N\**GYRLSLTNHGPTPVKEGSKDPRGGIFDAVFTRGDQSKLLTSRHDFKEKNL

KEISDLIKKELTEGKALGLSHTYANVRINHVINLWGADFDS*D*GNLKAIYVTDSDSNASIG

MKKYFVGVNSAGKVAISAKEIKEDNIGAQVLGLFTLSTGQDSWNQTN

SEQ ID NO.: 11

MRKRCYSTSAAVLAAVTLFVLSVDRGVIADSFSANQEIRYSEVTPYHVTSVWTKGVTPP

ANFTQGEDVFHAPYVANQGWYDITKTF*N\**GKDDLLCGAATAGNMLHWWFDQNKDQI

KRYLEEHPEKQKINF*N\**GEQMFDVKEAIDTKNHQLDSKLFEYFKEKAFPYLSTKHLGVF

PDHVIDMFI*L*GYRLSLTNHGPTPVKEGSKDPRGGIFDAVFTRGDQSKLLTSRHDFKEKNL

KEISDLIKKELTEGKALGLSHTYANVRINHVINLWGADFDS*D*GNLKAIYVTDSDSNASIG

MKKYFVGVNSAGKVAISAKEIKEDNIGAQVLGLFTLSTGQDSWNQTN

SEQ ID NO.: 12

MRKRCYSTSAAVLAAVTLFVLSVDRGVIADSFSANQEIRYSEVTPYHVTSVWTKGVTPP

ANFTQGEDVFHAPYVANQGWYDITKTF*D*GKDDLLCGAATAGNMLHWWFDQNKDQIK

RYLEEHPEKQKINF*R*GEQMFDVKEAIDTKNHQLDSKLFEYFKEKAFPYLSTKHLGVFPD

HVIDMFI*L*GYRLSLTNHGPTPVKEGSKDPRGGIFDAVFTRGDQSKLLTSRHDFKEKNLKE

ISDLIKKELTEGKALGLSHTYANVRINHVINLWGADFDS*N\**GNLKAIYVTDSDSNASIGM

KKYFVGVNSAGKVAISAKEIKEDNIGAQVLGLFTLSTGQDSWNQTN

SEQ ID NO.: 13

MRKRCYSTSAAVLAAVTLFVLSVDRGVIADSFSANQEIRYSEVTPYHVTSVWTKGVTPP

ANFTQGEDVFHAPYVANQGWYDITKTF*D*GKDDLLCGAATAGNMLHWWFDQNKDQIK

RYLEEHPEKQKINF*R*GEQMFDVKEAIDTKNHQLDSKLFEYFKEKAFPYLSTKHLGVFPD

HVIDMFI*N\**GYRLSLTNHGPTPVKEGSKDPRGGIFDAVFTRGDQSKLLTSRHDFKEKNLK

-continued

EISDLIKKELTEGKALGLSHTYANVRINHVINLWGADFDS*D*GNLKAIYVTDSDSNASIGM

KKYFVGVNSAGKVAISAKEIKEDNIGAQVLGLFTLSTGQDSWNQTN

SEQ ID NO.: 14
MRKRCYSTSAAVLAAVTLFVLSVDRGVIADSFSANQEIRYSEVTPYHVTSVWTKGVTPP

ANFTQGEDVFHAPYVANQGWYDITKTFDGKDDLLCGAATAGNMLHWWFDQNKDQIK

RYLEEHPEKQKINF*N*\*GEQMFDVKEAI*D*TKNHQLDSKLFEYFKEKAFPYLSTKHLGVFP

DHVIDMFI*L*GYRLSLTNHGPTPVKEGSKDPRGGIFDAVFTRGDQSKLLTSRHDFKEKNLK

EISDLIKKELTEGKALGLSHTYANVRINHVINLWGADFDS*D*GNLKAIYVTDSDSNASIGM

KKYFVGVNSAGKVAISAKEIKEDNIGAQVLGLFTLSTGQDSWNQTN

SEQ ID NO.: 15
MRKRCYSTSAAVLAAVTLFVLSVDRGVIADSFSANQEIRYSEVTPYHVTSVWTKGVTPP

ANFTQGEDVFHAPYVANQGWYDITKTF*N*\*GKDDLLCGAATAGNMLHWWFDQNKDQI

KRYLEEHPEKQKINF*R*GEQMFDVKEAIDTKNHQLDSKLFEYFKEKAFPYLSTKHLGVFP

DHVIDMFI*L*GYRLSLTNHGPTPVKEGSKDPRGGIFDAVFTRGDQSKLLTSRHDFKEKNLK

EISDLIKKELTEGKALGLSHTYANVRINHVINLWGADFDS*D*GNLKAIYVTDSDSNASIGM

KKYFVGVNSAGKVAISAKEIKEDNIGAQVLGLFTLSTGQDSWNQTN

SEQ ID NO.: 16
MRKRCYSTSAAVLAAVTLFVLSVDRGVIADSFSANQEIRYSEVTPYHVTSVWTKGVTPP

ANFTQGEDVFHAPYVANQGWYDITKTF*D*GKDDLLCGAATAGNMLHWWFDQNKDQIK

RYLEEHPEKQKINF*R*GEQMFDVKEAIDTKNHQLDSKLFEYFKEKAFPYLSTKHLGVFPD

HVIDMFI*L*GYRLSLTNHGPTPVKEGSKDPRGGIFDAVFTRGDQSKLLTSRHDFKEKNLKE

ISDLIKKELTEGKALGLSHTYANVRINHVINLWGADFDS*D*GNLKAIYVTDSDSNASIGMK

KYFVGVNSAGKVAISAKEIKEDNIGAQVLGLFTLSTGQDSWNQTN

In one embodiment, the polypeptide has an isolated amino acid sequence comprising at least 70% sequence identity over a full length of an isolated amino acid sequence as set forth in the group consisting of SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15 and SEQ ID NO.: 16. In one aspect, the isolated amino acid sequence has at least about 80% sequence identity over a full length of the isolated amino acid sequence. In another aspect, the isolated amino acid sequence has at least about 90% sequence identity over a full length of the isolated amino acid sequence. In another aspect, the isolated amino acid sequence has about 100% sequence identity over a full length of the isolated amino acid sequence. In one aspect, the polypeptide can be capable of cleaving a target protein into fragments. In a particular aspect, the target protein is an IgG. In another aspect, the target protein is a fusion protein. In yet another aspect, the fragments can comprise a Fab fragment and/or an Fc fragment.

The present disclosure also includes an isolated nucleic acid molecule encoding a polypeptide having an isolated amino acid sequence comprising at least 70% sequence identity over a full length of the isolated amino acid sequence as set forth in the group consisting of SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15 and SEQ ID NO.: 16. In one aspect, the isolated amino acid sequence has at least about 80% sequence identity over a full length of the isolated amino acid sequence. In another aspect, the isolated amino acid sequence has at least about 90% sequence identity over a full length of the isolated amino acid sequence. In another aspect, the isolated amino acid sequence has about 100% sequence identity over a full length of the isolated amino acid sequence. In one aspect, the polypeptide can be capable of cleaving a target protein into fragments. In a particular aspect, the target protein is an IgG. In another particular aspect, the target protein is a fusion protein. In yet another particular aspect, the fragments can comprise a Fab fragment and/or an Fc fragment.

The present disclosure also includes a vector which comprises a nucleic acid encoding a polypeptide having an isolated amino acid sequence comprising at least 70% sequence identity over a full length of the isolated amino acid sequence as set forth in the group consisting of SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15 and SEQ ID NO.: 16. In one aspect, the nucleic acid molecule is operatively linked to an expression control sequence capable of directing its expression in a host cell. In one aspect, the vector can be a plasmid. In one aspect, the isolated amino acid sequence has at least about 80% sequence identity over a full length of the isolated amino acid sequence. In another aspect, the isolated amino acid sequence has at least about 90% sequence identity over a full length of the isolated amino acid sequence. In another aspect, the isolated amino acid sequence has about 100% sequence identity over a full length of the isolated amino acid sequence. In one aspect, the polypeptide can be capable of cleaving a target protein into fragments. In a particular aspect, the target protein is an IgG. In another aspect, the target protein is a fusion protein. In yet another aspect, the fragments can comprise a Fab fragment and/or an Fc fragment.

In one embodiment, the isolated amino acid can comprise a parental amino acid sequence defined by SEQ ID NO.: 1 with an asparagine residue at position 87, 130, 182 and/or 274 mutated to an amino acid other than asparagine. In one aspect, the mutation can confer an increased chemical stability at alkaline pH-values compared to the parental amino acid sequence. In another aspect, the mutation can confer an increase in chemical stability by 50% at alkaline pH-values compared to the parental amino acid sequence. In one aspect, the amino acid can be selected from aspartic acid, leucine, and arginine. In a particular aspect, the asparagine residue at position 87 is mutated to an aspartic acid residue. In another aspect, the asparagine residue at position 130 is mutated to an arginine residue. In yet another aspect, the asparagine residue at position 182 is mutated to a leucine residue. In yet another aspect, the asparagine residue at position 274 is mutated to an aspartic acid residue. In yet another aspect, the asparagine residues at positions 87 and 130 are mutated. In yet another aspect, the asparagine residues at positions 87 and 182 are mutated. In yet another aspect, the asparagine residues at positions 87 and 274 are mutated. In yet another aspect, the asparagine residues at positions 130 and 182 are mutated. In yet another aspect, the asparagine residues at positions 130 and 274 are mutated. In yet another aspect, the asparagine residues at positions 182 and 274 are mutated. In yet another aspect, the asparagine residues at positions 87, 130 and 182 are mutated. In yet another aspect, the asparagine residues at positions 87, 182 and 274 are mutated. In yet another aspect, the asparagine residues at positions 130, 182 and 274 are mutated. In yet another aspect, the asparagine residues at positions 87, 130, 182 and 274 are mutated.

In a related embodiment, the disclosure includes an isolated nucleic acid molecule encoding a polypeptide having an isolated amino acid sequence comprising a parental amino acid sequence defined by SEQ ID NO.: 1 with asparagine residues at positions 87, 130, 182 and/or 274 mutated to an amino acid other than asparagine-see above. The mutation can confer an increased chemical stability at alkaline pH-values compared to the parental amino acid sequence.

In a further related embodiment, the disclosure includes a vector, which comprises a nucleic acid molecule encoding a polypeptide having an isolated amino acid sequence comprising a parental amino acid sequence defined by SEQ ID NO.: 1 with an asparagine residue at position 87, 130, 182 and/or 274 mutated to an amino acid other than asparagine-see above. The mutation can confer an increased chemical stability at alkaline pH-values compared to the parental amino acid sequence. In one aspect, the nucleic acid molecule is operatively linked to an expression control sequence capable of directing its expression in a host cell. In one aspect, the vector can be a plasmid.

Affinity-Based Production

The present disclosure also provides methods for reducing host cell proteins as well as other undesirable proteins and nucleic acids during production of an anti-VEGF protein using affinity chromatography.

In one embodiment, a method of producing a recombinant protein comprises: (a) providing a host cell genetically engineered to express a recombinant protein of interest; (b) culturing the host cell under suitable conditions in which the cell expresses the recombinant protein of interest; and (c) harvesting a preparation of the recombinant protein of interest produced by the cell. In one aspect, the recombinant protein of interest is an anti-VEGF protein. In a particular aspect, the anti-VEGF protein is selected from the group consisting of aflibercept, MiniTrap, recombinant MiniTrap (an example of which is disclosed in U.S. Pat. No. 7,279,159), a scFv and other anti-VEGF proteins.

In one aspect of the present embodiment, the recombinant protein of interest is expressed in a suitable host cell. Non-limiting examples of suitable host cells include, but are not limited to, CHO, CHO K1, EESYR®, NICE®, NS0, Sp2/0, embryonic kidney cells and BHK.

In one aspect of the present embodiment, the recombinant protein of interest is cultured in a CDM. A suitable CDM includes Dulbecco's Modified Eagle's (DME) medium, Ham's Nutrient Mixture, Excell medium, IS CHO-CD medium, and CDM1B. Other CDMs known to those skilled in the art are also contemplated to be within the scope of the present invention.

The production preparation can comprise at least one contaminant including one or more host cell proteins in addition to the recombinant protein of interest. The at least one contaminant can be derived from cell-substrate, cell culture or a downstream process.

In one embodiment, the invention is directed to methods for producing an anti-VEGF protein from a biological sample using affinity chromatography. In a particular aspect, methods disclosed herein can be used to separate, at least in part, the anti-VEGF protein from one or more host cell proteins and nucleic acids (e.g., DNA) formed during the culture production process of an anti-VEGF protein.

In one aspect, the method can comprise subjecting a biological sample comprising the anti-VEGF protein along with accompanying contaminants to an affinity chromatography under suitable conditions. In a particular aspect, the affinity chromatography can comprise material capable of selectively or specifically binding to the anti-VEGF protein ("capture"). Non-limiting examples of such chromatographic material include: Protein A, Protein G, chromatographic material comprising, for example, protein capable of binding to the anti-VEGF protein, and chromatographic material comprising an Fc binding protein. In a specific aspect, the protein capable of binding to or interacting with the anti-VEGF protein can be an antibody, fusion protein or a fragment thereof. Non-limiting examples of such material capable of selectively or specifically binding to the anti-VEGF protein are described in Example 7.

In one aspect of the present embodiment, the method can comprise subjecting a biological sample comprising an anti-VEGF protein and one or more host cell proteins/contaminants to affinity chromatography under suitable conditions, wherein the affinity chromatography stationary phase comprises a protein capable of selectively or specifically binding to the anti-VEGF protein. In a particular aspect, the protein can be an antibody, a fusion protein, a scFv or an antibody fragment. In a specific aspect, the protein can be $VEGF_{165}$, $VEGF_{121}$, or VEGF forms from other species, such as rabbit. For example, as exemplified in Table 7-1 and Table 7-10, using $VEGF_{165}$ as the protein capable of selectively or specifically binding to or interacting with the anti-VEGF protein led to a successful production of MT5 (an anti-VEGF protein), aflibercept and an anti-VEGF scFv fragment. In another specific aspect, the protein can be one or more of the proteins having an amino acid sequence as shown in SEQ ID NO.: 73-80. Table 7-1 also discloses successful production of MT5 using the proteins having amino acid sequences as shown in SEQ ID NO.: 73-80 as the protein capable of selectively or specifically binding to the anti-VEGF protein (MT5).

In one aspect of the present embodiment, the method can comprise subjecting a biological sample comprising the anti-VEGF protein and one or more host cell proteins/contaminants to affinity chromatography under suitable conditions, wherein the affinity chromatography stationary phase comprises a protein capable of selectively or specifically binding to or interacting with the anti-VEGF protein, wherein the anti-VEGF protein can be selected from aflibercept, VEGF MiniTrap, or an anti-VEGF antibody. In a particular aspect, the VEGF MiniTrap can be obtained from VEGF receptor components; further, it can be formed by recombinant expression of the VEGF MiniTrap in a host cell. Performing the method can reduce the amount of the one or more host cell proteins in the sample. For example, FIG. 35A and FIG. 35B show a significant reduction in total host cell proteins in the sample comprising MT5 (an anti-VEGF protein) on using five different affinity chromatography columns comprising (i) VEGF$_{165}$ (SEQ ID NO.: 72); (ii) mAb1 (a mouse anti-VEGFR1 mAb human IgG1 where SEQ ID NO.: 73 is a heavy chain and SEQ ID NO.: 74 is a light chain); (iii) mAb2 (a mouse anti-VEGFR1 mAb human IgG1 where SEQ ID NO.: 75 is a heavy chain and SEQ ID NO.: 76 is a light chain); (iv) mAb3 (a mouse anti-VEGFR1 mAb mouse IgG1 where SEQ ID NO.: 77 is a heavy chain and SEQ ID NO.: 78 is a light chain) and (v) mAb4 (a mouse anti-VEGFR1 mAb mouse IgG1 where SEQ ID NO.: 79 is a heavy chain and SEQ ID NO.: 80 is a light chain) as different proteins capable of selectively or specifically binding to MT5. As seen in FIG. 35A and FIG. 35B, the eluates from each of the affinity-based production processes reduced the host cell proteins from above 7000 ppm to about 25 ppm and to about 55 ppm, respectively.

Suitable conditions for employing affinity chromatography can include, but are not limited to, equilibration of an affinity chromatography column using an equilibration buffer. Following equilibration using, for example, Tris hydrochloride at a pH of about 8.3 to about 8.6, the affinity chromatography column is loaded with a biological sample. Following loading of the column, the column can be washed one or multiple times using, for example, the equilibrating buffer such as Dulbecco's Phosphate-Buffered Saline (DPBS). Other washes including washes employing different buffers can be used before eluting the column. Column elution can be affected by the buffer type and pH and conductivity. Other elution conditions well known to those skilled in the art can be applied. Following elution using one or more types of elution buffers, for example, glycine at a pH of about 2.0 to about 3.0, the eluted fractions can be neutralized with the addition of a neutralizing buffer, for example, 1 M Tris at pH 7.5.

In one aspect of the embodiment, the pH of both the wash and equilibration buffer can be from about 7.0 to about 8.6. In one aspect of the embodiment, the wash buffer can be DPBS. In one aspect, the elution buffer can comprise 100 mM glycine buffer with pH of about 2.5. In another aspect, the elution buffer can be a buffer with a pH of about 2.0 to about 3.0. In one aspect, the neutralizing buffer can comprise 1 M tris with pH of about 7.5.

In one aspect of the present embodiment, the method can further comprise washing the column with a wash buffer. In one aspect of the present embodiment, the method can further comprise eluting the column with an elution buffer to obtain elution fractions. In a particular aspect, the amount of host cell proteins in the eluted fractions is significantly reduced as compared to the amount of host cell proteins in the biological sample, for example, by about 70%, about 80%, 90%, about 95%, about 98%, or about 99%.

The present embodiment can include the addition of one or more steps, in no particular order, such as hydrophobic interaction chromatography, affinity-based chromatography, multimodal chromatography, viral inactivation (e.g., using low pH), viral filtration, and/or ultra/diafiltration.

In one aspect, the glycosylation profile of a composition of an anti-VEGF protein is as follows: about 40% to about 50% total fucosylated glycans, about 30% to about 55% total sialylated glycans, about 6% to about 15% mannose-5, and about 60% to about 79% galactosylated glycans.

In one aspect of this embodiment, the anti-VEGF protein has Man5 glycosylation at about 32.4% of asparagine 123 residues and/or about 27.1% of asparagine 196 residues. In a specific embodiment, the anti-VEGF protein can be aflibercept, anti-VEGF antibody or VEGF MiniTrap.

In one embodiment, the method can further comprise formulating a drug substance using a pharmaceutically acceptable excipient. In one aspect, the pharmaceutically acceptable excipient can be selected from the following: water, buffering agents, sugar, salt, surfactant, amino acid, polyol, chelating agent, emulsifier and preservative. Other well-known excipients to the skilled artisan are within the purview of this embodiment.

In one aspect of the embodiment, the formulation can be suitable for administration to a human subject. In one aspect of the present embodiment, administration can be effected by intravitreal injection. In one aspect, the formulation can have about 40 to about 200 mg/mL of the protein of interest. In a particular aspect, the protein of interest can be aflibercept, anti-VEGF antibody or VEGF MiniTrap.

The formulation can be used in a method of treating or preventing angiogenic eye disorders which can include: age-related macular degeneration (e.g., wet or dry), macular edema, macular edema following retinal vein occlusion, retinal vein occlusion (RVO), central retinal vein occlusion (CRVO), branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy in a subject with diabetic macular edema; or diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME).

Synthesis of Oxo-Species

One embodiment of the present invention is directed to one or more methods for synthesizing oxidized protein species using light. In one aspect of the present embodiment, the protein of interest is an anti-VEGF protein. In a particular aspect, the anti-VEGF protein is aflibercept. In another aspect, the anti-VEGF protein is a VEGF MiniTrap including recombinant VEGF MiniTrap. In yet another aspect of the present embodiment, the anti-VEGF protein is a single-chain variable fragment (scFv).

In one aspect of the present embodiment, a sample comprises a protein of interest, for example, aflibercept fusion protein with minimal or no oxo-variants. The sample is photo-stressed to synthesize oxidized species of aflibercept. In a particular aspect, the sample is photo-stressed by using cool-white light. In another particular aspect, the sample is photo-stressed by using ultraviolet light.

In a specific aspect of the embodiment, a sample comprising aflibercept or another anti-VEGF protein is exposed to cool-white light for about 30 hours to about 300 hours resulting in about 1.5 to about 50-fold increase in modified oligopeptide. These peptides are enzymatically digested and analyzed comprising one or more from the group consisting of:
DKTH*TC*PPC*PAPELLG (SEQ ID NO.: 17),
EIGLLTC*EATVNGH*LYK (SEQ ID NO.: 18),
QTNTIIDVVLSPSH*GIELSVGEK (SEQ ID NO.: 19),
TELNVGIDENWEYPSSKH*QHK (SEQ ID NO.: 20),
TNYLTH*R (SEQ ID NO.: 21),
SDTGRPFVEMYSEIPEIIH*MTEGR (SEQ ID NO.: 22),
VH*EKDK (SEQ ID NO.: 23),
SDTGRPFVEM*YSEIPEIIHMTEGR (SEQ ID NO.: 64),
SDTGRPFVEMYSEIPEIIHM*TEGR (SEQ ID NO.: 65),
TQSGSEM*K (SEQ ID NO.: 66),
SDQGLYTC*AASSGLM*TK (SEQ ID NO.: 67),
IIW*DSR (SEQ ID NO.: 28), RIIW*DSR (SEQ ID NO.: 115), IIW*DSRK (SEQ ID NO.: 114),
TELNVGIDENW*EYPSSK (SEQ ID NO.: 29),
GFIISNATY*K (SEQ ID NO.: 69), KF*PLDTLIPDGK (SEQ ID NO.: 70) F*LSTLTIDGVTR (SEQ ID NO.: 32), wherein H* is a histidine that is oxidized to 2-oxo-histidine, wherein C* is a cysteine that is carboxymethylated, wherein M* is an oxidized methionine, wherein W* is an oxidized tryptophan, wherein Y* is an oxidized tyrosine, and wherein F* is an oxidized phenylalanine. The digestion can be performed by proteases alluded to before, for example, trypsin. The oligopeptides can be analyzed using mass spectrometry.

In a specific aspect of the embodiment, a sample comprising aflibercept or other anti-VEGF protein is exposed to ultraviolet light for about 4 hours to about 40 hours resulting in about 1.5 to about 25-fold increase in modified oligopeptide products (obtained on performing digestion) wherein the sample comprises one or more modified oligopeptides selected from the group consisting of:
DKTH*TC*PPC*PAPELLG (SEQ ID NO.: 17),
EIGLLTC*EATVNGH*LYK (SEQ ID NO.: 18),
QTNTIIDVVLSPSH*GIELSVGEK (SEQ ID NO.: 19),
TELNVGIDENWEYPSSKH*QHK (SEQ ID NO.: 20),
TNYLTH*R (SEQ ID NO.: 21),
SDTGRPFVEMYSEIPEIIH*MTEGR (SEQ ID NO.: 22),
VH*EKDK (SEQ ID NO.: 23),
SDTGRPFVEM*YSEIPEIIHMTEGR (SEQ ID NO.: 64),
SDTGRPFVEMYSEIPEIIHM*TEGR (SEQ ID NO.: 65),
TQSGSEM*K (SEQ ID NO.: 66),
SDQGLYTC*AASSGLM*TK (SEQ ID NO.: 67),
IIW*DSR (SEQ ID NO.: 28), RIIW*DSR (SEQ ID NO.: 115), IIW*DSRK (SEQ ID NO.: 114),
TELNVGIDENW*EYPSSK (SEQ ID NO.: 29),
GFIISNATY*K (SEQ ID NO.: 69), KF*PLDTLIPDGK (SEQ ID NO.: 70) F*LSTLTIDGVTR (SEQ ID NO.: 32), wherein H* is a histidine that is oxidized to 2-oxo-histidine, wherein C* is a cysteine that is carboxymethylated, wherein M* is an oxidized methionine, wherein W* is an oxidized tryptophan, wherein Y* is an oxidized tyrosine, and wherein F* is an oxidized phenylalanine. The digestion can be performed by proteases alluded to before, for example, trypsin. The oligopeptides can be analyzed using mass spectrometry.

Methods to Minimize Yellow-Brown Color

The present disclosure provides methods for reducing yellow-brown coloration during production of aflibercept, MiniTrap or the like produced in a CDM.

In one embodiment, the method comprises culturing a host cell in a CDM under suitable conditions, wherein the host cell expresses a recombinant protein of interest, and then harvesting a preparation comprising the recombinant protein of interest. In one aspect, the recombinant protein of interest is an anti-VEGF protein. In a particular aspect, the anti-VEGF protein is selected from the group consisting of aflibercept, MiniTrap, recombinant MiniTrap (examples of which are disclosed in U.S. Pat. No. 7,279,159, which is incorporated herein by reference in its entirety), a scFv and other anti-VEGF proteins. In one aspect, the method can produce a preparation of the recombinant protein of interest, wherein the color of the preparation is characterized using the European BY method or the CIELAB method (b*). Additionally, the presence of oxo-variants can be analyzed using, for example, LC-MS.

In one aspect of the present embodiment, mitigation conditions include increasing or decreasing cumulative concentrations of one or more media components, for example, amino acids, metals or antioxidants, including, salts and precursors, corresponding to a reduction in color and protein variants of aflibercept and VEGF MiniTrap. Non-limiting examples of amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In a particular aspect, lowering of cysteine concentration can be effective in reducing the yellow-brown color of a preparation. Cysteine concentration can also affect oxo-variants.

In one embodiment, the method comprises culturing a host cell in a CDM under suitable conditions, wherein the host cell expresses a recombinant protein of interest, such as aflibercept, and harvesting a preparation of the protein of interest produced by the cell, wherein the suitable conditions are obtained, in part, by lowering the cumulative concentration of cysteine in the CDM to less than or equal to about 10 mM. Examples of suitable media include, but are not limited to, CDM1B, Excell or the like. As used herein, the term "cumulative amount" refers to the total amount of a particular component added to a bioreactor over the course of the cell culture to form the CDM, including amounts added at the beginning of the culture (CDM at day 0) and subsequently added amounts of the component. Amounts of a component added to a seed-train culture or inoculum prior to the bioreactor production (i.e., prior to the CDM at day 0) are also included when calculating the cumulative amount of the component. A cumulative amount is unaffected by the loss of a component over time during the culture (for example, through metabolism or chemical degradation). Thus, two cultures with the same cumulative amounts of a component may nonetheless have different absolute levels, for example, if the component is added to the two cultures at different times (e.g., if in one culture all of the component is added at the outset, and in another culture the component is added over time). A cumulative amount is also unaffected by in situ synthesis of a component over time during the culture (for example, via metabolism or chemical conversion). Thus, two cultures with the same cumulative amounts of a given component may nonetheless have different absolute levels, for example, if the component is synthesized in situ in one of the two cultures by way of a bioconversion process. A cumulative amount may be expressed in units such as, for example, grams or moles of the component.

As used herein, the term "cumulative concentration" refers to the cumulative amount of a component divided by the volume of liquid in the bioreactor at the beginning of the production batch, including the contribution to the starting volume from any inoculum used in the culture. For example, if a bioreactor contains 2 liters of cell culture medium at the beginning of the production batch, and one gram of component X is added at days 0, 1, 2, and 3, then the cumulative concentration after day 3 is 2 g/L (i.e., 4 grams divided by 2 liters). If, on day 4, an additional one liter of liquid not containing component X were added to the bioreactor, the cumulative concentration would remain 2 g/L. If, on day 5, some quantity of liquid were lost from the bioreactor (for example, through evaporation), the cumulative concentration would remain 2 g/L. A cumulative concentration may be expressed in units such as, for example, grams per liter or moles per liter.

In an aspect of this embodiment, the method comprises culturing a host cell in a CDM under suitable conditions, wherein the host cell expresses a recombinant protein of interest, harvesting a preparation of the protein produced by the cell, wherein the suitable conditions are obtained by lowering the ratio of cumulative cysteine concentration from about 1:10 to 1:29 to a cumulative total amino acid concentration from about 1:50 to about 1:30.

In one embodiment, the method comprises (i) culturing a host cell in a CDM under suitable conditions, wherein the host cell expresses a recombinant protein of interest, such as aflibercept, and (ii) harvesting a preparation of the recombinant protein of interest produced by the cell, wherein the suitable conditions are obtained by lowering the cumulative concentration of iron in the CDM to less than about 55.0 µM. In an aspect of this embodiment, the preparation obtained by this method shows lesser yellow-brown color than the preparation obtained by a method wherein the cumulative concentration of iron in the CDM is more than about 55.0 µM.

In one embodiment, the method comprises culturing a host cell in a CDM under suitable conditions, wherein the host cell expresses a recombinant protein of interest, such as aflibercept. The method further comprises harvesting a preparation of the recombinant protein of interest produced by the cell, wherein the suitable conditions are obtained by lowering the cumulative concentration of copper in the CDM to less than or equal to about 0.8 µM. In an aspect of this embodiment, the preparation obtained by this method shows lesser yellow-brown color than the preparation obtained by a method wherein the cumulative concentration of copper in the CDM is more than about 0.8 µM.

In one embodiment, the method comprises culturing a host cell in a CDM under suitable conditions, wherein the host cell expresses a recombinant protein of interest, such as aflibercept, and harvesting a preparation of the recombinant protein of interest produced by the cell, wherein the suitable conditions are obtained by lowering the cumulative concentration of nickel in the CDM to less than or equal to about 0.40 µM. In an aspect of this embodiment, the preparation obtained by this method shows lesser yellow-brown color than the preparation obtained by a method wherein the cumulative concentration of nickel in the CDM is more than about 0.40 µM.

In one embodiment, the method comprises culturing a host cell in a CDM under suitable conditions, wherein the host cell expresses a recombinant protein of interest, such as aflibercept. The method further comprises harvesting a preparation of the recombinant protein of interest produced by the cell, wherein the suitable conditions are obtained by lowering the cumulative concentration of zinc in the CDM to less than or equal to about 56 µM. In an aspect of this embodiment, the preparation obtained by this method shows lesser yellow-brown color than the preparation obtained by a method wherein the cumulative concentration of zinc in the CDM is more than about 56 µM.

In one embodiment, the method comprises culturing a host cell in a CDM under suitable conditions, wherein the host cell expresses a recombinant protein of interest, such as aflibercept. The method further comprises harvesting a preparation of the recombinant protein of interest produced by the cell, wherein the suitable conditions are obtained by presence of antioxidants in the CDM in a cumulative concentration of about 0.001 mM to about 10 mM for a single antioxidant and no more than about 30 mM cumulative concentration if multiple antioxidants are added in said CDM. In an aspect of this embodiment, the preparation obtained by this method shows lesser yellow-brown color than the preparation obtained by a method wherein antioxidants are present in the CDM in a cumulative concentration of less than about 0.01 mM or above about 100 mM. Non-limiting examples of the antioxidant can be taurine, hypotaurine, glycine, thioctic acid, glutathione, choline chloride, hydrocortisone, Vitamin C, Vitamin E, chelating agents, catalase, S-carboxymethyl-L-cysteine, and combinations thereof. Non-limiting examples of chelating agents include aurintricarboxylic acid (ATA), deferoxamine (DFO), EDTA and citrate.

In one embodiment, the method comprises culturing a host cell in a CDM under suitable conditions, wherein the host cell expresses a recombinant protein of interest, such as aflibercept. The method further comprises harvesting a preparation of the recombinant protein of interest produced by the cell, wherein the suitable conditions include a CDM with a: cumulative concentration of iron in said CDM that is less than about 55 µM, cumulative concentration of copper in said CDM that is less than or equal to about 0.8 UM, cumulative concentration of nickel in said CDM that is less than or equal to about 0.40 µM, cumulative concentration of zinc in said CDM that is less than or equal to about 56 µM, cumulative concentration of cysteine in said CDM that is less than 10 mM; and/or an antioxidant in said CDM in a concentration of about 0.001 mM to about 10 mM for a single antioxidant, and no more than about 30 mM cumulative concentration if multiple antioxidants are added in said CDM.

In one aspect of the present embodiment, the preparation obtained from using suitable conditions results in a reduction in protein variants of aflibercept and VEGF MiniTrap to a desired amount of protein variants of aflibercept and VEGF MiniTrap (referred to as a "target value" of protein variants of aflibercept and VEGF MiniTrap). In a further aspect of this embodiment, the preparation obtained from using suitable conditions results in a reduction in color of the preparations to a desired b* value or BY value (referred to as a "target b* value" "target BY value" respectively) when the preparation of protein, including variants of aflibercept and VEGF MiniTrap are normalized to a concentration of 5 g/L or 10 g/L. In a further aspect of the present embodiment, the target b* value (or target BY value) and/or target value of variants can be obtained in a preparation where the titer increases or does not significantly decrease.

These and other aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 11 depicts the relative abundance of the peptides identified from the peptide mapping analysis performed using oligopeptides from protease-digested AEX load and flowthrough (where underscoring represents oxidation of the residue in the peptide sequence), including fragments of aflibercept (SEQ ID NO.: 55), including SEQ ID NOS 22, 18, 21, 19-20, 118-119, and 28-29, respectively, in order of appearance.

FIG. 21 depicts the 3D SEC-PDA (size exclusion chromatography coupled to photodiode array detection) chromatograms on CWL-stressed MT1 with absorbance at ~350 nm (see, e.g., circle highlighting ~350 nm) according to an exemplary embodiment where A shows the chromatogram at T=0, B shows the chromatogram at 0.5×ICH, C shows the chromatogram at 2.0×ICH, and D shows images of MT1 in vials (normalized to 80 mg/mL) stressed by CWL for different time intervals.

FIG. 28C depicts the scaled estimated effects of incubation of various components with aflibercept in CDM on the generation of color (CIE L*, a*, b* predicted b value) in a shake flask culture.

FIG. 37 depicts a cartoon representation of the kinetic study of VEGF MiniTrap to $VEGF_{165}$, wherein the VEGF MiniTrap constructs studied were from before and after performing affinity chromatography production according to some exemplary embodiments.

FIG. 49B depicts a mass spectrum obtained on performing HILIC-UV/MS for VEGF MiniTrap MT6 showing the main peak at 47985.8 Da.

FIG. 49C depicts a mass spectra of O-glycans of VEGF MiniTrap MT6 obtained on performing HILIC-UV/MS.

FIG. 58A is a table of detailed glycan identification and quantification from VEGF MiniTrap samples MT1, MT5 and MT6.

FIG. 58B is a table of detailed glycan identification and quantification from VEGF MiniTrap samples MT1, MT5 and MT6.

FIG. 58C is a table of detailed glycan identification and quantification from VEGF MiniTrap samples MT1, MT5 and MT6.

DETAILED DESCRIPTION

Angiogenesis, the growth of new blood vessels from preexisting vasculature, is a highly orchestrated process that is critical for proper embryonic and postnatal vascular development. Abnormal or pathological angiogenesis is a hallmark of cancer and several retinal diseases where the upregulation of proangiogenic factors, such as vascular endothelial growth factor (VEGF) leads to increases in endothelial proliferation, changes in vasculature morphology, and increased vascular permeability. Elevated levels of VEGF have been found in the vitreous fluid and retinal vasculature of patients with various ocular diseases. Blocking VEGF activity has also become the therapy of choice for treating DME, wet AMD, CNV, retinal vein occlusions, and other ocular diseases where abnormal angiogenesis is the underlying etiology.

Figure 1:
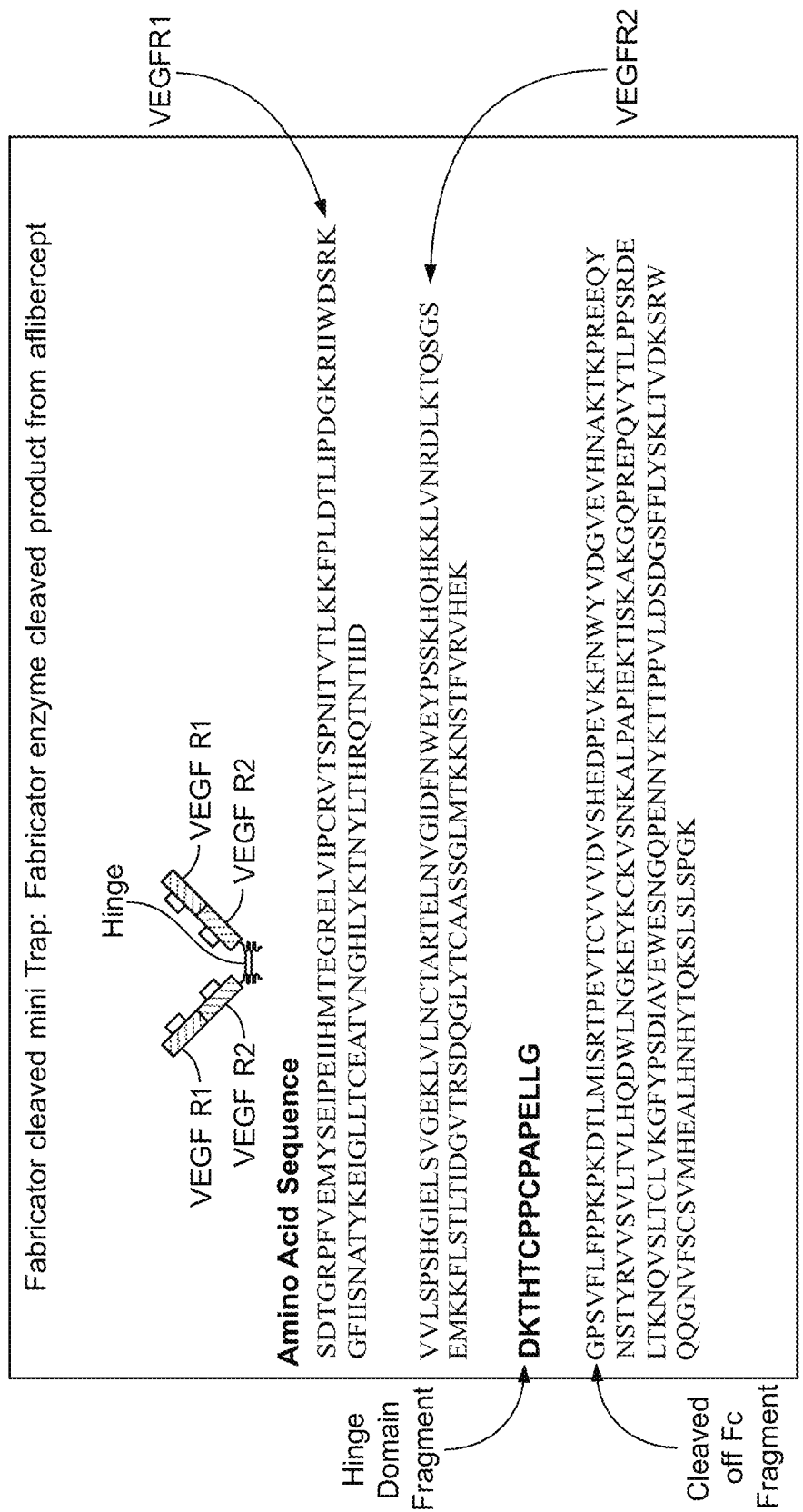
FIG. 1 depicts a VEGF MiniTrap generated using an exemplary embodiment, including VEGFR1 (SEQ ID NO.: 34), VEGFR2 (SEQ ID NO.: 36), Hinge domain fragment (SEQ ID NO.: 60) and the cleaved off Fc fragment from aflibercept (SEQ ID NO.: 113).

As used herein, aflibercept is one such anti-VEGF protein comprising an all-human amino acid sequence comprising the second Ig domain of human VEGFR1 and the third Ig domain of human VEGFR2 expressed as an inline fusion with a (Fc) of human IgG1. Aflibercept binds all forms of VEGF-A (VEGF) but in addition binds PIGF and VEGF-B. Several other homodimeric VEGF MiniTraps have been generated as enzymatically cleaved products from aflibercept or recombinantly expressed directly from host cell lines. One such example of a VEGF MiniTrap is shown in FIG. 1. In this figure, a terminal lysine is depicted (K); some culture processes remove this terminal lysine while others do not. FIG. 1 illustrates a process whereby the terminal lysine remains. In general, aflibercept encompasses both the presence and absence of the terminal lysine.

As demonstrated herein, the present invention, in part, discloses the production of anti-VEGF proteins (Example 1) using a CDM. Analysis of solutions comprising aflibercept produced using certain CDMs demonstrated a certain color property, such as an intense yellow-brown color. The intensity of the solution's color depended upon the CDM used. Not all CDMs examined produced a sample with a distinct yellow-brown color after the solutions were normalized to a concentration of 5 g/L.

A color, such as yellow-brown, in an injectable therapeutic drug solution can be an undesirable feature. It may be an important parameter employed for determining if a drug product satisfies a predetermined level of purity and quality for a particular therapeutic. A color such as yellow-brown observed along the manufacturing route of a biologic can be caused by chemical modifications of that biologic, degradation products of formulation excipients, or degradation products formed through the reaction of the biologic and formulation excipients. However, such information can be valuable for understanding the cause of the color change. It can also assist in designing short-term as well as long-term storage conditions to prevent modifications facilitating such a color change.

The inventors observed that use of AEX during the production of an anti-VEGF protein solution minimized yellow-brown coloration. Additionally, the inventors discovered that the yellow-brown coloration can be decreased by modifying the cell culture used to produce a recombinant protein, such as aflibercept or a modified aflibercept like MiniTrap.

The present invention encompasses anti-VEGF proteins and their production using CDM. Additionally, the present invention is based on the identification and optimization of upstream and downstream process technologies for protein production.

As demonstrated herein, some of the Examples set forth below describe the production of anti-VEGF proteins (Example 1), production of oxidized species of anti-VEGF proteins (Example 4), methods to reduce oxidized species of anti-VEGF proteins by optimizing culture medium (Example 5) and by optimizing production methods (Example 2).

A number of recent patent applications and granted patents purport to describe various aflibercept species and methods of producing the same, but none describe or suggest the anti-VEGF compositions and methods for producing the same described herein. See, e.g., U.S. application Ser. No. 16/566,847 to Coherus Biosciences Inc., U.S. Pat. No. 10,646,546 to Sam Chun Dang Pharm. Co., Ltd., U.S. Pat. No. 10,576,128 to Formycon AG, International Application No. PCT/US2020/015659 to Amgen Inc., and U.S. Pat. Nos. 8,956,830; 9,217,168; 9,487,810; 9,663,810; 9,926,583; and 10,144,944 to Momenta Pharmaceuticals, Inc.

I. Explanation of Selected Terms

Unless described otherwise, all technical and scientific terms used herein have the same meaning as commonly understood by one of ordinary skill in the art to which this invention belongs. Methods and materials similar or equivalent to those described herein known to the skilled artisan can be used in the practice of particular embodiments described herein. All publications mentioned are hereby incorporated by reference in their entirety.

The term "a" should be understood to mean "at least one" and the terms "about" and "approximately" should be understood to permit standard variation as would be understood by those of ordinary skill in the art and where ranges are provided, endpoints are included.

As used herein, the term "angiogenic eye disorder" means any disease of the eye, which is caused by or associated with the growth or proliferation of blood vessels or by blood vessel leakage.

As used herein, the term "chemically defined medium" or "chemically defined media" (both abbreviated "CDM") refers to a synthetic growth medium in which the identity and concentration of all the ingredients are defined. Chemically defined media do not contain bacterial, yeast, animal, or plant extracts, animal serum, or plasma, although individual plant or animal-derived components (e.g., proteins, polypeptides, etc.) may be added. Chemically defined media may contain inorganic salts such as phosphates, sulfates, and the like needed to support growth. The carbon source is defined, and is usually a sugar such as glucose, lactose, galactose, and the like, or other compounds such as glycerol, lactate, acetate, and the like. While certain chemically defined culture media also use phosphate salts as a buffer, other buffers may be employed such as sodium bicarbonate, HEPES, citrate, triethanolamine, and the like. Examples of commercially available chemically defined media include, but are not limited to, various Dulbecco's Modified Eagle's (DME) media (Sigma-Aldrich Co; SAFC Biosciences, Inc.), Ham's Nutrient Mixture (Sigma-Aldrich Co; SAFC Biosciences, Inc.), various EX-CELLS mediums (Sigma-Aldrich Co; SAFC Biosciences, Inc.), various IS CHO-CD mediums (FUJIFILM Irvine Scientific), combinations thereof, and the like. Methods of preparing chemically defined culture media are known in the art, for example, in U.S. Pat. Nos. 6,171,825 and 6,936,441, WO 2007/077217, and U.S. Patent Application Publication Nos. 2008/0009040 and 2007/0212770, the entire teachings of which are herein incorporated by reference.

As used herein, the term "cumulative amount" refers to the total amount of a particular component added to a bioreactor over the course of the cell culture to form the CDM, including amounts added at the beginning of the culture (CDM at day 0) and subsequently added amounts of the component. Amounts of a component added to a seed-train culture or inoculum prior to the bioreactor production (i.e., prior to the CDM at day 0) are also included when calculating the cumulative amount of the component. A cumulative amount is unaffected by the loss of a component over time during the culture (for example, through metabolism or chemical degradation). Thus, two cultures with the same cumulative amounts of a component may nonetheless have different absolute levels, for example, if the component is added to the two cultures at different times (e.g., if in one culture all of the component is added at the outset, and in another culture the component is added over time). A cumulative amount is also unaffected by in situ synthesis of a component over time during the culture (for example, via metabolism or chemical conversion). Thus, two cultures with the same cumulative amounts of a given component may nonetheless have different absolute levels, for example, if the component is synthesized in situ in one of the two cultures by way of a bioconversion process. A cumulative amount may be expressed in units such as, for example, grams or moles of the component.

As used herein, the term "cumulative concentration" refers to the cumulative amount of a component divided by the volume of liquid in the bioreactor at the beginning of the production batch, including the contribution to the starting volume from any inoculum used in the culture. For example, if a bioreactor contains 2 liters of cell culture medium at the beginning of the production batch, and one gram of component X is added at days 0, 1, 2, and 3, then the cumulative concentration after day 3 is 2 g/L (i.e., 4 grams divided by 2 liters). If, on day 4, an additional one liter of liquid not containing component X were added to the bioreactor, the cumulative concentration would remain 2 g/L. If, on day 5, some quantity of liquid were lost from the bioreactor (for example, through evaporation), the cumulative concentration would remain 2 g/L. A cumulative concentration may be expressed in units such as, for example, grams per liter or moles per liter.

As used herein, the term "formulation" refers to a protein of interest that is formulated together with one or more pharmaceutically acceptable vehicles. In one aspect, the protein of interest is aflibercept and/or MiniTrap. In some exemplary embodiments, the amount of protein of interest in the formulation can range from about 0.01 mg/mL to about 600 mg/mL. In some specific embodiments, the amount of the protein of interest in the formulation can be about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, about 500 mg/mL, about 525 mg/mL, about 550 mg/mL, about 575 mg/mL, or about 600 mg/mL. In some exemplary embodiments, pH of the composition can be greater than about 5.0. In one exemplary embodiment, the pH can be greater than about 5.0, greater than about 5.5, greater than about 6.0, greater than about 6.5, greater than about 7.0, greater than about 7.5, greater than about 8.0, or greater than about 8.5.

As used herein, the term "database" refers to a bioinformatics tool, which provides for the possibility of searching the uninterpreted MS-MS spectra against all possible sequences in the database(s). Non-limiting examples of such tools are Mascot (www.matrixscience.com), Spectrum Mill (www.chem.agilent.com), PLGS (www.waters.com), PEAKS (www.bioinformaticssolutions.com), Proteinpilot (download.appliedbiosystems.com//proteinpilot), Phenyx (www.phenyx-ms.com), Sorcerer (www.sagenresearch.com), OMSSA (www.pubchem.ncbi.nlm.nih.gov/omssa/), X!Tandem (www.thegpm.org/TANDEM/), Protein Prospector (www.prospector.ucsf.edu/prospector/mshome.htm), Byonic (www.protcinmetrics.com/products/byonic) or Sequest (fields.scripps.edu/sequest).

As used herein, the term "ultrafiltration" or "UF" can include a membrane filtration process similar to reverse osmosis, using hydrostatic pressure to force water through a semi-permeable membrane. Ultrafiltration is described in detail in: LEOS J. ZEMAN & ANDREW L. ZYDNEY, MICROFILTRATION AND ULTRAFILTRATION: PRINCIPLES AND APPLICATIONS (1996), the entire teaching of which is herein incorporated. Filters with a pore size of smaller than 0.1 μm can be used for ultrafiltration. By employing filters having such small pore size, the volume of the sample can be reduced through permeation of the sample buffer through the filter while proteins are retained behind the filter.

As used herein, "diafiltration" or "DF" can include a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to a solution being ultrafiltered at a rate approximately equal to the ultrafiltration rate. This washes microspecies from the solution at a constant volume. In certain exemplary embodiments of the present invention, a diafiltration step can be employed to exchange various buffers used in connection with the instant invention, for example, prior to chromatography or other production steps, as well as to remove impurities from the protein preparation. As used herein, the term "downstream process technology" refers to one or more techniques used after the upstream process technologies to produce a protein. Downstream process technology includes, for example, production of a protein product, using, for example, affinity chromatography, including Protein A affinity chromatography as well as affinity chromatography that uses a solid phase having a well-defined molecule like VEGF that can interact with its cognate like a VEGF receptor (VEGFR), ion exchange chromatography, such as anion or cation exchange chromatography, hydrophobic interaction chromatography, or displacement chromatography.

The phrase "recombinant host cell" (or simply "host cell") includes a cell into which a recombinant expression vector coding for a protein of interest has been introduced. It should be understood that such a term is intended to refer not only to a particular subject cell but to a progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the kingdoms of life. In one aspect, eukaryotic cells include protist, fungal, plant and animal cells. In a further aspect, host cells include eukaryotic cells such as plant and/or animal cells. The cells can be mammalian cells, fish cells, insect cells, amphibian cells or avian cells. In a particular aspect, the host cell is a mammalian cell. A wide variety of mammalian cell lines suitable for growth in culture are available from the American Type Culture Collection (Manassas, Va.) and other depositories as well as commercial vendors. Cells that can be used in the processes of the invention include, but not limited to, MK2.7 cells, PER-C6 cells, Chinese hamster ovary cells (CHO), such as CHO-K1 (ATCC CCL-61), DG44 (Chasin et al., 1986, *Som. Cell Molec. Genet.*, 12:555-556; Kolkekar et al., 1997, *Biochemistry*, 36: 10901-10909; and WO 01/92337 A2), dihydrofolate reductase negative CHO cells (CHO/-DHFR, Urlaub and Chasin, 1980, *Proc. Natl. Acad. Sci. USA*, 77:4216), and dp12.CHO cells (U.S. Pat. No. 5,721,121); monkey kidney cells (CV1, ATCC CCL-70); monkey kidney CV1 cells transformed by SV40 (COS cells, COS-7, ATCC CRL-1651); HEK 293 cells, and Sp2/0 cells, 5 L8 hybridoma cells, Daudi cells, EL4 cells, HeLa cells, HL-60 cells, K562 cells, Jurkat cells, THP-1 cells, Sp2/0 cells, primary epithelial cells (e.g., keratinocytes, cervical epithelial cells, bronchial epithelial cells, tracheal epithelial cells, kidney epithelial cells and retinal epithelial cells) and established cell lines and their strains (e.g., human embryonic kidney cells (e.g., 293 cells, or 293 cells subcloned for growth in suspension culture, Graham et al., 1977, *J. Gen. Virol.*, 36:59); baby hamster kidney cells (BHK, ATCC CCL-10); mouse sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals NY Acad. Sci.*, 383:44-68); MCR 5 cells; FS4 cells; PER-C6 retinal cells, MDBK (NBL-1) cells, 911 cells, CRFK cells, MDCK cells, BeWo cells, Chang cells, Detroit 562 cells, HeLa 229 cells, HeLa S3 cells, Hep-2 cells, KB cells, LS 180 cells, LS 174T cells, NCI—H-548 cells, RPMI 2650 cells, SW-13 cells, T24 cells, WI-28 VA13, 2RA cells, WISH cells, BS—C—I cells, LLC-MK$_2$ cells, Clone M-3 cells, 1-10 cells, RAG cells, TCMK-1 cells, Y-1 cells, LLC-PK$_1$ cells, PK(15) cells, GH$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CV-1 cells, COS-1 cells, COS-3 cells, COS-7 cells, African green monkey kidney cells (VERO-76, ATCC CRL-1587; VERO, ATCC CCL-81); DBS-FrhL-2 cells, BALB/3T3 cells, F9 cells, SV-T2 cells, M-MSV-BALB/3T3 cells, K-BALB cells, BLO-11 cells, NOR-10 cells, C$_3$H/IOTI/2 cells, HSDM$_1$C$_3$ cells, KLN205 cells, McCoy cells, Mouse L cells, Strain 2071 (Mouse L) cells, L-M strain (Mouse L) cells, L-MTK (Mouse L) cells, NCTC clones 2472 and 2555, SCC-PSA1 cells, Swiss/3T3 cells, Indian muntac cells, SIRC cells, C$_{II}$ cells, and Jensen cells, or derivatives thereof) or any other cell type known to one skilled in the art.

As used herein, the term "host cell proteins" (HCP) includes protein derived from a host cell and can be unrelated to the desired protein of interest. Host cell proteins can be a process-related impurity which can be derived from the manufacturing process and can include three major categories: cell substrate-derived, cell culture-derived and downstream derived. Cell substrate-derived impurities include, but are not limited to, proteins derived from a host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables.

In some exemplary embodiments, the host cell protein can have a pI in the range of about 4.5 to about 9.0. In an exemplary embodiment, the pI can be about 4.5, about 5.0, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0.

As used herein, the term "hydrolyzing agent" refers to any one or combination of a large number of different agents that can perform digestion of a protein. Non-limiting examples of hydrolyzing agents that can carry out enzymatic digestion include protease from *Aspergillus saitoi*, elastase, subtilisin, protease XIII, pepsin, trypsin, Tryp-N, chymotrypsin, aspergillopepsin I, LysN protease (Lys-N), LysC endoproteinase (Lys-C), endoproteinase Asp-N (Asp-N), endoproteinase Arg-C (Arg-C), endoproteinase Glu-C (Glu-C) or outer membrane protein T (OmpT), immunoglobulin-degrading enzyme of *Streptococcus pyogenes* (IdeS), thermolysin, papain, pronase, V8 protease or biologically active fragments or homologs thereof or combinations thereof. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion, see Switzar et al., "Protein Digestion: An Overview of the Available Techniques and Recent Developments" (Linda Switzar, Martin Giera & Wilfried M. A. Niessen, *Protein Digestion: An Overview of the Available Techniques and Recent Developments*, 12 JOURNAL OF PROTEOME RESEARCH 1067-1077 (2013), the entire teachings of which are herein incorporated). One or a combination of hydrolyzing agents can cleave peptide bonds in a protein or polypeptide, in a sequence-specific manner, generating a predictable collection of shorter peptides. The ratio of hydrolyzing agent to protein and the time required for digestion can be appropriately selected to obtain optimal digestion of the protein. When the enzyme to substrate ratio is unsuitably high, the correspondingly high digestion rate will not allow sufficient time for the peptides to be analyzed by mass spectrometer, and sequence coverage will be compromised. On the other hand, a low E/S ratio would need long digestion and thus long data acquisition time. The enzyme to substrate ratio can range from about 1:0.5 to about 1:200. As used herein, the term "digestion" refers to hydrolysis of one or more peptide bonds of a protein. There are several approaches to carrying out digestion of a protein in a biological sample using an appropriate hydrolyzing agent, for example, enzymatic digestion or non-enzymatic digestion. One of the widely accepted methods for digestion of proteins in a sample involves the use of proteases. Many proteases are available and each of them have their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes-aspartic, glutamic, and metalloproteases, cysteine, serine, and threonine proteases, as classified based on the mechanism of catalysis. The terms "protease" and "peptidase" are used interchangeably to refer to enzymes which hydrolyze peptide bonds.

The term "in association with" indicates that components, an anti-VEGF composition of the present invention, along with another agent such as anti-ANG2, can be formulated into a single composition for simultaneous delivery, or formulated separately into two or more compositions (e.g., a kit including each component). Components administered in association with each another can be administered to a subject at a different time than when the other component is administered; for example, each administration may be given non-simultaneously (e.g., separately or sequentially) at intervals over a given period of time. Separate components administered in association with each other may also be administered essentially simultaneously (e.g., at precisely the same time or separated by a non-clinically significant time period) during the same administration session. Moreover, the separate components administered in association with each other may be administered to a subject by the same or by a different route, for example, a composition of aflibercept along with another agent such as anti-ANG2, wherein the composition of aflibercept comprises about 15% or less of its variants.

As used herein, the term "liquid chromatography" refers to a process in which a biological/chemical mixture carried by a liquid can be separated into components as a result of differential distribution of the components as they flow through (or into) a stationary liquid or solid phase. Non-limiting examples of liquid chromatography include reverse phase liquid chromatography, ion-exchange chromatography, size exclusion chromatography, affinity chromatography, mixed-mode chromatography or hydrophobic chromatography.

As used herein, "affinity chromatography" can include separations including any method by which two substances are separated based upon their affinity to a chromatographic material. It can comprise subjecting the substances to a column comprising a suitable affinity chromatographic media. Non-limiting examples of such chromatographic media include, but are not limited to, Protein A resin, Protein G resin, affinity supports comprising an antigen against which a binding molecule (e.g., antibody) was produced, protein capable of binding to a protein of interest and affinity supports comprising an Fc binding protein. In one aspect, an affinity column can be equilibrated with a suitable buffer prior to sample loading. An example of a suitable buffer can be a Tris/NaCl buffer, pH around 7.0 to 8.0. A skilled artisan can develop a suitable buffer without undue burden. Following this equilibration, a sample can be loaded onto the column. Following the loading of the column, the column can be washed one or multiple times using, for example, the equilibrating buffer. Other washes, including washes employing different buffers, can be used before eluting the column. The affinity column can then be eluted using an appropriate elution buffer. An example of a suitable elution buffer can be an acetic acid/NaCl buffer, pH around 2.0 to 3.5. Again, the skilled artisan can develop an appropriate elution buffer without undue burden. The eluate can be monitored using techniques well known to those skilled in the art, including UV. For example, the absorbance at 280 nm can be employed, especially if the sample of interest comprises aromatic rings (e.g., proteins having aromatic amino acids like tryptophan).

As used herein, "ion exchange chromatography" can refer to separations including any method by which two substances are separated based on differences in their respective ionic charges, either on the molecule of interest and/or chromatographic material as a whole or locally on specific regions of the molecule of interest and/or chromatographic material, and thus can employ either cationic exchange material or anionic exchange material. Ion exchange chromatography separates molecules based on differences between the local charges of the molecules of interest and the local charges of the chromatographic material. A packed ion-exchange chromatography column or an ion-exchange membrane device can be operated in a bind-elute mode, a flowthrough mode, or a hybrid mode. After washing the column or the membrane device with an equilibration buffer or another buffer, product recovery can be achieved by increasing the ionic strength (i.e., conductivity) of the elution buffer to compete with the solute for the charged sites of the ion exchange matrix. Changing the pH and thereby altering the charge of the solute can be another way to achieve elution of the solute. The change in conductivity or pH may be gradual (gradient elution) or stepwise (step elution). Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate (S). Cellulose ion exchange medias or support can include DE23™, DE32™, DE52™, CM-23™, CM-32™, and CM-52™ are available from Whatman Ltd. Maidstone, Kent, U.K. SEPHADEX®-based and-locross-linked ion exchangers are also known. For example, DEAE-, QAE-, CM-, and SP-SEPHADEX® and DEAE-, Q-, CM- and S-SEPHAROSE® and SEPHAROSE® Fast Flow, and Capto™ S are all available from GE Healthcare. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa., or Nuvia S and UNO-Sphere™ S from BioRad, Hercules, Calif., Eshmuno® S from EMD Millipore, MA.

As used herein, the term "hydrophobic interaction chromatography resin" can include a solid phase, which can be covalently modified with phenyl, octyl, butyl or the like. It can use the properties of hydrophobicity to separate molecules from one another. In this type of chromatography, hydrophobic groups such as, phenyl, octyl, hexyl or butyl can form the stationary phase of a column. Molecules such as proteins, peptides and the like pass through a HIC (hydrophobic interactive chromatography) column that possess one or more hydrophobic regions on their surface or have hydrophobic pockets and are able to interact with hydrophobic groups comprising a HIC's stationary phase. Examples of HIC resins or support include Phenyl sepharose FF, Capto Phenyl (GE Healthcare, Uppsala, Sweden), Phenyl 650-M (Tosoh Bioscience, Tokyo, Japan) and Sartobind Phenyl (Sartorius corporation, New York, USA).

As used herein, the term "Mixed Mode Chromatography" or "multimodal chromatography" (both "MMC") includes a chromatographic method in which solutes interact with a stationary phase through more than one interaction mode or mechanism. MMC can be used as an alternative or complementary tool to traditional reversed-phased (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Mixed mode chromatography media can provide unique selectivity that cannot be reproduced by single mode chromatography. Mixed mode chromatography can also provide potential cost savings, longer column lifetimes and operation flexibility compared to affinity-based methods. In some exemplary embodiments, mixed mode chromatography media can be comprised of mixed mode ligands coupled to an organic or inorganic support, sometimes denoted a base matrix, directly or via a spacer. The support may be in the form of particles, such as essentially spherical particles, a monolith, filter, membrane, surface, capillaries, etc. In some exemplary embodiments, the support can be prepared from a native polymer such as cross-linked carbohydrate material, such as agarose, agPV, cellulose, dextran, chitosan, konjac, carrageenan, gellan, alginate, etc. To obtain high adsorption capacities, the support can be porous and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964), the entire teachings of which are herein incorporated). Alternatively, the support can be prepared from a synthetic polymer such as cross-linked synthetic polymers, for example, styrene or styrene derivatives, divinylbenzene, acrylamides, acrylate esters, methacrylate esters, vinyl esters, vinyl amides and the like. Such synthetic polymers can be produced according to standard methods, for example, "Styrene based polymer supports developed by suspension polymerization" (R Arshady: Chimica e L'Industria 70(9), 70-75 (1988), the entire teachings of which are herein incorporated). Porous native or synthetic polymer supports are also available from commercial sources, such as such as GE Healthcare, Uppsala, Sweden.

As used herein, the term "mass spectrometer" includes a device capable of identifying specific molecular species and measuring their accurate masses. The term is meant to include any molecular detector into which a polypeptide or peptide may be characterized. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends on the application. In some exemplary embodiments, the mass spectrometer can be a tandem mass spectrometer. As used herein, the term "tandem mass spectrometry" includes a technique where structural information on sample molecules is obtained by using multiple stages of mass selection and mass separation. A prerequisite is that the sample molecules be transformed into a gas phase and ionized so that fragments are formed in a predictable and controllable fashion after the first mass selection step. Multistage MS/MS, or MS$^n$, can be performed by first selecting and isolating a precursor ion (MS$^2$), fragmenting it, isolating a primary fragment ion (MS$^3$), fragmenting it, isolating a secondary fragment (MS$^4$), and so on, as long as one can obtain meaningful information, or the fragment ion signal is detectable. Tandem MS has been successfully performed with a wide variety of analyzer combinations. Which analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device. The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited to sequencing amino acids of the protein fragments, determining protein sequencing, determining protein de novo sequencing, locating post-translational modifications, or identifying post translational modifications, or comparability analysis, or combinations thereof.

As used herein, "Mini-Trap" or "MiniTrap" or "MiniTrap binding molecule" is capable of binding to a VEGF molecule. Such MiniTraps can include (i) chimeric polypeptides as well as (ii) multimeric (e.g., dimeric) molecules comprising two or more polypeptides which are bound non-covalently, for example, by one or more disulfide bridges. MiniTraps can be produced through chemical modification, enzymatic activity, or recombinantly manufactured.

As used herein, "VEGF MiniTrap" or "VEGF MiniTrap binding molecule" can be a molecule or complex of molecules that binds to VEGF and has one or more sets of VEGF receptor Ig-like domains (or variants thereof) (e.g., VEGFR1 Ig domain 2 and/or VEGFR2 Ig domain 3 and/or 4) and a modified or absent multimerizing component (MC), for example, wherein the MC is a modified immunoglobulin Fc. The modification may be the result of proteolytic digestion of a VEGF trap (e.g., aflibercept or conbercept) or direct expression of the resulting polypeptide chains with the shortened MC sequence. (See the molecular structure depicted in FIG. 1.) FIG. 1 is a depiction of a VEGF MiniTrap molecule, which is the product of proteolysis of aflibercept with *Streptococcus pyogenes* IdeS. The homodimeric molecule is depicted having an Ig hinge domain fragment connected by two parallel disulfide bonds. The VEGFR1 domain, the VEGFR2 domain and the hinge domain fragment (MC) is indicated. The point in aflibercept where IdeS cleavage occurs is indicated with a "//". The cleaved off Fc fragment from aflibercept is also indicated. A single such chimeric polypeptide, which is not dimerized, may also be a VEGF MiniTrap if it has VEGF binding activity. The term "VEGF MiniTrap" includes a single polypeptide comprising a first set of one or more VEGF receptor Ig domains (or variants thereof), lacking an MC, but fused with a linker (e.g., a peptide linker) to one or more further sets of one or more VEGF receptor Ig domains (or variants thereof). The VEGF binding domains in a VEGF MiniTrap of the present invention may be identical or different from another (see WO2005/00895, the entire teachings of which are herein incorporated).

For example, in an embodiment of the invention, the unmodified immunoglobulin Fc domain comprises the amino acid sequence or amino acids 1-226 thereof:

```
(SEQ ID NO.: 33; wherein X1 is L or P and X2 is
A or T)
DKTHTCPX1CPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKX2TPPVLDSDGSFFLYSKLTVDKSRWQ

QGNVFSCSVMHEALHNHYTQKSLSLSPGK
```

Inhibition of VEGF includes, for example, antagonism of VEGF binding to VEGF receptor, for example, by competition with VEGF receptor for VEGF (e.g., $VEGF_{110}$, $VEGF_{121}$ and/or $VEGF_{165}$) binding. Such inhibition may result in inhibition of VEGF-mediated activation of VEGFR, for example, inhibition of luciferase expression in a cell line (e.g., HEK293) expressing chimeric VEGF Receptor (e.g., a homodimer thereof) having VEGFR extracellular domains fused to IL18Rα and/or IL18Rβ intracellular domains on the cell surface and also having an NFkB-luciferase-IRES-eGFP reporter gene, for example, the cell line HEK293/D9/Flt-IL18Rα/Flt-IL18Rβ as set forth herein.

The VEGF receptor Ig domain components of the VEGF MiniTraps of the present invention can include:
  (i) one or more of the immunoglobulin-like (Ig) domain 2 of VEGFR1 (Flt1) (R1D2),
  (ii) one or more of the Ig domain 3 of VEGFR2 (Flk1 or KDR) (Flk1D3) (R2D3),
  (iii) one or more of the Ig domain 4 of VEGFR2 (Flk1 or KDR) (Flk1D4) (R2D4) and/or
  (iv) one or more of the Ig domain 3 of VEGFR3 (Flt4) (Flt1D3 or R3D3).

Immunoglobulin-like domains of VEGF receptors may be referred to herein as VEGFR "Ig" domains. VEGFR Ig domains which are referenced herein, for example, R1D2 (which may be referred to herein as VEGFR1(d2)), R2D3 (which may be referred to herein as VEGFR2(d3)), R2D4 (which may be referred to herein as VEGFR2(d4)) and R3D3 (which may be referred to herein as VEGFR3(d3)) are intended to encompass not only the complete wild-type Ig domain, but also variants thereof which substantially retain the functional characteristics of the wild-type domain, for example, retain the ability to form a functioning VEGF binding domain when incorporated into a VEGF MiniTrap. It will be readily apparent to one of skill in the art that numerous variants of the above Ig domains, which will retain substantially the same functional characteristics as the wild-type domain, can be obtained.

The present invention provides a VEGF MiniTrap polypeptide comprising the following domain structure:
  $((R1D2)\text{-}(R2D3))_a$-linker-$((R1D2)\text{-}(R2D3))_b$;
  $((R1D2)\text{-}(R2D3)\text{-}(R2D4))_c$-linker-$((R1D2)\text{-}(R2D3)\text{-}(R2D4))_d$;
  $((R1D2)\text{-}(R2D3))_e\text{-}(MC)_g$;
  $((R1D2)\text{-}(R2D3)\text{-}(R2D4))_f\text{-}(MC)_g$;
wherein,
  R1D2 is the VEGF receptor 1 (VEGFR1) Ig domain 2 (D2);
  R2D3 is the VEGFR2 Ig domain 3;
  R2D4 is the VEGFR2 Ig domain 4;
  MC is a multimerizing component (e.g., an IgG hinge domain or fragment thereof, for example from IgG1);
  linker is a peptide comprising about 5, 6, 7, 8, 9, 10, 11, 12, 13, 14, 15 or 16 amino acids, for example, $(GGGS)_g$ (SEQ ID NO.: 104);
and,
Independently,
  a=1, 2, 3, 4, 5, 6, 7, 8, 9, 10, 11, 12, 13, 14 or 15;
  b=1, 2, 3, 4, 5, 6, 7, 8, 9, 10, 11, 12, 13, 14 or 15;
  c=1, 2, 3, 4, 5, 6, 7, 8, 9, 10, 11, 12, 13, 14 or 15;
  d=1, 2, 3, 4, 5, 6, 7, 8, 9, 10, 11, 12, 13, 14 or 15;
  e=1, 2, 3, 4, 5, 6, 7, 8, 9, 10, 11, 12, 13, 14 or 15;
  f=1, 2, 3, 4, 5, 6, 7, 8, 9, 10, 11, 12, 13, 14 or 15; and
  g=1, 2, 3, 4, 5, 6, 7, 8, 9, 10, 11, 12, 13, 14 or 15.

In an embodiment of the invention, R1D2 comprises the amino acid sequence: SDTGRPFVEMYSEIPEIIHMTE-GRELVIPCRVT-SPNITVTLKKFPLDTLIPDGKRIIWDSRKG FIIS- NATYKEIGLLTCEATVNGHLYKTNYLTHRQTNTIID (SEQ ID NO.: 34). In one aspect, the R1D2 lacks the N-terminal SDT.

In an embodiment of the invention, R1D2 comprises the amino acid sequence:

(SEQ ID NO.: 35)
PFVEMYSEIPEIIHMTEGRELVIPCRVTSPNITVTLKKFPLDTLIPDGKR

IIWDSRKGFIISNATYKEIGLLTCEATVNGHLYKTNYLTHRQT.

In an embodiment of the invention, R2D3 comprises the amino acid sequence:

(SEQ ID NO.: 36)
VVLSPSHGIELSVGEKLVLNCTARTELNVGIDFNWEYPSSKHQHKKLVNR

DLKTQSGSEMKKFLSTLTIDGVTRSDQGLYTCAASSGLMTKKNSTFVRVH

EK.

In an embodiment of the invention, R2D4 comprises the amino acid sequence:

(SEQ ID NO.: 37)
PFVAFGSGMESLVEATVGERVRIPAKYLGYPPPEIKWYKNGIPLESNHTI

KAGHVLTIMEVSERDTGNYTVILTNPISKEKQSHVVSLVVYVPPGPG.

In an embodiment of the invention, R2D4 comprises the amino acid sequence:

(SEQ ID NO.: 38)
FVAFGSGMESLVEATVGERVRIPAKYLGYPPPEIKWYKNGIPLESNHTIK

AGHVLTIMEVSERDTGNYTVILTNPISKEKQSHVVSLVVYVP.

In an embodiment of the invention, a multimerizing component (MC) for use in a VEGF MiniTrap is a peptide, for example, a modified Fc immunoglobulin (e.g., from an IgG1) which is capable of binding to another multimerizing component. In one aspect, an MC is a modified Fc immunoglobulin that includes the immunoglobulin hinge region. For example, in an embodiment of the invention, an MC is a peptide comprising one or more (e.g., 1, 2, 3, 4, 5 or 6) cysteines that are able to form one or more cysteine bridges with cysteines in another MC, for example, DKTHTCPPC (SEQ ID NO.: 39), DKTHTCPPCPPC (SEQ ID NO.: 40), DKTHTCPPCPPCPPC (SEQ ID NO.: 41), DKTHTC (PPC)$_h$, wherein h is 1, 2, 3, 4, or 5 (SEQ ID NO.: 105), DKTHTCPPCPAPELLG (SEQ ID NO.: 60), DKTHTCPLCPAPELLG (SEQ ID NO.: 43), DKTHTC (SEQ ID NO.: 44) or DKTHTCPLCPAP (SEQ ID NO.: 45).

The present invention also provides a VEGF MiniTrap polypeptide comprising the following domain structure:
 (i) (R1D2)$_a$-(R2D3)$_b$-(MC)$_c$; or
 (ii) (R1D2)$_a$-(R2D3)$_b$-(R2D4)$_c$-(MC)$_d$;
which may be homodimerized with a second of said polypeptides, for example, by binding between the MCs of each polypeptide,
wherein
 (i) said R1D2 domains coordinate;
 (ii) said R2D3 domains coordinate; and/or
 (iii) said R2D4 domains coordinate,
to form a dimeric VEGF binding domain.

In an embodiment of the invention, the VEGF MiniTrap polypeptide comprises the amino acid sequence:

(SEQ ID NO.: 46; MC underscored)
SDTGRPFVEMYSEIPEIIHMTEGRELVIPCRVTSPN$_{36}$ITVTLKKFPLDT

LIPDGKRIIWDSRKGFIISN$_{68}$ATYKEIGLLTCEATVNGHLYKTNYLTHR

QTNTIIDVVLSPSHGIELSVGEKLVLN$_{123}$CTARTELNVGIDFNWEYPSS

KHQHKKLVNRDLKTQSGSEMKKFLSTLTIDGVTRSDQGLYTCAASSGLMT

KKN$_{196}$STFVRVHEK<u>DKTHTCPPCPAPELLG</u>;

(SEQ ID NO.: 47; MC underscored)
GRPFVEMYSEIPEIIHMTEGRELVIPCRVTSPNITVTLKKFPLDTLIPDG

KRIIWDSRKGFIISNATYKEIGLLTCEATVNGHLYKTNYLTHRQTNTIID

VVLSPSHGIELSVGEKLVLNCTARTELNVGIDFNWEYPSSKHQHKKLVNR

DLKTQSGSEMKKFLSTLTIDGVTRSDQGLYTCAASSGLMTKKNSTFVRVH

ENLSVAFGSGMESLVEATVGERVRIPAKYLGYPPPEIKWYKNGIPLESNH

TIKAGHVLTIMEVSERDTGNYTVILTNPISKEKQSHVVSLVVYVPPGPGD

KTHTCPLCPAPELLG;

(SEQ ID NO.: 48; MC underscored)
SDTGRPFVEMYSEIPEIIHMTEGRELVIPCRVTSPN$_{36}$ITVTLKKFPLDT

LIPDGKRIIWDSRKGFIISN$_{68}$ATYKEIGLLTCEATVNGHLYKTNYLTHR

QTNTIIDVVLSPSHGIELSVGEKLVLN$_{123}$CTARTELNVGIDFNWEYPSS

KHQHKKLVNRDLKTQSGSEMKKFLSTLTIDGVTRSDQGLYTCAASSGLMT

KKN$_{196}$STFVRVHEK<u>DKTHTCPPC</u>;

(SEQ ID NO.: 49; MC underscored)
SDTGRPFVEMYSEIPEIIHMTEGRELVIPCRVTSPN$_{36}$ITVTLKKFPLDT

LIPDGKRIIWDSRKGFIISN$_{68}$ATYKEIGLLTCEATVNGHLYKTNYLTHR

QTNTIIDVVLSPSHGIELSVGEKLVLN$_{123}$CTARTELNVGIDFNWEYPSS

KHQHKKLVNRDLKTQSGSEMKKFLSTLTIDGVTRSDQGLYTCAASSGLMT

KKN$_{196}$STFVRVHEK<u>DKTHTCPPCPPC</u>;

(SEQ ID NO.: 50; MC underscored)
SDTGRPFVEMYSEIPEIIHMTEGRELVIPCRVTSPN$_{36}$ITVTLKKFPLDT

LIPDGKRIIWDSRKGFIISN$_{68}$ATYKEIGLLTCEATVNGHLYKTNYLTHR

QTNTIIDVVLSPSHGIELSVGEKLVLN$_{123}$CTARTELNVGIDFNWEYPSS

KHQHKKLVNRDLKTQSGSEMKKFLSTLTIDGVTRSDQGLYTCAASSGLMT

KKN$_{196}$STFVRVHEK<u>DKTHTCPPCPPCPPC</u>;
or (SEQ ID NO.: 106)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEK<u>DKTHTC-(PPC)x</u>
(MC underscored; wherein x is 1, 2, 3, 4 or 5).

As discussed, such polypeptides may be multimerized (e.g., dimerized (e.g., homodimerized)) wherein binding between the polypeptides is mediated via the multimerizing components.

In an embodiment of the invention, the VEGFR1 Ig-like domain 2 of the monomeric VEGF MiniTraps of the present invention have N-linked glycosylation at N36 and/or N68; and/or an intrachain disulfide bridge between C30 and C79;

and/or, the VEGFR2 Ig-like domain 3 of the monomeric VEGF MiniTraps of the present invention, have N-linked glycosylation at N123 and/or N196; and/or an intrachain disulfide bridge between C124 and C185.

In an embodiment of the invention, the VEGF MiniTrap comprises the structure:
(R1D2)$_1$-(R2D3)$_1$-(G$_4$S)$_3$—(R1D2)$_1$-(R2D3)$_1$ ("(G$_4$S)$_3$" disclosed as SEQ ID NO.: 107);
(R1D2)$_1$-(R2D3)$_1$-(G$_4$S)$_6$—(R1D2)$_1$-(R2D3)$_1$ ("(G$_4$S)$_6$" disclosed as SEQ ID NO.: 108);
(R1D2)$_1$-(R2D3)$_1$-(G$_4$S)$_9$—(R1D2)$_1$-(R2D3)$_1$ ("(G$_4$S)$_9$" disclosed as SEQ ID NO.: 109); or
(R1D2)$_1$-(R2D3)$_1$-(G$_4$S)$_{12}$—(R1D2)$_1$-(R2D3)$_1$ ("(G$_4$S)$_{12}$" disclosed as SEQ ID NO.: 110).
G4S is-Gly-Gly-Gly-Gly-Ser (SEQ ID NO.: 111)

In an embodiment of the invention, the VEGF MiniTrap comprises the amino acid sequence:

(i)
(SEQ ID NO.: 51; linker underscored)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEK<u>GGGGSGGGGSGGGGSGGGGSGGGGSGGGGS</u>SDTGRPFVEMYSEIP

EIIHMTEGRELVIPCRVTSPNITVTLKKFPLDTLIPDGKRIIWDSRKGFI

ISNATYKEIGLLTCEATVNGHLYKTNYLTHRQTNTIIDVVLSPSHGIELS

VGEKLVLNCTARTELNVGIDFNWEYPSSKHQHKKLVNRDLKTQSGSEMKK

FLSTLTIDGVTRSDQGLYTCAASSGLMTKKNSTFVRVHEK;

(iii)
(SEQ ID NO.: 52; linker underscored)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEK<u>GGGGSGGGGSGGGGS</u>SDTGRPFVEMYSEIPEIIHMTEGRELVIPC

RVTSPNITVTLKKFPLDTLIPDGKRIIWDSRKGFIISNATYKEIGLLTCE

ATVNGHLYKTNYLTHRQTNTIIDVVLSPSHGIELSVGEKLVLNCTARTEL

NVGIDFNWEYPSSKHQHKKLVNRDLKTQSGSEMKKFLSTLTIDGVTRSDQ

GLYTCAASSGLMTKKNSTFVRVHEK;

(iv)
(SEQ ID NO.: 53; linker underscored)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEK<u>GGGGSGGGGSGGGGSGGGGSGGGGSGGGGSGGGGSGGGGSGGGGS</u>

SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEK (v)
(SEQ ID NO.: 54; linker underscored);
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEK<u>GGGGSGGGGSGGGGSGGGGSGGGGSGGGGSGGGGSGGGGSGGGGS

GGGGSGGGGSGGGGS</u>SDTGRPFVEMYSEIPEIIHMTEGRELVIPCRVTSP

NITVTLKKFPLDTLIPDGKRIIWDSRKGFIISNATYKEIGLLTCEATVNG

HLYKTNYLTHRQTNTIIDVVLSPSHGIELSVGEKLVLNCTARTELNVGID

FNWEYPSSKHQHKKLVNRDLKTQSGSEMKKFLSTLTIDGVTRSDQGLYTC

AASSGLMTKKNSTFVRVHEK or (vi)
(SEQ ID NO.: 112)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEK-(GGGGS)x - SDTGRPFVEMYSEIPEIIHMTEGRELVIPCRVT

SPNITVTLKKFPLDTLIPDGKRIIWDSRKGFIISNATYKEIGLLTCEATV

NGHLYKTNYLTHRQTNTIIDVVLSPSHGIELSVGEKLVLNCTARTELNVG

IDFNWEYPSSKHQHKKLVNRDLKTQSGSEMKKFLSTLTIDGVTRSDQGLY

TCAASSGLMTKKNSTFVRVHEK (wherein x is 1, 2, 3, 4, 5, 6, 7, 8, 9, 10, 11, 12, 13, 14 or 15). As discussed herein, these polypeptides may comprise a secondary structure wherein like VEGFR Ig domains associate to form an intra-chain VEGF binding domain (e.g., FIG. 2). In an embodiment of the invention, two or more of such polypeptides multimerize (e.g., dimerize (e.g., homodimerize)) wherein the VEGFR Ig domains of each chain associate with like Ig domains of another chain to form an inter-chain VEGF binding domain.

In a certain embodiment of the invention, a VEGF MiniTrap of the present invention lacks any significant modification of the amino acid residues of a VEGF MiniTrap polypeptide (e.g., directed chemical modification such as PEGylation or iodoacetamidation, for example at the N- and/or C-terminus).

Figure 2:
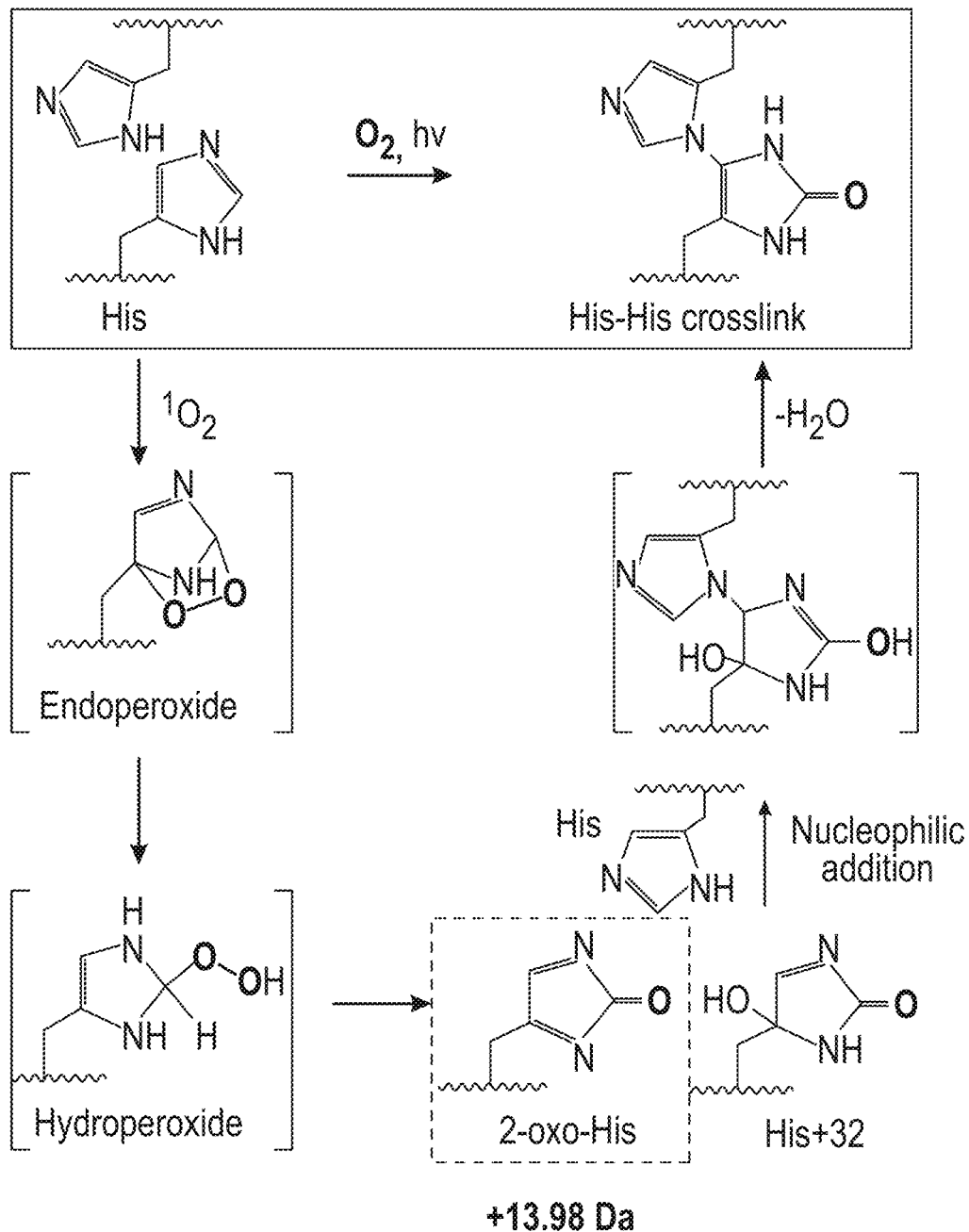
FIG. 2 depicts a proposed mechanism for histidine oxidation to 2-oxo-histidine (14 Da).

In an embodiment of the invention, the polypeptide comprises a secondary structure wherein like VEGFR Ig domains in a single chimeric polypeptide (e.g., (R1D2)$_a$-(R2D3)$_b$-linker-(R1D2)$_c$-(R2D3)$_d$; or (R1D2)$_a$-(R2D3)$_b$-(R2D4)$_c$-linker-(R1D2)$_d$-(R2D3)$_e$-(R2D4)$_f$) or in separate chimeric polypeptides (e.g., homodimers) coordinate to form a VEGF binding domain. For example, wherein
(i) said R1D2 domains coordinate;
(ii) said R2D3 domains coordinate; and/or
(iii) said R2D4 domains coordinate,
to form a VEGF binding domain. FIG. 2 is a description of a single chain VEGF MiniTrap depicting such domain coordination. The VEGFR1, VEGFR2 and linker domains are indicated. The linker shown is $(G_4S)_6$ (SEQ ID NO.: 108). The present invention includes single chain VEGF MiniTraps with a $(G_4S)_3$ (SEQ ID NO.: 107); $(G_4S)_9$ (SEQ ID NO.: 109) or $(G_4S)_{12}$ (SEQ ID NO.: 110) linker.

In addition, the present invention also provides a complex comprising a VEGF MiniTrap as discussed herein complexed with a VEGF polypeptide or a fragment thereof or fusion thereof. In an embodiment of the invention, the VEGF (e.g., $VEGF_{165}$) is homodimerized and/or the VEGF MiniTrap is homodimerized in a 2:2 complex (2 VEGFs:2 MiniTraps) and/or VEGF MiniTrap is homodimerized in a 1:1 complex. Complexes can include homodimerized VEGF molecules bound to homodimerized VEGF MiniTrap polypeptides. In an embodiment of the invention, the complex is in vitro (e.g., immobilized to a solid substrate) or is in the body of a subject. The present invention also includes a composition of complexes of a VEGF dimer (e.g., $VEGF_{165}$) complexed with a VEGF MiniTrap.

As used herein, the term "protein" or "protein of interest" can include any amino acid polymer having covalently linked amide bonds. Examples of proteins of interest include, but are not limited to, aflibercept and MiniTrap. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds. "Synthetic peptide or polypeptide" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may comprise one or multiple polypeptides to form a single functioning biomolecule. In another exemplary aspect, a protein can include antibody fragments, nanobodies, recombinant antibody chimeras, cytokines, chemokines, peptide hormones, and the like. Proteins of interest can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In a particular aspect, the protein of interest is an anti-VEGF fusion protein (e.g., aflibercept or MiniTrap). Proteins may be produced using recombinant cell-based production systems, such as the insect baculovirus system, yeast systems (e.g., *Pichia* sp.), and mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation" (Darius Ghaderi et al., Production platforms for biotherapeutic glycoproteins. Occurrence, impact, and challenges of non-human sialylation, 28 BIOTECHNOLOGY AND GENETIC ENGINEERING REVIEWS 147-176 (2012), the entire teachings of which are herein incorporated). In some exemplary embodiments, proteins comprise modifications, adducts, and other covalently linked moieties. These modifications, adducts and moieties include, for example, avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as globular proteins and fibrous proteins; conjugated proteins, such as nucleoproteins, glycoproteins, mucoproteins, chromoproteins, phosphoproteins, metalloproteins, and lipoproteins; and derived proteins, such as primary derived proteins and secondary derived proteins.

In some exemplary embodiments, the protein of interest can be a recombinant protein, an antibody, a bispecific antibody, a multispecific antibody, antibody fragment, monoclonal antibody, fusion protein, scFv and combinations thereof.

As used herein, the term "recombinant protein" refers to a protein produced as the result of the transcription and translation of a gene carried on a recombinant expression vector that has been introduced into a suitable host cell. In certain exemplary embodiments, the recombinant protein can be a fusion protein. In a particular aspect, the recombinant protein is an anti-VEGF fusion protein (e.g., aflibercept or MiniTrap). In certain exemplary embodiments, the recombinant protein can be an antibody, for example, a chimeric, humanized, or fully human antibody. In certain exemplary embodiments, the recombinant protein can be an antibody of an isotype selected from group consisting of: IgG, IgM, IgA1, IgA2, IgD, or IgE. In certain exemplary embodiments the antibody molecule is a full-length antibody (e.g., an IgG1) or alternatively the antibody can be a fragment (e.g., an Fc fragment or a Fab fragment).

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. In different embodiments of the invention, the FRs of the anti-big-ET-1 antibody (or antigen-binding portion thereof) may be identical to the human germline sequences or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, for example, commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')$_2$ fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment comprises a sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively, or additionally, an antibody fragment may be wholly or partially synthetically produced. An antibody fragment may optionally comprise a single chain antibody fragment. Alternatively, or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The term "bispecific antibody" includes an antibody capable of selectively binding two or more epitopes. Bispecific antibodies generally comprise two different heavy chains with each heavy chain specifically binding a different epitope-either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions and such sequences can be expressed in a cell that expresses an immunoglobulin light chain.

A typical bispecific antibody has two heavy chains each having three heavy chain CDRs, followed by a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding of one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats such as, but not limited to, triomab, knobs into holes IgG (kih IgG), crossMab, orth-Fab IgG, Dual-variable domains Ig (DVD-Ig), two-in-one or dual action Fab (DAF), IgG-single-chain Fv (IgG-scFv), or κλ-bodies. The non-IgG-like different formats include tandem scFvs, diabody format, single-chain diabody, tandem diabodies (TandAbs), Dual-affinity retargeting molecule (DART), DART-Fc, nanobodies, or antibodies produced by the dock-and-lock (DNL) method (Gaowei Fan, Zujian Wang & Mingju Hao, Bispecific antibodies and their applications, 8 JOURNAL OF HEMATOLOGY & ONCOLOGY 130; Dafne Müller & Roland E. Kontermann, Bispecific Antibodies, HANDBOOK OF THERAPEUTIC ANTIBODIES 265-310 (2014), the entire teachings of which are herein incorporated). The methods of producing bsAbs are not limited to quadroma technology based on the somatic fusion of two different hybridoma cell lines, chemical conjugation, which involves chemical cross-linkers, and genetic approaches utilizing recombinant DNA technology. Examples of bsAbs include those disclosed in the following patent applications, which are hereby incorporated by reference: U.S. Ser. No. 12/823,838, filed Jun. 25, 2010; U.S. Ser. No. 13/488,628, filed Jun. 5, 2012; U.S. Ser. No. 14/031,075, filed Sep. 19, 2013; U.S. Ser. No. 14/808,171, filed Jul. 24, 2015; U.S. Ser. No. 15/713,574, filed Sep. 22, 2017; U.S. Ser. No. 15/713, 569, field Sep. 22, 2017; U.S. Ser. No. 15/386,453, filed Dec. 21, 2016; U.S. Ser. No. 15/386,443, filed Dec. 21, 2016; U.S. Ser. No. 15/22,343 filed Jul. 29, 2016; and U.S. Ser. No. 15/814,095, filed Nov. 15, 2017. Low levels of homodimer impurities can be present at several steps during the manufacturing of bispecific antibodies. The detection of such homodimer impurities can be challenging when performed using intact mass analysis due to low abundances of the homodimer impurities and the co-elution of these impurities with main species when carried out using a regular liquid chromatographic method.

As used herein "multispecific antibody" refers to an antibody with binding specificities for at least two different antigens. While such molecules normally will only bind two antigens (i.e., bispecific antibodies, bsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

In some exemplary embodiments, the protein of interest can have a pI in the range of about 4.5 to about 9.0. In one exemplary specific embodiment, the pI can be about 4.5, about 5.0, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In some exemplary embodiments, the types of protein of interest in the compositions can be more than one.

In some exemplary embodiments, the protein of interest can be produced from mammalian cells. The mammalian cells can be of human origin or non-human origin can include primary epithelial cells (e.g., keratinocytes, cervical epithelial cells, bronchial epithelial cells, tracheal epithelial cells, kidney epithelial cells and retinal epithelial cells), established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LSI80 cells, LS174T cells, NCI—H-548 cells, RPMI2650 cells, SW-13 cells, T24 cells, WI-28 VA13, 2RA cells, WISH cells, BS—C—I cells, LLC-MK2 cells, Clone M-3 cells, 1-10 cells, RAG cells, TCMK-1 cells, Y-1 cells, LLC-PKi cells, PK(15) cells, GHi cells, GH3 cells, L2 cells, LLC-RC 256 cells, MHiCi cells, XC cells, MDOK cells, VSW cells, and TH-I, B1 cells, BSC-1 cells, RAf cells, RK-cells, PK-15 cells or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, Midi cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDMiC3 cells, KLN205 cells, McCoy cells, Mouse L cells, Strain 2071 (Mouse L) cells, L-M strain (Mouse L) cells, L-MTK' (Mouse L) cells, NCTC clones 2472 and 2555, SCC-PSA1 cells, Swiss/3T3 cells, Indian muntjac cells, SIRC cells, Cn cells, and Jensen cells, Sp2/0, NS0, NS1 cells or derivatives thereof).

As used herein, the term "protein alkylating agent" refers to an agent used for alkylating certain free amino acid residues in a protein. Non-limiting examples of protein alkylating agents are iodoacetamide (IOA), chloroacetamide (CAA), acrylamide (AA), N-ethylmaleimide (NEM), methyl methanethiosulfonate (MMTS), and 4-vinylpyridine or combinations thereof.

As used herein, "protein denaturing" can refer to a process in which the three-dimensional shape of a molecule is changed from its native state. Protein denaturation can be carried out using a protein denaturing agent. Non-limiting examples of a protein denaturing agent include heat, high or low pH, reducing agents like DTT (see below) or exposure to chaotropic agents. Several chaotropic agents can be used as protein denaturing agents. Chaotropic solutes increase the entropy of the system by interfering with intramolecular interactions mediated by non-covalent forces such as hydrogen bonds, van der Waals forces, and hydrophobic effects. Non-limiting examples for chaotropic agents include butanol, ethanol, guanidinium chloride, lithium perchlorate, lithium acetate, magnesium chloride, phenol, propanol, sodium dodecyl sulfate, thiourea, N-lauroylsarcosine, urea, and salts thereof.

As used herein, the term "protein reducing agent" refers to the agent used for reduction of disulfide bridges in a protein. Non-limiting examples of the protein reducing agents used to reduce the protein are dithiothreitol (DTT), ß-mercaptoethanol, Ellman's reagent, hydroxylamine hydrochloride, sodium cyanoborohydride, tris(2-carboxyethyl)phosphine hydrochloride (TCEP-HCl), or combinations thereof.

As used herein, the term "variant" of a polypeptide (e.g., of a VEGFR Ig domain) refers to a polypeptide comprising an amino acid sequence that is at least about 70-99.9% (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9%) identical or similar to a referenced or native amino acid sequence of a protein of interest. A sequence comparison can be performed by, for example, a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment). Variants of a polypeptide (e.g., of a VEGFR Ig domain) may also refer to a polypeptide comprising a referenced amino acid sequence except for one or more (e.g., 1, 2, 3, 4, 5, 6, 7, 8, 9 or 10) mutations such as, for example, missense mutations (e.g., conservative substitutions), nonsense mutations, deletions, or insertions. The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.; the entire teachings of which are herein incorporated.

Some variants can be covalent modifications that polypeptides undergo, either during (co-translational modification) or after (post-translational modification "PTM") their ribosomal synthesis. PTMs are generally introduced by specific enzymes or enzyme pathways. Many occur at the site of a specific characteristic protein sequence (e.g., signature sequence) within the protein backbone. Several hundred PTMs have been recorded and these modifications invariably influence some aspect of a protein's structure or function (Walsh, G. "Proteins" (2014) second edition, published by Wiley and Sons, Ltd., ISBN: 9780470669853, the entire teachings of which are herein incorporated). In certain exemplary embodiments, a protein composition can comprise more than one type of protein variant of a protein of interest.

Protein variants in the case of aflibercept (and proteins sharing structural characteristics of aflibercept, for example, one or more heavy or light chain regions of aflibercept) can comprise, but are not limited to, oxidation variants which can result from oxidation of one or more amino acid residues occurring at, for example, histidine, cysteine, methionine, tryptophan, phenylalanine and/or tyrosine residues; deamidation variants which can result from deamidation at asparagine residues and/or deoxyglucosonation at arginine residues.

With respect to aflibercept (and proteins sharing structural characteristics of aflibercept, for example, one or more heavy or light chain regions of aflibercept) oxidation variants can comprise oxidation of histidine residue at His86, His110, His145, His209, His95, His19 and/or His203 (or equivalent residue positions on proteins sharing certain structural characteristics of aflibercept); oxidation of tryptophan residues at Trp58 and/or Trp138 (or equivalent residue positions on proteins sharing certain structural characteristics of aflibercept); oxidation of tyrosine residues at Tyr64 (or equivalent positions on proteins sharing certain structural characteristics of aflibercept); oxidation of phenylalanine residues at Phe44 and/or Phe166 (or equivalent residue positions on proteins sharing certain structural characteristics of aflibercept); and/or oxidation of methionine residues at Met10, Met20, Met163 and/or Met192 (or equivalent residue positions on proteins sharing certain structural characteristics of aflibercept).

With respect to aflibercept (and proteins sharing structural characteristics of aflibercept, for example, one or more heavy or light chain regions of aflibercept) deamidation variants can comprise deamidation of asparagine residue at Asn84 and/or Asn99 (or equivalent residue positions on proteins sharing certain structural characteristics of aflibercept).

With respect to aflibercept (and proteins sharing structural characteristics of aflibercept for example, one or more heavy or light chain regions of aflibercept) deoxyglucosonation variant can comprise 3-deoxyglucosonation of arginine residue at Arg5 (or equivalent residue position on proteins sharing certain structural characteristics of aflibercept).

Protein variants can include both acidic species and basic species. Acidic species are typically the variants that elute earlier than the main peak from CEX or later than the main peak from AEX, while basic species are the variants that elute later than the main peak from CEX or earlier than the main peak from AEX.

Figure 16:
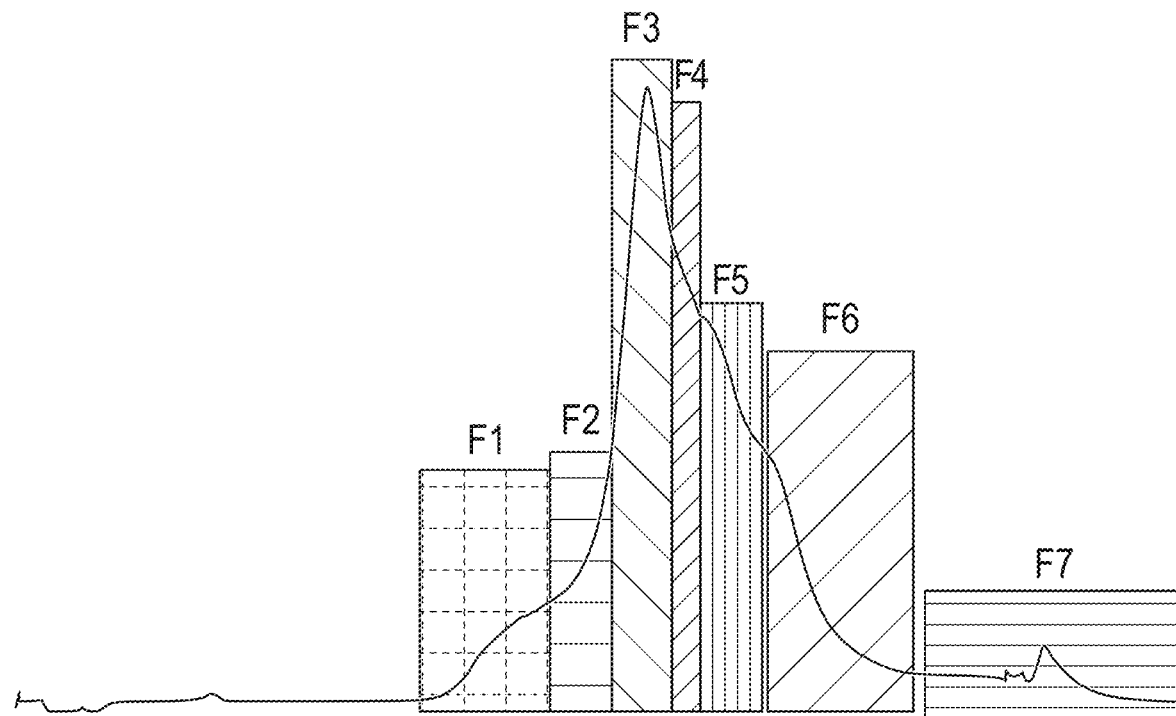
FIG. 16 depicts the fractions from performing strong cation exchange chromatography according to an exemplary embodiment.
Figure 17:
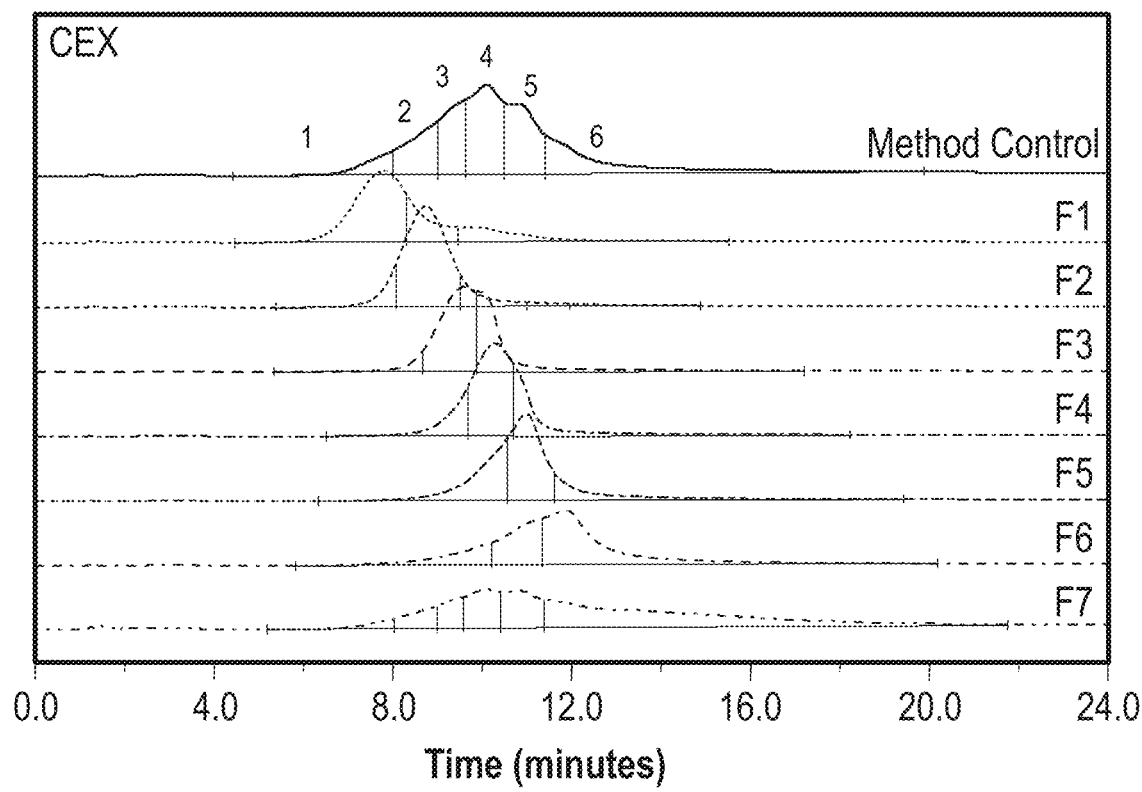
FIG. 17 depicts strong cation exchange chromatograms performed according to an exemplary embodiment for the MT1 production (prior to any production procedure, ≤BY3) subjected to CEX and for enriched variants of desialylated MiniTrap (dsMT1) using a dual salt-pH gradient.

As used herein, the terms "acidic species," "AS," "acidic region," and "AR," refer to the variants of a protein which are characterized by an overall acidic charge. For example, in recombinant protein preparations such acidic species can be detected by various methods, such as ion exchange, for example, WCX-10 HPLC (a weak cation exchange chromatography), or IEF (isoelectric focusing). Acidic species of an antibody may include variants, structure variants, and/or fragmentation variants. Exemplary variants can include, but are not limited to, deamidation variants, afucosylation variants, oxidation variants, methylglyoxal (MGO) variants, glycation variants, and citric acid variants. Exemplary structure variants include, but are not limited to, glycosylation variants and acetonation variants. Exemplary fragmentation variants include any modified protein species from the target molecule due to dissociation of peptide chain, enzymatic and/or chemical modifications, including, but not limited to, Fc and Fab fragments, fragments missing a Fab, fragments missing a heavy chain variable domain, C-terminal truncation variants, variants with excision of N-terminal Asp in the light chain, and variants having N-terminal truncation of the light chain. Other acidic species variants include variants comprising unpaired disulfides, host cell proteins, and host nucleic acids, chromatographic materials, and media components. Commonly, acidic species elute earlier than the main peak during CEX or later than the main peak during AEX analysis (See FIGS. 16 and 17).

In certain embodiments, a protein composition can comprise more than one type of acidic species variant. For example, but not by way of limitation, the total acidic species can be categorized based on chromatographic retention time of the peaks appearing. Another example in which the total acidic species can be categorized can be based on the type of variant-variants, structure variants, or fragmentation variant.

The term "acidic species" or "AS" does not refer to process-related impurities. The term "process-related impurity," as used herein, refers to impurities that are present in a composition comprising a protein, but are not derived from the protein itself. Process-related impurities include, but are not limited to, host cell proteins (HCPs), host cell nucleic acids, chromatographic materials, and media components.

In one exemplary embodiment, the amount of acidic species in the anti-VEGF composition compared to the protein of interest can be at most about 20%, 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0% and ranges within one or more of the preceding. Examples of anti-VEGF compositions are discussed in Section III below. In one aspect, the anti-VEGF composition can comprise an anti-VEGF protein selected from the group consisting of aflibercept, recombinant MiniTrap (examples of which are disclosed in U.S. Pat. No. 7,279,159), a scFv and other anti-VEGF proteins. In a preferred aspect, the recombinant protein of interest is aflibercept.

Among the chemical degradation pathways responsible for acidic or basic species, the two most commonly observed covalent modifications occurring in proteins and peptides are deamination and oxidation. Methionine, cysteine, histidine, tryptophan, and tyrosine are some of the amino acids that are most susceptible to oxidation: Met and Cys because of their sulfur atoms and His, Trp, and Tyr because of their aromatic rings.

As used herein, the terms "oxidative species," "OS," or "oxidation variant" refer to the variants of a protein formed by oxidation. Such oxidative species can also be detected by various methods, such as ion exchange, for example, WCX-10 HPLC (a weak cation exchange chromatography), or IEF (isoelectric focusing). Oxidation variants can result from oxidation occurring at histidine, cysteine, methionine, tryptophan, phenylalanine and/or tyrosine residues. With respect, in particular, to aflibercept (and proteins sharing structural characteristics of aflibercept e.g., one or more heavy or light chain regions of aflibercept), oxidation variants can comprise oxidation of histidine residue at His86, His110, His145, His209, His95, His19 and/or His203 (or equivalent residue positions on proteins sharing certain structural characteristics of aflibercept); oxidation of tryptophan residues at Trp58 and/or Trp138 (or equivalent residue positions on proteins sharing certain structural characteristics of aflibercept); oxidation of tyrosine residues at Tyr64 (or equivalent positions on proteins sharing certain structural characteristics of aflibercept); oxidation of phenylalanine residues at Phe44 and/or Phe166 (or equivalent residue positions on proteins sharing certain structural characteristics of aflibercept); and/or oxidation of methionine residues at Met10, Met20, Met163 and/or Met192 (or equivalent residue positions on proteins sharing certain structural characteristics of aflibercept).

In one exemplary embodiment, the amount of oxidative species in the anti-VEGF composition compared to the protein of interest can be at most about 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0% and ranges within one or more of the preceding. Examples of anti-VEGF compositions are discussed in Section III below. In one aspect, the anti-VEGF composition can comprise an anti-VEGF protein selected from the group consisting of aflibercept, recombinant Mini-Trap (examples of which are disclosed in U.S. Pat. No. 7,279,159), a scFv and other anti-VEGF proteins. In a preferred aspect, the recombinant protein of interest is aflibercept or MiniTrap.

Cysteine residues may undergo spontaneous oxidation to form either intra- or intermolecular disulfide bonds or monomolecular byproducts such as sulfenic acid.

Histidine residues are also highly sensitive to oxidation through reaction with their imidazole rings, which can subsequently generate additional hydroxyl species (Li, S, C Schoneich, and RT. Borchardt. 1995. Chemical Instability of Protein Pharmaceuticals: Mechanisms of Oxidation and Strategies for Stabilization. Biotechnol. Bioeng. 48:490-500, the entire teaching of which is herein incorporated). Proposed mechanisms for histidine oxidation are highlighted in FIG. 2 and FIG. 3. Detailed mechanistic studies are available in Anal. Chem. 2014, 86, 4940-4948 and J. Pharm. Biomed. Anal. 21 (2000) 1093-1097, the entire teaching of which is herein incorporated.

Oxidation of methionine can lead to formation of methionine sulfoxide (Li, S, C Schoneich, and RT. Borchardt. 1995. Chemical Instability of Protein Pharmaceuticals: Mechanisms of Oxidation and Strategies for Stabilization. Biotechnol. Bioeng. 48:490-500). The various possible oxidation mechanisms of the methionine residues have been discussed in the literature (Brot, N., Weissbach, H. 1982. The biochemistry of methionine sulfoxide residues in proteins. Trends Biochem. Sci. 7: 137-139, the entire teaching of which is herein incorporated).

Figure 4:
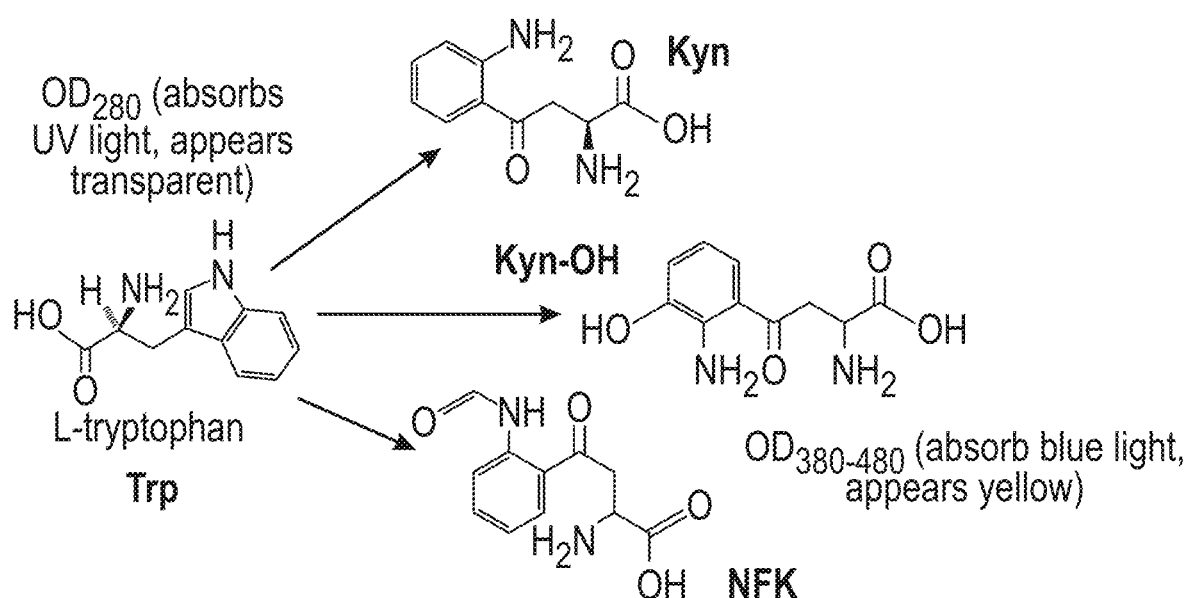
FIG. 4 depicts a proposed mechanism for oxidation of tryptophan to N-formylkynurenine and kynurenine.

Oxidation of tryptophan can give a complex mixture of products. The primary products can be N-formylkynurenine and kynurenine along with mono-oxidation, di-oxidation and/or tri-oxidation products (FIG. 4). Peptides bearing oxidized Trp modifications generally exhibit mass increases of 4, 16, 32 and 48 Da, corresponding to the formation of kynurenine (KYN), hydroxytryptophan ($W_{ox1}$), and N-formylkynurenine/dihydroxytryptophan (NFK/$W_{ox2}$, referred to also as "doubly oxidized Trp"), trihydroxytryptophan ($W_{ox3}$, referred to also as "triply oxidized Trp"), and their combinations, such as hydroxykynurenine ($KYN_{ox1}$, +20 Da). Oxidation to hydroxytryptophan ($W_{ox1}$) has been discussed in the literature (Mass spectrometric identification of oxidative modifications of tryptophan residues in proteins: chemical artifact or post-translational modification? J. Am. Soc. Mass Spectrom. 2010 July; 21(7): 1114-1117, the entire teaching of which is herein incorporated). Tryptophan oxidation, but not methionine and histidine oxidation, has been found to produce a color change in protein products (Characterization of the Degradation Products of a Color-Changed Monoclonal Antibody: Tryptophan-Derived Chromophores. dx.doi.org/10.1021/ac404218t| Anal. Chem. 2014, 86, 6850-6857). Similar to tryptophan, oxidation of tyrosine primarily yields 3,4-dihydroxyphenylalanine (DOPA) and dityrosine (Li, S, C Schoneich, and RT. Borchardt. 1995. Chemical Instability of Protein Pharmaceuticals: Mechanisms of Oxidation and Strategies for Stabilization. Biotechnol. Bioeng. 48:490-500).

As used herein, the terms "basic species," "basic region," and "BR," refer to the variants of a protein, for example, an antibody or antigen-binding portion thereof, which are characterized by an overall basic charge, relative to the primary charge variant species present within the protein. For example, in recombinant protein preparations, such basic species can be detected by various methods, such as ion exchange, for example, WCX-10 HPLC (a weak cation exchange chromatography), or IEF (isoelectric focusing). Exemplary variants can include, but are not limited to, lysine variants, isomerization of aspartic acid, succinimide formation at asparagine, methionine oxidation, amidation, incomplete disulfide bond formation, mutation from serine to arginine, aglycosylation, fragmentation and aggregation. Commonly, basic species elute later than the main peak during CEX or earlier than the main peak during AEX analysis. (Chromatographic analysis of the acidic and basic species of recombinant monoclonal antibodies. MAbs. 2012 Sep. 1; 4(5): 578-585. doi: 10.4161/mabs.21328, the entire teaching of which is herein incorporated.)

In certain embodiments, a protein composition can comprise more than one type of basic species variant. For example, but not by way of limitation, the total basic species can be divided based on chromatographic retention time of the peaks appearing. Another example in which the total basic species can be divided can be based on the type of variant-variants, structure variants, or fragmentation variant.

As discussed for acidic species, the term "basic species" does not include process-related impurities and the basic species may be the result of product preparation (referred to herein as "preparation-derived basic species"), or the result of storage (referred to herein as "storage-derived basic species").

In one exemplary embodiment, the amount of basic species in the anti-VEGF composition compared to the protein of interest can be at most about 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0% and ranges within one or more of the preceding. Examples of anti-VEGF compositions are discussed in Section III below. In one aspect, the anti-VEGF composition can comprise an anti-VEGF protein selected from the group consisting of aflibercept, recombinant Mini-Trap (examples of which are disclosed in U.S. Pat. No. 7,279,159), a scFv and other anti-VEGF proteins. In a preferred aspect, the recombinant protein of interest is aflibercept.

As used herein, "sample matrix" or "biological sample" can be obtained from any step of the bioprocess, such as cell culture fluid (CCF), harvested cell culture fluid (HCCF), any step in the downstream processing, drug substance (DS), or a drug product (DP) comprising the final formulated product. In some other specific exemplary embodiments, the biological sample can be selected from any step of the downstream process of clarification, chromatographic production, viral inactivation, or filtration. In some specific exemplary embodiments, the drug product can be selected from manufactured drug product in the clinic, shipping, storage, or handling.

As used herein, the term "subject" refers to a mammal (e.g., rat, mouse, cat, dog, cow, sheep, horse, goat, rabbit), preferably a human in need of prevention and/or treatment of a cancer or an angiogenic eye disorder. The subject may have cancer or angiogenic eye disorder or be predisposed to developing cancer or angiogenic eye disorder.

In terms of protein formulation, the term "stable," as used herein refers to the protein of interest within the formulation being able to retain an acceptable degree of chemical structure or biological function after storage under exemplary conditions defined herein. A formulation may be stable even though the protein of interest contained therein does not maintain 100% of its chemical structure or biological function after storage for a defined amount of time. Under certain circumstances, maintenance of about 90%, about 95%, about 96%, about 97%, about 98% or about 99% of a protein's structure or function after storage for a defined amount of time may be regarded as "stable."

The term "treat" or "treatment" refers to a therapeutic measure that reverses, stabilizes or eliminates an undesired disease or disorder (e.g., an angiogenic eye disorder or cancer), for example, by causing the regression, stabilization or elimination of one or more symptoms or indicia of such disease or disorder by any clinically measurable degree, for example, with regard to an angiogenic eye disorder, by causing a reduction in or maintenance of diabetic retinopathy severity score (DRSS), by improving or maintaining vision (e.g., in best corrected visual acuity, for example, as measured by an increase in ETDRS letters), increasing or maintaining visual field and/or reducing or maintaining central retinal thickness and, with respect to cancer, stopping or reversing the growth, survival and/or metastasis of cancer cells in the subject. Typically, the therapeutic measure is administration of one or more doses of a therapeutically effective amount of VEGF MiniTrap to the subject with the disease or disorder.

As used herein, the term "upstream process technology," in the context of protein preparation, refers to activities involving the production and collection of proteins from cells during or following the cell culture of a protein of interest. As used herein, the term "cell culture" refers to methods for generating and maintaining a population of host cells capable of producing a recombinant protein of interest, as well as the methods and techniques for optimizing the production and collection of the protein of interest. For example, once an expression vector has been incorporated into an appropriate host cell, the host cell can be maintained under conditions suitable for expression of the relevant nucleotide coding sequences, and the collection and production of the desired recombinant protein.

When using the cell culture techniques of the instant invention, a protein of interest can be produced intracellularly, in the periplasmic space, or directly secreted into the medium. In embodiments where the protein of interest is produced intracellularly, particulate debris-either host cells or lysed cells (e.g., resulting from homogenization) can be removed by a variety of means, including, but not limited to, centrifugation or ultrafiltration. Where the protein of interest is secreted into the medium, supernatants from such expression systems can be first concentrated using a commercially available protein concentration filter, for example, using an Amicon™ or Millipore Pellicon™ ultrafiltration unit. In one aspect, the protein of interest may be harvested by centrifugation followed by depth filtration and then affinity capture chromatography.

As used herein, a "VEGF antagonist" is any protein or peptide that binds to or interacts with VEGF. Typically, this binding to or interacting with inhibits the binding of VEGF to its receptors (VEGFR1 and VEGFR2), and/or inhibits the biological signaling and activity of VEGF. VEGF antagonists include molecules which interfere with the interaction between VEGF and a natural VEGF receptor, for example, molecules which bind to VEGF or a VEGF receptor and prevent or otherwise hinder the interaction between VEGF and a VEGF receptor. Specific exemplary VEGF antagonists include anti-VEGF antibodies (e.g., ranibizumab [LUCENTIS®]), anti-VEGF receptor antibodies (e.g., anti-VEGFR1 antibodies, anti-VEGFR2 antibodies and the like), and VEGF receptor-based chimeric molecules or VEGF-inhibiting fusion proteins (also referred to herein as "VEGF-Traps" or "VEGF MiniTraps"), such as aflibercept, ziv-aflibercept and a protein having an amino acid having SEQ ID NO.: 60. Other examples of VEGF-Traps are ALT-L9, M710, FYB203 and CHS-2020. Additional examples of VEGF-Traps can be found in U.S. Pat. Nos. 7,070,959; 7,306,799; 7,374,757; 7,374,758; 7,531,173; 7,608,261; 5,952,199; 6,100,071; 6,383,486; 6,897,294 & 7,771,721, which are specifically incorporated herein by reference in their entirety.

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also comprise a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) (also known as aflibercept; marketed under the product name EYLEA®). In certain exemplary embodiments, aflibercept comprises the amino acid sequence set forth as

```
                                    (SEQ ID NO.: 55)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEKDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK.
```

As used herein, "viral filtration" can include filtration using suitable filters including, but not limited to, Planova 20N™, 50N or BioEx from Asahi Kasei Pharma, Viresolve™ filters from EMD Millipore, ViroSart CPV from Sartorius, or Ultipor DV20 or DV50™ filter from Pall Corporation. It will be apparent to one of ordinary skill in the art to select a suitable filter to obtain desired filtration performance.

II. Color Determination

As used herein, color observed during the production of a recombinant protein, specifically, an anti-VEGF protein, can be measured by various methods. Non-limiting examples include using the iodine color number, hazen color number, gardner color number, lovibond color number, Saybolt color number, Mineral oil color number, European pharmacopoeia color number, US pharmacopoeia color number, CIE L*, a*, b* (or CIELAB), Klett color number, Hess-Ives color number, the yellowness index, ADMI color number, and ASBC and EBC brewery color number. Details on such scales can be found in Application Report No. 3.9 e by Lange, the entire teaching of which is herein incorporated.

Visual color matching on the basis of the European Pharmacopoeia (Ph Eur) (European Color Standards, see European Pharmacopoeia. Chapter 2.2.2. Degree of coloration of liquids. $8^{th}$ ed. EP, the entire teaching of which is herein incorporated) can include preparing a color reference solution as described in Ph. Eur. (EP 2.2.2. Degree of Coloration of Liquids 2)—three parent solutions for red (cobaltous (II) chloride), yellow (ferrous (III) chloride) and blue colors (cuprous (II) sulphate) and 1% hydrochloric acid, five color reference solutions for yellow (Y), greenish-yellow (GY), brownish-yellow (BY), brown (B) and red (R) hues are prepared. With these five reference solutions in turn, a total of thirty-seven color reference solutions are prepared (Y1-Y7, GY1-GY7, BY1-BY7, B1-B9 and R1-R7). Each reference solution is clearly defined in the CIE-Lab color space, for example, by lightness, hue and chroma. Of the seven yellow-brown standards (BY standards), BY1 is the darkest standard and BY7 is the least dark. Matching a given sample to that of a BY color standard is typically done under diffused daylight. The compositions of European yellow-brown color standards are described in Table 1, below.

TABLE 1

Composition of European Brown-Yellow Standards

| Reference Solution | Volumes in mL | |
|---|---|---|
| | Standard Solution BY | Hydrochloric acid (10 g/1 HCl) |
| BY1 | 100.0 | 0.0 |
| BY2 | 75.0 | 25.0 |
| BY3 | 50.0 | 50.0 |
| BY4 | 25.0 | 75.0 |
| BY5 | 12.5 | 87.5 |
| BY6 | 5.0 | 95.0 |
| BY7 | 2.5 | 97.5 |

Brownish-Yellow Standard Solution (BY): 10.8 g/L $FeCl_3 \cdot 6H_2O$, 6.0 g/L $CoCl_2 \cdot 6H_2O$ and 2.5 g/L $CuSO_4 \cdot 5H_2O$ The test for color of liquids is carried out by comparing a test solution with a standard color solution. The composition of the standard color solution is selected depending on the hue and intensity of the color of the test solution. Typically, comparison is carried out in flat-bottomed tubes of colorless, transparent, neutral glass that are matched as closely as possible in internal diameter and in all other respects (e.g., tubes of about 12, 15, 16 or 25 mm diameter). For example, a comparison can be between 2 or 10 mL of the test solution and standard color solution. The depth of liquids, for example, can be about 15, 25, 40 or 50 mm. The color assigned to the test solution should not be more intense than that of the standard color. Color comparisons are typically carried out in diffused light (e.g., daylight) against a white background. Colors can be compared down the vertical axis or horizontal axis of the tubes.

In contrast to the EP color measurement, the USP Monograph 1061 Color-Instrumental Measurement references the use of CIE L*, a*, b* (or CIELAB) color measurement to quantify colors precisely and objectively. A total of twenty color reference solutions (identified sequentially by the letters A to T) are defined in U.S. Pharmacopoeia. The color of the measured sample is automatically correlated to the color reference solutions. This means that the color reference solution that is closest to the sample (i.e., the reference solution with the smallest color difference $\Delta E^*$ to the color of the sample) is displayed. The $\Delta L^*$, $\Delta a^*$ and $\Delta b^*$ values give the quantitative differences between the L*, a and b* values of the sample and those of the displayed USP solutions. In the CIE L*a*b* coordinate system, L* represents the degree of lightness of a color on a scale of 0-100, with 0 being the darkest and 100 the lightest, a* represents the redness or greenness of a color (positive values of a* represent red, whereas negative values of a* represent green), and b* represents the yellowness or blueness of a sample, with positive values of b* representing yellow and negative values of b* representing blue. Color difference from a standard, or from an initial sample in an evaluation, can be represented by a change in the individual color components $\Delta L^*$, $\Delta a^*$, and $\Delta b^*$. The composite change, or difference in color, can be calculated as a simple Euclidian distance in space using the formula: $dE^* = \sqrt{(\Delta L^*)^2 + (\Delta a^*)^2 + (\Delta b^*)^2}$. CIE L*, a*, b* color coordinates can be generated, for example, using the Hunter Labs UltrascanPro (Hunter Associates Laboratory, Reston, Virginia) or on the BYK Gardner LCS IV (BYK-Gardner, Columbia, Maryland). For the Hunter Labs UltraScan Pro, the Didymium Filter Test can be executed for wavelength calibration. The instrument can be standardized in TTRAN with the 0.780-inch port insert and DIW before use; thus, establishing the top (L=100) and bottom (L=0) of the photometric scale using a light trap and black card. See Pack et al., Modernization of Physical Appearance and Solution Color Tests Using Quantitative Tristimulus Colorimetry: Advantages, Harmonization, and Validation Strategies, J. Pharmaceutical Sci. 104: 3299-3313 (2015), the entire teaching of which is herein incorporated. The color of the BY standards can also be expressed under the CIE L*, a*, b* color space ("CIELAB" or "CIELab" color space). See Table 2.

TABLE 2

Characterization of European Brown-Yellow Color Standards in the CIE L*, a*, b* Color Space

| Std. | L*^ | a*^ | b*^ | L*~ | a*~ | b*~ |
|---|---|---|---|---|---|---|
| BY1 | 93.95 | −2.76 | 28.55 | 92.84 | −3.16 | 31.15 |
| BY2 | 94.76 | −2.96 | 22.69 | 94.25 | −3.77 | 26.28 |
| BY3 | 96.47 | −2.84 | 16.41 | 95.92 | −3.44 | 18.52 |
| BY4 | 97.17 | −1.94 | 9.07 | 97.67 | −2.63 | 10.70 |
| BY5 | 98.91 | −1.19 | 4.73 | 98.75 | −1.61 | 5.77 |
| BY6 | 99.47 | −0.59 | 2.09 | 99.47 | −0.71 | 2.38 |
| BY7 | 99.37 | −0.31 | 1.13 | 99.71 | −0.37 | 1.17 |

^Reported by Pack et al.
~Measured experimentally herein-the L* and b* values, for each BY color standard To enable a high throughput screening for the color assay, the spectrophotometric assay method (CIELAB) is a more suitable and quantitative measure than BY color standards. The surrogate assay was further optimized as described in the Example section.

For any of the samples evaluated for color, the protein concentration of the test samples must be standardized for protein concentration in the samples, for example, 5 g/L, 10 g/L and the like for comparison.

III. Anti-VEGF Compositions

There are at least five members of the VEGF family of proteins that regulate the VEGF signaling pathway: VEGF-A, VEGF-B, VEGF-C, VEGF-D, and placental growth factor (PIGF). Anti-VEGF compositions can comprise a VEGF antagonist, which specifically interacts with one or more members of the VEGF family of proteins and inhibits one or more of its biological activities, for example, its mitogenic, angiogenic and/or vascular permeability activity.

In one embodiment, a method of producing an anti-VEGF protein comprises: (a) providing a host cell genetically engineered to express the anti-VEGF protein; (b) culturing the host cell in a CDM under conditions suitable in which the cell expresses the anti-VEGF protein; and (c) harvesting a preparation of the anti-VEGF protein produced by the cell. In one aspect, the anti-VEGF protein is selected from the group consisting of aflibercept, recombinant MiniTrap (examples of which are disclosed in U.S. Pat. No. 7,279,159), a scFv and other anti-VEGF proteins. In a preferred aspect, the recombinant protein of interest is aflibercept.

The inventors discovered that manufacturing anti-VEGF proteins (e.g., aflibercept) in certain CDMs produced a biological sample exhibiting a distinctive color. The distinct color properties were observed in different manufacturing steps and even in the final formulation comprising the anti-VEGF protein. As observed in Example 9, for the production of VEGF MiniTrap, culturing cells in a CDM produced anti-VEGF proteins (e.g., aflibercept) with an intense yellow-brown color. The affinity capture step following harvesting also produced an eluate exhibiting a certain color—a yellow-brown color. Further production steps using AEX also exhibited a yellow-brown color, however with reduced intensity.

As described in more detail below, color may be assessed using (i) the European Color Standard BY in which a qualitative visual inspection is made or (ii) a colorimetric assay, CIELAB, which is more quantitative than the BY system. However, in either case, color assessment between multiple samples was normalized against protein concentration in order to assure a meaningful assessment/comparison. For example, referring to Example 9, in particular Table 9-2, the Protein A eluate has a b* value of around 2.52 which corresponds to approximately a BY value of BY5 (when measured at a concentration of 5 g/L protein in the Protein A eluate). If the color of the Protein A eluate is to be compared to another sample, then the comparison should be made using the same protein concentration. Thus, comparing the Protein A eluate to the AEX pool which has a b* value of around 0.74 (when measured at a concentration of 5 g/L protein in the protein A eluate), the method of production shows a substantial reduction in the yellow-brown color of the sample from the Protein A eluate to the AEX pool following AEX chromatography.

Compositions of the present invention can be characterized by a yellow-brown color as discussed herein, for example, no darker/more intense than the European Brown-Yellow Color Standard BY2-BY3, BY3-BY4, BY4-BY5 or BY5-BY6 and/or having a b* value 17-23, 10-17, 5-10, 3-5, or 1-3, wherein the composition comprises about 5 g/L of the anti-VEGF protein or about 10 g/L of the anti-VEGF protein and wherein the composition is obtained as a sample from a clarified harvest or a Protein A eluate of the clarified harvest.

In one embodiment, the compositions of the invention produced using CDM produces a biological sample having a distinct yellow-brown color, wherein the sample may be characterized by a recognized standard color characterization:
  (i) no more yellow-brown than European Color Standard BY2;
  (ii) no more yellow-brown than European Color Standard BY3;
  (iii) no more yellow-brown than European Color Standard BY4;
  (iv) no more yellow-brown than European Color Standard BY5;
  (v) between European Color Standard BY2 and BY3;
  (vi) between European Color Standard BY3 and BY4;
  (vii) between European Color Standard BY4 and BY5, wherein the composition comprises about 5 g/L or about 10 g/L of the anti-VEGF protein and wherein the composition is obtained as a sample from a Protein A eluate of a clarified harvest.

In another embodiment, the compositions of the invention produced using a CDM produces a biological sample having a distinct yellow-brown color, wherein the composition is characterized by a recognized standard color characterization in the CIELAB scale:
  (i) no more yellow-brown than a b* value of about 22-23;
  (ii) no more yellow-brown than a b* value of about 16-17;
  (iii) no more yellow-brown than a b* value of 9-10;
  (iv) no more yellow-brown than a b* value of 4-5;
  (v) no more yellow-brown than a b* value of 2-3;
  (vi) between b* value of 17-23;
  (vii) between b* value of 10-17;
  (viii) between b* value of 5-10;
  (ix) between b* value of 3-5; or
  (x) between b* value of 1-3, wherein the composition comprises about 5 g/L or about 10 g/L of the anti-VEGF protein and wherein the composition is obtained as a sample from a Protein A eluate of a clarified harvest.

In one embodiment, the compositions of the invention produced using CDM can comprise other species or variants of the anti-VEGF protein. These variants include anti-VEGF protein isoforms that comprise one or more oxidized amino acid residues collectively referred to as oxo-variants. The enzymatic digestion of such compositions comprising the anti-VEGF protein and its oxo-variants can comprise one or more of:
  EIGLLTC*EATVNGH*LYK (SEQ ID NO.: 18) which comprises about 0.004-0.013%2-oxo-histidines,
  QTNTIIDVVLSPSH*GIELSVGEK (SEQ ID NO.: 19) which comprises about 0.006-0.028%2-oxo-histidines,
  TELNVGIDENWEYPSSKH*QHK (SEQ ID NO.: 20) which comprises about 0.049-0.085%2-oxo-histidines,
  DKTH*TC*PPC*PAPELLG (SEQ ID NO.: 17) which comprises about 0.057-0.092%2-oxo-histidines,
  TNYLTH*R (SEQ ID NO.: 21) which comprises about 0.008-0.022%2-oxo-histidines, and/or
  IIWDSR (SEQ ID NO.: 56) which comprises about 0.185-0.298% deoxidized tryptophan; or
  EIGLLTC*EATVNGH*LYK (SEQ ID NO.: 18) which comprises about 0.008%2-oxo-histidines,
  QTNTIIDVVLSPSH*GIELSVGEK (SEQ ID NO.: 19) which comprises about 0.02%2-oxo-histidines,
  TELNVGIDENWEYPSSKH*QHK (SEQ ID NO.: 20) which comprises about 0.06%2-oxo-histidines, DKTH*TC*PPC*PAPELLG (SEQ ID NO.: 17) which comprises about 0.07% 2-oxo-histidines, TNYLTH*R (SEQ ID NO.: 21) which comprises about 0.01% 2-oxo-histidines, and/or IIWDSR (SEQ ID NO.: 56) which comprises about 0.23% di-oxo-tryptophans, wherein H* is a histidine that may be oxidized to 2-oxo-histidine and wherein C* is a cysteine which may be carboxymethylated. In a particular embodiment, the anti-VEGF protein is aflibercept. In another embodiment, the anti-VEGF protein is a VEGF MiniTrap.

In one exemplary embodiment of the invention, the compositions of the invention can comprise an anti-VEGF protein, wherein no more than about 1%, no more than about 0.1%, or about 0.1-1%, 0.2-1%, 0.3-1%, 0.4-1%, 0.5-1%, 0.6-1%, 0.7-1%, 0.8-1% or 0.9-1% of histidine residues of the anti-VEGF protein are 2-oxo-histidine. In such compositions, there can be a heterogeneous population of the anti-VEGF protein variants each having a varying amount of 2-oxo-histidine residues and un-oxidized histidine residues. Thus, the percentage of 2-oxo-histidine anti-VEGF protein in a composition refers to the site-specific 2-oxo-histidines among the anti-VEGF molecules divided by total site-specific histidines in the molecules of the anti-VEGF protein (oxidized plus un-oxidized) times 100. One method to quantitate the level of 2-oxo-histidines in a composition is to digest the polypeptide with a protease (e.g., Lys-C and/or trypsin) and analyze the quantity of 2-oxo-histidines in the resulting peptides by, for example, mass spectrometry (MS).

Before digestion of the anti-VEGF protein, cysteine sulfhydryl groups are blocked by reaction with iodoacetamide (IAM) resulting in a residue represented by the following chemical structure:

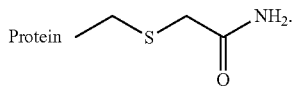

Such modification protects free thiols from reforming disulfide bridges and prevents disulfide bond scrambling. The present invention includes compositions (e.g., aqueous compositions) comprising anti-VEGF protein and its variants which, when modified with IAM and digested with protease (e.g., Lys-C and trypsin) and analyzed by mass spectrometry comprise the following peptides:

EIGLLTC*EATVNGH*LYK (SEQ ID NO.: 18) which comprises about 0.004-0.013% 2-oxo-histidines, QTNTIIDVVLSPSH*GIELSVGEK (SEQ ID NO.: 19) which comprises about 0.006-0.028% 2-oxo-histidines, TELNVGIDENWEYPSSKH*QHK (SEQ ID NO.: 20) which comprises about 0.049-0.085% 2-oxo-histidines, DKTH*TC*PPC*PAPELLG (SEQ ID NO.: 17) which comprises about 0.057-0.092% 2-oxo-histidines, TNYLTH*R (SEQ ID NO.: 21) which comprises about 0.008-0.022% 2-oxo-histidines, and/or IIWDSR (SEQ ID NO.: 56) which comprises about 0.185-0.298% deoxidized tryptophan; or EIGLLTC*EATVNGH*LYK (SEQ ID NO.: 18) which comprises about 0.008% 2-oxo-histidines, QTNTIIDVVLSPSH*GIELSVGEK (SEQ ID NO.: 19) which comprises about 0.02% 2-oxo-histidines, TELNVGIDENWEYPSSKH*QHK (SEQ ID NO.: 20) which comprises about 0.06% 2-oxo-histidines, DKTH*TC*PPC*PAPELLG (SEQ ID NO.: 17) which comprises about 0.07% 2-oxo-histidines, TNYLTH*R (SEQ ID NO.: 21) which comprises about 0.01% 2-oxo-histidines, and/or IIWDSR (SEQ ID NO.: 56) which comprises about 0.23% di-oxo-tryptophans, wherein H* is 2-oxo-histidine and wherein C* is carboxymethylated cysteine. In one embodiment of the invention, the peptides are deglycosylated with PNGase F.

The present invention includes compositions comprising anti-VEGF protein, wherein about 0.1%-10% of all histidines of the anti-VEGF protein are modified to 2-oxo-histidine. Further, the color of the composition is no darker/more intense than, for example, the European Brown-Yellow Color Standard BY2-BY3, BY3-BY4, BY4-BY5 or BY5-BY6, or, alternatively, having a b* value, as characterized using CIE L*, a*, b*, of about 17-23, 10-17, 5-10, 3-5, or 1-3, wherein the composition comprises about 5 g/L or about 10 g/L of the anti-VEGF protein. The composition is obtained either as a sample from a clarified harvest or a Protein A eluate of the clarified harvest. Such compositions can be obtained from the clarified harvest when the harvest material is subjected to a capture chromatography procedure. In one aspect, the capture step is an affinity chromatography procedure using, for example, a Protein A affinity column. When an affinity sample is analyzed using liquid chromatography-mass spectrometry (LC-MS), one or more variants may be detected.

The present invention includes compositions comprising anti-VEGF protein, wherein about 0.1%-10% of all tryptophans of the anti-VEGF protein are modified to kynurenine. Further, the color of the composition is no darker/more intense than the European Brown-Yellow Color Standard BY2-BY3, BY3-BY4, BY4-BY5 or BY5-BY6 and/or having a b* value, as characterized by CIE L*, a*, b*, of about 17-23, 10-17, 5-10, 3-5, or 1-3, wherein the composition comprises about 5 g/L of the anti-VEGF protein or about 10 g/L of the anti-VEGF protein. The composition is obtained as a sample from a clarified harvest or a Protein A eluate of the clarified harvest. Such compositions can be obtained from the clarified harvest when subjected to a capture chromatography procedure. The capture step is an affinity chromatography procedure using, for example, a Protein A affinity column. When an affinity sample is analyzed using liquid chromatography-mass spectrometry (LC-MS), one or more of these variants may be detected.

The present invention includes compositions comprising anti-VEGF protein, wherein about 0.1%-10% of all tryptophans of the anti-VEGF protein are modified to mono-hydroxyl tryptophan. Further, the color of the composition is no darker/more intense than the European Brown-Yellow Color Standard BY2-BY3, BY3-BY4, BY4-BY5 or BY5-BY6 and/or having a b* value characterized by CIE L*, a*, b* of about 17-23, 10-17, 5-10, 3-5, or 1-3, wherein the composition comprises about 5 g/L of the anti-VEGF protein or about 10 g/L of the anti-VEGF protein. The composition is obtained as a sample from a clarified harvest or a Protein A eluate of the clarified harvest. Such compositions can be obtained from the clarified harvest when subjected to a capture chromatography procedure. The capture step is an affinity chromatography procedure using, for example, a Protein A affinity column. When a sample extracted from the affinity step is analyzed using liquid chromatography-mass spectrometry (LC-MS), one or more of these variants may be detected.

The present invention includes compositions comprising anti-VEGF protein, wherein about 0.1%-10% of all tryptophans of the anti-VEGF protein are modified to di-hydroxyl tryptophan. Further, the color is no darker/more intense than the European Brown-Yellow Color Standard BY2-BY3, BY3-BY4, BY4-BY5 or BY5-BY6 and/or having a b* value characterized using CIE L*, a*, b* of about 17-23, 10-17, 5-10, 3-5, or 1-3, wherein the composition comprises about 5 g/L of the anti-VEGF protein or about 10 g/L of the anti-VEGF protein. The composition is obtained as a sample from a clarified harvest or a Protein A eluate of the clarified harvest. Such compositions can be obtained from the clarified harvest made using CDM comprising the anti-VEGF protein as well as its oxo-variants subjected to a capture chromatography procedure. The capture step is an affinity chromatography procedure using, for example, a Protein A affinity column. When a sample extracted from the affinity step is analyzed using liquid chromatography-mass spectrometry (LC-MS), one or more of these variants may be detected.

The present invention includes compositions comprising anti-VEGF protein, wherein about 0.1%-10% of all tryptophans of the anti-VEGF protein are modified to tri-hydroxyl tryptophan. Further, the color of the composition is no darker/more intense than the European Brown-Yellow Color Standard BY2-BY3, BY3-BY4, BY4-BY5 or BY5-BY6 and/or having a b* value characterized by CIE L*, a*, b* of about 17-23, 10-17, 5-10, 3-5, or 1-3, wherein the composition comprises about 5 g/L of the anti-VEGF protein or about 10 g/L of the anti-VEGF protein. The composition is obtained as a sample from a clarified harvest or a Protein A eluate of the clarified harvest. Such compositions can be obtained using capture chromatography. The capture step is an affinity chromatography procedure using, for example, a Protein A affinity column. When a sample extracted from the affinity is analyzed using liquid chromatography-mass spectrometry (LC-MS), one or more of these variants may be detected.

In one embodiment, the compositions of the invention can comprise an anti-VEGF protein, wherein the anti-VEGF protein can comprise modifications of one or more residues as follows: one or more asparagines are deamidated; one or more aspartic acids are converted to iso-aspartate and/or asparagine; one or more methionines are oxidized; one or more tryptophans are converted to N-formylkynurenine; one or more tryptophans are mono-hydroxyl tryptophan; one or more tryptophans are di-hydroxyl tryptophan; one or more tryptophans are tri-hydroxyl tryptophan; one or more arginines are converted to Arg 3-deoxyglucose; the C-terminal glycine is not present; and/or there are one or more non-glycosylated glycosites.

Such compositions can be obtained from a clarified harvest made using CDM comprising the anti-VEGF protein as well as its variants subjected to, for example, a capture chromatography procedure. The capture step is an affinity chromatography procedure using, for example, a Protein A column. When a sample extracted from the affinity step is analyzed using, for example, liquid chromatography-mass spectrometry (LC-MS), one or more of these variants may be detected.

In one exemplary embodiment, the compositions of the invention can comprise an anti-VEGF protein sharing structural characteristics of aflibercept which can be oxidized at one or more of the following: His86, His110, His145, His209, His95, His19 and/or His203 (or equivalent residue positions on proteins sharing certain structural characteristics of aflibercept); Trp58 and/or Trp138 (or equivalent residue positions on proteins sharing certain structural characteristics of aflibercept); Tyr64 (or equivalent positions on proteins sharing certain structural characteristics of aflibercept); Phe44 and/or Phe166 (or equivalent residue positions on proteins sharing certain structural characteristics of aflibercept); and/or Met10, Met20, Met163 and/or Met192 (or equivalent residue positions on proteins sharing certain structural characteristics of aflibercept). Such compositions can be obtained from a clarified harvest made using CDM comprising aflibercept as well as its oxo-variants subjected to a capture chromatography procedure. The capture step can be an affinity chromatography procedure using, for example, a Protein A column. When a sample extracted from the affinity step is analyzed using, for example, liquid chromatography-mass spectrometry (LC-MS), one or more of these variants may be detected.

In one embodiment, the compositions of the invention can comprise a VEGF MiniTrap having the amino acid sequence of SEQ ID NO.: 46, which can be oxidized at His86, His110, His145, His209, His95, His19 and/or His203; Trp58 and/or Trp138; Tyr64; Phe44 and/or Phe166; and/or Met10, Met20, Met163 and/or Met192. Such compositions can be obtained from the clarified harvest made using CDM comprising the VEGF MiniTrap as well as its oxo-variants subjected to a capture chromatography procedure. The capture step is an affinity chromatography procedure using, for example, a Protein A column-when analyzed using liquid chromatography-mass spectrometry (LC-MS), one or more of these variants may be detected.

In some exemplary embodiments, compositions of the present invention can comprise an anti-VEGF protein and its variants (including oxo-variants), wherein the amount of the protein variants in the composition can be at most about 20%, 19%, 18%, 17%, 16%, 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0% and ranges within one or more of the preceding. Such compositions can be obtained from the clarified harvest made using CDM comprising the anti-VEGF protein as well as its variants subjected to a capture chromatography procedure. The capture step is an affinity chromatography procedure using, for example, a Protein A column-when analyzed using liquid chromatography-mass spectrometry (LC-MS), one or more of these variants may be detected. In one aspect, the color of such a composition is no darker/more intense than, for example, the European Brown-Yellow Color Standard BY2-BY3, BY3-BY4, BY4-BY5 or BY5-BY6 and/or having a b* value characterized by CIE L*, a*, b* of about 17-23, 10-17, 5-10, 3-5, or 1-3, wherein the composition comprises about 5 g/L or about 10 g/L of the anti-VEGF protein.

In other exemplary embodiments, compositions of the present invention can comprise an anti-VEGF protein and its variants, wherein the amount of the protein variants in the composition can be about 0% to about 20%, for example, about 0% to about 20%, about 0.05% to about 20%, about 0.1% to about 20%, about 0.2% to about 20%, about 0.3% to about 20%, about 0.4% to about 20%, about 0.5% to about 20%, about 0.6% to about 20%, about 0.7% to about 20%, about 0.8% to about 20%, about 0.9% to about 20%, about 1% to about 20%, about 1.5% to about 20%, about 2% to about 20%, about 3% to about 20%, about 4% to about 20%, about 5% to about 20%, about 6% to about 20%, about 7% to about 20%, about 8% to about 20%, about 9% to about 20%, about 10% to about 20%, about 0% to about 10%, about 0.05% to about 10%, about 0.1% to about 10%, about 0.2% to about 10%, about 0.3% to about 10%, about 0.4% to about 10%, about 0.5% to about 10%, about 0.6% to about 10%, about 0.7% to about 10%, about 0.8% to about 10%, about 0.9% to about 10%, about 1% to about 10%, about 1.5% to about 10%, about 2% to about 10%, about 3% to about 10%, about 4% to about 10%, about 5% to about 10%, about 6% to about 10%, about 7% to about 10%, about 8% to about 10%, about 9% to about 10%, about 0% to about 7.5%, about 0.05% to about 7.5%, about 0.1% to about 7.5%, about 0.2% to about 7.5%, about 0.3% to about 7.5%, about 0.4% to about 7.5%, about 0.5% to about 7.5%, about 0.6% to about 7.5%, about 0.7% to about 7.5%, about 0.8% to about 7.5%, about 0.9% to about 7.5%, about 1% to about 7.5%, about 1.5% to about 7.5%, about 2% to about 7.5%, about 3% to about 7.5%, about 4% to about 7.5%, about 5% to about 7.5%, about 6% to about 7.5%, about 7% to about 7.5%, about 0% to about 5%, about 0.05% to about 5%, about 0.1% to about 5%, about 0.2% to about 5%, about 0.3% to about 5%, about 0.4% to about 5%, about 0.5% to about 5%, about 0.6% to about 5%, about 0.7% to about 5%, about 0.8% to about 5%, about 0.9% to about 5%, about 1% to about 5%, about 1.5% to about 5%, about 2% to about 5%, about 3% to about 5%, about 4% to about 5% and ranges within one or more of the preceding. Such compositions can be obtained performing capture chromatography on a harvest sample. The capture step is an affinity chromatography procedure using, for example, a Protein A column. When a sample is analyzed using liquid chromatography-mass spectrometry (LC-MS), one or more of these variants may be detected. In one aspect, the color of such a composition is no darker/more intense than, for example, the European Brown-Yellow Color Standard BY2-BY3, BY3-BY4, BY4-BY5 or BY5-BY6 and/or having a b* value characterized by CIE L*, a*, b* of about 17-23, 10-17, 5-10, 3-5, or 1-3, wherein the composition comprises about 5 g/L or about 10 g/L of the anti-VEGF protein.

In one embodiment, compositions of the present invention can comprise an anti-VEGF protein including its acidic species, wherein the amount of the acidic species in the composition can be about 20%, 19%, 18%, 17%, 16%, 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0% and ranges within one or more of the preceding. As discussed supra, such acidic species can be detected by various methods such as ion exchange, for example, WCX (WCX-10 HPLC, a weak cation exchange chromatography), or IEF (isoelectric focusing). Commonly, acidic species elute earlier than the main peak during CEX or later than the main peak during AEX analysis (see FIG. 16 and FIG. 17). Compositions comprising acidic species can be obtained from biological material such as harvest or affinity produced material using ion exchange chromatography.

In one aspect, the color of such a composition is no darker/more intense than, for example, the European Brown-Yellow Color Standard BY2-BY3, BY3-BY4, BY4-BY5 or BY5-BY6 and/or having a b* value characterized by CIE L*, a*, b* of about 17-23, 10-17, 5-10, 3-5, or 1-3, wherein the composition comprises about 5 g/L or about 10 g/L. As an example, referring to FIG. 16 and FIG. 17, fractions F1 and F2 represent acidic fractions which comprise the majority of the acidic species. Peaks 1 and 2 of MT1 in FIG. 17 comprise the acidic species and fractions F1 and F2 comprise the majority of the acidic fractions. The fractions comprising such acidic species (F1 and F2) also showed a yellow-brown color compared to other fractions (FIG. 18B and FIG. 18C).

In another embodiment, compositions of the instant invention comprise an anti-VEGF protein including its acidic species, wherein the amount of acidic species in the composition can be about 0% to about 20%, for example, about 0% to about 20%, about 0.05% to about 20%, about 0.1% to about 20%, about 0.2% to about 20%, about 0.3% to about 20%, about 0.4% to about 20%, about 0.5% to about 20%, about 0.6% to about 20%, about 0.7% to about 20%, about 0.8% to about 20%, about 0.9% to about 20%, about 1% to about 20%, about 1.5% to about 20%, about 2% to about 20%, about 3% to about 20%, about 4% to about 20%, about 5% to about 20%, about 6% to about 20%, about 7% to about 20%, about 8% to about 20%, about 9% to about 20%, about 10% to about 20%, about 0% to about 10%, about 0.05% to about 10%, about 0.1% to about 10%, about 0.2% to about 10%, about 0.3% to about 10%, about 0.4% to about 10%, about 0.5% to about 10%, about 0.6% to about 10%, about 0.7% to about 10%, about 0.8% to about 10%, about 0.9% to about 10%, about 1% to about 10%, about 1.5% to about 10%, about 2% to about 10%, about 3% to about 10%, about 4% to about 10%, about 5% to about 10%, about 6% to about 10%, about 7% to about 10%, about 8% to about 10%, about 9% to about 10%, about 0% to about 7.5%, about 0.05% to about 7.5%, about 0.1% to about 7.5%, about 0.2% to about 7.5%, about 0.3% to about 7.5%, about 0.4% to about 7.5%, about 0.5% to about 7.5%, about 0.6% to about 7.5%, about 0.7% to about 7.5%, about 0.8% to about 7.5%, about 0.9% to about 7.5%, about 1% to about 7.5%, about 1.5% to about 7.5%, about 2% to about 7.5%, about 3% to about 7.5%, about 4% to about 7.5%, about 5% to about 7.5%, about 6% to about 7.5%, about 7% to about 7.5%, about 0% to about 5%, about 0.05% to about 5%, about 0.1% to about 5%, about 0.2% to about 5%, about 0.3% to about 5%, about 0.4% to about 5%, about 0.5% to about 5%, about 0.6% to about 5%, about 0.7% to about 5%, about 0.8% to about 5%, about 0.9% to about 5%, about 1% to about 5%, about 1.5% to about 5%, about 2% to about 5%, about 3% to about 5%, about 4% to about 5% and ranges within one or more of the preceding. As discussed above, such acidic species can be detected by various methods, such as ion exchange, for example, WCX (WCX-10 HPLC, a weak cation exchange chromatography), or IEF (isoelectric focusing). Typically, acidic species elute earlier than the main peak during CEX or later than the main peak during AEX analysis (See FIG. 16 and FIG. 17).

Using a cation exchange column, all peaks eluting prior to the main peak of interest were summed as the acidic region, and all peaks eluting after the protein of interest were summed as the basic region. In exemplary embodiments, the acidic species can be eluted as two or more acidic regions and can be numbered AR1, AR2, AR3 and so on based on a certain retention time of the peaks and on the ion exchange column used.

In one embodiment, compositions can comprise an anti-VEGF protein including acidic species, wherein AR1 is 20%, 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0%, and ranges within one or more of the preceding. In one aspect, compositions can comprise an anti-VEGF protein including its acidic species, wherein AR1 is about 0.0% to about 10%, about 0.0% to about 5%, about 0.0% to about 4%, about 0.0% to about 3%, about 0.0% to about 2%, about 3% to about 5%, about 5% to about 8%, about 8% to about 10%, or about 10% to about 15%, and ranges within one or more of the preceding. As discussed above, such acidic regions can be detected by various methods, such as ion exchange, for example, WCX (WCX-10 HPLC, a weak cation exchange chromatography), or IEF (isoelectric focusing). Commonly, acidic species elute earlier than the main peak during CEX or later than the main peak during AEX analysis (See FIG. 16 and FIG. 17).

In another embodiment, compositions can comprise an anti-VEGF protein including acidic species, wherein AR2 is 20%, 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0%, and ranges within one or more of the preceding. In one aspect, compositions can comprise an anti-VEGF protein including acidic species, wherein AR2 is about 0.0% to about 10%, about 0.0% to about 5%, about 0.0% to about 4%, about 0.0% to about 3%, about 0.0% to about 2%, about 3% to about 5%, about 5% to about 8%, about 8% to about 10%, or about 10% to about 15%, and ranges within one or more of the preceding.

In one embodiment, compositions can comprise an anti-VEGF protein including basic species, wherein the amount of the basic species in the composition can be at most about 20%, 19%, 18%, 17%, 16%, 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0% and ranges within one or more of the preceding. In one aspect, compositions can comprise an anti-VEGF protein and its basic species, wherein the amount of the basic species in the composition compared to the anti-VEGF protein can be 0% to about 20%, e.g., about 0% to about 20%, about 0.05% to about 20%, about 0.1% to about 20%, about 0.2% to about 20%, about 0.3% to about 20%, about 0.4% to about 20%, about 0.5% to about 20%, about 0.6% to about 20%, about 0.7% to about 20%, about 0.8% to about 20%, about 0.9% to about 20%, about 1% to about 20%, about 1.5% to about 20%, about 2% to about 20%, about 3% to about 20%, about 4% to about 20%, about 5% to about 20%, about 6% to about 20%, about 7% to about 20%, about 8% to about 20%, about 9% to about 20%, about 10% to about 20%, about 0% to about 10%, about 0.05% to about 10%, about 0.1% to about 10%, about 0.2% to about 10%, about 0.3% to about 10%, about 0.4% to about 10%, about 0.5% to about 10%, about 0.6% to about 10%, about 0.7% to about 10%, about 0.8% to about 10%, about 0.9% to about 10%, about 1% to about 10%, about 1.5% to about 10%, about 2% to about 10%, about 3% to about 10%, about 4% to about 10%, about 5% to about 10%, about 6% to about 10%, about 7% to about 10%, about 8% to about 10%, about 9% to about 10%, about 0% to about 7.5%, about 0.05% to about 7.5%, about 0.1% to about 7.5%, about 0.2% to about 7.5%, about 0.3% to about 7.5%, about 0.4% to about 7.5%, about 0.5% to about 7.5%, about 0.6% to about 7.5%, about 0.7% to about 7.5%, about 0.8% to about 7.5%, about 0.9% to about 7.5%, about 1% to about 7.5%, about 1.5% to about 7.5%, about 2% to about 7.5%, about 3% to about 7.5%, about 4% to about 7.5%, about 5% to about 7.5%, about 6% to about 7.5%, about 7% to about 7.5%, about 0% to about 5%, about 0.05% to about 5%, about 0.1% to about 5%, about 0.2% to about 5%, about 0.3% to about 5%, about 0.4% to about 5%, about 0.5% to about 5%, about 0.6% to about 5%, about 0.7% to about 5%, about 0.8% to about 5%, about 0.9% to about 5%, about 1% to about 5%, about 1.5% to about 5%, about 2% to about 5%, about 3% to about 5%, about 4% to about 5% and ranges within one or more of the preceding.

The basic species can be eluted as two or more basic regions and can be numbered BR1, BR2, BR3 and so on based on a certain retention time of the peaks and ion exchange used.

In one embodiment, compositions can comprise an anti-VEGF protein including its basic species, wherein BR1 is 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0%, and ranges within one or more of the preceding. In one aspect, compositions can comprise an anti-VEGF protein and its basic species, wherein BR1 is about 0.0% to about 10%, about 0.0% to about 5%, about 0.0% to about 4%, about 0.0% to about 3%, about 0.0% to about 2%, about 3% to about 5%, about 5% to about 8%, about 8% to about 10%, or about 10% to about 15%, and ranges within one or more of the preceding.

In another embodiment, the composition can comprise an anti-VEGF protein and its basic species, wherein BR2 is 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0%, and ranges within one or more of the preceding. In one aspect, compositions can comprise an anti-VEGF protein and its basic species of the anti-VEGF protein, wherein BR2 is about 0.0% to about 10%, about 0.0% to about 5%, about 0.0% to about 4%, about 0.0% to about 3%, about 0.0% to about 2%, about 3% to about 5%, about 5% to about 8%, about 8% to about 10%, or about 10% to about 15%, and ranges within one or more of the preceding.

In another embodiment, the composition can comprise an anti-VEGF protein and its basic species, wherein BR3 is 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or 0.0%, and ranges within one or more of the preceding. In one aspect, compositions can comprise an anti-VEGF protein and its basic species of the anti-VEGF protein, wherein BR3 is about 0.0% to about 10%, about 0.0% to about 5%, about 0.0% to about 4%, about 0.0% to about 3%, about 0.0% to about 2%, about 3% to about 5%, about 5% to about 8%, about 8% to about 10%, or about 10% to about 15%, and ranges within one or more of the preceding.

Photo-Induced Oxidation of Aflibercept

In addition to discovering the different color characteristics or variants of the anti-VEGF protein compositions produced using CDM, the inventors also discovered that such compositions can be artificially produced in the laboratory by exposure to light.

Modified, including oxidized, variants of an anti-VEGF composition can be produced by exposing an anti-VEGF protein to cool-white light or ultraviolet light. In one aspect, the anti-VEGF composition can comprise about 1.5 to about 50-fold increase in one or more modified oligopeptides, compared to the sample, wherein the oligopeptides are selected from the group consisting of:

DKTH*TC*PPC*PAPELLG (SEQ ID NO.: 17), EIGLLTC*EATVNGH*LYK (SEQ ID NO.: 18), QTNTIIDVVLSPSH*GIELSVGEK (SEQ ID NO.: 19), TELNVGIDENWEYPSSKH*QHK (SEQ ID NO.: 20), TNYLTH*R (SEQ ID NO.: 21), SDTGRPFVEMYSEIPEIIH*MTEGR (SEQ ID NO.: 22), VH*EKDK (SEQ ID NO.: 23), SDTGRPFVEM*YSEIPEIIHMTEGR (SEQ ID NO.:

64), SDTGRPFVEMYSEIPEIIHM*TEGR (SEQ ID NO.: 65), TQSGSEM*K (SEQ ID NO.: 66), SDQGLYTC*AASSGLM*TK (SEQ ID NO.: 67), IIW*DSR (SEQ ID NO.: 28), RIIW*DSR (SEQ ID NO.: 115), IIW*DSRK (SEQ ID NO.: 114), TELNVGIDENW*EYPSSK (SEQ ID NO.: 29), GFIISNATY*K (SEQ ID NO.: 69), KF*PLDTLIPDGK (SEQ ID NO.: 70) F*LSTLTIDGVTR (SEQ ID NO.: 32), wherein H* is a histidine is oxidized to 2-oxo-histidine, wherein C* is a cysteine is carboxymethylated, wherein M* is a oxidized methionine, wherein W* is a oxidized tryptophan, wherein Y* is a oxidized tyrosine, and wherein F* is a oxidized phenylalanine. In a further aspect, the anti-VEGF composition can comprise about 1.5 to about 10-fold increase in one or more modified oligopeptides by exposing an anti-VEGF composition to cool-white light for a period of time, for example, about 30 hours. In another aspect, the anti-VEGF composition can comprise about 1.5 to about 10-fold increase in one or more modified oligopeptides by exposing a sample to cool-white light for about 75 hours. In yet another aspect, the anti-VEGF composition can comprise about 1.5 to about 20-fold increase in one or more oligopeptides by exposing the sample to cool-white light for about 100 hours. In yet another aspect, the anti-VEGF composition can comprise about 1.5 to about 20-fold increase in one or more oligopeptides by exposing the sample to cool-white light for about 150 hours. In still another aspect, the anti-VEGF composition can comprise about 1.5 to about 50-fold increase in one or more oligopeptides by exposing the sample to cool-white light for about 300 hours-see Example 4 below.

The anti-VEGF composition can comprise about 1.5 to about 3-fold increase in one or more oligopeptides, as described above, by exposing a sample of an anti-VEGF composition to ultraviolet light for about 4 hours. In another aspect, the anti-VEGF composition can comprise about 1.5 to about 10-fold increase in one or more oligopeptides by exposing the sample to ultraviolet light for about 10 hours. In yet another aspect, the anti-VEGF composition can comprise about 1.5 to about 10-fold increase in one or more oligopeptides by exposing the sample to ultraviolet light for about 16 hours. In yet another aspect, the anti-VEGF composition can comprise about 1.5 to about 25-fold increase in one or more oligopeptides by exposing the sample to ultraviolet light for about 20 hours. In yet another aspect, the anti-VEGF composition can comprise about 1.5 to about 25-fold increase in one or more oligopeptides by exposing the sample matrix to ultraviolet light for about 40 hours. See Example 4.

Glycodiversity—Anti-VEGF Protein Produced Using CDM

The compositions of this invention comprise an anti-VEGF protein, wherein the anti-VEGF protein produced in CDM has a variety of glycodiversity. The different glycosylation profiles of the anti-VEGF protein are within the scope of this invention.

In some exemplary embodiments of the invention, the composition can comprise an anti-VEGF protein glycosylated at one or more asparagines as follows: G0-GlcNAc glycosylation; G1-GlcNAc glycosylation; G1S-GlcNAc glycosylation; G0 glycosylation; G1 glycosylation; G1S glycosylation; G2 glycosylation; G2S glycosylation; G2S2 glycosylation; G0F glycosylation; G2F2S glycosylation; G2F2S2 glycosylation; G1F glycosylation; G1FS glycosylation; G2F glycosylation; G2FS glycosylation; G2FS2 glycosylation; G3FS glycosylation; G3FS3 glycosylation; G0-2GlcNAc glycosylation; Man4 glycosylation; Man4_A1G1 glycosylation; Man4_A1G1S1 glycosylation; Man5 glycosylation; Man5_A1G1 glycosylation; Man5_A1G1S1 glycosylation; Man6 glycosylation; Man6_G0+Phosphate glycosylation; Man6+Phosphate glycosylation; and/or Man7 glycosylation. In one aspect, the protein of interest can be aflibercept, anti-VEGF antibody or VEGF MiniTrap.

In one embodiment, the composition can have a glycosylation profile as follows: about 40% to about 50% total fucosylated glycans, about 30% to about 50% total sialylated glycans, about 6% to about 15% mannose-5, and about 60% to about 79% galactosylated glycans. (Example 6).

In one embodiment, the composition can comprise an anti-VEGF protein, wherein the protein of interest has Man5 glycosylation at about 32.4% of asparagine 123 residues and/or about 27.1% of asparagine 196 residues. In one aspect, the protein of interest can be aflibercept, anti-VEGF antibody or VEGF MiniTrap.

In another embodiment, the composition can have about 40%, about 41%, about 42%, about 43%, about 44%, about 45%, about 46%, about 47%, about 48%, about 49% or about 50% total fucosylated glycans.

In yet another embodiment, the composition can have about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49% or about 50% total sialylated glycans.

In one embodiment, the composition can have about 6%, about 7%, about 8%, about 9%, about 10%, about 11%, about 12%, about 13%, about 14%, or about 15% mannose-5.

In another embodiment, the composition can have about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, or about 79% total galactosylated glycans.

In one embodiment, the anti-VEGF protein can have a decreased level of fucosylated glycans by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. The anti-VEGF protein can have a decreased level of fucosylated glycans by ranges within one or more of the preceding values, for example, 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 1-99% compared to the level of fucosylated glycans in an anti-VEGF protein produced using a soy hydrolysate.

In one embodiment, the anti-VEGF protein can have a decreased level of sialylated glycans by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. The anti-VEGF protein can have a decreased level of sialylated glycans by ranges within one or more of the preceding values, for example, 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 1-99% compared to the level of sialylated glycans in an anti-VEGF protein produced using a soy hydrolysate.

In another embodiment, the anti-VEGF protein can have a decreased level of galactosylated glycans by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. The anti-VEGF protein can have a decreased level of galactosylated glycans by ranges within one or more of the preceding values, for example, 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 1-99% compared to the level of galactosylated glycans in an anti-VEGF protein produced using a soy hydrolysate.

In one embodiment, the anti-VEGF protein can have an increased level of mannosylated glycans by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95% or 99%. The anti-VEGF protein can have an increased level of mannosylated glycans by ranges within one or more of the preceding values, for example, 1-10%, 1-15%, 1-20%, 1-25%, 1-30%, 1-35%, 1-40%, 1-41%, 1-42%, 1-43%, 1-44%, 1-45%, 1-46%, 1-47%, 1-48%, 1-49%, 1-50%, 2-10%, 2-15%, 2-20%, 2-25%, 2-30%, 2-35%, 2-40%, 2-41%, 2-42%, 2-43%, 2-44%, 2-45%, 2-46%, 2-47%, 2-48%, 2-49%, 2-50%, 3-10%, 3-15%, 3-20%, 3-25%, 3-30%, 3-35%, 3-40%, 3-41%, 3-42%, 3-43%, 3-44%, 3-45%, 3-46%, 3-47%, 3-48%, 3-49%, 3-50%, 4-10%, 4-15%, 4-20%, 4-25%, 4-30%, 4-35%, 4-40%, 4-41%, 4-42%, 4-43%, 4-44%, 4-45%, 4-46%, 4-47%, 4-48%, 4-49%, 4-50% or 1-99% compared to the level of mannosylated glycans in an anti-VEGF protein produced using a soy hydrolysate.

The compositions described in this section can be produced by several upstream and downstream parameters as described below in sections IV and V, respectively.

IV. Preparation of Compositions Using Upstream Process Technologies

For biologics, the implementation of a robust and flexible upstream process is desirable. An efficient upstream process can lead to desirable production and scale-up of a protein of interest. The inventors discovered that the compositions of the invention comprising an anti-VEGF protein can be produced by modulating conditions during upstream protein production, such as changes in media components of a CDM. Each step in an upstream process may affect quality, purity and quantity of the manufactured protein.

The present disclosure provides evidence for the existence of certain variants of aflibercept and/or MiniTrap produced using CDM. These variants include isoforms that comprise one or more oxidized amino acid residues. Examples of oxidized residues include, but are not limited to, one or more histidine, tryptophan, methionine, phenylalanine or tyrosine residues. The compositions produced by using the modified CDM can produce a preparation of anti-VEGF protein with a desired target value of protein variants of aflibercept and/or MiniTrap. As alluded to above, there can also be a yellow-brownish color associated with fractions produced using a CDM. (As mentioned above, not all CDMs tested by the inventors manifested a distinct discoloration.)

This invention includes culturing a host cell in a modified CDM under suitable conditions in which the cell expresses a recombinant protein of interest followed by harvesting a preparation of the recombinant protein of interest produced by the cell. Such a modified CDM can be used to produce the compositions as described above in Section III.

In one embodiment, the method comprises culturing a host cell in a CDM under suitable conditions, wherein the host cell expresses a recombinant protein of interest, such as aflibercept. The method further comprises harvesting a preparation of the recombinant protein of interest produced by the cell, wherein the suitable conditions include a CDM with a: cumulative concentration of iron in said CDM that is less than about 55 μM, cumulative concentration of copper in said CDM that is less than or equal to about 0.8 UM, cumulative concentration of nickel in said CDM that is less than or equal to about 0.40 μM, cumulative concentration of zinc in said CDM that is less than or equal to about 56 μM, cumulative concentration of cysteine in said CDM that is less than about 10 mM; and/or an antioxidant in said CDM in a concentration of about 0.001 mM to about 10 mM for a single antioxidant and no more than about 30 mM cumulative concentration if multiple antioxidants are added in said CDM.

In one aspect of the present embodiment, the preparation obtained from using suitable conditions results in a reduction in protein variants of aflibercept and VEGF MiniTrap to a desired amount of protein variants of aflibercept and VEGF MiniTrap (referred to as a "target value" of protein variants of aflibercept and VEGF MiniTrap). In a further aspect of this embodiment, the preparation obtained from using suitable conditions results in a reduction in color of the preparations to a desired BY value (referred to as a "target BY value") when the preparation of protein, including variants of aflibercept and VEGF MiniTrap, are normalized to a concentration of 5 g/L, 10 g/L or even higher.

In a further aspect of the present embodiment, the target BY value and/or target value of variants can be obtained in a preparation where the titer increases or does not significantly decrease (see Example 5).

In some embodiments, the compositions produced by using the modified CDM can produce a preparation of anti-VEGF protein with a desired target BY value, wherein the color of the preparation is characterized as follows:
 (i) no more yellow-brown than European Color Standard BY2;
 (ii) no more yellow-brown than European Color Standard BY3;
 (iii) no more yellow-brown than European Color Standard BY4;
 (iv) no more yellow-brown than European Color Standard BY5;

(v) between European Color Standard BY2 and BY3;
(vi) between European Color Standard BY3 and BY4;
(vii) between European Color Standard BY4 and BY5, wherein the composition comprises about 5 g/L or about 10 g/L of the anti-VEGF protein and wherein a sample of the composition can be obtained as a sample from a Protein A eluate of a clarified harvest. As seen in Example 9, Table 9-3 below, the Protein A eluate comprising 5 g/L aflibercept exhibited a yellow-brown color measured as having a b* value of 1.77. Such a sample when produced downstream following AEX had a b* value of 0.50 demonstrating the utility of AEX to lower the yellow-brown coloration of a sample (Table 9-3).

The compositions produced by using the modified CDM can produce a preparation of anti-VEGF protein, wherein the color of the preparation is characterized by a recognized standard color characterization in the CIELAB scale:
(i) no more yellow-brown than a b* value of about 22-23;
(ii) no more yellow-brown than a b* value of about 16-17;
(iii) no more yellow-brown than a b* value of 9-10;
(iv) no more yellow-brown than a b* value of 4-5;
(v) no more yellow-brown than a b* value of 2-3;
(vi) between b* value of 17-23;
(vii) between b* value of 10-17;
(viii) between b* value of 5-10;
(ix) between b* value of 3-5; or
(x) between b* value of 1-3, wherein the composition comprises about 5 g/L or about 10 g/L of the anti-VEGF protein and wherein the composition is obtained as a sample from a Protein A eluate of a clarified harvest. See Example 9, Table 9-3.

For components added to the cell culture to form the modified CDM, the term "cumulative amount" refers to the total amount of a particular component added to a bioreactor over the course of the cell culture to form the CDM, including amounts added at the beginning of the culture (CDM at day 0) and subsequently added amounts of the component. Amounts of a component added to a seed-train culture or inoculum prior to the bioreactor production (i.e., prior to the CDM at day 0) are also included when calculating the cumulative amount of the component. A cumulative amount is unaffected by the loss of a component over time during the culture (for example, through metabolism or chemical degradation). Thus, two cultures with the same cumulative amounts of a component may nonetheless have different absolute levels, for example, if the component is added to the two cultures at different times (e.g., if in one culture all of the component is added at the outset, and in another culture the component is added over time). A cumulative amount is also unaffected by in situ synthesis of a component over time during the culture (for example, via metabolism or chemical conversion). Thus, two cultures with the same cumulative amounts of a given component may nonetheless have different absolute levels, for example, if the component is synthesized in situ in one of the two cultures by way of a bioconversion process. A cumulative amount may be expressed in units such as, for example, grams or moles of the component. The term "cumulative concentration" refers to the cumulative amount of a component divided by the volume of liquid in the bioreactor at the beginning of the production batch, including the contribution to the starting volume from any inoculum used in the culture. For example, if a bioreactor contains 2 liters of cell culture medium at the beginning of the production batch, and one gram of component X is added at days 0, 1, 2, and 3, then the cumulative concentration after day 3 is 2 g/L (i.e., 4 grams divided by 2 liters). If, on day 4, an additional one liter of liquid not containing component X were added to the bioreactor, the cumulative concentration would remain 2 g/L. If, on day 5, some quantity of liquid were lost from the bioreactor (for example, through evaporation), the cumulative concentration would remain 2 g/L. A cumulative concentration may be expressed in units such as, for example, grams per liter or moles per liter.

Figures 25A, 25B:
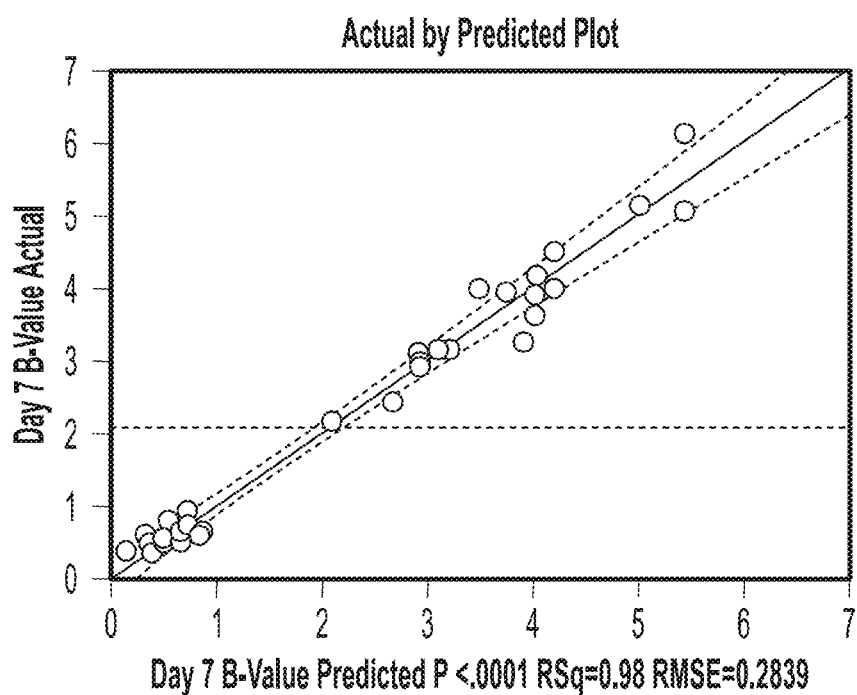
FIG. 25A depicts a scaled estimate of the effect that incubation of various components with aflibercept have on the generation of color (CIE L*, a*, b* predicted b value)
FIG. 25B depicts actual against predicted b value plot.
Figure 26A:
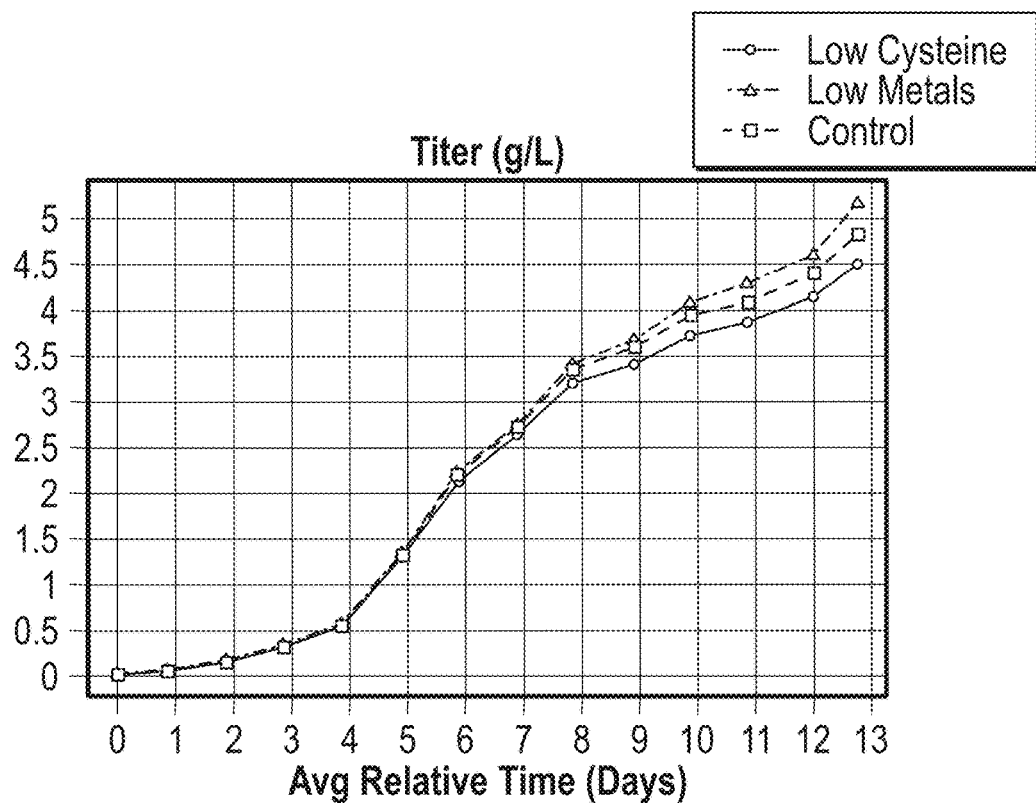
FIG. 26A depicts the effect of CDMs comprising low cysteine and low metals on the titer of aflibercept.
Figure 26B:
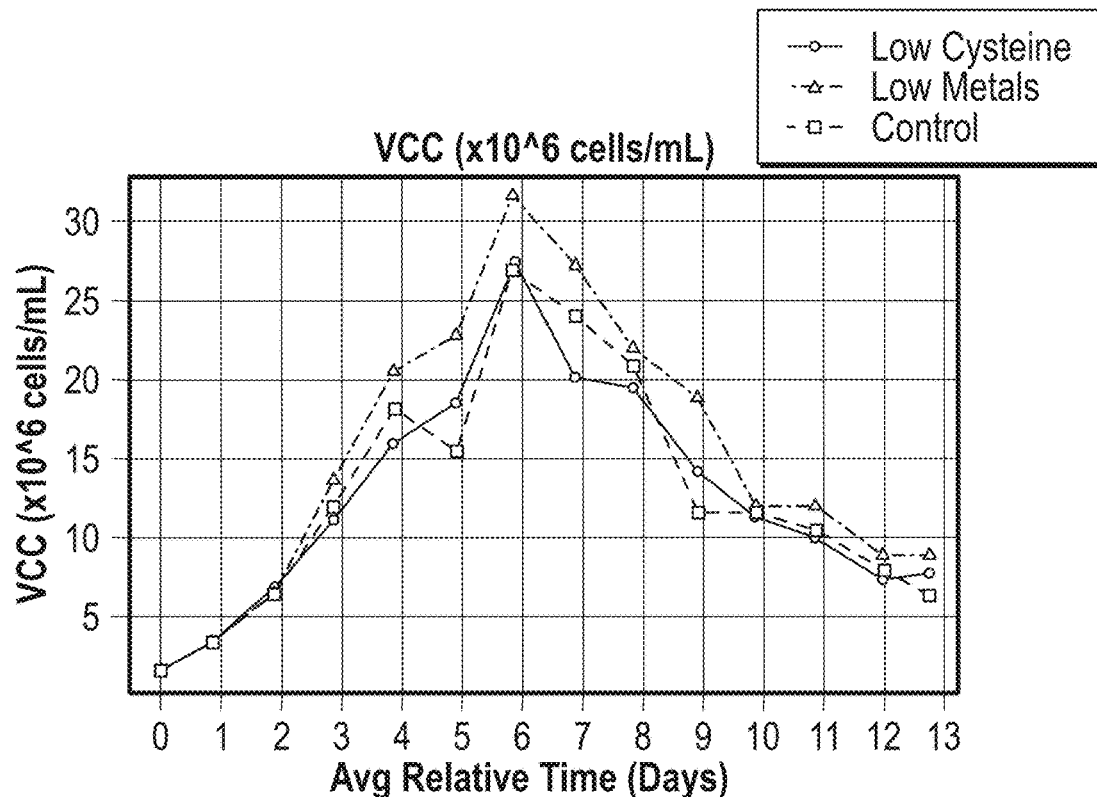
FIG. 26B depicts effect of CDMs comprising low cysteine and low metals on the viable cell concentration.
Figure 26C:
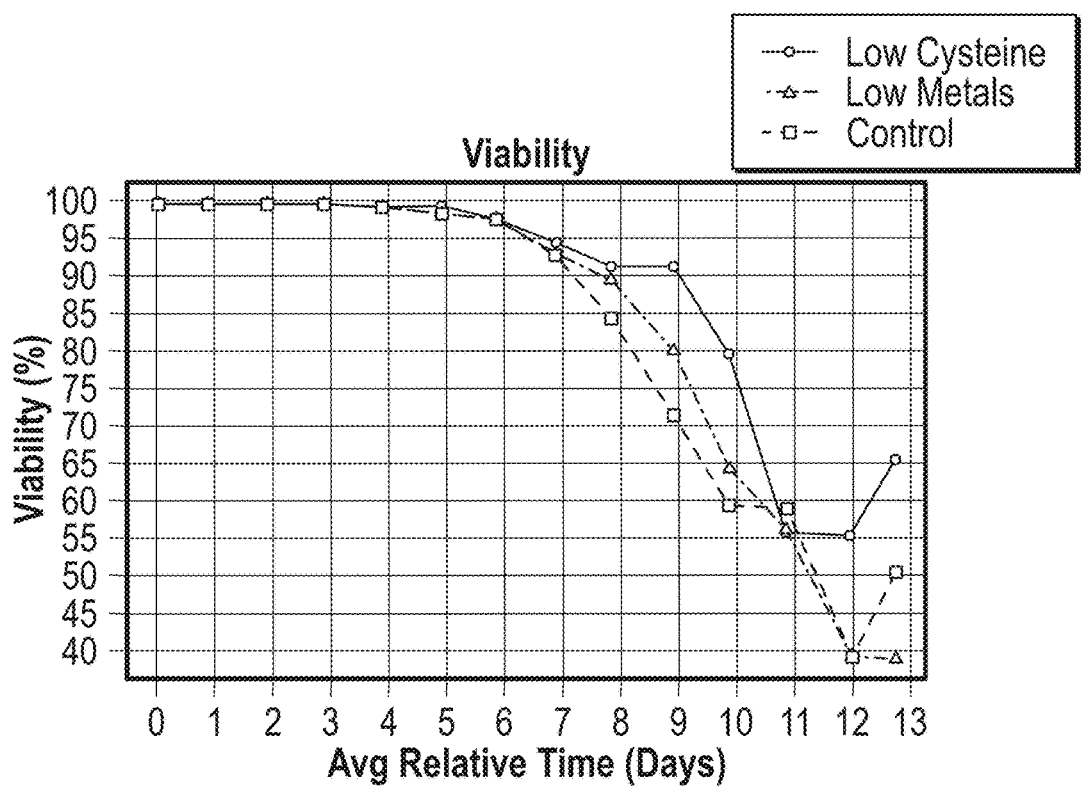
FIG. 26C depicts effect of CDMs comprising low cysteine and low metals on the viability.
Figure 26D:
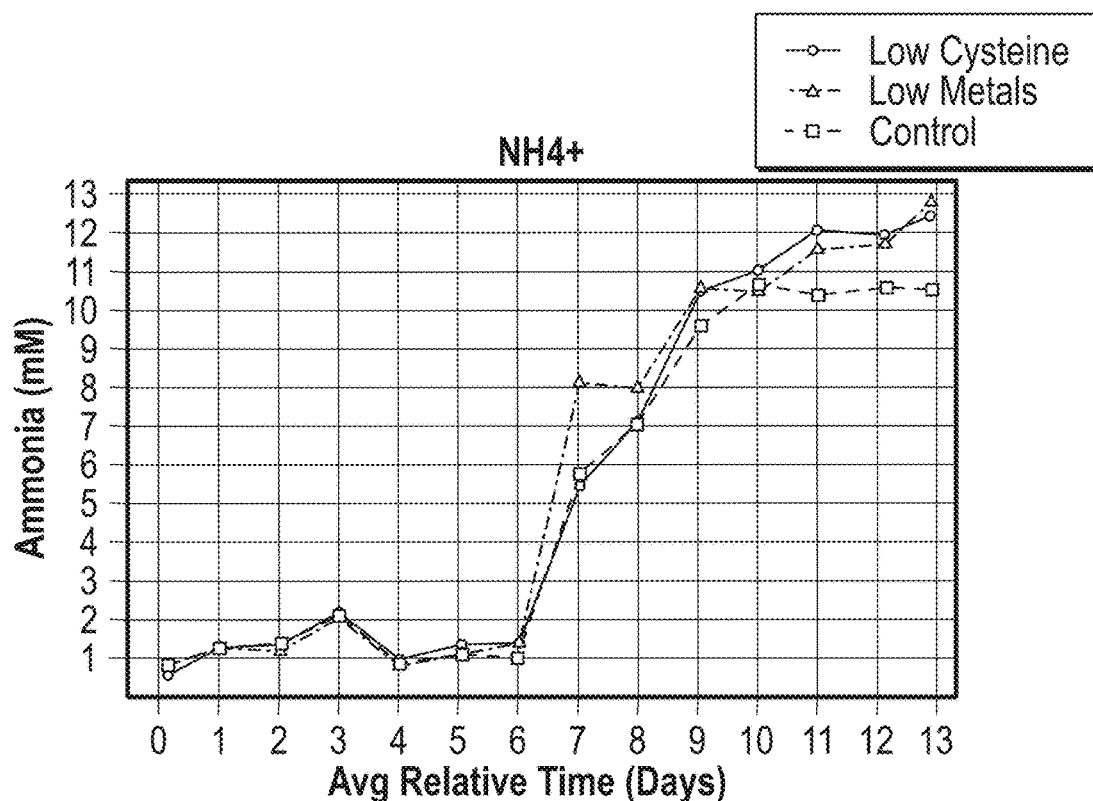
FIG. 26D depicts effect of CDMs comprising low cysteine and low metals on the ammonia.
Figure 26E:
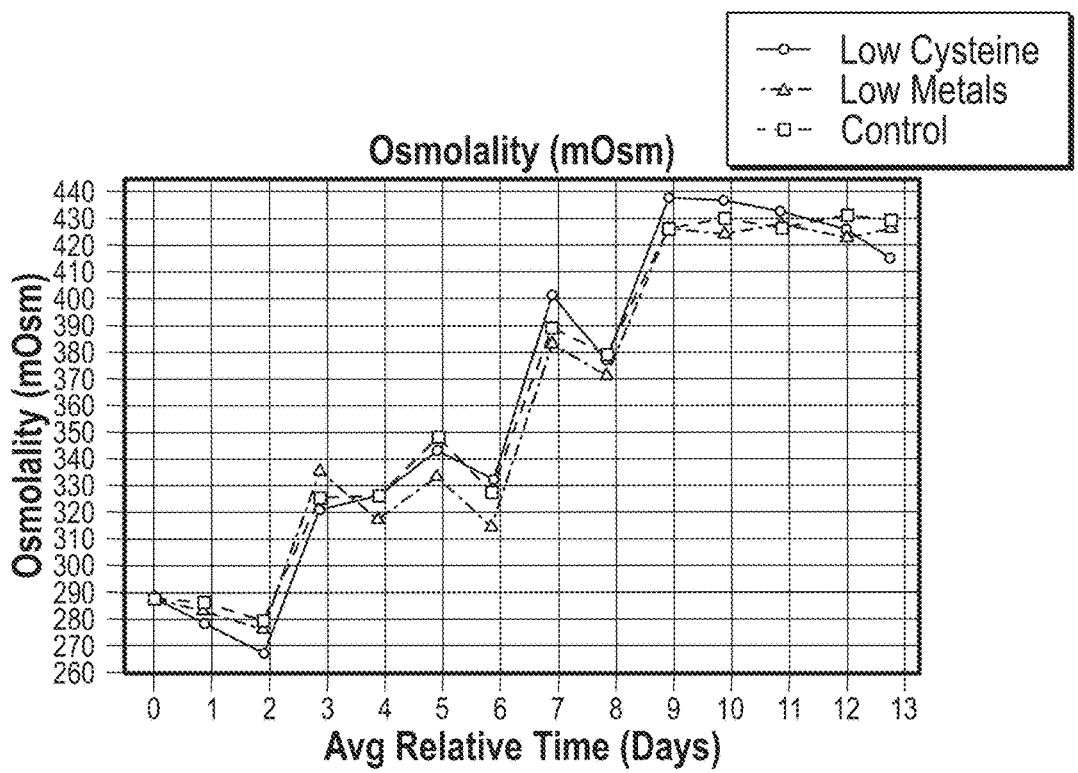
FIG. 26E depicts effect of CDMs comprising low cysteine and low metals on the osmolality.
Figure 27:
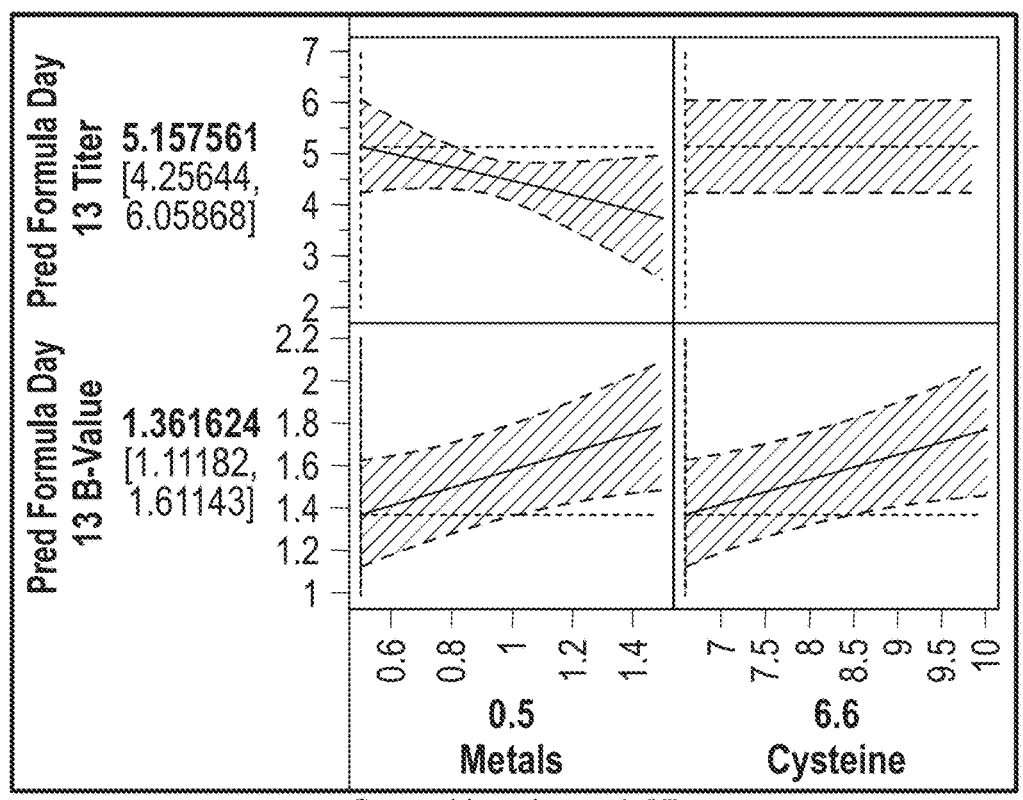
FIG. 27 is a chart showing prediction profile of the color of the harvest (seen as Day 13 b* values) on increasing/decreasing concentrations of metals and cysteine according to an exemplary embodiment.

A. Amino Acids:

In some embodiments, a modified CDM can be obtained by decreasing or increasing cumulative concentrations of amino acids in a CDM. Non-limiting examples of such amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine (or salts thereof). The increase or decrease in the cumulative amount of these amino acids in the modified CDM can be of about 1%, 5%, 10%, 15%, 20%, 25%, 30%, 35%, 40%, 45%, 50%, 55%, 60%, 65%, 70%, 75%, 80%, 85%, 90%, 95%, 100% as compared to the starting CDM, and ranges within one or more of the preceding. Alternatively, the increase or decrease in the cumulative amount of the one or more amino acids in the modified CDM can be about 5% to about 20%, about 10% to about 30%, about 30% to about 40%, about 30% to about 50%, about 40% to about 60%, about 60% to about 70%, about 70% to about 80%, about 80% to about 90%, or about 90% to about 100% as compared to the unmodified CDM, and ranges within one or more of the preceding (see FIGS. 25-27 and Example 5).

In some embodiments, the modified CDM can be obtained by decreasing the cumulative concentration of cysteine in a CDM. The decrease in the amount of the cysteine in the CDM to form the modified CDM can be about 1%, 5%, 10%, 15%, 20%, 25%, 30%, 35%, 40%, 45%, 50%, 55%, 60%, 65%, 70%, 75%, 80%, 85%, 90%, 95%, or 100% as compared to the unmodified CDM, and ranges within one or more of the preceding. Alternatively, the decrease in the cumulative amount of the cysteine in the modified CDM can be about 5% to about 20%, about 10% to about 30%, about 30% to about 40%, about 30% to about 50%, about 40% to about 60%, about 60% to about 70%, about 70% to about 80%, about 80% to about 90%, or about 90% to about 100% as compared to the CDM, and ranges within one or more of the preceding. In one aspect, the amount of cumulative cysteine in modified CDM is less than about 1 mM, about 2 mM, about 3 mM, about 4 mM, about 5 mM, about 6 mM, about 7 mM, about 8 mM, about 9 mM or about 10 mM (see FIGS. 25-27 and Example 5).

In some embodiments, the modified CDM can be obtained by replacing at least a certain percentage of cumulative cysteine in a CDM with cystine. The replacement can be about 1%, 5%, 10%, 15%, 20%, 25%, 30%, 35%, 40%, 45%, 50%, 55%, 60%, 65%, 70%, 75%, 80%, 85%, 90%, 95%, or 100% as compared to the unmodified CDM, and ranges within one or more of the preceding. Alternatively, the replacement can be about 5% to about 20%, about 10% to about 30%, about 30% to about 40%, about 30% to about 50%, about 40% to about 60%, about 60% to about 70%, about 70% to about 80%, about 80% to about 90%, or about 90% to about 100% as compared to the unmodified CDM, and ranges within one or more of the preceding (see FIGS. 25-27 and Example 5).

In some embodiments, the modified CDM can be obtained by replacing at least a certain percentage of cumulative cysteine in a CDM with cysteine sulfate. The replacement can be about 1%, 5%, 10%, 15%, 20%, 25%, 30%, 35%, 40%, 45%, 50%, 55%, 60%, 65%, 70%, 75%, 80%, 85%, 90%, 95%, or 100% as compared to the unmodified CDM, and ranges within one or more of the preceding. Alternatively, the replacement can be about 5% to about 20%, about 10% to about 30%, about 30% to about 40%, about 30% to about 50%, about 40% to about 60%, about 60% to about 70%, about 70% to about 80%, about 80% to about 90%, or about 90% to about 100% as compared to the unmodified CDM, and ranges within one or more of the preceding.

B. Metals:

In some embodiments, the modified CDM can be obtained by decreasing or increasing cumulative concentration of metals in a CDM. Non-limiting examples of metals include iron, copper, manganese, molybdenum, zinc, nickel, calcium, potassium and sodium. The increase or decrease in the amount of the one or more metals in the modified CDM can be of about 1%, 5%, 10%, 15%, 20%, 25%, 30%, 35%, 40%, 45%, 50%, 55%, 60%, 65%, 70%, 75%, 80%, 85%, 90%, 95%, or 100% as compared to the unmodified CDM, and ranges within one or more of the preceding. Alternatively, the increase or decrease in the cumulative amount of the one or more metals in the modified CDM can be about 5% to about 20%, about 10% to about 30%, about 30% to about 40%, about 30% to about 50%, about 40% to about 60%, about 60% to about 70%, about 70% to about 80%, about 80% to about 90%, or about 90% to about 100% as compared to the unmodified CDM, and ranges within one or more of the preceding (see FIGS. 25-27 and Example 5).

C. Antioxidants:

In some embodiments, the modified CDM comprises one or more antioxidants. Non-limiting examples of antioxidants can include taurine, hypotaurine, glycine, thioctic acid, glutathione, choline chloride, hydrocortisone, Vitamin C, Vitamin E and combinations thereof (see FIG. 28A-E and Example 5).

In some embodiments, the modified CDM comprises about 0.01 mM to about 20 mM of taurine, i.e., about 0.01 mM to about 1 mM, about 0.01 mM to about 5 mM, about 0.01 mM to about 10 mM, about 0.1 mM to about 1 mM, about 0.1 mM to about 5 mM, about 0.1 mM to about 10 mM, about 1 mM to about 5 mM, about 1 mM to about 10 mM, and ranges within one or more of the preceding.

In some embodiments, the modified CDM comprises about 0.01 mM to about 20 mM of hypotaurine, i.e., about 0.01 mM to about 1 mM, about 0.01 mM to about 5 mM, about 0.01 mM to about 10 mM, about 0.1 mM to about 1 mM, about 0.1 mM to about 5 mM, about 0.1 mM to about 10 mM, about 1 mM to about 5 mM, about 1 mM to about 10 mM, and ranges within one or more of the preceding.

In some embodiments, the modified CDM comprises about 0.01 mM to about 20 mM of glycine, i.e., about 0.01 mM to about 1 mM, about 0.01 mM to about 5 mM, about 0.01 mM to about 10 mM, about 0.1 mM to about 1 mM, about 0.1 mM to about 5 mM, about 0.1 mM to about 10 mM, about 1 mM to about 5 mM, about 1 mM to about 10 mM, and ranges within one or more of the preceding.

In some embodiments, the modified CDM comprises about 0.01 µM to about 5 µM of thioctic acid, i.e., about 0.01 µM to about 0.1 µM, about 0.1 µM to about 1 µM, about 1 µM to about 2.5 µM, about 1 µM to about 3 µM, about 1 µM to about 5 µM, and ranges within one or more of the preceding.

In some embodiments, the modified CDM comprises about 0.01 M to about 5 mM of glutathione, i.e., about 0.01 mM to about 1 mM, about 0.1 mM to about 1 mM, about 0.1 mM to about 5 mM, about 1 mM to about 5 mM, and ranges within one or more of the preceding.

In some embodiments, the modified CDM comprises about 0.01 µM to about 5 µM of hydrocortisone, i.e., about 0.01 µM to about 0.1 µM, about 0.1 µM to about 1 µM, about 1 µM to about 2.5 µM, about 1 µM to about 3 µM, about 1 µM to about 5 µM, and ranges within one or more of the preceding.

In some embodiments, the modified CDM comprises about 1 µM to about 50 µM of vitamin C, i.e., about 1 µM to about 5 µM, about 5 µM to about 20 µM, about 10 µM to about 30 µM, about 5 µM to about 30 µM, about 20 µM to about 50 µM, about 25 µM to about 50 µM, and ranges within one or more of the preceding.

D. Changes to the Media to Modulate Glycosylation:

This disclosure also includes methods of modulating glycosylation of an anti-VEGF protein by varying cumulative concentrations of certain components in a CDM. Based on the cumulative amounts of components added to the CDM, the total % fucosylation, total % galactosylation, total % sialylation and mannose-5 can be varied.

In exemplary embodiments, the method of modulating glycosylation of an anti-VEGF protein can comprise supplementing the CDM with uridine. The anti-VEGF protein can have about 40% to about 50% total fucosylated glycans, about 30% to about 55% total sialylated glycans, about 2% to about 15% mannose-5, and about 60% to about 79% galactosylated glycans. (See Example 6 below).

In some embodiments, the method of modulating glycosylation of an anti-VEGF protein can comprise supplementing a CDM with manganese. In one aspect, the CDM is devoid of manganese before supplementation. The anti-VEGF protein can have about 40% to about 50% total fucosylated glycans, about 30% to about 55% total sialylated glycans, about 2% to about 15% mannose-5, and about 60% to about 79% galactosylated glycans. (See Example 6 below).

In some embodiments, the method of modulating glycosylation of an anti-VEGF protein can comprise supplementing a CDM with galactose. In one aspect, the CDM is devoid of galactose before supplementation. The anti-VEGF protein can have about 40% to about 50% total fucosylated glycans, about 30% to about 55% total sialylated glycans, about 2% to about 15% mannose-5, and about 60% to about 79% galactosylated glycans. (See Example 6 below).

In some embodiments, the method of modulating glycosylation of an anti-VEGF protein can comprise supplementing a CDM with dexamethasone. In one aspect, the CDM is devoid of dexamethasone before supplementation. The anti-VEGF protein can have about 40% to about 50% total fucosylated glycans, about 30% to about 55% total sialylated glycans, about 2% to about 15% mannose-5, and about 60% to about 79% galactosylated glycans. (See Example 6 below).

In some embodiments, the method of modulating glycosylation of an anti-VEGF protein can comprise supplementing a CDM with one or more of uridine, manganese, galactose and dexamethasone. In one aspect, the CDM is devoid of one or more of uridine, manganese, galactose and dexamethasone before supplementation. The anti-VEGF protein can have about 40% to about 50% total fucosylated glycans, about 30% to about 55% total sialylated glycans, about 2% to about 15% mannose-5, and about 60% to about 79% galactosylated glycans. (See Example 6 below).

V. Preparation of Compositions Using Downstream Process Technologies

The compositions comprising an anti-VEGF protein of the invention can be produced by modulating conditions during downstream protein production. The inventors discovered that optimizing the downstream procedures can lead to minimization of certain variants of the anti-VEGF protein as well as discoloration. Optimization of the downstream process may produce a composition with reduced oxo-variants as well as optimized color characteristics.

The downstream process technologies may be used alone or in combination with the upstream process technologies described in Section IV, supra.

A. Anion-Exchange Chromatography:

In some embodiments, a composition of the invention can involve a process comprising: expressing an anti-VEGF protein in a host cell in a CDM, wherein the anti-VEGF protein is secreted from the host cell into the medium and a clarified harvest is obtained. The harvest is subjected to the following steps: (a) loading a biological sample obtained from the harvest onto an anion-exchange chromatography (AEX) column; (b) washing the AEX column with a suitable wash buffer, (c) collecting the flowthrough fraction(s), optionally, (d) washing the column with a suitable strip buffer and (e) collecting stripped fractions.

The flowthrough fractions can comprise oxo-variants of the anti-VEGF protein which are about 1%, 5%, 10%, 15%, 20%, 25%, 30%, 35%, 40%, 45%, 50%, 55%, 60%, 65%, 70%, 75%, 80%, 85%, 90%, or 95% of the anti-VEGF protein sample when compared to the oxo-variants in the stripped fraction of the anion-exchange chromatography column. For example, referring to Table 9-5 and Table 9-6, the flowthrough fractions comprise oxidized variants of anti-VEGF protein where several histidine and tryptophan residues are about 1%, 5%, 10%, 15%, 20%, 25%, 30%, 35%, 40%, 45%, 50%, 55%, 60%, 65%, 70%, 75%, 80%, 85%, 90%, 95% (and ranges within one or more of the preceding) oxidized when compared against the oxidized variants in the stripped fractions.

The pH of both the equilibration and wash buffers for the AEX column can be from about 8.20 to about 8.60. In another aspect, the conductivity of both the equilibration and wash buffers for the AEX column can be from about 1.50 to about 3.0 mS/cm. In one aspect, the equilibration and wash buffers can be about 50 mM Tris hydrochloride. In one aspect, the strip buffer comprises 2 M sodium chloride or 1N sodium hydroxide or both (see Table 2-2). Example 2 further illustrates optimizing the concentration and conductivity of the equilibration and wash buffers.

Protein variants can include modifications of one or more residues as follows: one or more asparagines are deamidated; one or more aspartic acids are converted to iso-aspartate and/or Asn; one or more methionines are oxidized; one or more tryptophans are converted to N-formylkynurenine; one or more tryptophans are mono-hydroxyl tryptophan; one or more tryptophans are di-hydroxyl tryptophan; one or more tryptophans are tri-hydroxyl tryptophan; one or more arginines are converted to Arg 3-deoxyglucosone; the C-terminal glycine is not present; and/or there are one or more non-glycosylated glycosites.

The protein of interest can be aflibercept, anti-VEGF antibody or a VEGF MiniTrap. The protein variants can be formed by one or more of (i) oxidation of histidines from the histidine residues selected from His86, His110, His145, His209, His95, His19 and/or His203 (or equivalent residue positions on proteins sharing certain structural characteristics of aflibercept); (ii) oxidation of tryptophan residues selected from tryptophan residues at Trp58 and/or Trp138 (or equivalent residue positions on proteins sharing certain structural characteristics of aflibercept); (iii) oxidation tyrosine residue at Tyr64 (or equivalent positions on proteins sharing certain structural characteristics of aflibercept); (iv) oxidation of phenylalanine residues selected from Phe44 and/or Phe166 (or equivalent residue positions on proteins sharing certain structural characteristics of aflibercept); and/or (v) oxidation of methionine residues selected from Met10, Met20, Met163 and/or Met192 (or equivalent residue positions on proteins sharing certain structural characteristics of aflibercept).

The flowthrough fractions can comprise one or more of the following:

(a) a percentage of histidine residues which have been oxidized to 2-oxo-histidine wherein their color characterization is as follows:
  (i) no more yellow-brown than European Color Standard BY2;
  (ii) no more yellow-brown than European Color Standard BY3;
  (iii) no more yellow-brown than European Color Standard BY4;
  (iv) no more yellow-brown than European Color Standard BY5;
  (v) between European Color Standard BY2 and BY3;
  (vi) between European Color Standard BY3 and BY4;
  (vii) between European Color Standard BY4 and BY5, wherein the composition comprises about 5 g/L or about 10 g/L of the anti-VEGF protein, and wherein the composition is obtained as a sample from the flowthrough fractions.

(b) a percentage of histidine residues which have been oxidized to 2-oxo-histidine. Further, their color is characterized by having a yellow-brown color which approximates that of BY2, BY3, BY4, BY5, BY6, BY7; or is no darker/more intense than BY2, no darker than BY3, no darker than BY4, no darker than BY5, no darker than BY6, no darker than BY7; or is between that of BY2 and BY3, between that of BY2 and BY4, between that of BY3 and BY4 or between that of BY3 and BY5.

(c) a percentage of histidine residues which have been oxidized to 2-oxo-histidine wherein their color is characterized by a color in the CIE L*, a*, b* color space as follows:
  (i) no more yellow-brown than a b* value of about 22-23;
  (ii) no more yellow-brown than a b* value of about 16-17;
  (iii) no more yellow-brown than a b* value of 9-10;
  (iv) no more yellow-brown than a b* value of 4-5;
  (v) no more yellow-brown than a b* value of 2-3;
  (vi) between b* value of 17-23;
  (vii) between b* value of 10-17;
  (viii) between b* value of 5-10;
  (ix) between b* value of 3-5; or
  (x) between b* value of 1-3, wherein the composition comprises about 5 g/L or about 10 g/L of the anti-VEGF protein and wherein the composition is obtained as a sample from the flowthrough fractions.

(d) no more than about 1%, no more than about 0.1%, or about 0.1-1%, 0.2-1%, 0.3-1%, 0.4-1%, 0.5-1%, 0.6-1%, 0.7-1%, 0.8-1% or 0.9-1% of histidine residues in the composition are oxidized to 2-oxo-histidine. The percentage calculation is described in Section II.

B. Affinity Chromatography:

In some embodiments, compositions of the invention can be produced using a process comprising: expressing an anti-VEGF protein in a host cell wherein anti-VEGF protein is secreted from the host cell into the medium and a clarified harvest is obtained. The harvest is subjected to the following steps, comprising (a) loading a biological sample obtained from the clarified harvest onto an affinity chromatography column, wherein the affinity chromatography comprises a protein capable of selectively or specifically binding to the anti-VEGF protein; (b) washing the affinity chromatography column with a suitable elution buffer, and (c) collecting the eluted fraction(s). For example, as exemplified in Table 7-1 and Table 7-7 through 7-10, using $VEGF_{165}$ as the protein capable of selectively or specifically binding to the anti-VEGF protein and collecting the eluted fractions as per the method above led to a successful production of MT5 (an anti-VEGF protein), aflibercept and an anti-VEGF scFv fragment. Table 7-1 also discloses successful production of MT5 using (i) mAb1 (a mouse anti-VEGFR1 mAb human IgG1 where SEQ ID NO.: 73 is a heavy chain and SEQ ID NO.: 74 is a light chain); (ii) mAb2 (a mouse anti-VEGFR 1 mAb human IgG1 where SEQ ID NO.: 75 is a heavy chain and SEQ ID NO.: 76 is a light chain); (iii) mAb3 (a mouse anti-VEGF-R1 mAb mouse IgG1 where SEQ ID NO.: 77 is a heavy chain and SEQ ID NO.: 78 is a light chain) and (iv) mAb4 (a mouse anti-VEGFR1 mAb mouse IgG1 where SEQ ID NO.: 79 is a heavy chain and SEQ ID NO.: 80 is a light chain) as different proteins capable of selectively or specifically binding to MT5.

With respect to step (a) above, the biological sample to be loaded onto the affinity column can come from a sample in which the clarified harvest can be subjected to chromatography prior to affinity including, but not limited to, ion exchange chromatography (either anion or cation). Other chromatographic procedures well known to the skilled artisan can also be employed prior to use of the affinity step. The important point is that a biological sample comprising an anti-VEGF protein can be subjected to affinity chromatography.

In some embodiments, compositions of the invention can be produced using a process comprising: expressing a VEGF MiniTrap protein in a host cell wherein the VEGF MiniTrap is secreted from the host cell into the medium and wherein the medium can be further processed forming a clarified harvest. This harvest can be further processed by known chromatographic procedures yielding a biological sample comprising a VEGF MiniTrap. This biological sample can be further processed by employing the following steps, comprising (a) loading the biological sample onto an affinity chromatography column, wherein the affinity chromatography comprises a protein capable of selectively or specifically binding to or interacting with the VEGF MiniTrap protein; (b) washing the affinity chromatography column with a suitable elution buffer and (c) collecting the eluted fraction(s). Referring again to Table 7-1, disclosed in this Table is a successful production of MT5 (VEGF MiniTrap) using (i) $VEGF_{165}$; (ii) mAb1 (a mouse anti-VEGFR 1 mAb human IgG1 where SEQ ID NO.: 73 is a heavy chain and SEQ ID NO.: 74 is a light chain); (iii) mAb2 (a mouse anti-VEGFR1 mAb human IgG1 where SEQ ID NO.: 75 is a heavy chain and SEQ ID NO.: 76 is a light chain); (iv) mAb3 (a mouse anti-VEGF-R1 mAb mouse IgG1 where SEQ ID NO.: 77 is a heavy chain and SEQ ID NO.: 78 is a light chain) and (v) mAb4 (a mouse anti-VEGFR1 mAb mouse IgG1 where SEQ ID NO.: 79 is a heavy chain and SEQ ID NO.: 80 is a light chain) as different proteins capable of selectively or specifically binding to of interacting with MT5.

In one embodiment, affinity chromatography can also be used to isolate other MiniTrap proteins. Following cleavage of an aflibercept, a sample comprising the cleaved aflibercept can be subjected to affinity chromatography using a binder specific for the cleaved aflibercept. In one aspect, the binder can be an antibody or portion thereof.

Cleaving of the aflibercept can be facilitated using proteolytic digestion of aflibercept with, for example, IdeS protease (FabRICATOR) or a variant thereof to generate the VEGF MiniTrap. Cleaving of the aflibercept with IdeS protease or a variant thereof can produce a mixture of products including a Fc fragment and the VEGF MiniTrap. The VEGF MiniTrap can be further processed by using one or more of the production strategies described herein.

In some exemplary embodiments, a protein capable of selectively or specifically binding ("binder") to or interacting with an anti-VEGF protein, such as aflibercept or MiniTrap, can originate from a human or a mouse.

The affinity production process can further comprise equilibrating an affinity column using an equilibration buffer before loading the biological sample. Exemplary equilibration buffers can be 20 mM sodium phosphate, pH 6-8 (esp. 7.2), 10 mM sodium phosphate, 500 mM NaCl, pH 6-8 (esp. 7.2), 50 mM Tris pH 7-8, DPBS pH 7.4.

The biological sample can be loaded using a suitable buffer, such as, DPBS.

This affinity production process can further comprise washing an affinity column with one or more wash buffers. The column can be washed one or multiple times. Further, the washes can also be collected as wash fractions. The pH of the wash buffer can be from about 7.0 to about 8.60. In one aspect, the wash buffer can be DPBS. In another aspect, the wash buffer can be 20 mM sodium phosphate, pH 6-8 (esp. 7.2), 10 mM sodium phosphate, 500 mM NaCl, pH 6-8 (esp. 7.2), 50 mM Tris pH 7-8, or DPBS pH 7.4.

This affinity process can further comprise washing an affinity column with one or more suitable elution buffers and collecting the eluted fractions. The column can be washed one or multiple times. Non-limiting examples of such a suitable elution buffer includes: ammonium acetate (pH of about 2.0 to about 3.0), acetic acid (pH of about 2.0 to about 3.2), glycine-HCl (pH of about 2.0 to about 3.0), sodium citrate (pH of about 2.0 to about 3.0), citric acid (pH of about 2.0 to about 3.0), potassium isothiocyanate (pH of about 2.0 to about 3.0), or combinations thereof.

In some aspects, the eluted fractions can be neutralized using a neutralizing buffer. An example of such a neutralizing buffer is Tris to Tris-HCl (pH of about 7.0 to about 9.0).

C. IdeS Mutants:

The IdeS protease used for the cleavage of an Fc fusion protein such as aflibercept will rapidly lose enzymatic activity under basic pH conditions, which can limit its use during the manufacture of VEGF MiniTrap. Thus, variants have been developed to be more stable at basic pH, for example, in the presence of a strong base such as NaOH. Such basic conditions can be 0.05N NaOH for 1 hr or 0.1N NaOH for 0.5 hr.

In some embodiments, an IdeS mutant can have an amino acid sequence comprising at least about 70% sequence identity over its full length to the amino acid sequences set forth in the group consisting of SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15 and SEQ ID NO.: 16. In some aspects, the amino acid sequence has about 75%, 80%, 85%, 90%, 95% or about 100% sequence identity over its full length to the amino acid sequences mentioned directly above.

In some embodiments, an IdeS mutant can have an isolated nucleic acid molecule encoding a polypeptide with an amino acid sequence comprising at least 70% sequence identity over its full length to the amino acid sequences as set forth in the group consisting of SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15 and SEQ ID NO.: 16. In some aspects, the amino acid sequence has about 75%, 80%, 85%, 90%, 95% or about 100% sequence identity over its full length to the amino acid sequences mentioned directly above.

In some embodiments, the polypeptide can have an amino acid sequence comprising at least 70% sequence identity over its full length to the amino acid sequences as set forth in the group consisting of SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15 and SEQ ID NO.: 16 and can be expressed by a host cell with a suitable vector comprising nucleic acid coding for the identified peptides. In one aspect, the nucleic acid molecule is operatively linked to an expression control sequence capable of directing its expression in a host cell. In one aspect, the vector can be a plasmid. In some aspects, the amino acid sequence has about 75%, 80%, 85%, 90%, 95% or about 100% sequence identity over its full length to the amino acid sequences mentioned directly above. In some aspects, an isolated nucleic acid molecule can be used to encode the polypeptide.

In some embodiments, an IdeS mutant can have an amino acid sequence comprising a parental amino acid sequence defined by SEQ ID NO.: 1 (IdeS) with an asparagine residue at position 87, 130, 182 and/or 274 mutated to an amino acid other than asparagine. In one aspect, the mutation can confer an increased chemical stability at alkaline pH-values compared to the parental amino acid sequence. In another aspect, the mutation can confer an increase in chemical stability by 50% at alkaline pH-values compared to the parental amino acid sequence. In one aspect, the amino acid can be selected from aspartic acid, leucine, and arginine. In a particular aspect, the asparagine residue at position 87 is mutated to an aspartic acid residue. In another particular aspect, the asparagine residue at position 130 is mutated to an arginine residue. In yet another particular aspect, the asparagine residue at position 182 is mutated to a leucine residue. In yet another particular aspect, the asparagine residue at position 274 is mutated to an aspartic acid residue. In yet another particular aspect, the asparagine residues at position 87 and 130 are mutated. In yet another particular aspect, the asparagine residues at position 87 and 182 are mutated. In yet another particular aspect, the asparagine residues at position 87 and 274 are mutated. In yet another particular aspect, the asparagine residues at position 130 and 182 are mutated. In yet another particular aspect, the asparagine residues at position 130 and 274 are mutated. In yet another particular aspect, the asparagine residues at position 182 and 274 are mutated. In yet another particular aspect, the asparagine residues at position 87, 130 and 182 are mutated. In yet another particular aspect, the asparagine residues at position 87, 182 and 274 are mutated. In yet another particular aspect, the asparagine residues at position 130, 182 and 274 are mutated. In yet another particular aspect, the asparagine residues at position 87, 130, 182 and 274 are mutated. In some aspects, the amino acid sequence has about 75%, 80%, 85%, 90%, 95% or about 100% sequence identity over its full length to the amino acid sequences described above. In some aspects, an isolated nucleic acid molecule can be used to encode the polypeptide.

Those of ordinary skill in the art familiar with standard molecular biology techniques can without undue burden prepare and use IdeS mutants of the present invention. Standard techniques can be used for recombinant DNA, oligonucleotide synthesis, tissue culture, and transformation (e.g., electroporation, lipofection). See, for example, Sambrook et al., *Molecular Cloning: A Laboratory Manual*, supra, which is incorporated herein by reference for any purpose. Enzymatic reactions and production techniques can be performed according to manufacturer's specification or as described herein.

VI. Protein Production Generally

A variety of different production techniques, including, but not limited to, affinity, ion exchange, mixed mode, size exclusion, and hydrophobic interaction chromatography, singularly or in combination, are envisaged to be within the scope of the present invention. These chromatographic steps separate mixtures of proteins of a biological sample on the basis of their charge, degree of hydrophobicity, or size, or a combination thereof, depending on the particular form of separation. Several different chromatography resins are available for each of the techniques alluded to supra, allowing accurate tailoring of the production scheme to a particular protein involved. Each separation method results in the protein traversing at different rates through a column to achieve a physical separation that increases as they pass further through the column or adhere selectively to a separation medium. The proteins are then either (i) differentially eluted using an appropriate elution buffer and/or (ii) collected from flowthrough fractions obtained from the column used, optionally, from washing the column with an appropriate equilibration buffer. In some cases, the protein of interest is separated from impurities (HCPs, protein variants, etc.) when the impurities preferentially adhere to the column and the protein of interest less so, i.e., the protein of interest does not adsorb to the solid phase of a particular column and thus flows through the column. In some cases, the impurities are separated from the protein of interest when they fail to adsorb to the column and thus flow through the column.

The production process may begin at the separation step after the recombinant protein has been produced using upstream production methods described above and/or by alternative production methods conventional in the art. Once a clarified solution or mixture comprising the protein of interest, for example, a fusion protein, has been obtained, separation of the protein of interest from process-related impurities (such as the other proteins produced by the cell (like HCPs), as well as product-related substances, such acidic or basic variants) is performed. A combination of one or more different production techniques, including affinity, ion exchange (e.g., CEX, AEX), mixed-mode (MM), and/or hydrophobic interaction chromatography can be employed. Such production steps separate mixtures of components within a biological sample on the basis of their, for example, charge, degree of hydrophobicity, and/or apparent size. Numerous chromatography resins are commercially available for each of the chromatography techniques mentioned herein, allowing accurate tailoring of the production scheme to a particular protein involved. Each of the separation methods allow proteins to either traverse at different rates through a column achieving a physical separation that increases as they pass further through the column or to adsorb selectively to a separation resin (or medium). The proteins can then be differentially collected. In some cases, the protein of interest is separated from components of a biological sample when other components specifically adsorb to a column's resin while the protein of interest does not.

A. Primary Recovery and Virus Inactivation

In certain embodiments, the initial steps of the production methods disclosed herein involve the clarification and primary recovery of a protein of interest from a biological sample. The primary recovery will include one or more centrifugation steps to separate the protein of interest from a host cell and attendant cellular debris. Centrifugation of the sample can be performed at, for example, but not by way of limitation, 7,000×g to approximately 12,750×g. In the context of large-scale production, such centrifugation can occur on-line with a flow rate set to achieve, for example, a turbidity level of 150 NTU in the resulting supernatant. Such supernatant can then be collected for further processing or in-line filtered through one or more depth filters for further clarification of the sample.

In certain embodiments, the primary recovery may include the use of one or more depth filtration steps to clarify the sample and, thereby, aid in processing the protein of interest. In other embodiments, the primary recovery may include the use of one or more depth filtration steps post centrifugation. Non-limiting examples of depth filters that can be used in the context of the instant invention include the Millistak+X0HC, F0HC, D0HC, A1HC, B1HC depth filters (EMD Millipore), 3M™ model 30/60ZA, 60/90 ZA, VR05, VR07, delipid depth filters (3M Corp.). A 0.2 μm filter such as Sartorius's 0.45/0.2 μm Sartopore™ bi-layer or Millipore's Express SHR or SHC filter cartridges typically follows the depth filters. Other filters well known to the skilled artisan can also be used.

In certain embodiments, the primary recovery process can also be a point to reduce or inactivate viruses that can be present in a biological sample. Any one or more of a variety of methods of viral reduction/inactivation can be used during the primary recovery phase of production including heat inactivation (pasteurization), pH inactivation, buffer/detergent treatment, UV and γ-ray irradiation and the addition of certain chemical inactivating agents such as β-propiolactone or, for example, copper phenanthroline as described in U.S. Pat. No. 4,534,972, the entire teaching of which is incorporated herein by reference. In certain exemplary embodiments of the present invention, the sample is exposed to detergent viral inactivation during the primary recovery phase. In other embodiments, the sample may be exposed to low pH inactivation during the primary recovery phase.

In those embodiments where viral reduction/inactivation is employed, a biological sample can be adjusted, as needed, for further production steps. For example, following low pH viral inactivation, the pH of the sample is typically adjusted to a more neutral pH, for example, from about 4.5 to about 8.5, prior to continuing the production process. Additionally, the mixture may be diluted with water for injection (WFI) to obtain a desired conductivity.

B. Affinity Chromatography

In certain exemplary embodiments, it may be advantageous to subject a biological sample to affinity chromatography for production of a protein of interest. The chromatographic material is capable of selectively or specifically binding to or interacting with the protein of interest. Non-limiting examples of such chromatographic material include: Protein A and Protein G. Also included is chromatographic material comprising, for example, a protein or portion thereof capable of binding to or interacting with the protein of interest. In one aspect, the protein of interest is an anti-VEGF protein such as aflibercept, MiniTrap or a protein related thereto.

Affinity chromatography can involve subjecting a biological sample to a column comprising a suitable Protein A resin. When used herein, the term "Protein A" encompasses Protein A recovered from a native source thereof. Protein A produced synthetically (e.g., by peptide synthesis or by recombinant techniques), and variants thereof which retain the ability to bind proteins which have a $C_H2/C_H3$ region. In certain aspects, Protein A resin is useful for affinity-based production and isolation of a variety of antibody isotypes by interacting specifically with the Fc portion of a molecule should it possess that region.

There are several commercial sources for Protein A resin. One suitable resin is MabSelect™ from GE Healthcare. Suitable resins include, but are not limited to, MabSelect SuRe™, MabSelect SuRe LX, MabSelect, MabSelect SuRe pcc, MabSelect Xtra, rProtein A Sepharose from GE Healthcare, ProSep HC, ProSep Ultra, and ProSep Ultra Plus from EMD Millipore, MapCapture from Life Technologies. A non-limiting example of a suitable column packed with MabSelect™ is an about 1.0 cm diameter× about 21.6 cm long column (17 mL bed volume). A suitable column may comprise a resin such as MabSelect™ SuRe or an analogous resin. Protein A can also be purchased commercially from Repligen. Pharmacia and Fermatech.

An affinity column can be equilibrated with a suitable buffer prior to sample loading. Following loading of the column, the column can be washed one or multiple times using a suitable wash buffer. The column can then be eluted using an appropriate elution buffer, for example, glycine-HCl, acetic acid, or citric acid. The eluate can be monitored using techniques well known to those skilled in the art such as a UV detector. The eluted fractions of interest can be collected and then prepared for further processing.

In one aspect, the eluate may be subjected to viral inactivation, for example, either by detergent or low pH. A suitable detergent concentration or pH (and time) can be selected to obtain a desired viral inactivation result. After viral inactivation, the eluate is usually pH and/or conductivity adjusted for subsequent production steps.

The eluate may be subjected to filtration through a depth filter to remove turbidity and/or various impurities from the protein of interest prior to additional chromatographic polishing steps. Examples of suitable depth filters include, but are not limited to, Millistak+X0HC, F0HC, D0HC, A1HC, X0SP, and B1HC Pod filters (EMD Millipore), or Zeta Plus 30ZA/60ZA, 60ZA/90ZA, delipid, VR07, and VR05 filters (3M). The Emphaze AEX Hybrid Purifier multi-mechanism filter may also be used to clarify the eluate. The eluate pool may need to be adjusted to a particular pH and conductivity in order to obtain desired impurity removal and product recovery from the depth filtration step.

C. Anion Exchange Chromatography

In certain embodiments, a protein of interest is produced by subjecting a biological sample to at least one anion exchange separation step. In one scenario, the anion exchange step can occur following an affinity chromatography procedure (e.g., Protein A affinity). In other scenarios, the anion exchange step can occur before the affinity chromatography step. In yet other protocols, anion exchange can occur both before and after an affinity chromatography step. In one aspect, the protein of interest is either aflibercept or MiniTrap.

The use of an anionic exchange material versus a cationic exchange material is based, in part, on the local charges of the protein of interest. Anion exchange chromatography can be used in combination with other chromatographic procedures such as affinity chromatography, size exclusion chromatography, hydrophobic interaction chromatography as well as other modes of chromatography known to the skilled artisan.

In performing a separation, the initial protein composition (biological sample) can be placed in contact with an anion exchange material by using any of a variety of techniques, for example, using a batch production technique or a chromatographic technique.

In the context of batch production, anion exchange material is prepared in, or equilibrated to, a desired starting buffer. Upon preparation, a slurry of the anion exchange material is obtained. The biological sample is contacted with the slurry to allow for protein adsorption to the anion exchange material. A solution comprising acidic species that do not bind to the AEX material is separated from the slurry by allowing the slurry to settle and removing the supernatant. The slurry can be subjected to one or more washing steps and/or elution steps.

In the context of chromatographic separation, a chromatographic column is used to house chromatographic support material (resin or solid phase). A sample comprising a protein of interest is loaded onto a particular chromatographic column. The column can then be subjected to one or more wash steps using a suitable wash buffer. Components of a sample that have not adsorbed onto the resin will likely flow through the column. Components that have adsorbed to the resin can be differentially eluted using an appropriate elution buffer.

A wash step is typically performed in AEX chromatography using conditions similar to the load conditions or alternatively by decreasing the pH and/or increasing the ionic strength/conductivity of the wash in a step wise or linear gradient manner. In one aspect, the aqueous salt solution used in both the loading and wash buffer has a pH that is at or near the isoelectric point (pI) of the protein of interest. Typically, the pH is about 0 to 2 units higher or lower than the pI of the protein of interest, however it may be in the range of 0 to 0.5 units higher or lower. It may also be at the pI of the protein of interest.

The anionic agent may be selected from the group consisting of acetate, chloride, formate and combinations thereof. The cationic agent may be selected from the group consisting of Tris, arginine, sodium and combinations thereof. In a particular example, the buffer solution is a Tris/formate buffer. The buffer may be selected from the group consisting of pyridine, piperazine, L-histidine, Bis-Tris, Bis-Tris propane, imidazole, N-ethylmorpholine, TEA (triethanolamine), Tris, morpholine, N-methyldiethanolamine, AMPD (2-amino-2-methyl-1,3-propanediol), diethanolamine, ethanolamine, AMP (2-amino-2-methyl-1-propanol), piperazine, 1,3-diaminopropane and piperidine.

A packed anion-exchange chromatography column, anion-exchange membrane device, anion-exchange monolithic device, or depth filter media can be operated either in bind-elute mode, flowthrough mode, or a hybrid mode wherein proteins exhibit binding to the chromatographic material and yet can be washed from such material using a buffer that is the same or substantially similar to the loading buffer.

In the bind-elute mode, a column or membrane device is first conditioned with a buffer with appropriate ionic strength and pH under conditions where certain proteins will adsorb to the resin-based matrix. For example, during the feed load, a protein of interest can be adsorbed to the resin due to electrostatic attraction. After washing the column or the membrane device with the equilibration buffer or another buffer with a different pH and/or conductivity, the product recovery is achieved by increasing the ionic strength (i.e., conductivity) of the elution buffer to compete with the solute for the charged sites of the anion exchange matrix. Changing the pH and thereby altering the charge of the solute is another way to achieve elution of the solute. The change in conductivity or pH may be gradual (gradient elution) or stepwise (step elution).

In the flowthrough mode, a column or membrane device is operated at a selected pH and conductivity such that the protein of interest does not bind to the resin or the membrane while the acidic species will either be retained on the column or will have a distinct elution profile as compared to the protein of interest. In the context of this strategy, acidic species will interact with or bind to the chromatographic material under suitable conditions while the protein of interest and certain aggregates and/or fragments of the protein of interest will flow through the column.

Non-limiting examples of anionic exchange resins include diethylaminoethyl (DEAE), quaternary aminoethyl (QAE) and quaternary amine (Q) groups. Additional non-limiting examples include: Poros 50PI and Poros 50HQ, which are a rigid polymeric bead with a backbone consisting of cross-linked poly[styrene-divinylbenzene]; Capto Q Impres and Capto DEAE, which are a high flow agarose bead; Toyopearl QAE-550, Toyopearl DEAE-650, and Toyopearl GigaCap Q-650, which are a polymeric base bead; Fractogel® EMD TMAE Hicap, which is a synthetic polymeric resin with a tentacle ion exchanger; Sartobind STIC® PA nano, which is a salt-tolerant chromatographic membrane with a primary amine ligand; Sartobind Q nano, which is a strong anion exchange chromatographic membrane; CUNO BioCap, which is a zeta-plus depth filter media constructed from inorganic filter aids, refined cellulose, and an ion exchange resin; and XOHC, which is a depth-filter media constructed from inorganic filter aid, cellulose, and mixed cellulose esters.

In certain embodiments, the protein load of a sample may be adjusted to a total protein load to the column of between about 50 g/L and about 500 g/L, or between about 75 g/L and about 350 g/L, or between about 200 g/L and about 300 g/L. In other embodiments, the protein concentration of the load protein mixture is adjusted to a protein concentration of the material loaded to the column of about 0.5 g/L and about 50 g/L, between about 1 g/L and about 20 g/L, or between about 3 g/L and about 10 g/L. In yet other embodiments, the protein concentration of the load protein mixture is adjusted to a protein concentration of the material to the column of about 37 g/L.

Additives such as polyethylene glycol (PEG), detergents, amino acids, sugars, chaotropic agents can be added to enhance the performance of the separation to achieve better separation, recovery and/or product quality.

In certain embodiments, including those relating to aflibercept and/or VEGF MiniTrap, the methods of the instant invention can be used to selectively remove, significantly reduce, or essentially remove at least 10% of protein variants, thereby producing protein compositions that have reduced protein variants.

The protein variants can include modifications of one or more residues as follows: one or more asparagines are deamidated; one or more aspartic acids are converted to aspartate-glycine and/or Asn-Gly; one or more methionines are oxidized; one or more tryptophans are converted to N-formylkynurenine; one or more tryptophans are mono-hydroxyl tryptophan; one or more tryptophans are di-hydroxyl tryptophan; one or more tryptophans are tri-hydroxyl tryptophan; one or more arginines are converted to Arg 3-deoxyglucosone; the C-terminal glycine is not present; and/or there are one or more non-glycosylated glycosites. The use of AEX was also observed to reduce oxidized and acidic species of anti-VEGF variants in said affinity eluate. Compared to the affinity eluate, following use of AEX, the flowthrough fraction may show a reduction of at least about 20%, 19%, 18%, 17%, 16%, 15%, 14%, 13%, 12%, 11%, 10%, 9%, 8%, 7%, 6%, or 5% in oxidized and/or acidic species of anti-VEGF variants.

Protein variants of aflibercept and/or VEGF MiniTrap can include one or more of (i) oxidated histidines from the histidine residues selected from His86, His110, His145, His209, His95, His19 and/or His203; (ii) oxidated tryptophan residues selected from tryptophan residues at Trp58 and/or Trp138; (iii) oxidated tyrosine residue at Tyr64; (iv) oxidated phenylalanine residues selected from Phe44 and/or Phe166; and/or (v) oxidated methionine residues selected from Met10, Met20, Met163 and/or Met192.

D. Cation Exchange Chromatography

The compositions of the present invention can be produced by subjecting a biological sample comprising a protein of interest to at least one cation exchange (CEX) step. In certain exemplary embodiments, the CEX step will be in addition to an AEX step and occur either before or after the AEX step. In one aspect, the protein of interest is either aflibercept, MiniTrap or a molecule related thereto.

The use of a cationic exchange material versus an anionic exchange material, such as those anionic exchange materials discussed supra, is based, in part, on the local charges of the protein of interest in a given solution and the separation conditions desired. It is within the scope of this invention to employ a cationic exchange step prior to the use of an anionic exchange step, or an anionic exchange step prior to the use of a cationic exchange step. Furthermore, it is within the scope of this invention to employ only a cationic exchange step in combination with other chromatography procedures.

In performing cation exchange, a sample comprising a protein of interest can be contacted with a cation exchange material by using any of a variety of techniques, for example, using a batch production technique or a chromatographic technique, as described above for AEX.

An aqueous salt solution may be used as both a loading and wash buffer having a pH that is lower than the isoelectric point (pI) of the protein of interest. In one aspect, the pH is about 0 to 5 units lower than the pI of the protein. In another aspect, it is in the range of 1 to 2 units lower than the pI of the protein. In yet another aspect, it is in the range of 1 to 1.5 units lower than the pI of the protein.

In certain embodiments, the concentration of the anionic agent in aqueous salt solution is increased or decreased to achieve a pH of between about 3.5 and about 10.5, or between about 4 and about 10, or between about 4.5 and about 9.5, or between about 5 and about 9, or between about 5.5 and about 8.5, or between about 6 and about 8, or between about 6.5 and about 7.5. In one aspect, the concentration of anionic agent is increased or decreased in the aqueous salt solution in order to achieve a pH of 5, or 5.5, or 6, or 6.5, or 6.8, or 7.5. Buffer systems suitable for use in the CEX methods include, but are not limited to, Tris formate, Tris acetate, ammonium sulfate, sodium chloride, and sodium sulfate.

In certain embodiments, the conductivity and pH of the aqueous salt solution is adjusted by increasing or decreasing the concentration of a cationic agent. In one aspect, the cationic agent is maintained at a concentration ranging from about 20 mM to about 500 mM, about 50 mM to about 350 mM, about 100 mM to about 300 mM, or about 100 mM to about 200 mM. Non-limiting examples of the cationic agent can be selected from the group consisting of sodium, Tris, triethylamine, ammonium, arginine, and combinations thereof.

A packed cation-exchange chromatography column or a cation-exchange membrane device can be operated either in bind-elute mode, flowthrough mode, or a hybrid mode wherein the product exhibits binding to or interacting with a chromatographic material yet can be washed from such material using a buffer that is the same or substantially similar to the loading buffer (details of these modes are outlined above).

Cationic substituents include carboxymethyl (CM), sulfoethyl (SE), sulfopropyl (SP), phosphate (P) and sulfonate (S). Additional cationic materials include, but are not limited to: Capto SP ImpRes, which is a high flow agarose bead; CM Hyper D grade F, which is a ceramic bead coated and permeated with a functionalized hydrogel, 250-400 ionic groups μeq/mL; Eshmuno S, which is a hydrophilic polyvinyl ether base matrix with 50-100 μeq/mL ionic capacity; Nuvia C Prime, which is a hydrophobic cation exchange media composed of a macroporous highly crosslinked hydrophilic polymer matrix 55-75με/mL; Nuvia S, which has a UNOsphere base matrix with 90-150με/mL ionic groups; Poros HS, which is a rigid polymeric bead with a backbone consisting of cross-linked poly[styrene-divinylbenzene]; Poros XS, which is a rigid polymetric bead with a backbone consisting of cross-linked poly[styrene divinylbenzene]; Toyo Pearl Giga Cap CM 650M, which is a polymeric base bead with 0.225 meq/mL ionic capacity; Toyo Pearl Giga Cap S 650M, which is a polymeric base bead; and Toyo Pearl MX TRP, which is a polymeric base bead. It is noted that CEX chromatography can be used with MM resins, described herein.

The protein load of a sample comprising a protein of interest is adjusted to a total protein load to the column of between about 5 g/L and about 150 g/L, or between about 10 g/L and about 100 g/L, between about 20 g/L and about 80 g/L, between about 30 g/L and about 50 g/L, or between about 40 g/L and about 50 g/L. In certain embodiments, the protein concentration of the load protein mixture is adjusted to a protein concentration of the material to be loaded onto the column of about 0.5 g/L and about 50 g/L, or between about 1 g/L and about 20 g/L.

Additives such as polyethylene glycol, detergents, amino acids, sugars, chaotropic agents can be added to enhance the performance of the separation so as to achieve better separation, recovery and/or product quality.

In certain embodiments, including those relating to aflibercept or anti-VEGF antibody or VEGF MiniTrap, the methods of the instant invention can be used to selectively remove, significantly reduce, or essentially remove all of the oxo-variants in a sample where the protein of interest will essentially be in the flowthrough of a CEX procedure while the oxo-variants will be substantially captured by the column media.

E. Mixed Mode Chromatography

Mixed mode ("MM") chromatography may also be used to prepare the compositions of the invention. MM chromatography, also referred to herein as "multimodal chromatography", is a chromatographic strategy that utilizes a support comprising a ligand that is capable of providing at least two different interactions with an analyte or protein of interest from a sample. One of these sites provides an attractive type of charge-charge interaction between the ligand and the protein of interest and the other site provides for electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole, etc.

The column resin employed for a mixed mode separation can be Capto Adhere. Capto Adhere is a strong anion exchanger with multimodal functionality. Its base matrix is a highly cross-linked agarose with a ligand (N-benzyl-N-methyl ethanol amine) that exhibits different functionalities for interaction, such as ionic interaction, hydrogen bonding and hydrophobic interaction. In certain aspects, the resin employed for a mixed mode separation is selected from PPA-HyperCel and HEA-HyperCel. The base matrices of PPA-HyperCel and HEA-HyperCel are high porosity cross-linked cellulose. Their ligands are phenylpropylamine and hexylamine, respectively. Phenylpropylamine and hexylamine offer different selectivity and hydrophobicity options for protein separations. Additional mixed mode chromatographic supports include, but are not limited to, Nuvia C Prime, Toyo Pearl MX Trp 650M, and Eshmuno® HCX. In certain aspects, the mixed mode chromatography resin is comprised of ligands coupled to an organic or inorganic support, sometimes denoted by a base matrix, directly or via a spacer. The support may be in the form of particles, such as essentially spherical particles, a monolith, filter, membrane, surface, capillaries, and the like. In certain aspects, the support is prepared from a native polymer, such as cross-linked carbohydrate material, such as agarose, agar, cellulose, dextran, chitosan, konjac, carrageenan, gellan, alginate and the like. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964), the entire teaching of which is incorporated herein by reference). Alternatively, the support can be prepared from a synthetic polymer, such as cross-linked synthetic polymers, for example, styrene or styrene derivatives, divinylbenzene, acrylamides, acrylate esters, methacrylate esters, vinyl esters, vinyl amides, and the like. Such synthetic polymers can be produced according to standard methods, see "Styrene based polymer supports developed by suspension polymerization" (R Arshady: Chimica e L'Industria 70(9), 70-75 (1988), the entire teaching of which is incorporated herein by reference). Porous native or synthetic polymer supports are also available from commercial sources, such as GE Healthcare, Uppsala, Sweden.

The protein load of a biological sample mixture comprising a protein of interest can be adjusted to a total protein load to the column of between about 25 g/L and about 750 g/L, or between about 75 g/L and about 500 g/L, or between about 100 g/L and about 300 g/L. In certain exemplary embodiments, the protein concentration of the load protein mixture is adjusted to a protein concentration of the material loaded to the column of about 1 g/L and about 50 g/L, or between about 9 g/L and about 25 g/L.

Additives such as polyethylene glycol, detergents, amino acids, sugars, chaotropic agents can be added to enhance the performance of the separation, so as to achieve better separation, recovery and/or product quality.

In certain embodiments, including those relating to aflibercept and/or MiniTrap, the methods of the instant invention can be used to selectively remove, significantly reduce, or essentially remove all of the PTMs, including oxo-variants.

The methods for producing the composition of the invention can also be implemented in a continuous chromatography mode. In this mode, at least two columns are employed (referred to as a "first" column and a "second" column). In certain embodiments, this continuous chromatography mode can be performed such that the eluted fractions and/or stripped fractions comprising PTMs, for example, oxo-variants, can then be loaded subsequently or concurrently onto the second column (with or without dilution).

In one embodiment, the media choice for continuous mode can be one of many chromatographic resins with pendant hydrophobic and anion exchange functional groups, monolithic media, membrane adsorbent media or depth filtration media.

F. Hydrophobic Interaction Chromatography

The compositions of the invention may also be prepared using hydrophobic interaction chromatography (HIC).

In performing the separation, a biological sample is contacted with a HIC material, for example, using a batch production technique or using a column or membrane chromatography. Prior to HIC processing it may be desirable to adjust the concentration of the salt buffer to achieve desired protein binding/interaction to the resin or the membrane.

Whereas ion exchange chromatography relies on the local charge of the protein of interest for selective separation, hydrophobic interaction chromatography exploits the hydrophobic properties of proteins to achieve selective separation. Hydrophobic groups on or within a protein interact with hydrophobic groups of chromatography resin or a membrane. Typically, under suitable conditions, the more hydrophobic a protein is (or portions of a protein) the stronger it will interact with the column or the membrane. Thus, under suitable conditions, HIC can be used to facilitate the separation of process-related impurities (e.g., HCPs) as well as product-related substances (e.g., aggregates and fragments) from a protein of interest in a sample.

Like ion exchange chromatography, a HIC column or a HIC membrane device can also be operated in an elution mode, a flowthrough, or a hybrid mode wherein the product exhibits binding to or interacting with a chromatographic material yet can be washed from such material using a buffer that is the same or substantially similar to the loading buffer. (The details of these modes are outlined above in connection with AEX processing.) As hydrophobic interactions are strongest at high ionic strength, this form of separation is conveniently performed following a salt elution step such as those typically used in connection with ion exchange chromatography. Alternatively, salts can be added to a sample before employing a HIC step. Adsorption of a protein to a HIC column is favored by high salt concentrations, but the actual concentrations can vary over a wide range depending on the nature of the protein of interest, salt type and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{2+}$; $Ca^{2+}$; $Mg^{2+}$; $Li^+$; $Cs^+$; $Na^+$; $K^+$; $Rb^+$; $NH4^+$, while anions may be ranked in terms of increasing chaotropic effect as $PO_4^{3-}$; $SO_4^{2-}$; $CH_3CO_3^-$; $Cl^-$; $Br^-$; $NO_3^-$; $ClO_4^-$; $I^-$; $SCN^-$.

In general, $Na^+$, $K^+$ or $NH4^+$ sulfates effectively promote ligand-protein interaction using HIC. Salts may be formulated that influence the strength of the interaction as given by the following relationship: $(NH_4)_2SO_4 > Na_2SO_4 > NaCl > NH_4Cl > NaBr > NaSCN$. In general, salt concentrations of between about 0.75 M and about 2 M ammonium sulfate or between about 1 M and about 4 M NaCl are useful.

HIC media normally comprise a base matrix (e.g., cross-linked agarose or synthetic copolymer material) to which hydrophobic ligands (e.g., alkyl or aryl groups) are coupled. A suitable HIC media comprises an agarose resin or a membrane functionalized with phenyl groups (e.g., a Phenyl Sepharose™ from GE Healthcare or a Phenyl Membrane from Sartorius). Many HIC resins are available commercially. Examples include, but are not limited to, Capto Phenyl, Phenyl Sepharose™ 6 Fast Flow with low or high substitution, Phenyl Sepharose™ High Performance, Octyl Sepharose™ High Performance (GE Healthcare); Fractogel™ EMD Propyl or Fractogel™ EMD Phenyl (E. Merck, Germany); Macro-Prep™ Methyl or Macro-Prep™ t-Butyl columns (Bio-Rad, California); WP HI-Propyl (C3)™ (J. T. Baker, New Jersey); and Toyopearl™ ether, phenyl or butyl (TosoHaas, PA); ToyoScreen PPG; ToyoScreen Phenyl; ToyoScreen Butyl; ToyoScreen Hexyl; GE HiScreen and Butyl FF HiScreen Octyl FF.

The protein load of a sample comprising a protein of interest is adjusted to a total protein load to the column of between about 50 g/L to about 1000 g/L; about 5 g/L and about 150 g/L, between about 10 g/L and about 100 g/L, between about 20 g/L and about 80 g/L, between about 30 g/L and about 50 g/L, or between about 40 g/L and about 50 g/L. In certain embodiments, the protein concentration of the load protein mixture is adjusted to a protein concentration of the material to be loaded onto the column of about 0.5 g/L and about 50 g/L, or between about 1 g/L and about 20 g/L.

Because the pH selected for any particular production process must be compatible with protein stability and activity, particular pH conditions may be specific for each application. However, because at pH 5.0-8.5 particular pH values have very little significance on the final selectivity and resolution of a HIC separation, such conditions may be favored. An increase in pH weakens hydrophobic interactions and retention of proteins changes more drastically at pH values above 8.5 or below 5.0. In addition, changes in ionic strength, the presence of organic solvents, temperature and pH (especially at the isoelectric point, pI, when there is no net surface charge) can impact protein structure and solubility and, consequently, the interaction with other hydrophobic surfaces, such as those in HIC media and hence, in certain embodiments, the present invention incorporates production strategies wherein one or more of the foregoing are adjusted to achieve the desired reduction in process-related impurities and/or product-related substances.

In certain embodiments, spectroscopy methods such as UV, NIR, FTIR, Fluorescence, and Raman may be used to monitor the protein of interest and impurities in an on-line, at-line or in-line mode, which can then be used to control the level of aggregates in the pooled material collected from the HIC adsorbent effluent. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, and moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

G. Size Exclusion Chromatography

Size exclusion chromatography or gel filtration relies on the separation of components as a function of their molecular size. Separation depends on the amount of time that the substances spend in the porous stationary phase as compared to time in the fluid. The probability that a molecule will reside in a pore depends on the size of the molecule and the pore. In addition, the ability of a substance to permeate into pores is determined by the diffusion mobility of macromolecules which is higher for small macromolecules. Very large macromolecules may not penetrate the pores of the stationary phase at all; and, for very small macromolecules the probability of penetration is close to unity. While components of larger molecular size move more quickly past the stationary phase, components of small molecular size have a longer path length through the pores of the stationary phase and are thus retained longer in the stationary phase.

The chromatographic material can comprise a size exclusion material wherein the size exclusion material is a resin or membrane. The matrix used for size exclusion is preferably an inert gel medium which can be a composite of cross-linked polysaccharides, for example, cross-linked agarose and/or dextran in the form of spherical beads. The degree of cross-linking determines the size of pores that are present in the swollen gel beads. Molecules greater than a certain size do not enter the gel beads and thus move through the chromatographic bed the fastest. Smaller molecules, such as detergent, protein, DNA and the like, which enter the gel beads to varying extent depending on their size and shape, are retarded in their passage through the bed. Molecules are thus generally eluted in the order of decreasing molecular size.

Porous chromatographic resins appropriate for size-exclusion chromatography of viruses may be made of dextrose, agarose, polyacrylamide, or silica which have different physical characteristics. Polymer combinations can also be also used. Most commonly used are those under the tradename, "SEPHADEX" available from Amersham Biosciences.

Other size exclusion supports from different materials of construction are also appropriate, for example Toyopearl 55F (polymethacrylate, from Tosoh Bioscience, Montgomery Pa.) and Bio-Gel P-30 Fine (BioRad Laboratories, Hercules, CA).

The protein load of a sample comprising a protein of interest can be adjusted to a total protein load to the column of between about 50 g/L and about 1000 g/L; about 5 g/L and about 150 g/L, between about 10 g/L and about 100 g/L, between about 20 g/L and about 80 g/L, between about 30 g/L and about 50 g/L, or between about 40 g/L and about 50 g/L. In certain embodiments, the protein concentration of the load protein mixture is adjusted to a protein concentration of the material to be loaded onto the column of between about 0.5 g/L and about 50 g/L, or between about 1 g/L and about 20 g/L.

H. Viral Filtration

Viral filtration is a dedicated viral reduction step in a production process. This step is usually performed post chromatographic polishing. Viral reduction can be achieved via the use of suitable filters including, but not limited to, Planova 20N™, 50N or BioEx from Asahi Kasei Pharma, Viresolve™ filters from EMD Millipore, ViroSart CPV from Sartorius, or Ultipor DV20 or DV50™ filter from Pall Corporation. It will be apparent to one of ordinary skill in the art to select a suitable filter to obtain desired filtration performance.

I. Ultrafiltration/Diafiltration

Certain embodiments of the present invention employ ultrafiltration and diafiltration to further concentrate and formulate a protein of interest. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9); the entire teachings of which are incorporated herein by reference. One filtration process is Tangential Flow Filtration as described in the Millipore catalogue entitled "Pharmaceutical Process Filtration Catalogue" pp. 177-202 (Bedford, Mass., 1995/96), the entire teaching of which is incorporated herein by reference. Ultrafiltration is generally considered to mean filtration using filters with a pore size of smaller than 0.1μm. By employing filters having such a small pore size, the volume of sample can be reduced through permeation of the sample buffer through the filter membrane pores while proteins are retained above the membrane surface.

One of ordinary skill in the art can select an appropriate membrane filter device for the UF/DF operation. Examples of membrane cassettes suitable for the present invention include, but not limited to, Pellicon 2 or Pellicon 3 cassettes with 10 kD, 30 kD or 50 kD membranes from EMD Millipore, Kvick 10 kD, 30 kD or 50 kD membrane cassettes from GE Healthcare, and Centramate or Centrasette 10 kD, 30 kD or 50 kD cassettes from Pall Corporation.

J. Exemplary Production Strategies

Primary recovery can proceed by sequentially employing pH reduction, centrifugation, and filtration to remove cells and cellular debris (including HCPs) from a production bioreactor harvest. The present invention is directed to subjecting a biological sample comprising a protein of interest from the primary recovery to one or more production steps, including (in no particular order) AEX, CEX, SEC, HIC and/or MM. Certain aspects of the present invention include further processing steps. Examples of additional processing procedures include ethanol precipitation, isoelectric focusing, reverse phase HPLC, chromatography on silica, chromatography on heparin Sepharose™, further anion exchange chromatography and/or further cation exchange chromatography, chromatofocusing, SDS-PAGE, ammonium sulfate precipitation, hydroxyapatite chromatography, gel electrophoresis, dialysis, and affinity chromatography (e.g., using Protein A or G, an antibody, a specific substrate, ligand or antigen as the capture reagent). In certain aspects, the column temperature (as well as other parameters) can be independently varied to improve the separation efficiency and/or yield of any particular production step.

In certain embodiments, unbound flowthrough and wash fractions can be further fractionated and a combination of fractions providing a target product purity can be pooled.

Column loading and washing steps can be controlled by in-line, at-line or off-line measurement of the product related impurity/substance levels, either in the column effluent, or the collected pool or both, so as to achieve a particular target product quality and/or yield. In certain embodiments, the loading concentration can be dynamically controlled by in-line or batch or continuous dilutions with buffers or other solutions to achieve the partitioning necessary to improve the separation efficiency and/or yield.

Examples of such production procedures are depicted in FIGS. 5-8.

Figure 5:
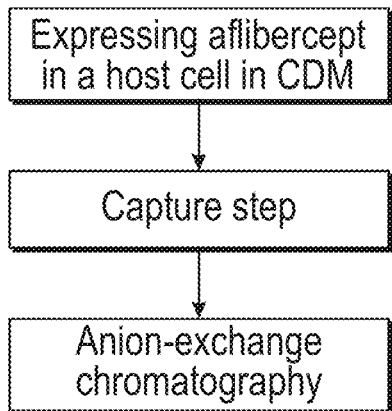
FIG. 5 depicts an exemplary embodiment for production of aflibercept.

FIG. 5 represents one exemplary embodiment used for the production of aflibercept. Referring to FIG. 5, the method comprises: (a) expressing aflibercept in a host cell cultured in a CDM; (b) capturing aflibercept using a first chromatography support, which can include affinity capture resin; and (c) contacting at least a portion of aflibercept with a second chromatography support, which can include anion-exchange chromatography. Step (c) can further comprise washing an AEX column and collecting flowthrough fraction(s) of a sample comprising aflibercept. Optionally, step (c) can comprise stripping the second chromatographic support and collecting stripped fractions. The steps can be carried out by routine methodology in conjunction with methodology mentioned supra. It should be understood that one skilled in the art might opt to employ CEX rather than or in addition to AEX. In no particular order, additional chromatographic steps may be employed as well including, but not limited to, HIC and SEC.

In addition to the exemplary embodiment in FIG. 5, other additional exemplary embodiments can include (d) contacting at least a portion of said aflibercept of step (c) with a third chromatography support. In one aspect, the protocol can include (e) contacting at least a portion aflibercept of step (d) with a fourth chromatography support. In one aspect of this embodiment, the protocol can optionally comprise subjecting the sample comprising aflibercept of step (c) to a pH less than 5.5. In one aspect, the present method comprises a clarification step prior to step (a).

Figure 6:
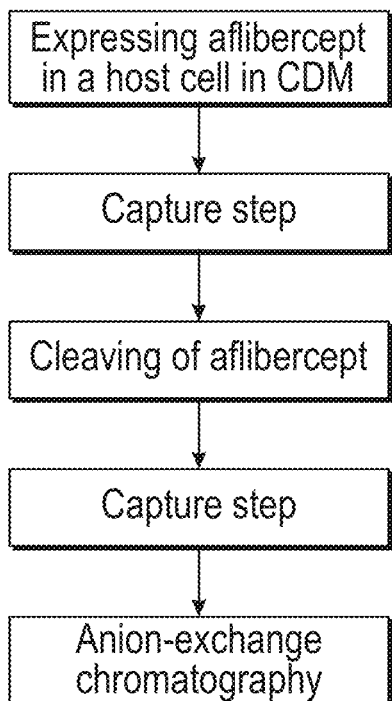
FIG. 6 depicts an exemplary embodiment for production of VEGF MiniTrap.

FIG. 6 represents one exemplary embodiment used for the production of VEGF MiniTrap. This method comprises: (a) expressing aflibercept in a host cell cultured in a CDM; (b) capturing aflibercept using a first chromatography support which can include affinity chromatography resin; (c) cleaving the aflibercept thereby removing the Fc domain and forming a sample comprising VEGF MiniTrap; (d) contacting the sample of step (c) with a second chromatographic support which can be affinity chromatography and (e) contacting the flowthrough of step (d) to a third chromatography support which can include an anion-exchange chromatography. Step (d) comprises the collection of flowthrough fraction(s) where due to the absence of an Fc domain, the MiniTrap should reside while the aflibercept or any other protein having an Fc domain should essentially interact with the affinity column of step (d). Optionally, step (d) can comprise stripping the third chromatographic support and collecting stripped fractions. The steps can be carried out by routine methodology in conjunction with methodology outlined above. In no particular order, additional chromatographic steps can be employed including, but not limited to, HIC and SEC.

Figure 7:
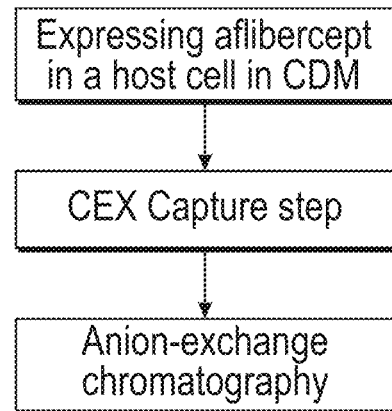
FIG. 7 depicts an exemplary embodiment for production of aflibercept.

FIG. 7 represents one exemplary embodiment for the production of aflibercept. This method comprises: (a) expressing aflibercept in a host cell cultured in a CDM; (b) capturing aflibercept using a first chromatography support, which can include cation exchange chromatography; and (c) contacting a flowthrough of step (b) to a second chromatography support which can include an anion-exchange chromatography. Optionally, step (c) can comprise stripping the second chromatographic support and collecting stripped fractions. The steps can be carried out by routine methodology in conjunction with protocols alluded to above. In no particular order, other chromatographic procedures may be employed including, but not limited to, HIC and SEC.

Figure 8:
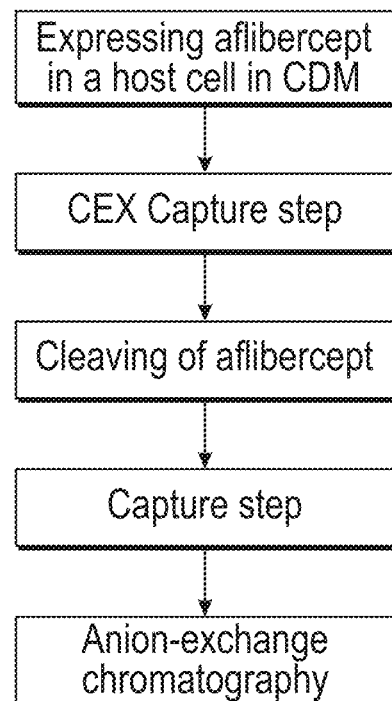
FIG. 8 depicts an exemplary embodiment for production of VEGF MiniTrap.

FIG. 8 represents one exemplary embodiment for producing VEGF MiniTrap. This method comprises: (a) expressing aflibercept in a host cell cultured in a CDM; (b) capturing aflibercept using a first chromatography support which can include an ion exchange chromatography; (c) subjecting a flowthrough fraction of (b) comprising aflibercept to affinity chromatography; eluting, wherein the elution comprises aflibercept; (d) subjecting the aflibercept of (c) to a cleavage activity, whereby the Fc domain is cleaved thus forming VEGF MiniTrap. In one aspect, the ion exchange of step (b) comprises AEX. Alternatively, step (b) may comprise CEX. In no particular order, additional chromatographic steps may be included such as further ion exchange chromatography steps following step (d), the addition of HIC and/or SEC.

VII. Pharmaceutical Formulations Comprising the Compositions

The invention also discloses formulations comprising anti-VEGF compositions (as described above). Suitable formulations for anti-VEGF proteins include, but are not limited to, formulations described in U.S. Pat. Nos. 7,608,261, 7,807,164, 8,092,803, 8,481,046, 8,802,107, 9,340,594, 9,914,763, 9,580,489, 10,400,025, 8,110,546, 8,404,638, 8,710,004, 8,921,316, 9,416,167, 9,511,140, 9,636,400, and 10,406,226, which are all incorporated herein by reference in their entirety.

The upstream process technologies (described in Section IV, supra) and downstream process technologies (described in Section V, supra) may be used alone or in combination with each other to effect formulation production.

The present invention discloses formulations comprising anti-VEGF compositions in association with one or more ingredients/excipients as well as methods of use thereof and methods of making such compositions. In an embodiment of the invention, a pharmaceutical formulation of the present invention has a pH of approximately 5.5, 5.6, 5.7, 5.8, 5.9, 6.0, 6.1 or 6.2.

To prepare pharmaceutical formulations for anti-VEGF compositions, an anti-VEGF composition is admixed with a pharmaceutically acceptable carrier or excipient. See, for example, Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, N.Y.; Weiner and Kotkoskie (2000) Excipient Toxicity and Safety, Marcel Dekker, Inc., New York, N.Y.; the entire teachings of which are incorporated herein by reference. In an embodiment of the invention, the pharmaceutical formulation is sterile.

Pharmaceutical formulations of the present invention include an anti-VEGF composition and a pharmaceutically acceptable carrier including, for example, water, buffering agents, preservatives and/or detergents.

The present invention provides a pharmaceutical formulation comprising any of the anti-VEGF compositions set forth herein and a pharmaceutically acceptable carrier, for example, wherein the concentration of polypeptide is about 40 mg/mL, about 60 mg/mL, about 80 mg/mL, about 90 mg/mL, about 100 mg/mL, about 110 mg/mL, about 120 mg/mL, about 130 mg/mL, about 140 mg/mL, about 150 mg/mL, about 200 mg/mL or about 250 mg/mL.

The scope of the present invention includes desiccated, for example, freeze-dried, compositions comprising an anti-VEGF protein and a pharmaceutically acceptable carrier substantially (about 85% to about 99% or greater) lacking water.

In one embodiment, a further therapeutic agent that is administered to a subject in association with an anti-VEGF composition disclosed herein is administered to the subject in accordance with the Physicians' Desk Reference 2003 (Thomson Healthcare; 57th edition (Nov. 1, 2002), the teaching of which is incorporated herein by reference).

The present invention provides a vessel (e.g., a plastic or glass vial with a cap or a chromatography column, hollow bore needle or a syringe cylinder) comprising any of the anti-VEGF compositions or a pharmaceutical formulation comprising a pharmaceutically acceptable carrier described herein. The present invention also provides an injection device comprising the anti-VEGF composition or formulation set forth herein, for example, a syringe, a pre-filled syringe or an autoinjector. In one aspect, the vessel is tinted (e.g., brown) to block out light, natural or otherwise.

The present invention includes combinations including anti-VEGF compositions in association with one or more further therapeutic agents. The anti-VEGF composition and the further therapeutic agent can be in a single composition or in separate compositions. For example, the therapeutic agent is an Ang-2 inhibitor (e.g., nesvacumab), a Tie-2 receptor activator, an anti-PDGF antibody or antigen-binding fragment thereof, an anti-PDGF receptor or PDGF receptor beta antibody or antigen-binding fragment thereof and/or an additional VEGF antagonist such as aflibercept, conbercept, bevacizumab, ranibizumab, an anti-VEGF aptamer such as pegaptanib (e.g., pegaptanib sodium), a single chain (e.g., VL-VH) anti-VEGF antibody such as brolucizumab, an anti-VEGF DARPin such as the Abicipar Pegol DARPin, a bispecific anti-VEGF antibody, for example, which also binds to ANG2, such as RG7716, or a soluble form of human vascular endothelial growth factor receptor-3 (VEGFR-3) comprising extracellular domains 1-3, expressed as an Fc-fusion protein.

VIII. Methods of Treatment

The present invention provides methods for treating or preventing a cancer (e.g., whose growth and/or metastasis is mediated, at least in part, by VEGF, for example, VEGF-mediated angiogenesis) or an angiogenic eye disorder, in a subject, comprising administering a therapeutically effective amount of compositions as disclosed herein (Section III supra).

Upstream process technologies (Section IV supra), downstream process technologies (Sections V and VI supra) may be used alone or in combination with the each other to produce the compositions as described in Section III and/or the formulations as described in Section VII which can be used for treating or preventing a variety of disorders including ophthalmological and oncological disease.

The present invention also provides a method for administering compositions set forth herein (Section III and Section VII) to a subject (e.g., a human) comprising introducing the compositions with about 0.5 mg, 2 mg, 4 mg, 6 mg, 8 mg, 10 mg, 12 mg, 14 mg, 16 mg, 18 mg or 20 mg of the protein of interest (e.g., aflibercept or MiniTrap) in no more than about 100 µL, for example, about 50 µL, about 70 µL or about 100 µL, and optionally a further therapeutic agent, into the body of the subject by, for example, intraocular injection such as by intravitreal injection.

The present invention provides a method for treating cancer whose growth and/or metastasis is mediated, at least in part, by VEGF, for example, VEGF-mediated angiogenesis or an angiogenic eye disorder in a subject in need thereof, the method comprising administering a therapeutically effective amount of the compositions set forth herein (Section III and Section VII above), for example, 2 mg, 4 mg, 6 mg, 8 mg or 10 mg of the protein of interest, in no more than about 100 µl, and optionally a further therapeutic agent, to a subject. In one embodiment of the invention, administration is done by intravitreal injection. Non-limiting examples of angiogenic eye disorders that are treatable or preventable using the methods herein, include:

- age-related macular degeneration (e.g., wet or dry),
- macular edema,
- macular edema following retinal vein occlusion,
- retinal vein occlusion (RVO),
- central retinal vein occlusion (CRVO),
- branch retinal vein occlusion (BRVO),
- diabetic macular edema (DME),
- choroidal neovascularization (CNV),
- iris neovascularization,
- neovascular glaucoma,
- post-surgical fibrosis in glaucoma,
- proliferative vitreoretinopathy (PVR),
- optic disc neovascularization,
- corneal neovascularization,
- retinal neovascularization,
- vitreal neovascularization,
- pannus,
- pterygium,
- vascular retinopathy,
- diabetic retinopathy in a subject with diabetic macular edema; and
- diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME).

The mode of administration of such compositions or formulations (Section III and Section VII) can vary and can be determined by a skilled practitioner. Routes of administration include parenteral, non-parenteral, oral, rectal, transmucosal, intestinal, parenteral, intramuscular, subcutaneous, intradermal, intramedullary, intrathecal, direct intraventricular, intravenous, intraperitoneal, intranasal, intraocular, inhalation, insufflation, topical, cutaneous, intraocular, intravitreal, transdermal or intra-arterial.

In one embodiment of the invention, intravitreal injection of a pharmaceutical formulation of the present invention (which includes a compositions or formulations of the present invention) includes the step of piercing the eye with a syringe and needle (e.g., 30-gauge injection needle) comprising the formulation and injecting the formulation (e.g., less than or equal to about 100 microliters; about 40, 50, 55, 56, 57, 57.1, 58, 60 or 70 microliters) into the vitreous of the eye with a sufficient volume as to deliver a therapeutically effective amount as set forth herein, for example, of about 2, 4, 6, 8.0, 8.1, 8.2, 8.3, 8.4, 8.5, 8.6, 8.7, 8.8, 8.9, 10 or 20 mg of the protein of interest. Optionally, the method includes the steps of administering a local anesthetic (e.g., proparacaine, lidocaine or tetracaine), an antibiotic (e.g., a fluoroquinolone), antiseptic (e.g., povidone-iodine) and/or a pupil dilating agent to the eye being injected. In one aspect, a sterile field around the eye to be injected is established before the injection. Following intravitreal injection, the subject is monitored for elevations in intraocular pressure, inflammation and/or blood pressure.

An effective or therapeutically effective amount of protein of interest for an angiogenic eye disorder refers to the amount of the protein of interest sufficient to cause the regression, stabilization or elimination of the cancer or angiogenic eye disorder, for example, by regressing, stabilizing or eliminating one or more symptoms or indicia of the cancer or angiogenic eye disorder by any clinically measurable degree, for example, with regard to an angiogenic eye disorder, by causing a reduction in or maintenance of diabetic retinopathy severity score (DRSS), by improving or maintaining vision (e.g., in best corrected visual acuity as measured by an increase in ETDRS letters), increasing or maintaining visual field and/or reducing or maintaining central retinal thickness and, with respect to cancer, stopping or reversing the growth, survival and/or metastasis of cancer cells in the subject.

In one embodiment of the invention, an effective or therapeutically effective amount of a protein of interest such as aflibercept for treating or preventing an angiogenic eye disorder is about 0.5 mg, 2 mg, 3 mg, 4 mg, 5 mg, 6 mg, 7 mg, 7.25 mg, 7.7 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9 mg, 10 mg, 11 mg, 12 mg, 13 mg, 14 mg, 15 mg, 16 mg, 17 mg, 18 mg, 19 mg or 20 mg, e.g., in no more than about 100 µL. The amount may vary depending upon the age and the size of a subject to be administered, target disease, conditions, route of administration, and the like. In certain exemplary embodiments, the initial dose may be followed by administration of a second or a plurality of subsequent doses of the protein of interest in an amount that can be approximately the same or less or more than that of the initial dose, wherein the subsequent doses are separated by at least 1 day to 3 days; at least one week, at least 2 weeks, at least 3 weeks, at least 4 weeks, at least 5 weeks, at least 6 weeks, at least 7 weeks, at least 8 weeks, at least 9 weeks, at least 10 weeks, at least 12 weeks, or at least 14 weeks.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

IX. Method of Assaying Protein Variants

The levels of protein variants in a chromatographic sample produced using the techniques described herein may be analyzed as described in the Examples below. In certain embodiments, a cIEF method is employed using an iCE3 analyzer (ProteinSimple) with a fluorocarbon coated capillary cartridge (100µπιx5 cm). The ampholyte solution consists of a mixture of 0.35% methyl cellulose (MC), 4% Pharmalyte 3-10 carrier ampholytes, 4% Pharmalyte 5-8 carrier ampholytes, 10 mM L-Arginine HCl, 24% formamide, and pI markers 5.12 and 9.77 in purified water. The anolyte was 80 mM phosphoric acid, and the catholyte was 100 mM sodium hydroxide, both in 0.10% methylcellulose. Samples were diluted in purified water to 10 mg/mL. Samples were mixed with the ampholyte solution and then focused by introducing a potential of 1500 V for one minute, followed by a potential of 3000 V for 7 minutes. An image of the focused variants was obtained by passing 280 nm ultraviolet light through the capillary and into the lens of a charge coupled device digital camera. This image was then analyzed to determine the distribution of the various charge variants. Persons of skill in the art may vary the precise parameters while still achieving the desired outcome.

Various publications, including patents, patent applications, published patent applications, accession numbers, technical articles and scholarly articles are cited throughout the specification. Each of these cited references is incorporated by reference, in its entirety.

The present invention will be more fully understood by reference to the following Examples. They should not, however, be construed as limiting the scope of the invention.

EXAMPLES

The MiniTraps (MT) 1-6 discussed in the Examples are as follows:
- MT1: VEGF MiniTrap obtained by cleavage of aflibercept produced using CDM1.
- MT2: VEGF MiniTrap obtained by cleavage of aflibercept produced using CDM2.
- MT3: VEGF MiniTrap obtained by cleavage of aflibercept produced using CDM3.
- MT4: VEGF MiniTrap obtained by cleavage of aflibercept produced using soy hydrolysate.
- MT5: recombinant VEGF MiniTrap (dimer).
- MT6: recombinant VEGF MiniTrap (scFv).

Characterization of MT1, MT5 and MT6 are described below in Example 8.

Color Assessment of Samples

The spectrophotometric assay method of measuring the b* value (CIELAB) was found suitable for performing color assessment.

The absorbance of a 1 mL protein sample was quantified over the visible light spectrum (380 to 780 nm) and the absorbance curve was transformed into the CIELAB color space using a set of matrix operations. The instrument can process approximately 6 samples per hour. The high throughput format of the assay used a CLARIOstar plate reader (BMG Labtech). Up to 96 samples can be analyzed using a 96-well plate requiring 0.3 mL of sample.

To convert the BY standards into the b* values, BY reference standards (BY1 to BY7) were quantified using the high throughput assay format.

Figure 9:
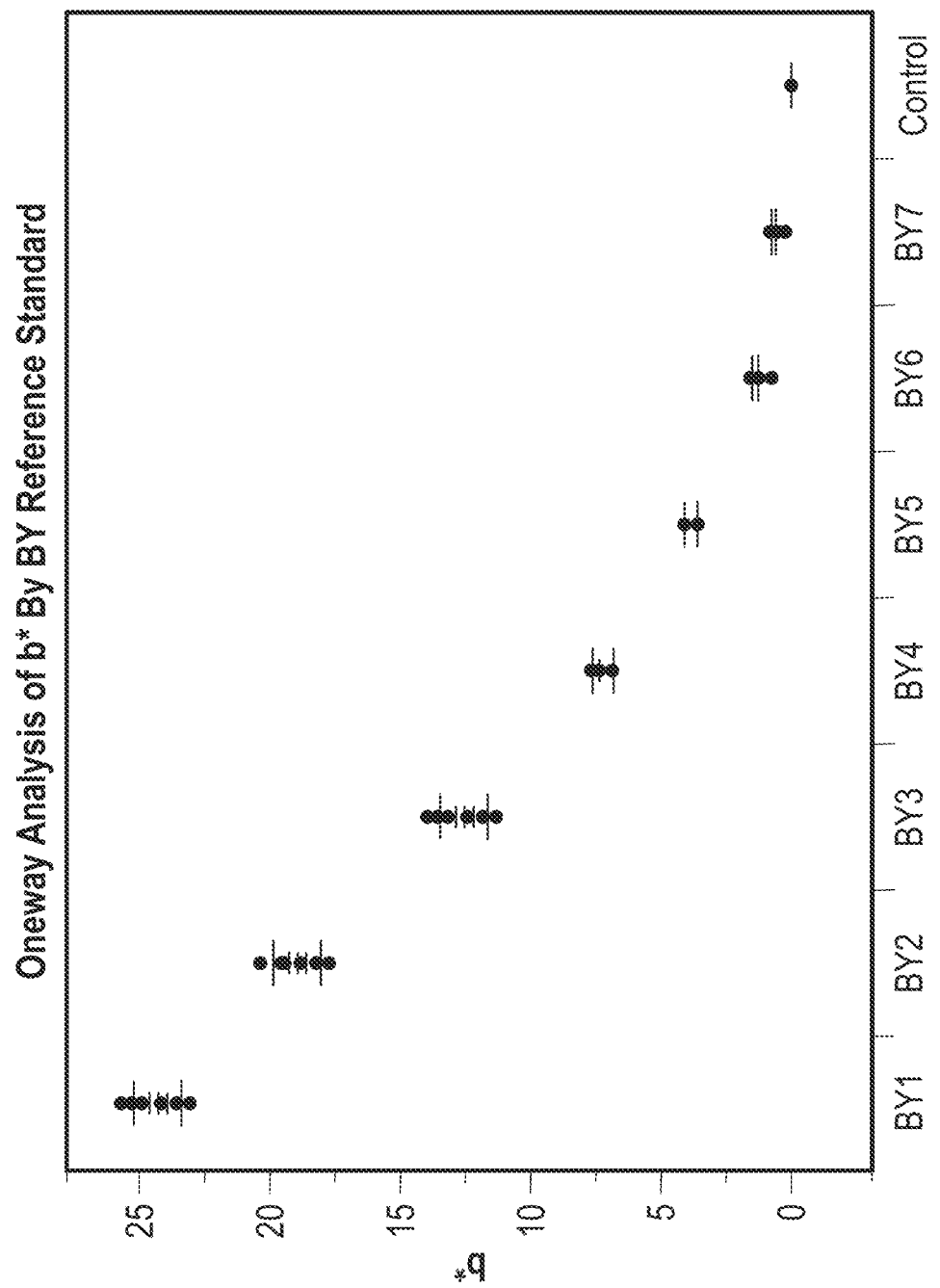
FIG. 9 depicts a chart of calculated BY standards versus b* value calculated according to an exemplary embodiment.

The solutions were prepared as per the BY standards discussed above. The b* value for each of the standards are as shown in FIG. 9. This method provided a faster assay with a smaller sample requirement and shorter run times as shown in Table 3 below. For all the samples evaluated using this method, the protein concentration of the test samples was standardized to either 5 g/L or 10 g/L.

TABLE 3

| | Original | High-throughput |
|---|---|---|
| Amount/Sample | 1 mL | 0.3 mL |
| Measurement Format | cuvette (individual) | 96-well-plate (bulk) |
| Run Time | 6 samples per hour | 96 samples per 5 minutes |
| Data Entry | manual | automated |
| Data Storage | Excel | LIMS |

Example 1: Production of a Protein Using a Chemically Defined Medium 1.1 Cell Source and Harvest An aflibercept producing cell line was employed in the present study. Aflibercept producing cell lines were cultured and harvested using chemically defined media (CDM).

1.2 Proteolytic Cleavage of Aflibercept

A column with an immobilized IdeS enzyme (FabRICATOR® obtained from Genovis (Cambridge, MA)) was used to generate MT1. Aflibercept obtained from a cell culture harvest (20 mg in 1.0 mL cleavage buffer) was added to the column and incubated for 30 min at 18° C. After 30 min, the column was washed with the cleavage buffer (1.0 mL). The digestion mixture and washing solutions were combined. The mixture was loaded onto and eluted from an analytical Protein A affinity column (Applied Biosystems™, POROS™ 20 μM Protein A Cartridge 2.1×30 mm, 0.1 mL (Cat #2-1001-00)). The processing was carried out according to Applied Biosystems'™ protocol for POROS™ 20 μM Protein A Cartridge 2.1×30 mm, 0.1 mL (Cat #2-1001-00). The column height was 20±1.0 cm, residence time was 15 minutes and equilibration/wash was performed using 40 mM Tris, 54 mM Acetate pH 7.0±0.1.

Example 2. Anion Exchange Chromatography (AEX) for Color Minimization (A) AEX was Employed to Reduce Color Formation AEX chromatography was performed to remove the coloration obtained during production of aflibercept expressed using CDM1.

2.1 Design

Five AEX separations were performed for this study as detailed in Table 2-1 with the AEX protocol as described in Table 2-2. A 15.7 mL Q Sepharose Fast Flow column (19.5 cm bed height, 1.0 cm I.D.) and a 14.1 mL POROS 50 HQ column (18.0 cm bed height, 1.0 cm I.D.) were integrated into an AKTA Avant benchtop liquid chromatography controller.

AEX load pH was adjusted to target+0.05 pH units using 2 M Tris base or 2 M acetic acid. AEX load conductivity was adjusted to target+0.1 mS/cm using 5 M sodium chloride or deionized water. All pool samples were analyzed for high molecular weight (HMW), color and yield.

TABLE 2-1

Summary of the Study Design for AEX Color Reduction

| AEX Separation | Condition Evaluated | Resin |
|---|---|---|
| 1 | pH 8.30-8.50, 1.90-2.10 mS/cm | POROS 50 HQ |
| 2 | pH 7.90-8.10, 2.40-2.60 mS/cm | Q Sepharose FF |
| 3 | pH 7.90-8.10, 2.40-2.60 mS/cm | POROS 50 HQ |
| 4 | pH 7.70-7.90, 3.90-4.10 mS/cm | Q Sepharose FF |
| 5 | pH 7.70-7.90, 3.90-4.10 mS/cm | POROS 50 HQ |

TABLE 2-2

AEX Protocol for Color Reduction

| Step | Description | Mobile Phase | Column Volumes (CVs) | Linear Velocity (cm/h) |
|---|---|---|---|---|
| 1 | Pre-Equilibration | 2M Sodium Chloride (NaCl) | 2 | 200 |

TABLE 2-2-continued

AEX Protocol for Color Reduction

| Step | Description | Mobile Phase | Column Volumes (CVs) | Linear Velocity (cm/h) |
|---|---|---|---|---|
| 2 | Equilibration | 50 mM Tris, Variable mM NaCl Variable pH and Conductivity | 2 | 200 |
| 3 | Load | AEX Load Variable pH and Conductivity | 40 g/L-resin | 200 |
| 4 | FT/Wash | 50 mM Tris, Variable mM NaCl Variable pH and Conductivity | 2 | 200 |
| 5 | Strip 1 | 2M Sodium Chloride (NaCl) | 2 | 200 |
| 6 | Strip 2 | 1N Sodium Hydroxide (NaOH) | 2 | 200 |

2.2 Results

Employing AEX separations for production exhibited a significant reduction in color. (Table 2-3). For example, as seen in Table 2-3, the color observed in the flowthrough (FT) and wash in AEX separation 1 (pH 8.30-8.50, 1.90-2.10 mS/cm) had a b* value of 1.05, as compared to the color of the Load for AEX ("AEX Load") with a b* value of 3.06. The increase in b* value reflects the intensity of yellow-brown coloration of a sample.

Five AEX separations were performed to evaluate the impact of resin (Q Sepharose FF or POROS 50 HQ) and pH and conductivity setpoint (pH 8.40 and 2.00 mS/cm, pH 8.00 and 2.50 mS/cm, or pH 7.80 and 4.00 mS/cm) on color reduction. For POROS 50 HQ, yields (64.4, 81.9, and 91.4%) and pool HMW levels (1.02, 1.29, and 1.83%) increased as the setpoint was changed to a lower pH and higher conductivity. Color (b* values) also increased (1.05, 1.33, and 1.55) as the setpoint was changed to a lower pH and higher conductivity. The higher pH levels and lower conductivities provided the most reduction in color over the AEX separation for POROS 50 HQ.

For Q Sepharose Fast Flow, yields (49.5 and 77.7%) and pool HMW levels (0.59 and 1.25%) also increased as the setpoint was changed to a lower pH and higher conductivity. Color (b* values) also increased (0.96 and 1.35) as the setpoint was changed to a lower pH and higher conductivity.

The use of AEX reduces yellow-brown coloration-see Table 2-3. Additionally, it was determined that Q Sepharose Fast Flow reduced color more than POROS 50 HQ for the two set points evaluated on both resins. At pH 8.00 and 2.50 mS/cm setpoint, POROS 50 HQ pool had a b* value of 1.33 while Q Sepharose Fast Flow pool had a b* value of 0.96. Similarly, at pH 7.80 and 4.00 mS/cm setpoint, POROS 50 HQ pool had a b* value of 1.55 while Q Sepharose Fast Flow pool had a b* value of 1.35 (Table 2-3).

TABLE 2-3

Summary of Experimental Results of the AEX Color Reduction Study

| AEX Separation | Fraction | Yield (%) | HMW (%) | Color (L*) | Color (a*) | Color (b*) |
|---|---|---|---|---|---|---|
| 1 | FT/wash | 64.4 | 1.02 | 98.89 | 0.01 | 1.05 |
| 2 | FT/wash | 49.5 | 0.59 | 98.30 | −0.03 | 0.96 |
| 3 | FT/wash | 81.9 | 1.29 | 99.07 | −0.07 | 1.33 |
| 4 | FT/wash | 77.7 | 1.25 | 99.42 | −0.04 | 1.35 |
| 5 | FT/wash | 91.4 | 1.83 | 99.19 | −0.09 | 1.55 |
| — | filtered pool (AEX Load) | — | 3.66-3.98 | 98.73 | −0.21 | 3.06 |

AEX, anion exchange chromatography;
HMW, high molecular weight species;
N/A, not applicable
The fractions were adjusted to a protein concentration of 10 g/L for color measurements.

2.3 Conclusion

Use of AEX was found to reduce the yellow-brown coloration, see Table 2-3. Referring to Table 2-3, the AEX Load has a b* value of 3.06, but when subjected to AEX chromatography (AEX Separation 1-5), the b* value decreases indicating a decrease in yellow-brown coloration. Again, as the b* value decreases so does the coloration; as the b* value increases it is reflective of the yellow-brown color increasing in a given sample.

Color reduction was evaluated using two AEX resins (POROS 50 HQ and Q Sepharose Fast Flow) and three set points (pH 8.40 and 2.00 mS/cm, pH 8.00 and 2.50 mS/cm, and pH 7.80 and 4.00 mS/cm). For both resins, color reduction was higher for the higher pH and lower conductivity set points. In addition, Q Sepharose Fast Flow provided more color reduction than POROS 50 HQ at the two set points evaluated on both resins (pH 8.00 and 2.50 mS/cm and pH 7.80 and 4.00 mS/cm). However, all the five AEX separation methods led to a significant color reduction when compared to the loading solution for AEX ("AEX Load"), demonstrating the importance of AEX production in the process of aflibercept production expressed using a CDM. The initial b* value of the AEX Load (at a concentration of 10 g/L) may range from about 0.5 to about 30, more particularly from about 1.0 to about 25.0, and even more particularly from about 2.0 to about 20.0. Following use of AEX, the b* value for the flowthrough (at a concentration of 10 g/L) may range from 0.5 to about 10.0, more particularly from about 0.5 to about 7.0, and even more particularly from about 0.5 to about 5.0.

2.4 Peptide Mapping

Sample preparation. Tryptic mapping of reduced and alkylated aflibercept samples obtained from AEX Load and flowthrough of the above experiment (Table 2-3) were performed to identify and quantify post-translational modification (PTM). An aliquot of each sample (Load and flowthrough) was denatured using 8.0 M Urea, 0.1 M Tris-HCl, pH 7.5, reduced with DTT and then alkylated with iodoacetamide. The denatured, reduced and alkylated sample was first digested with recombinant Lys-C (rLys-C) at an enzyme to substrate ratio of 1:100 (w/w) at 37° C. for 30 minutes, diluted with 0.1 M Tris-HCl, pH 7.5 such that a final urea concentration was 1.8 M, subsequently digested with trypsin at an enzyme to substance ratio of 1:20 (w/w) at 37° C. for 2 hours and then deglycosylated with PNGase F at an enzyme substrate ratio of 1:5 (w/w) for 37° C. for 1 hour. The digestion was stopped by bringing the pH below 2.0 using formic acid (FA).

Figure 10:
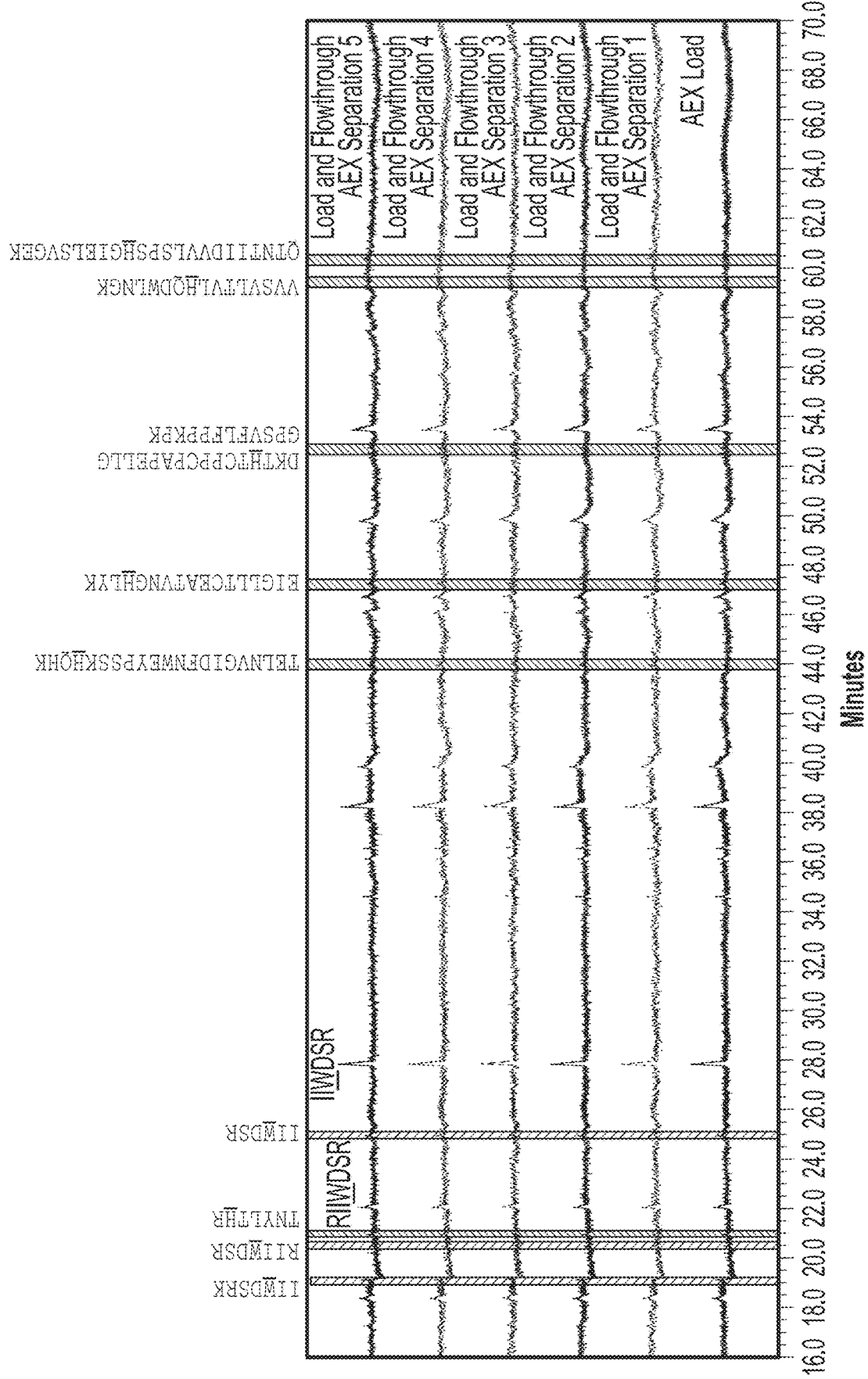
FIG. 10 depicts results of an experiment performed to evaluate the percentage of 2-oxo-histidines and tryptophan oxidation (where underscoring represents oxidation of the residue) in oligopeptides from protease-digested AEX load and flowthrough, including fragments of reduced and alkylated aflibercept (SEQ ID NO.: 55), including SEQ ID NOS 114-115, 21, 115, 28, 28, 20, 18, 17, 116-117, and 19, respectively, in order of appearance.

LC-MS analysis. A 20 µg aliquot of resulting rLys-C/tryptic peptides from each sample was separated and analyzed by reverse-phase ultra-performance liquid chromatography (UPLC) using Waters ACQUITY UPLC CSH C18 column (130 Å, 1.7 µm, 2.1×150 mm) followed by on-line PDA detection (at wavelengths of 280 nm, 320 nm and 350 nm) and mass spectrometry analysis. Mobile phase A was 0.1% FA in water, and mobile phase B was 0.1% FA in acetonitrile. After sample injection, a gradient was initiated with a 5 minute hold at 0.1% B followed by a linear increase to 35% B over 75 minutes for optimum peptide separation. MS and MS/MS experiments were conducted using a Thermo Scientific Q Exactive Hybrid Quadrupole-Orbitrap mass spectrometer with higher-energy collisional dissociation (HCD) employed for peptide fragmentation for MS/MS experiments. Peptide identity assignments were based on the experimentally determined accurate mass of a given peptide in the full MS spectrum as well as the b and y fragment ions in the corresponding HCD MS/MS spectrum. Extracted ion chromatograms of the peptides from the Load and flowthrough were generated (see FIG. 10). As seen in the extracted ion chromatogram in FIG. 10, the peptide fragments identified in "AEX Load" and "AEX FT/wash" from AEX separations 1-5 (as identified in Table 2-3) are shown. The relative abundance of some of these peptides identified in FIG. 10 from the peptide mapping analysis are shown in FIG. 11.

Referring to FIG. 11, this figure identifies various peptide fragments analyzed and their relative levels of oxidation. In particular, the third column identifies the amino acid residues ("Peptide Sequence") of peptide fragments that were isolated and analyzed. Each Peptide Sequence has an amino acid residue that is underscored. The underscored amino acid residue identifies the amino acid in the Peptide Sequence that is oxidized. The oxidized amino acids correspond to either histidine (H) oxidation or tryptophan (W) oxidation. There is also depicted in this figure rows to the right of each of the Peptide Sequences showing the abundance of oxidized species. This shading in the rows indicates differences in the relative amount of oxidized residues in a particular sample using different AEX separations identified in the respective column headings. For example, referring to the second peptide, EIGLLTCEATVNGHLYK (SEQ ID NO.: 18) in FIG. 11, when read across along in a horizontal manner, the relative total population of this peptide in a particular sample ("aflibercept AEX Load") that is oxidized is approximately 0.013% oxidized. As progression is made across the same row, there is a shift in the shading, indicating a change in the relative abundance of oxidized species. For example, using this same Peptide Sequence, the relative abundance of oxidized species for AEX separation are 0.006% to 0.010% when following different AEX separation protocols. Thus, it can be appreciated that AEX chromatography decreases the abundance of oxidized species.

(B) AEX was Employed to Reduce the Color Formation in MiniTrap Production

AEX chromatography was performed to remove the coloration obtained during production of MT1 which was obtained on performing cleavage of full-length aflibercept expressed using CDM1.

2.5 Design

Four AEX separations were performed for this study as described in Table 2-4. The AEX Load was obtained from a filtration sample of MT1 ("MT1 filtered pool"). A 15.7 mL Capto Q column (20.0 cm bed height, 1.0 cm I.D.), a 14.1 mL POROS 50 HQ column (18.0 cm bed height, 1.0 cm I.D.), and a 16.5 mL Q Sepharose FF column (21.0 cm bed height, 1.0 cm I.D.) were integrated into an AKTA Avant benchtop liquid chromatography controller for this experiment.

AEX load pH was adjusted to target±0.05 pH units using 2 M tris base or 2 M acetic acid. AEX load conductivity was adjusted to target±0.1 mS/cm using 5 M sodium chloride or deionized water. All pool samples were analyzed for HMW, color and yield.

TABLE 2-4

Summary of the Study Design for the AEX Color Reduction Study

| AEX Separation | Resin | AEX Protocol |
|---|---|---|
| 1 | Capto Q | Table 2-6 |
| 2 | POROS 50 HQ | Table 2-6 |
| 3 | Q Sepharose FF | Table 2-6 |
| 4 | POROS 50 HQ | Table 2-5 |

TABLE 2-5

Flowthrough AEX Protocol Used for the Color Reduction Study

| Step | Description | Mobile Phase | Column Volumes (CVs) | Linear Velocity (cm/h) |
|---|---|---|---|---|
| 1 | Pre-Equilibration | 2M Sodium Chloride (NaCl) | 2 | 200 |
| 2 | Equilibration | 50 mM Tris, 40 mM NaCl pH 7.90-8.10, 6.50-7.50 mS/cm | 2 | 200 |
| 3 | Load | AEX Load pH 7.90-8.10, 6.50-7.50 mS/cm | 30 g/L-resin | 200 |
| 4 | Wash | 50 mM Tris, 40 mM NaCl pH 7.90-8.10, 6.50-7.50 mS/cm | 2 | 200 |
| 5 | Strip 1 | 2M Sodium Chloride (NaCl) | 2 | 200 |
| 6 | Strip 2 | 1N Sodium Hydroxide (NaOH) | 2 | 200 |

AEX, anion exchange chromatography;
CV, column volume

TABLE 2-6

Bind and Elute AEX Protocol Used for the Color Reduction Study

| Step | Description | Mobile Phase | Column Volumes (CVs) | Linear Velocity (cm/h) |
|---|---|---|---|---|
| 1 | Pre-Equilibration | 2M Sodium Chloride (NaCl) | 2 | 200 |
| 2 | Equilibration | 50 mM Tris pH 8.30-8.50, 1.90-2.10 mS/cm | 2 | 200 |
| 3 | Load | AEX Load pH 8.30-8.50, 1.90-2.10 mS/cm | 30 g/L-resin | 200 |
| 4 | Wash | 50 mM Tris pH 8.30-8.50, 1.90-2.10 mS/cm | 2 | 200 |
| 5 | Elution | 50 mM Tris, 70 mM NaCl pH 8.30-8.50, 8.50-9.50 mS/cm | 2 | 200 |
| 6 | Strip 1 | 2M Sodium Chloride (NaCl) | 2 | 200 |
| 7 | Strip 2 | 1N Sodium Hydroxide (NaOH) | 2 | 200 |

AEX, anion exchange chromatography;
CV, column volume 2.6 Results

All four AEX separations led to reduction in color as seen for coloration of the flowthrough and wash for AEX separations 1-4 (Table 2-7). While the first three AEX separations were evaluated in a bind and elute mode (Table 2-6), it was observed that the majority of the product was present in the load and wash blocks (62%-94%).

The first three separations evaluated the pH 8.4 and 2.0 mS/cm setpoint for Capto Q, POROS 50 HQ, and Q Sepharose FF resins. All three separations had a good yield (>80%). The POROS 50 HQ AEX pool showed the lowest yellow color in AEX pool (b* value of 2.09) followed by the Q Sepharose FF AEX pool (b* value of 2.22) and the Capto Q AEX pool (b* value of 2.55).

TABLE 2-7

Summary of Experimental Results of the AEX Color Reduction Study

| AEX Separation | Fraction | Yield (%) | HMW (%) | Color (L*) | Color (a*) | Color (b*) |
|---|---|---|---|---|---|---|
| 1 | FT/wash | 90.7 | 0.49 | 99.11 | −0.27 | 2.55 |
| 2 | FT/wash | 93.8 | 0.33 | 99.20 | −0.28 | 2.09 |
| 3 | FT/wash | 86.7 | 0.23 | 98.88 | −0.23 | 2.22 |
| 4 | FT/wash | 99.5 | 1.13 | 98.90 | −0.39 | 3.40 |
| — | MT1 Filtered Pool (AEX Load) | — | 0.65 | 98.18 | −0.37 | 4.17 |

AEX, anion exchange chromatography; HMW, high molecular weight species.
The fractions were adjusted to a protein concentration of 5 g/L for color measurements.

2.7 Conclusion

As seen for aflibercept (see Section 2.3 above), use of AEX was found to reduce yellow-brown coloration (Table 2-7) for MiniTrap production. Referring to Table 2-7, the AEX Load has a b* value of 4.17, but when subjected to AEX chromatography (AEX Separation 1-4), the b* value decreases indicating a decrease in yellow-brown coloration. Again, as the b* value decreases so too does the coloration. The initial b* value of the AEX Load (at a concentration of 5 g/L) may range from about 0.5 to about 25, more particularly from about 1.0 to about 20.0, and even more particularly from about 1.5 to about 15.0. Following use of AEX, the b* value of the flowthrough (at a concentration of 5 g/L) may range from 0.5 to about 10.0, more particularly from about 0.5 to about 7.0, and even more particularly from about 0.5 to about 5.0.

Example 3. Oxidized Peptide Study 3.1 Peptide Mappings

Sample Preparation. Tryptic mapping of reduced and alkylated MiniTrap (MT1) and MT4 (MiniTrap similar to MT1 using a different full-length aflibercept one produced using soy hydrolysate cell culture) samples were performed to identify and quantify post-translational modification. An aliquot of sample was denatured using 8.0 M Urea in 0.1 M Tris-HCl, pH 7.5, reduced with DTT and then alkylated with iodoacetamide. The denatured, reduced and alkylated drug substance was first digested with recombinant Lys-C (rLys-C) at an enzyme to substrate ratio of 1:100 (w/w) at 37° C. for 30 minutes, diluted with 0.1 M Tris-HCl, pH 7.5 such that the final urea concentration was 1.8 M, subsequently digested with trypsin at an enzyme to substance ratio of 1:20 (w/w) at 37° C. for 2 hours and then deglycosylated with PNGase F at an enzyme substrate ratio of 1:5 (w/w) for 37° C. for 1 hour. The digestion was stopped by bringing the pH below 2.0 using formic acid (FA).

LC-MS Analysis. A 20 μg aliquot of resulting rLys-C/tryptic peptides from each sample was separated and analyzed by reverse-phase ultra-performance liquid chromatography (UPLC) using Waters ACQUITY UPLC CSH C18 column (130 Å, 1.7 μm, 2.1×150 mm) followed by on-line PDA detection (at wavelengths of 280 nm, 320 nm and 350 nm) and mass spectrometry analysis. Mobile phase A was 0.1% FA in water and mobile phase B was 0.1% FA in acetonitrile. After sample injection, a gradient started with a 5 min hold at 0.1% B followed by a linear increase to 35% B over 75 minutes for optimum peptide separation. MS and MS/MS experiments were conducted on a Thermo Scientific Q Exactive Hybrid Quadrupole-Orbitrap mass spectrometer with higher-energy collisional dissociation (HCD) employed for peptide fragmentation for MS/MS experiments. Peptide identity assignments were based on the experimentally determined accurate mass of a given peptide in the full MS spectrum as well as the b and y fragment ions in the corresponding HCD MS/MS spectrum. Extracted ion chromatograms of oxidized peptides and corresponding native peptide were generated with the peak areas integrated to calculate the site-specific percentage of oxidized amino acid residue(s) within the MT1 sample.

Peptide Fragments Linked to Increased Absorbance at 350 nm

Figure 12A:
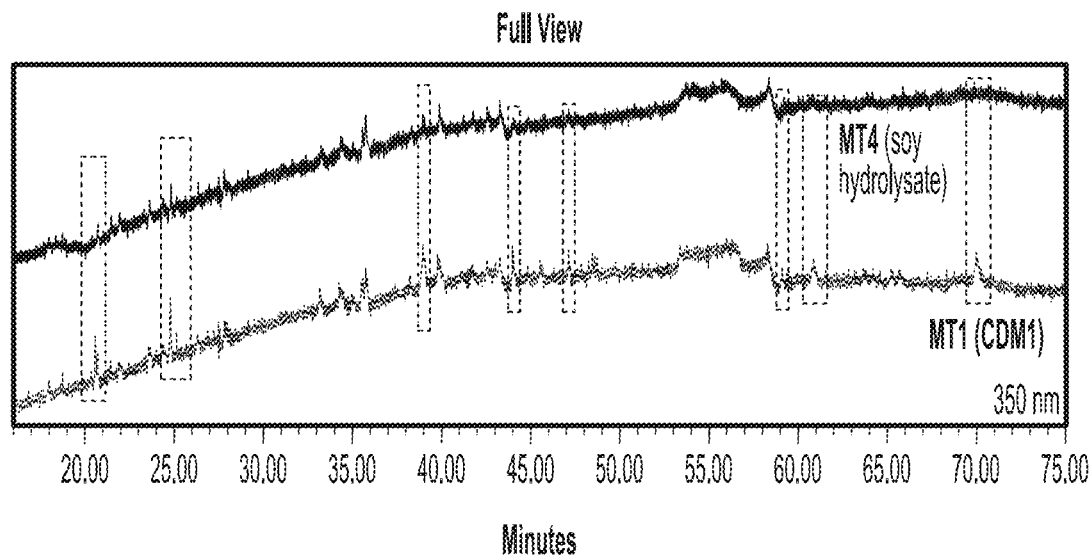
FIG. 12A depicts a full-view of the chromatogram chart of absorbance versus time (minutes) for MT4 and MT1 at 350 nm.
Figure 12B:
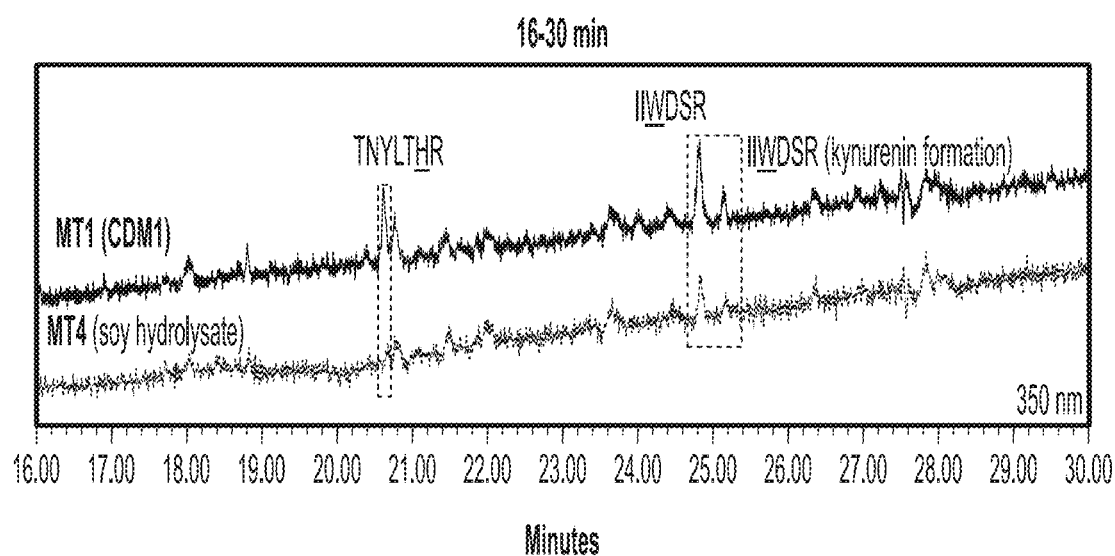
FIG. 12B depicts an expanded-view of the chromatogram chart of absorbance versus time (16-30 minutes) for MT4 and MT1 at 350 nm, including SEQ ID NOS 21, 28, and 28, respectively, in order of appearance.
Figure 12C:
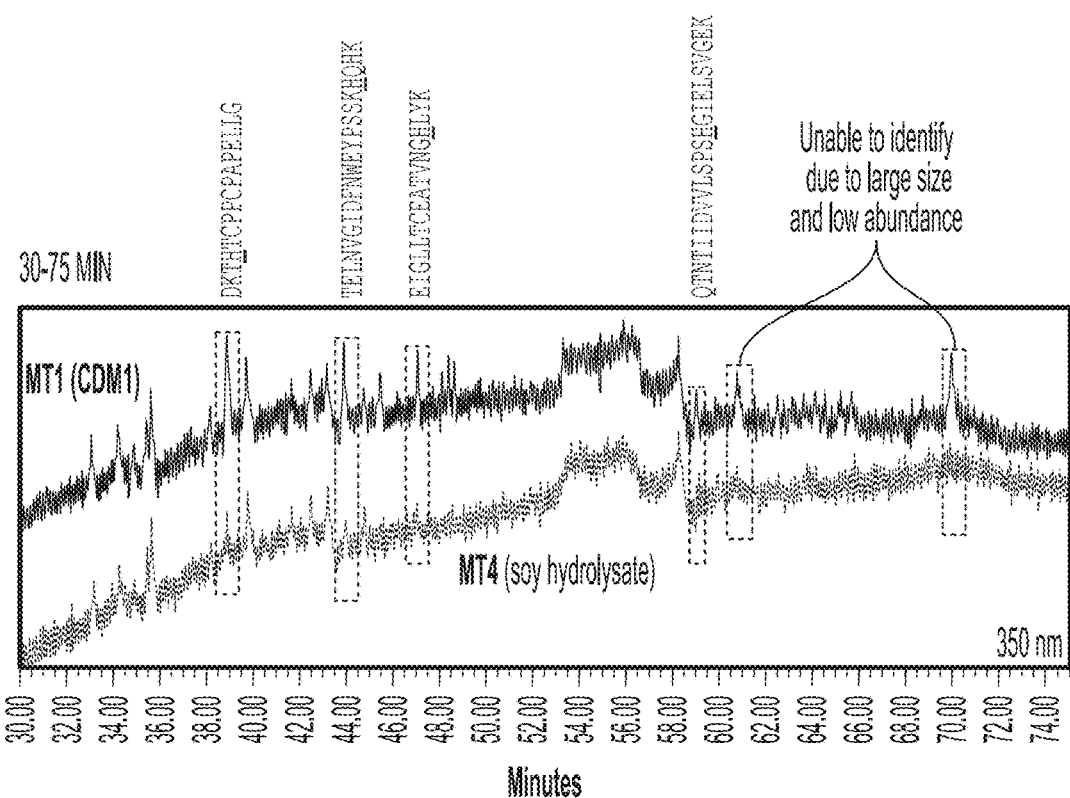
FIG. 12C depicts an expanded-view of the chromatogram chart of absorbance versus time (30-75 minutes) for MT4 and MT1 at 350 nm, including SEQ ID NOS 17, 20, 18, and 19, respectively, in order of appearance.

The PTMs on MT1 were observed upon comparing the tryptic peptide maps for MT1 and MT4 (FIG. 12A shows the absorbance of peptides eluted from 20.0 to 75 minutes). The peptides with varying UV peaks are highlighted. The expanded view of the chromatogram is shown in FIG. 12B which shows the absorbance of peptides eluted from 16 to 30 minutes. The peptides with sharp contrast in UV absorbance between MT1 and MT4 were TNYLTH*R (SEQ ID NO.: 21), IIW(+4)DSR (SEQ ID NO.: 28) and IIIW(+132)DSR (SEQ ID NO.: 124) (* or underscoring represents oxidation of the residue). Further, the expanded view of the chromatogram is shown in FIG. 12C, which shows the absorbance of peptides eluted from 30 to 75 minutes. The peptides with sharp contrast in UV absorbance between MT1 and MT4 were DKTH*TC*PPC*PAPELLG (SEQ ID NO.: 17), TELNVGIDENWEYPSSKH*QHK (SEQ ID NO.: 20), EIGLLTCEATVNGH*LYK (SEQ ID NO.: 18) and QTNTIIDVVLSPSH*GIELSVGEK (SEQ ID NO.: 19) (* represents oxidation of the residue). The peptide mapping revealed identity of peptides that are significantly different in abundance between the VEGF MiniTraps. The relative abundance of the peptides identified from the peptide mapping analysis is shown in Table 3-1. The amount of 2-oxo-histidines in MT1 (produced in a CDM) were higher than MT4 (produced in soy hydrolysate), suggesting that the media used to express aflibercept can have a significant effect on the relative abundance of peptides with oxidized histidines or oxidized tryptophans. For example, for the peptide QTNTIIDVVLSPSH*GIELSVGEK (SEQ ID NO.: 19), the percent relative abundance of the peptide in MT1 (CDM produced) was 0.015% compared to percent relative abundance of the peptide in MT4 (soy hydrolysate produced; which is about 15-fold less as compared to MT1).

TABLE 3-1

| Peptide | Peptide Modified Sequence | MT1 | MT4 | Fold change MT1/MT4 |
|---|---|---|---|---|
| EIGLLTCEATVNGH LYK (SEQ ID NO.: 57) | EIGLLTC[+57]EATVN GH[+14]LYK (SEQ ID NO.: 18) | 0.011% | 0.004% | 2.75 |

TABLE 3-1-continued

| Peptide | Peptide Modified Sequence | MT1 | MT4 | Fold change MT1/MT4 |
|---|---|---|---|---|
| QTNTIIDVVLSPSH GIELSVGEK (SEQ ID NO.: 58) | QTNTIIDVVLSPSH[+14] GIELSVGEK (SEQ ID NO.: 19) | 0.015% | 0.001% | 15.00 |
| TELNVGIDFNWEYP SSKHQHK (SEQ ID NO.: 59) | TELNVGIDFNWEYPS SKH[+14]QHK (SEQ ID NO.: 20) | 0.204% | 0.026% | 7.85 |
| DKTHTCPPCPAPEL LG (SEQ ID NO.: 60) | DKTH[+14]TC[+57]PP C[+57]PAPELLG (SEQ ID NO.: 17) | 0.115% | 0.018% | 6.39 |
| TNYLTHR (SEQ ID NO.: 61) | TNYLTH[+14]R (SEQ ID NO.: 21) | 0.130% | 0.020% | 6.50 |

Color and 2-oxo-Histidine Quantitation. The percentage of 2-oxo-histidines in the oligopeptides that were generated by protease digestion, as measured by mass spectrometry, are also shown (Table 3-2). (Values were normalized against unmodified peptides.) Table 3-2 (I) shows the percent of oxidized histidines/tryptophans observed for AEX flowthrough: MT1 lot 1, AEX flowthrough for MT1 lot 2, and AEX flowthrough for MT1 lot 3. Table 3-2 (II) shows the percent of oxidized histidines/tryptophans observed for acidic fraction 1, acidic fraction 2, and main fraction obtained on performing CEX separation for MT1 lot 3. From this Table, it is clear that the acidic variants are comprised of oxidized species. From Table 3-2(I), it is clear that the % of 2-oxo-histidines and tryptophan dioxidation comprising peptides/protein is reduced in the AEX flowthrough compared to the AEX Strip. It is evident that stripping the AEX column enriches for the percentage of such modified peptides. For example, the % of the modified peptide "EIGLLTC[+57]EATVNGH[+14]LYK (SEQ ID NO.: 18)" in the AEX Flowthrough (MT1 lot 1) was 0.013% and in the "AEX Strip" was 0.080%. This also corroborates that the AEX column captures modified peptides, thus reducing the percentage of modified peptides in the AEX flowthrough.

TABLE 3-2 (I)

Percentage of 2-oxo-Histidines/Tryptophans

| | | AEX Flowthrough | | |
|---|---|---|---|---|
| Modified Peptides | AEX Strip Intense yellow | MT1 lot 1 BY1,110 mg/mL | MT1 lot 2 ≤BY3,110 mg/mL | MT1 lot 3 ≤BY3,110 mg/mL |
| EIGLLTC[+57]EATVNGH[+14]LYK (SEQ ID NO.: 18) | 0.080% | 0.013% | 0.008% | 0.006% |
| QTNTIIDVVLSPSH[+14]GIELSVGEK (SEQ ID NO.: 19) | 0.054% | 0.028% | 0.023% | 0.019% |
| TELN VGIDFNWEYPSSKH[+14]QHK (SEQ ID NO.: 20) | 0.235% | 0.085% | 0.049% | 0.049% |
| DKTH[+14]TC[+57]PPC[+57]PAPELLG (SEQ ID NO.: 17) | 0.544% | 0.092% | 0.077% | 0.057% |
| TNYLTH[+14]R (SEQ ID NO.: 21) | 0.089% | 0.022% | 0.011% | 0.010% |
| IIW[+32]DSR (SEQ ID NO.: 28) | 0.738% | 0.252% | 0.198% | 0.298% |

TABLE 3-2 (II)

Percentage of 2-oxo-Histidines/Tryptophans

| | CEX flowthrough | | |
|---|---|---|---|
| Modified Peptides | Acidic fraction 1 from MT1 lot 3 Yellow | Acidic fraction 2 from MT1 lot 3 Yellow | Main fraction from MT1 lot 3 No Color |
| EIGLLTC[+57]EATVNGH[+14]LYK (SEQ ID NO.: 18) | 0.009% | 0.008% | 0.004% |

TABLE 3-2 (II)-continued

| | Percentage of 2-oxo-Histidines/Tryptophans | | |
|---|---|---|---|
| | CEX flowthrough | | |
| Modified Peptides | Acidic fraction 1 from MT1 lot 3 Yellow | Acidic fraction 2 from MT1 lot 3 Yellow | Main fraction from MT1 lot 3 No Color |
| QTNTIIDVVLSPSH[+14]GIELSVGEK (SEQ ID NO.: 19) | 0.013% | 0.015% | 0.006% |
| TELN VGIDFNWEYPSSKH[+14]QHK (SEQ ID NO.: 20) | 0.131% | 0.151% | 0.049% |
| DKTH[+14]TC[+57]PPC[+57]PAPELLG (SEQ ID NO.: 17) | 0.117% | 0.132% | 0.068% |
| TNYLTH[+14]R (SEQ ID NO.: 21) | 0.014% | 0.008% | 0.008% |
| IIW[+32]DSR (SEQ ID NO.: 28) | 0.458% | 0.269% | 0.185% |

In Table 3-2(II), [+57] represent alkylation of cysteine by iodoacetamide, which adds a carboxymethyl amine moiety on the cysteine, which is a net mass increase of about +57 over unmodified cysteine:

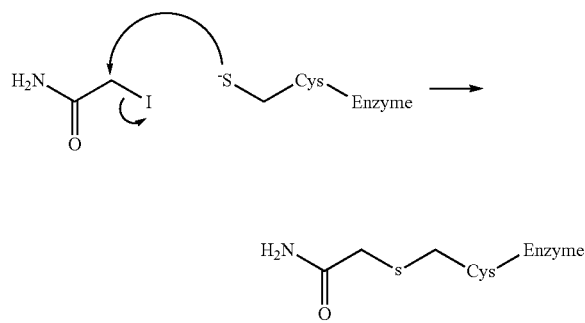

In Table 3-2(II), [+14] represent conversion from His to 2-oxo-His. One oxygen atom is added on carbon 2, but two hydrogen atoms are lost (one from Carbon 2, the other from nitrogen 3), which is a net mass increase of about +14 over unmodified histidine.

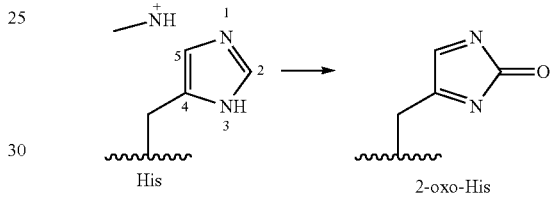

In Table 3-2(II), [+32] represents tryptophan dioxidation resulting in the formation of N-formylkynurenine, which is a net mass increase of about +32 over unmodified tryptophan (FIG. 4).

Figure 13:
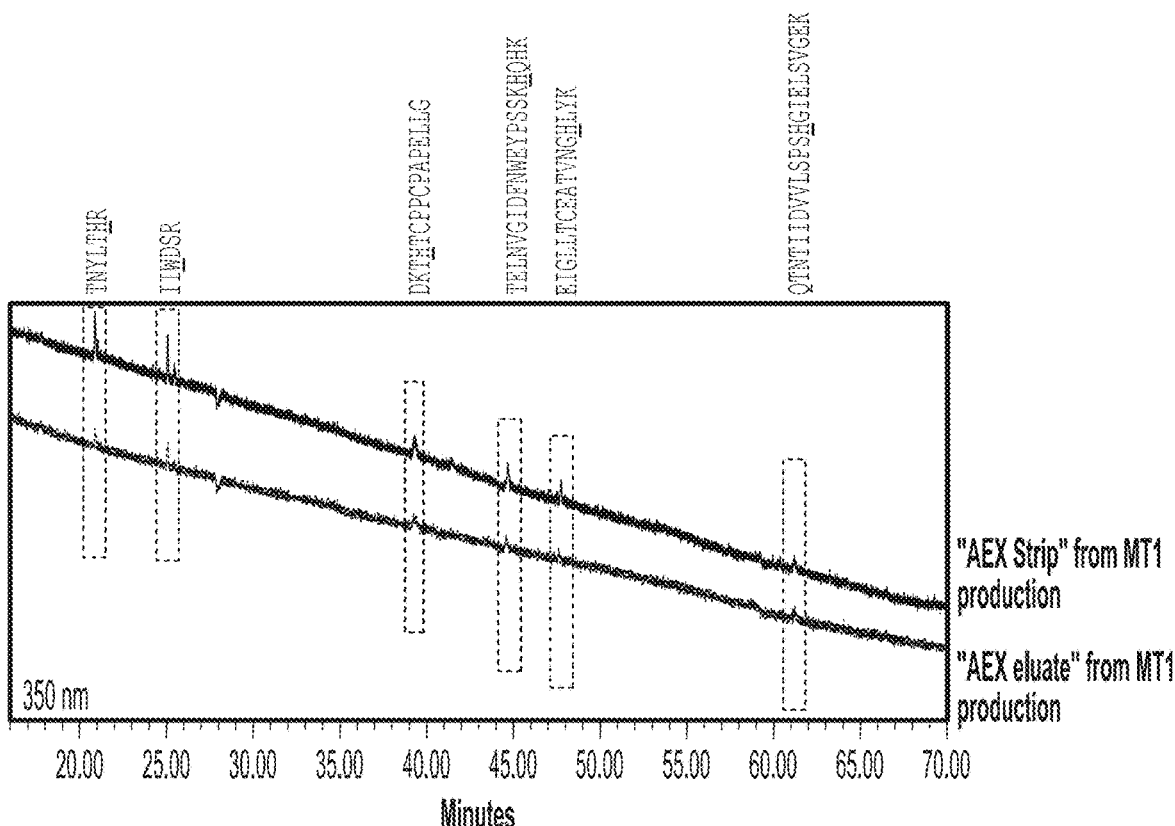
FIG. 13 depicts results of an experiment performed to evaluate the percentage of 2-oxo-histidines (and tryptophan dioxidation) in oligopeptides from protease digested MT1 which has been processed by AEX chromatography and oligopeptides from protease digested MT1 which has been stripped from AEX chromatography, including SEQ ID NOS 21, 28, 17, 20, and 18-19, respectively, in order of appearance.

A second set of experiments were performed to evaluate the percentage of 2-oxo-histidines (and tryptophan dioxidation) in oligopeptides from protease digested FabRICATOR-cleaved aflibercept (MT4) which was processed by AEX chromatography (FIG. 13 and Table 3-3 below). The percent of 2-oxo-histidines and tryptophan dioxidation in AEX strip for oligopeptides from protease digested FabRICATOR-cleaved aflibercept (MT4) was significantly more than the percent of 2-oxo-histidines and tryptophan dioxidation in the AEX flowthrough (referring to "MT1" in Table 3-3 below).

TABLE 3-3

| | Percentage of 2-oxo-Histidines | | | |
|---|---|---|---|---|
| Modified peptides | Full length aflibercept | MT1 | AEX Strip from MT1 | fold change AEX Strip/MT1 |
| IIW[+32]DSR (SEQ ID NO.: 28) | 0.22% | 0.34% | 0.81% | 2.4 |
| EIGLLTC[+57]EATVNGH[+14]LYK (SEQ ID NO.: 18) | 0.00% | 0.02% | 0.08% | 4.0 |
| QTNTIIDVVLSPSH[+14]GIELSVGEK (SEQ ID NO.: 19) | 0.01% | 0.04% | 0.07% | 1.8 |
| TELNVGIDFNWEYPSSKH[+14]QHK (SEQ ID NO.: 20) | 0.01% | 0.19% | 0.42% | 2.2 |

TABLE 3-3-continued

Percentage of 2-oxo-Histidines

| Modified peptides | Full length aflibercept | MT1 | AEX Strip from MT1 | fold change AEX Strip/MT1 |
|---|---|---|---|---|
| DKTH[+14]TC[+57]PPC[+57]PAPELLG (SEQ ID NO.: 17) | 0.01%[a] | 0.11% | 0.63% | 5.7 |
| TNYLTH[+14]R (SEQ ID NO.: 21) | 0.00% | 0.03% | 0.10% | 3.3 |

[a] value calculated using a different peptide for full-length aflibercept, as the C-terminal peptide is different from MiniTrap.

Figure 14:
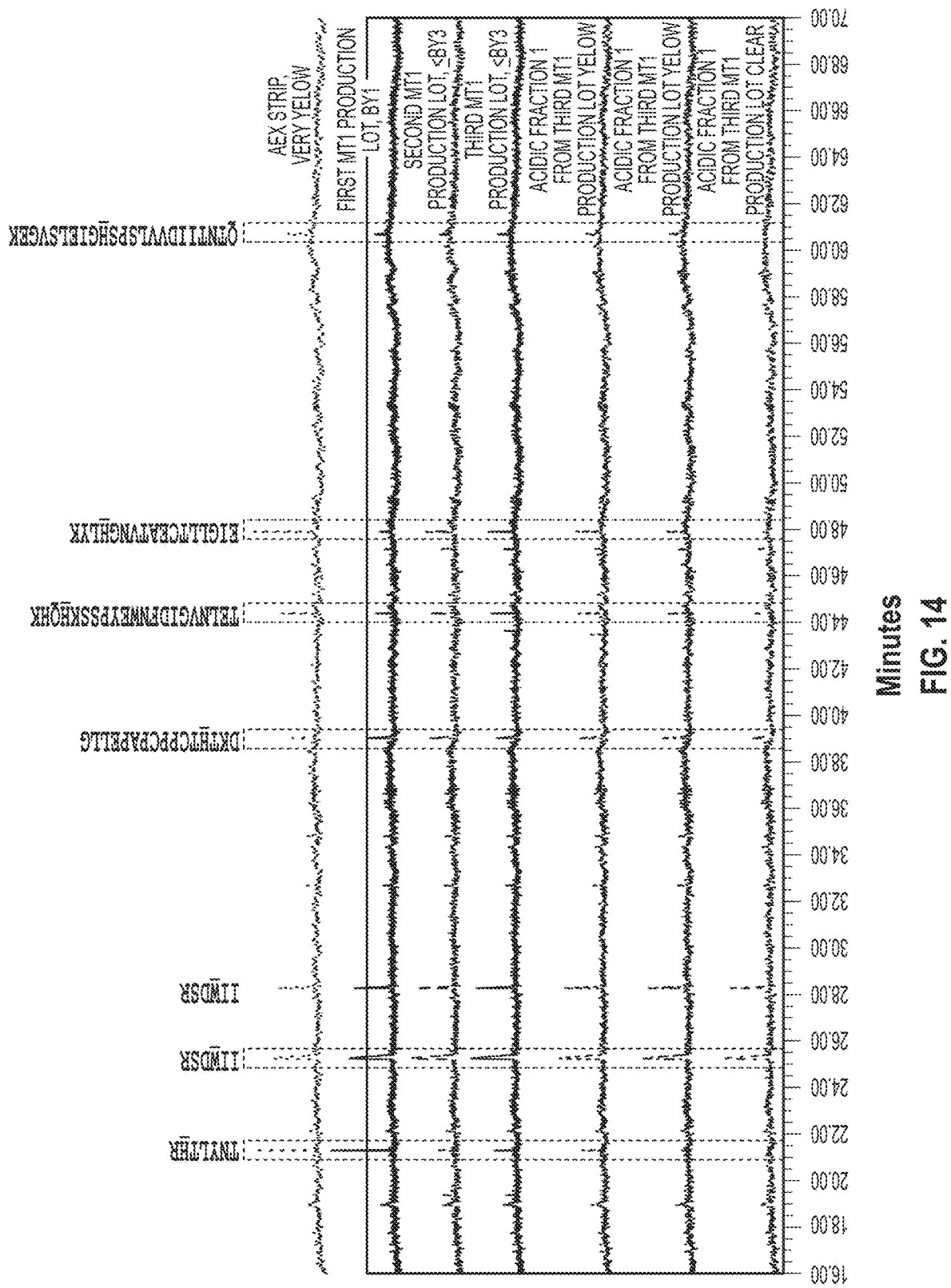
FIG. 14 depicts results of an experiment performed to compare the acidic species present in different production lots of MT1 and the acidic acid fractions obtained on performing a strong cation exchange (CEX) chromatography, including SEQ ID NOS 21, 28, 28, 17, 20, and 18-19, respectively, in order of appearance.

The percent of 2-oxo-histidines and tryptophan dioxidation in AEX strip was significantly more than the percent of 2-oxo-histidines and tryptophan dioxidation in the AEX flowthroughs during the MT1 productions (referring to "MT1" in Table 3-3 above). Compared to Table 3-2, Table 3-3 shows similar results that stripping the AEX column produced a sample with a significantly higher percent of 2-oxo-histidines and tryptophan dioxidation compared to the percent of 2-oxo-histidines and tryptophan dioxidation in AEX flowthrough, suggesting that the 2-oxo-histidines and tryptophan dioxidation species are bound to the AEX column during the separation and are removed upon stripping the AEX column. This is further evident in the extracted ion chromatogram as seen in FIG. 14.

Strong Cation Exchange Chromatogram (CEX)

A series of experiments were conducted in order to identify acidic species and other variants present in samples comprising anti-VEGF proteins.

Strong cation exchange chromatography was performed using a MonoS (10/100) GL column (GE Life Sciences, Marlborough, MA). For the sample separations, the mobile phases used were 20 mM 2-(N-morpholino)ethanesulfonic acid (MES), pH 5.7 (Mobile phase A) and 40 mM sodium phosphate, 100 mM sodium chloride pH 9.0 (Mobile phase B). A non-linear pH gradient was used to elute charge variants of MT1 with detection at 280 nm. Peaks that elute at a relative residence time earlier than the main peak are designated herein as acidic species.

Figure 15:
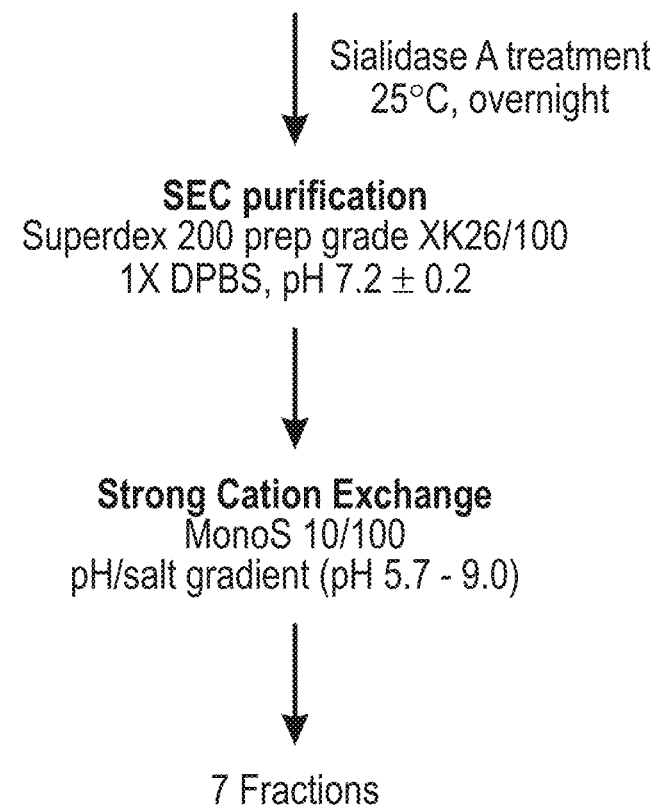
FIG. 15 depicts an exemplary method for the enrichment of the acidic species and other variants present in cell culture harvest samples using strong cation exchange chromatography.

A sample from the MT1 lot 2 (≤BY3), prior to any enrichment, was subjected to CEX using the method as depicted in FIG. 15. Desilylation was applied to the sample in order to reduce the complexity of variants of MT1. This was followed by preparative SEC processing (Superdex 200 prep grade XK26/100) using 1×DPBS, pH 7.2±0.2, as the mobile phase. The fractions obtained from the preparative SEC column comprising desialyated MiniTrap (dsMT1) were combined and further subjected to strong cation exchange (SCX) chromatography to enrich for charge variants of MT1 using a dual salt-pH gradient. The procedure resulted in a total of 7 fractions (F1-F7; MC represents the method control, FIG. 16 and FIG. 17).

On performing CEX, the acidic species elute earlier than the main peaks and basic species elute after the main peaks. As observed in FIG. 17, peaks 3-5 are the main peaks. Peaks 1 and 2 are eluted before elution of the main species of MT1 (peaks 3-5), and thus, comprise the acidic species. Peak 6 is eluted after the elution of the main species of MT1 (peaks 3-5), and thus, comprises the basic species. Table 3-4 shows the relative abundance of the peaks in MC (as identified in FIG. 16). For example, row two of Table 3-4 (labeled MC) shows that the total relative amount of acidic species in MC is about 19.8% (i.e., peak 1+ peak 2). Table-3-4 also shows the relative abundance of the peaks for each individual fraction. While there are overlapping species in the different fractions (as reflected in FIG. 16 and FIG. 17), the majority of fractions F1 and F2 are acidic species (i.e., peak 1 and peak 2). For example, fraction F1 is comprised of 63.7% peak 1 and 19.2% peak 2 (for a total of 82.9% acidic species). Fraction F2 is comprised of 9.6% peak 1 and 75.9% peak 2 (for a total of 85.5% acidic species). The majority of fractions F3-F5 are the main species of MT1 (peaks 3-5). Lastly, the majority of fractions F6-F7 are the basic species (peak 6) but do include some portions of the main species (e.g., peaks 4 and 5).

It was also observed that fractions F1 and F2 (which comprises the acidic species) had an intense yellow-brown coloration compared to the fractions F3-F5 (which comprises the main species or "MT1"). All the fractions were inspected for color at concentrations ≥13 mg/mL. As evident from this Example, the presence of acidic species in the sample tracked with the appearance of yellow-brown coloration, removal (or minimization) of which can be accomplished by removing (or minimizing) the acidic species from MT1.

TABLE 3-4

Relative abundance of peaks based on analytical CEX

| | Peak Area (%) | | | | | |
|---|---|---|---|---|---|---|
| Sample | Peak 1 | Peak 2 | Peak 3 | Peak 4 | Peak 5 | Peak 6 |
| MC | 5.9 | 13.9 | 15.0 | 25.4 | 20.9 | 19.0 |
| MT1 F1 | 63.7 | 19.2 | 17.1 | ND | ND | ND |
| MT1 F2 | 9.6 | 75.9 | 10.6 | 2.2 | 1.6 | ND |
| MT1 F3 | ND | 5.0 | 57.2 | 37.8 | ND | ND |
| MT1 F4 | ND | ND | 16.3 | 56.3 | 27.4 | ND |
| MT1 F5 | ND | ND | ND | 33.1 | 50.4 | 16.5 |
| MT1 F6 | ND | ND | ND | 16.0 | 27.7 | 56.3 |
| MT1 F7 | 2.8 | 7.7 | 8.0 | 16.1 | 16.5 | 48.9 |

ND: Not Detected

Figure 18A:
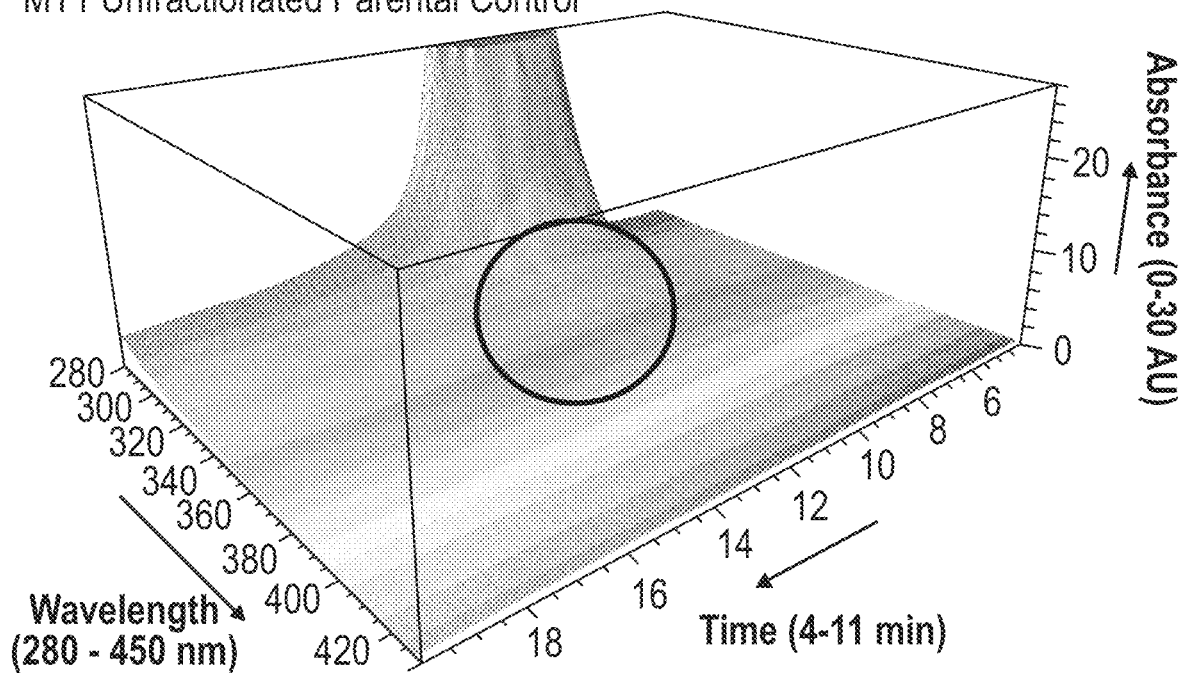
FIG. 18A depicts a 3D chromatogram for unfractionated parental control carried out by strong cation exchange chromatography according to an exemplary embodiment.
Figure 18B:
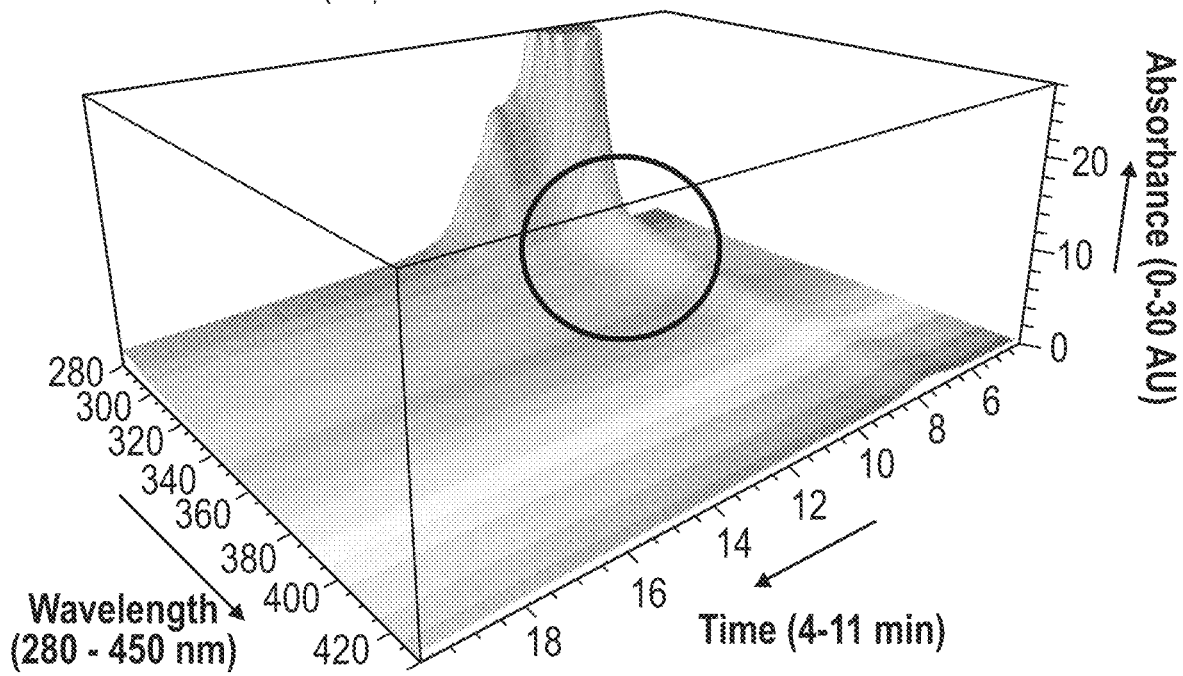
FIG. 18B depicts a 3D chromatogram for MT1, fraction 1 representing some of the tailing feature for the experiment carried out by strong cation exchange chromatography according to an exemplary embodiment.
Figure 18C:
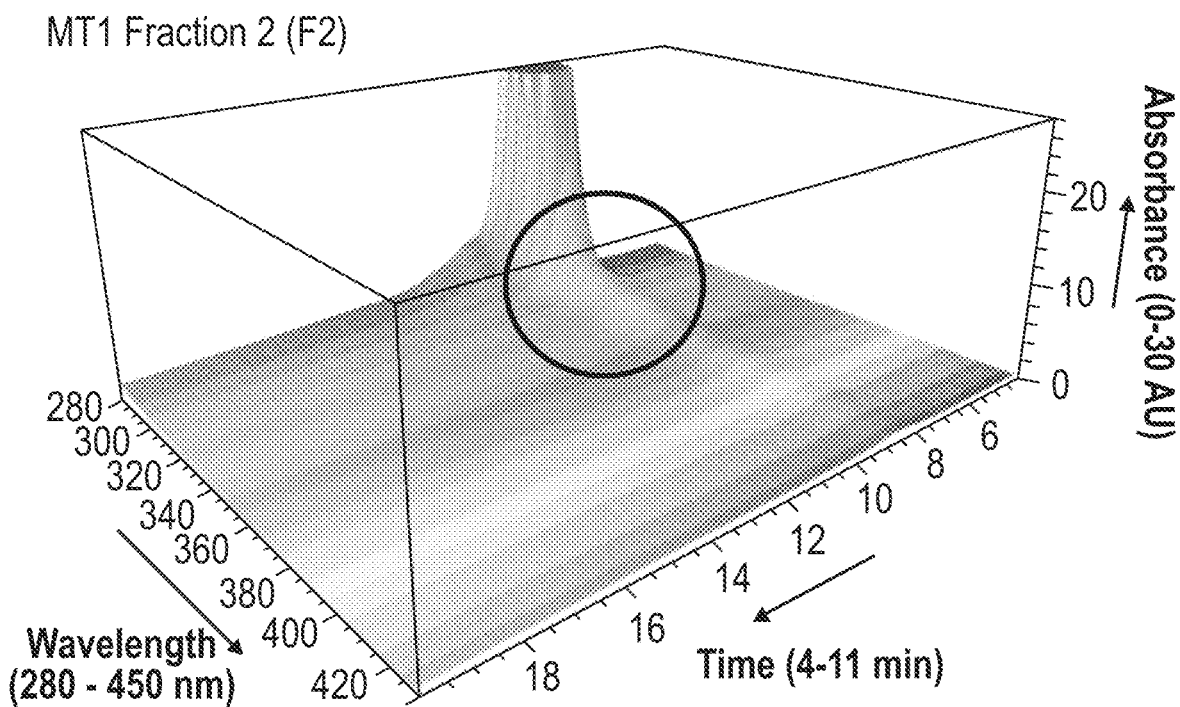
FIG. 18C depicts a 3D chromatogram for MT1, fraction 2 feature carried out by strong cation exchange chromatography according to an exemplary embodiment.
Figure 18D:
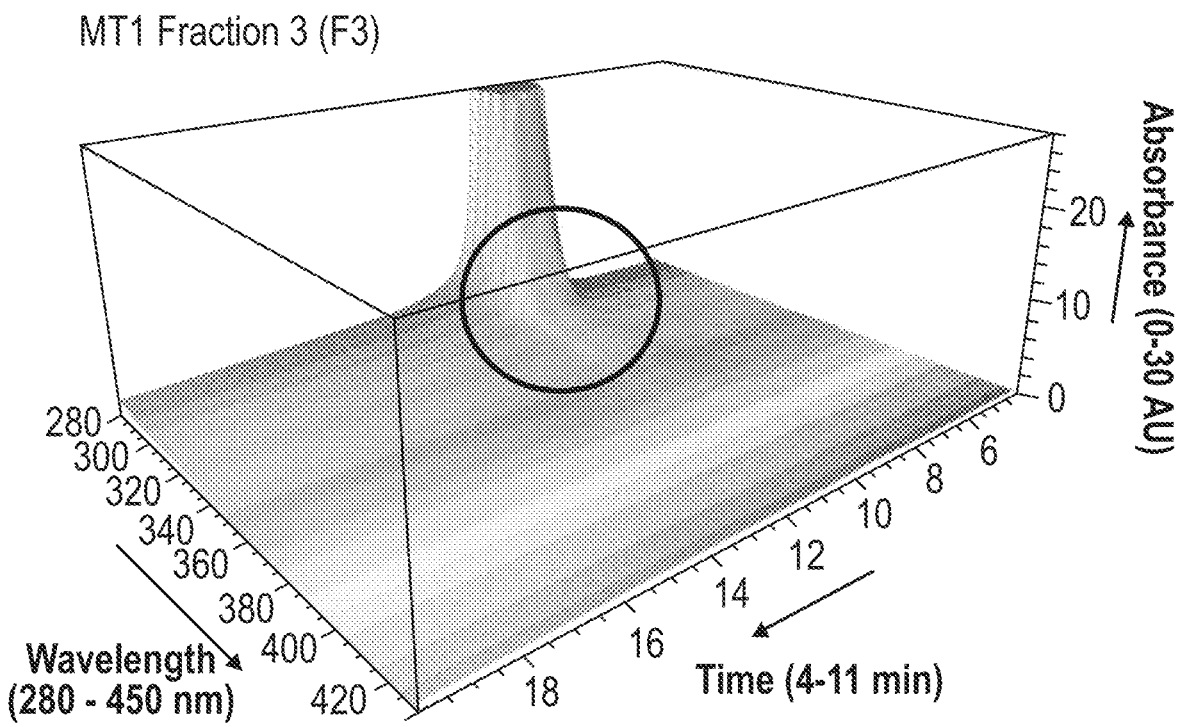
FIG. 18D depicts a 3D chromatogram for MT1, fraction 3 feature carried out by strong cation exchange chromatography according to an exemplary embodiment.
Figure 18E:
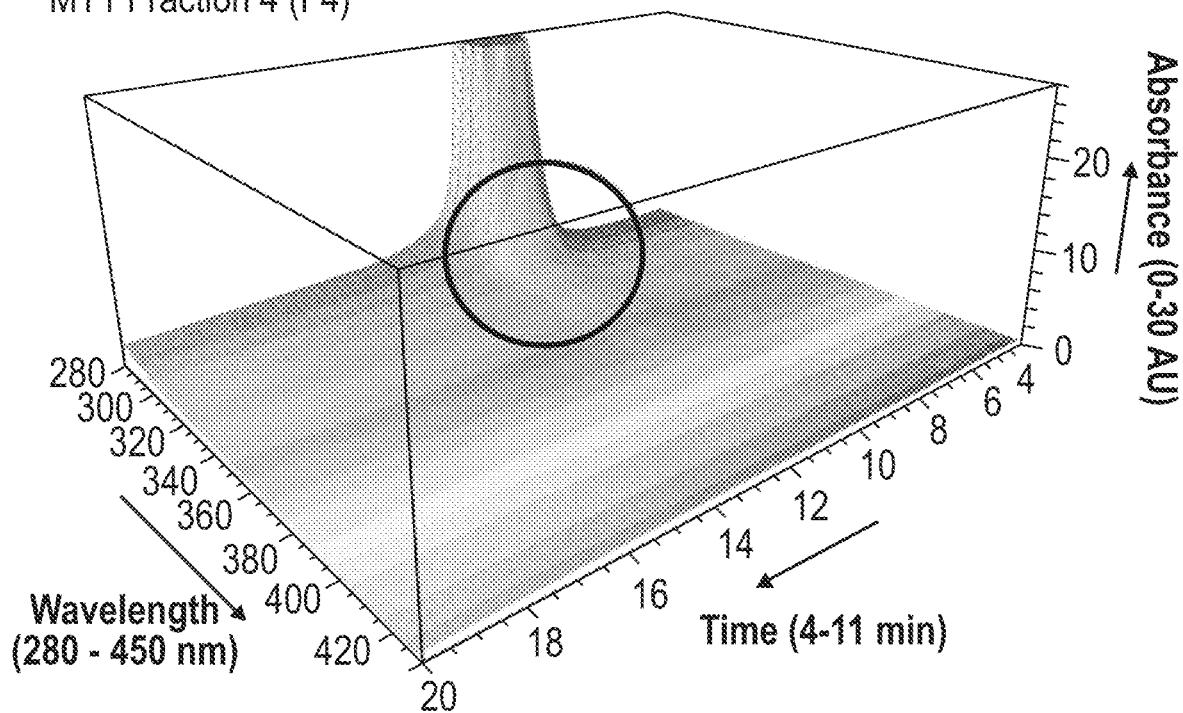
FIG. 18E depicts a 3D chromatogram for MT1, fraction 4 feature carried out by strong cation exchange chromatography according to an exemplary embodiment.
Figure 18F:
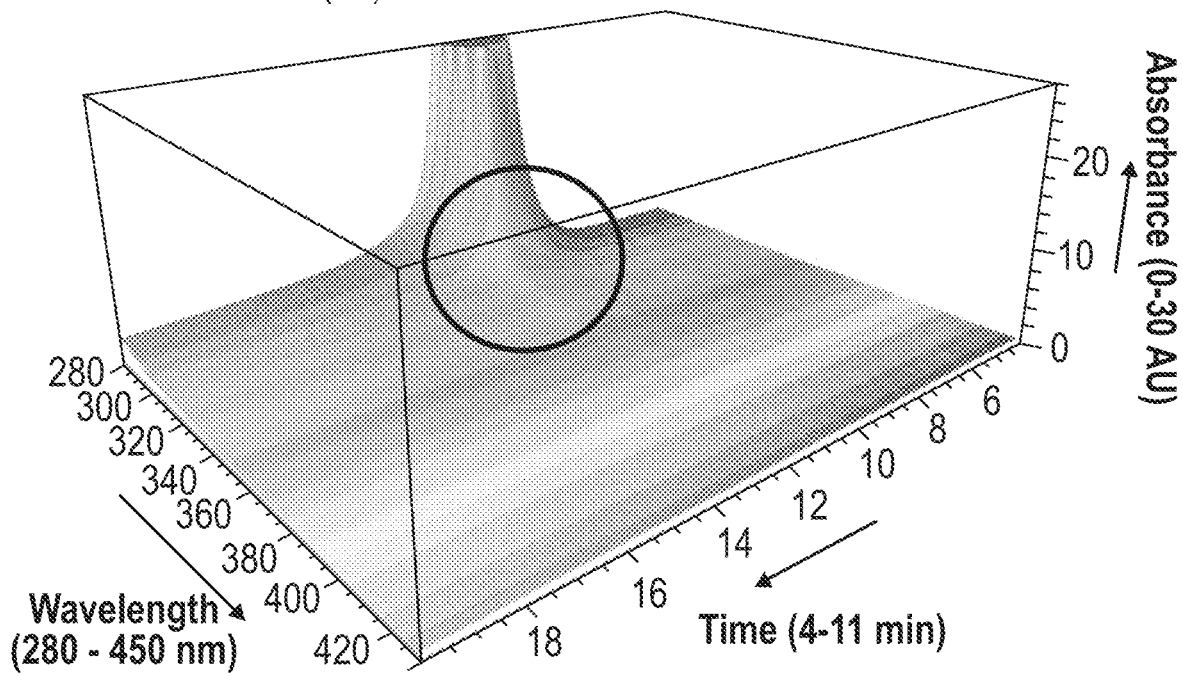
FIG. 18F depicts a 3D chromatogram for MT1, fraction 5 feature carried out by strong cation exchange chromatography according to an exemplary embodiment.
Figure 18G:
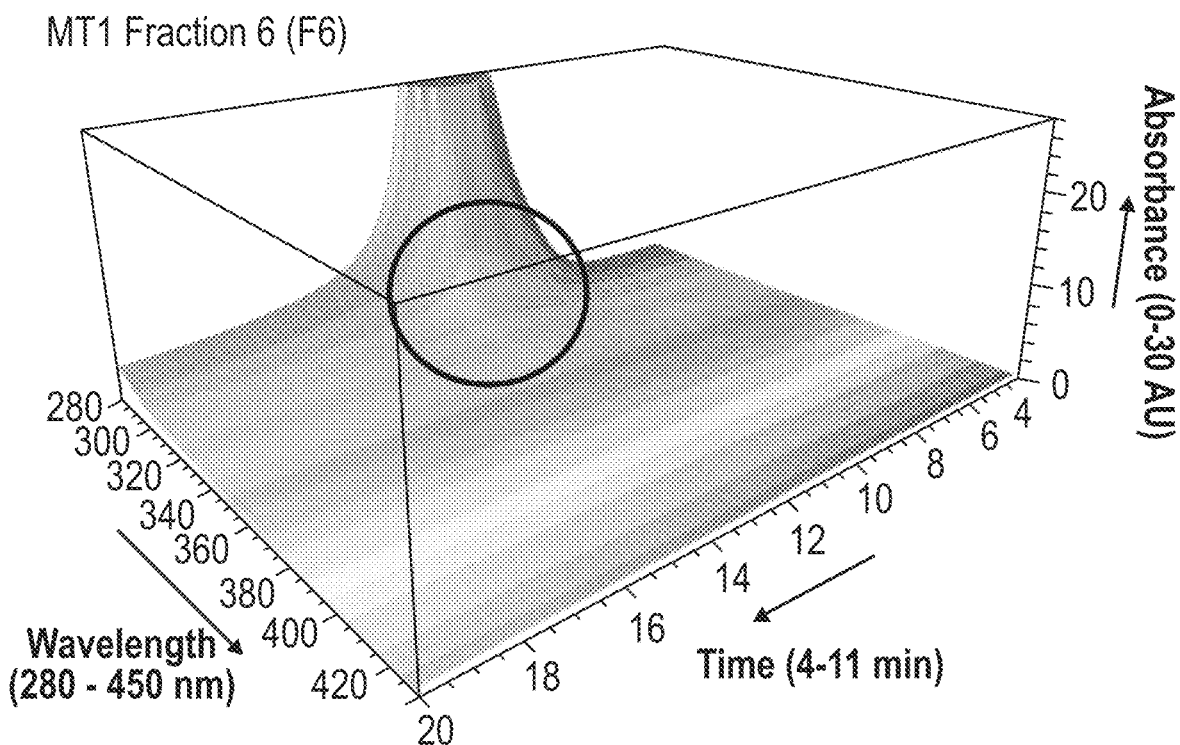
FIG. 18G depicts a 3D chromatogram for MT1, fraction 6 feature carried out by strong cation exchange chromatography according to an exemplary embodiment.
Figure 18H:
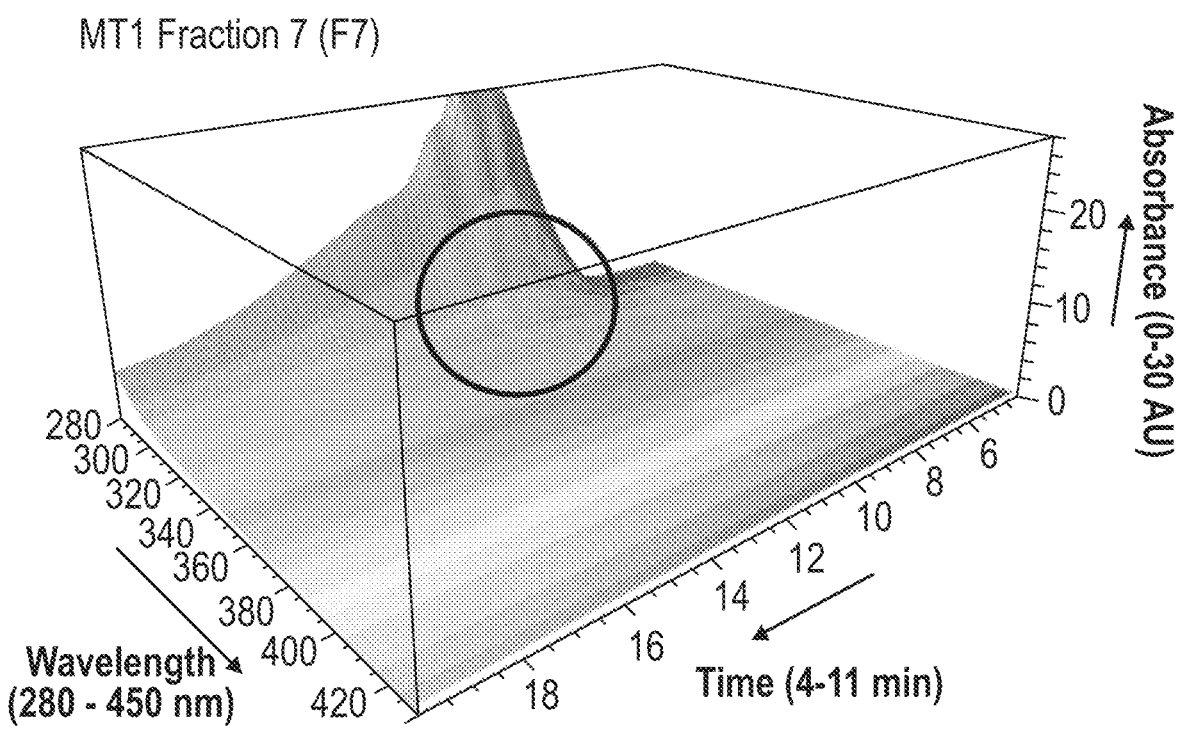
FIG. 18H depicts a 3D chromatogram for MT1, fraction 7 feature carried out by strong cation exchange chromatography according to an exemplary embodiment.

The 3D chromatograms for MT1 lot 2 and fractions F1-F7 are shown in FIGS. 18A-H. MT1 lot 2 did not exhibit any significant spectral features (FIG. 18A). Fractions 1 and 2 (comprising the acidic species) exhibited a spectral signature between 320-360 nm (see the circle in FIG. 18B). This feature was more prominent in fraction 1 compared to fraction 2 (FIGS. 18B and 18C) and was absent in fraction 3 and fractions 4-7 (main species, MT1) (FIGS. 18D and 18H), which did not exhibit yellow-brown coloration.

Thus, as observed above, CEX led to identification of acidic species/acidic fractions (fractions 1 and 2) which show an intense yellow-brown coloration as compared to the main species/fractions (fractions 3-6). This result was also observed in the form of a distinct spectral signature present in the 3D chromatograms of fractions F1-F2 and absent in fractions F3-F7.

Imaged Capillary Isoelectric Focusing (icIEF) Electropherograms

Figure 19:
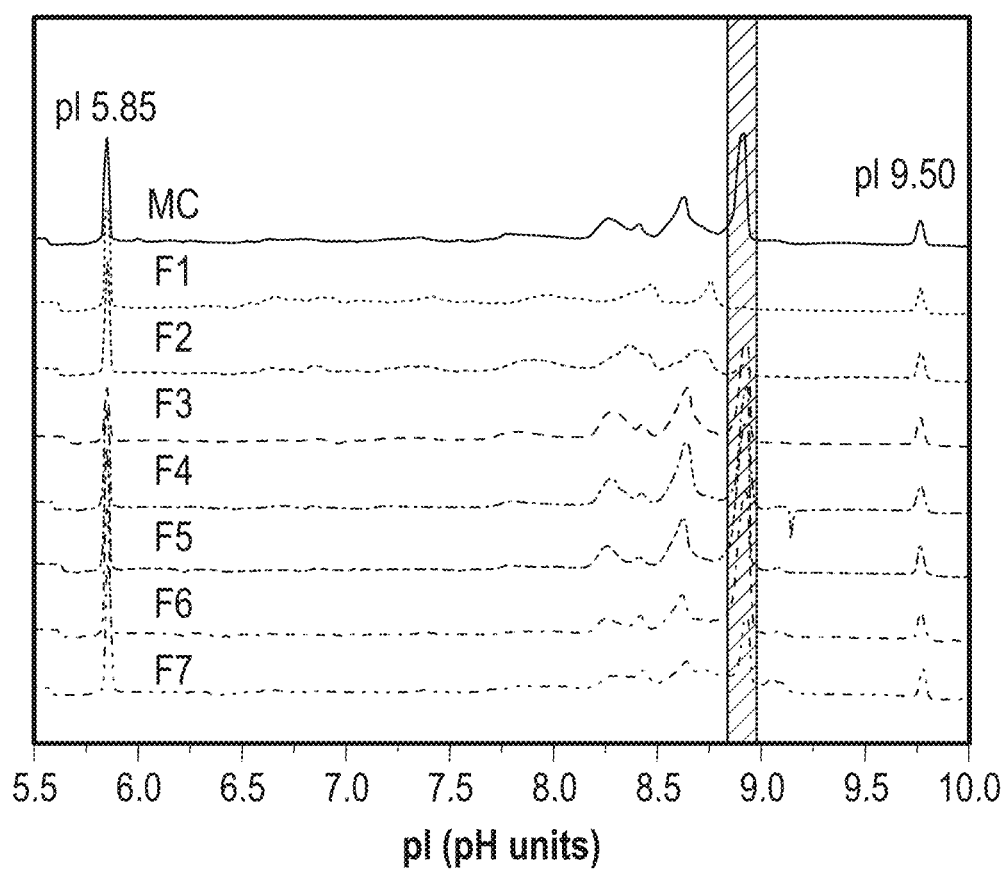
FIG. 19 depicts imaged capillary isoelectric focusing (icIEF) electropherograms performed according to an exemplary embodiment for the MT1 production.

The distribution of variants in fractions F1-F7 and MC (from MT1-lot 2 after CEX) was further assessed by icIEF (FIG. 19).

The distribution of variants in fractions F1-F7 and MC (from MT1-lot 2 after CEX) was further assessed by icIEF using an iCE3 analyzer (ProteinSimple) with a fluorocarbon coated capillary cartridge (100 μm×5 cm). The ampholyte solution consisted of a mixture of 0.35% methyl cellulose (MC), 0.75% Pharmalyte 3-10 carrier ampholytes, 4.2% Pharmalyte 8-10.5 carrier ampholytes, and 0.2% pI marker 7.40 and 0.15% pI marker 9.77 in purified water. The anolyte was 80 mM phosphoric acid, and the catholyte was 100 mM sodium hydroxide, both in 0.10% methylcellulose. Samples were diluted in purified water and sialidase A was added to each diluted sample at an enzyme to substrate ratio of 1:200 (units of sialidase A per milligram of MT1) followed by incubation at ambient temperature for approximately 16 hours. The sialidase A treated samples were mixed with the ampholyte solution and then focused by introducing a potential of 1500 V for one minute followed by a potential of 3000 V for 7 minutes. An image of the focused MT1 variants was obtained by passing 280 nm ultraviolet light through the capillary and into the lens of a charge coupled device digital camera. This image was then analyzed to determine the distribution of the various charge variants (FIG. 19). Referring to FIG. 19, fractions F1 and F2 (or the acidic fractions) showed an absence of the peak for MT1, which is clearly observed for MC and fractions F3-F7 (main species, MT1). Thus, icIEF electropherograms were considered able to detect and determine the distribution of the different charge variants of the protein under consideration, MT1 in this case. Thus, it was evident that acidic fractions on performing CEX analysis showed (a) increased relative abundance of percent of 2-oxo-histidine or dioxo-tryptophan (Table 3-2 (II)); (b) increased yellow-brown coloration (data not shown); and (c) presence of a spectral signature as seen on the 3D chromatograms for fractions 1 and 2 (FIG. 18B and FIG. 18C).

Example 4. Photo-Induction Study

In this Example, photo-induction of VEGF MiniTrap (MT), for example MT1, was performed by exposure of a protein sample to varying amounts of cool white (CW) fluorescent light or ultra-violet A (UVA) light. The color and oxidized amino acid content of the light exposed samples was determined. LCMS analysis was performed following exposure, as explained above. Exposure of MT to cool white light or UVA light produced an increase in oxidized amino acid residues, for example, histidine (Table 4-1, Table 4-2 and Table 4-3).

TABLE 4-1

Photo-Induction Study Design

| Cumulative Exposure | 0.2 (×ICH) | 0.5 (×ICH) | 0.8 (×ICH) | 1.0 (×ICH)H | 2.0 (×ICH) |
|---|---|---|---|---|---|
| CW fluorescent exposure (lux*hr) | 0.24 million lux*hr | 0.6 million lux*hr | 0.96 million lux*hr | 1.2 million lux*hr | 2.4 million lux*hr |
| Incubation time with CW fluorescent light (at 8 klux) | 30 hours | 75 hours | 100 hours | 150 hours | 300 hours |
| UVA exposure (W*hr/m²) | 40 | 100 | 160 | 200 | 400 |
| Incubation time with UVA (at 10 W/m²) | 4 hours | 10 hours | 16 hours | 20 hours | 40 hours |

ICH refers to ICH Harmonised Tripartite Guideline: Stability Testing: Photostability Testing of New Drug Substances and Products Q1B which specifies photostability studies to be conducted with not less than 1.2 million lux*hours cool white fluorescent light and near ultraviolet energyof not less than 200 W*hr/m².

Table 4-2 depicts the increase in coloration of the MT sample exposed to cool-white light and ultra-violet light. For example, b-value for sample (t=0) was 9.58. On exposing this sample to cool-white light at 2.4 million lux*hr, the b-value increases to 22.14. This increase in b-value indicates that the exposure of MT to cool-white light at 2.4 million lux*hr increases yellow-brown coloration of the sample as compared to sample (t=0). Similarly, on exposing MT sample (t=0) to ultra-violet light at 400 W*h/m², the b-value increases to 10.72 from 9.58. This increase in b-value indicates that the exposure of MT sample to ultra-violet light at 400 W*h/m² produces an increased yellow-brown coloration of the sample as compared to sample (t=0).

TABLE 4-2

Color of Samples Exposed to Cool White Light and Ultra-Violet Light

| Photo exposure × ICH (lux*hr) | L* | a* | b* | BY Value |
|---|---|---|---|---|
| Cool White Light | | | | |
| T = 0 | 97.37 | −1.12 | 9.58 | 4.0 |
| 0.2 × (0.24 million lux*hr) | 96.46 | −0.72 | 11.75 | 3.7 |
| 0.5 × (0.6 million lux*hr) | 95.47 | −0.4 | 11.3 | 3.7 |
| Cool White Light | | | | |
| 0.8 × (0.96 million lux*hr) | 95.33 | −0.38 | 11.96 | 3.6 |
| 1.0 × (1.2 million lux*hr) | 94.42 | −0.2 | 13.72 | 3.3 |
| 2.0 × (2.4 million lux*hr) | 92.70 | 0.41 | 22.14 | 2.0 |
| UVA | | | | |
| 0.2 × (40 W*h/m²) | 97.26 | −0.92 | 12.66 | 3.5 |
| 0.5 × (100 W*h/m²) | 100.39 | −1.01 | 11.83 | 3.7 |
| 0.8 × (160 W*h/m²) | 79.69 | −0.18 | 10.1 | 3.6 |
| 1.0 × (200 W*h/m²) | 97.48 | −0.95 | 11.36 | 3.7 |
| 2.0 × (400 W*h/m²) | 97.76 | −0.98 | 10.72 | 3.8 |

Sample colors are indicated using the CIELAB color space (L*, a* and b* variables) and relative to the EP BY color standard;

L* = white to black (L* is lightness);

a* = magenta to aqua;

b* = yellow to blue, the higher the b-value the more yellow.

TABLE 4-3 (I)

2-oxo-His Levels in Peptides from Ultra-Violet Light Stressed MiniTrap

| Peptides | Site | t0 | UV_4 h | UV_10 h | UV_16 h | UV_20 h | UV_40 h |
|---|---|---|---|---|---|---|---|
| DKTHTCPPCPAPELLG (SEQ ID NO.: 17) | H209 | 0.056% | 0.067% | 0.081% | 0.088% | 0.077% | 0.091% |
| EIGLLTCEATVNGHLYK (SEQ ID NO.: 18) | H86 | 0.010% | 0.020% | 0.034% | 0.037% | 0.033% | 0.035% |
| QTNTIIDVVLSPSHGIELSVGEK (SEQ ID NO.: 19) | H110 | 0.024% | 0.031% | 0.028% | 0.028% | 0.027% | 0.027% |
| TELNVGIDFNWEYPSSKHQHK (SEQ ID NO.: 20) | H145 | 0.096% | 0.147% | 0.163% | 0.173% | 0.147% | 0.125% |
| TNYLTHR (SEQ ID NO.: 21) | H95 | 0.014% | 0.032% | 0.044% | 0.056% | 0.058% | 0.078% |
| SDTGRPFVEMYSEIPEIIHMTEGR (SEQ ID NO.: 22) | H19 | 0.007% | 0.013% | 0.021% | 0.025% | 0.024% | 0.034% |
| VHEKDK (SEQ ID NO.: 23) | H203 | 0.040% | 0.105% | 0.238% | 0.255% | 0.269% | 0.324% |

TABLE 4-3 (II)

2-oxo-His Levels in Peptides from Cool White Light Stressed MiniTrap

| Peptides | Site | t0 | CW_30 h | CW_75 h | CW_100 h | CW_150 h | CW_300 h |
|---|---|---|---|---|---|---|---|
| DKTHTCPPCPAPELLG (SEQ ID NO.: 17) | H209 | 0.056% | 0.152% | 0.220% | 0.243% | 0.258% | 0.399% |
| EIGLLTCEATVNGHLYK (SEQ ID NO.: 18) | H86 | 0.010% | 0.063% | 0.110% | 0.132% | 0.170% | 0.308% |
| QTNTIIDVVLSPSHGIELSVGEK (SEQ ID NO.: 19) | H110 | 0.024% | 0.085% | 0.120% | 0.128% | 0.148% | 0.180% |
| TELNVGIDFNWEYPSSKHQHK (SEQ ID NO.: 20) | H145 | 0.096% | 0.423% | 0.585% | 0.634% | 0.697% | 0.748% |
| TNYLTHR (SEQ ID NO.: 21) | H95 | 0.014% | 0.103% | 0.175% | 0.198% | 0.267% | 0.437% |
| SDTGRPFVEMYSEIPEIIHMTEGR (SEQ ID NO.: 22) | H19 | 0.007% | 0.025% | 0.043% | 0.049% | 0.058% | 0.115% |
| VHEKDK (SEQ ID NO.: 23) | H203 | 0.040% | 0.426% | 0.542% | 0.622% | 0.702% | 1.309% |

Exposure of aflibercept MT to cool white light or UVA light tracked with the appearance of oxidized histidines (2-oxo-his) (Table 4-3). Referring to Table 4-3, the peptide "SDTGRPFVEMYSEIPEIIHMTEGR (SEQ ID NO.: 22)" with oxo-histidine was 0.007% in MT sample (t=0), whereas its abundance increased to 0.324% on exposure to ultraviolet light for 40 hours (Table 4-3(I)) and to 1.309% on exposure to cool-white light for 300 hours (Table 4-3(II)).

Figure 3:
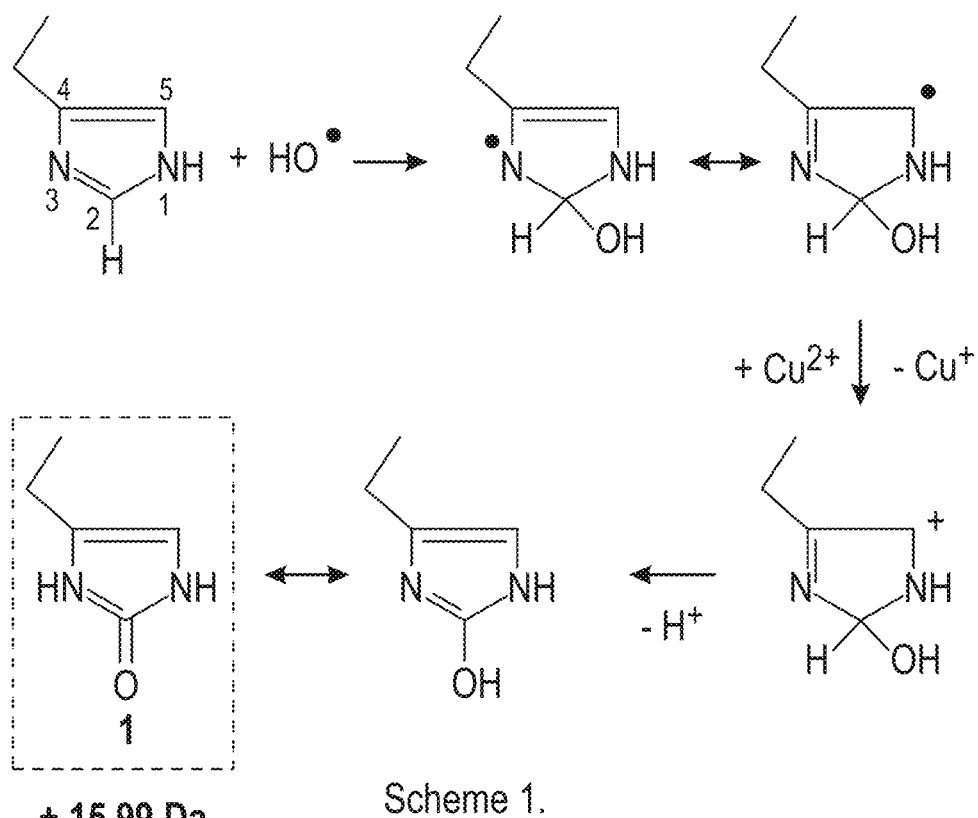
FIG. 3 depicts a proposed mechanism for histidine oxidation to 2-oxo-histidine (16 Da).

Two species of 2-oxo-histidine were observed, a 13.98 Da species (as shown in FIG. 2) and a 15.99 Da species (as shown in FIG. 3), with the 13.98 Da species being predominant in light stressed MiniTrap samples. The 15.99 Da species is known to be a product of a copper metal-catalyzed process (Schöneich, *J. Pharm. Biomed Anal.*, 21:1093-1097 (2000)). Moreover, the 13.98 Da species is a product of a light-driven process (Liu et al., *Anal. Chem.*, 86, 10, 4940-4948 (2014)).

Similar to the increased abundance of oxidized histidines in samples exposed to cool white light and UVA light, exposure of MT to cool white light or UVA light also induced formation of other PTMs (Table 4-4 and Table 4-5).

TABLE 4-4 (I)

Other PTMs in Peptides from Ultra-Violet Light Stressed MiniTrap

| Peptides | Site | t0 | UV_4 h | UV_10 h | UV_16 h | UV_20 h | UV_40 h |
|---|---|---|---|---|---|---|---|
| Deamidation | | | | | | | |
| EIGLLTCEATVNGHLYK (SEQ ID NO.: 62) | N84 | 20.8% | 21.7% | 21.5% | 21.5% | 22.7% | 22.4% |
| QTNTIIDVVLSPSHGIELSVGEK (SEQ ID NO.: 63) | N99 | 5.3% | 5.4% | 5.5% | 5.4% | 5.5% | 5.6% |
| Oxidation | | | | | | | |
| SDTGRPFVEMYSEIPEIIHMTEGR (SEQ ID NO.: 64) | M10 | 4.5% | 8.2% | 11.1% | 13.3% | 13.8% | 19.3% |
| SDTGRPFVEMYSEIPEIIHMTEGR (SEQ ID NO.: 65) | M20 | 1.1% | 2.0% | 2.8% | 3.4% | 3.4% | 4.6% |
| TQSGSEMK (SEQ ID NO.: 66) | M163 | 2.0% | 2.7% | 4.1% | 4.6% | 7.9% | 8.7% |
| SDQGLYTCAASSGLMTK (SEQ ID NO.: 67) | M192 | 5.4% | 8.1% | 10.9% | 12.1% | 12.5% | 18.3% |
| 3-deoxygluconasone | | | | | | | |
| SDTGRPFVEMYSEIPEIIHMTEGR (SEQ ID NO.: 68) | R5 | 9.9% | 10.0% | 9.9% | 9.7% | 9.8% | 9.3% |

TABLE 4-4 (II)

Other PTMs in Peptides from Cool White Light Stressed MiniTrap

| Peptides | Site | t0 | CW_30 h | CW_75 h | CW_100 h | CW_150 h | CW_300 h |
|---|---|---|---|---|---|---|---|
| Deamidation | | | | | | | |
| EIGLLTCEATVNGHLYK (SEQ ID NO.: 62) | N84 | 20.8% | 22.0% | 22.9% | 20.3% | 21.8% | 21.3% |
| QTNTIIDVVLSPSHGIELSVGEK (SEQ ID NO.: 63) | N99 | 5.3% | 5.6% | 5.2% | 5.6% | 5.5% | 5.8% |
| Oxidation | | | | | | | |
| SDTGRPFVEMYSEIPEIIHMTEGR (SEQ ID NO.: 64) | M10 | 4.5% | 11.7% | 17.3% | 19.9% | 25.1% | 39.7% |
| SDTGRPFVEMYSEIPEIIHMTEGR (SEQ ID NO.: 65) | M20 | 1.1% | 3.1% | 4.3% | 5.1% | 6.1% | 8.2% |
| TQSGSEMK (SEQ ID NO.: 66) | M163 | 2.0% | 3.3% | 15.7% | 11.7% | 26.4% | 20.5% |
| SDQGLYTCAASSGLMTK (SEQ ID NO.: 67) | M192 | 5.4% | 10.7% | 15.3% | 18.7% | 22.8% | 37.6% |
| 3-deoxygluconasone | | | | | | | |
| SDTGRPFVEMYSEIPEIIHMTEGR (SEQ ID NO.: 68) | R5 | 9.9% | 9.9% | 9.6% | 9.3% | 9.3% | 9.0% |

TABLE 4-5(I)

Oxidation Levels of Tryptophan/Tyrosine/Phenylalanine in Peptides from Ultra-Violet Light Stressed MiniTrap

| Peptides | Modification | Site | t0 | UV_4 h | UV_10 h | UV_16 h | UV_20 h | UV_40 h |
|---|---|---|---|---|---|---|---|---|
| SDQGLYTCAASSGLMTK (SEQ ID NO.: 67) | +4 | W58 | 0.016% | 0.049% | 0.089% | 0.119% | 0.132% | 0.221% |
| | +16 | | 0.047% | 0.109% | 0.177% | 0.225% | 0.242% | 0.514% |
| | +32 | | 0.200% | 0.487% | 0.415% | 0.481% | 0.423% | 0.498% |
| | +48 | | 0.000% | 0.000% | 0.000% | 0.001% | 0.001% | 0.001% |

TABLE 4-5(I)-continued

Oxidation Levels of Tryptophan/Tyrosine/Phenylalanine in Peptides from Ultra-Violet Light Stressed MiniTrap

| Peptides | Modification | Site | t0 | UV_4 h | UV_10 h | UV_16 h | UV_20 h | UV_40 h |
|---|---|---|---|---|---|---|---|---|
| TELNVGIDFNWEYPSS K (SEQ ID NO.: 29) | +4 | W138 | 0.435% | 0.462% | 0.550% | 0.557% | 0.502% | 0.512% |
| | +16 | | 0.083% | 0.100% | 0.161% | 0.206% | 0.239% | 0.448% |
| | +32 | | 0.009% | 0.018% | 0.027% | 0.039% | 0.044% | 0.115% |
| | +48 | | 0.284% | 0.278% | 0.270% | 0.302% | 0.343% | 0.275% |
| GFIISNATYK (SEQ ID NO.: 69) | +16 | Y64 | 0.032% | 0.041% | 0.046% | 0.053% | 0.054% | 0.073% |
| KFPLDTLIPDGK (SEQ ID NO.: 70) | +16 | F44 | 0.068% | 0.077% | 0.087% | 0.084% | 0.070% | 0.096% |
| FLSTLTIDGVTR (SEQ ID NO.: 71) | +16 | F166 | 0.066% | 0.075% | 0.085% | 0.089% | 0.089% | 0.124% |

TABLE 4-5 (II)

Oxidation Levels of Tryptophan/Tyrosine/Phenylalanine in Peptides from Cool White Light Stressed MiniTrap

| Peptides | Modification | Site | t0 | CW_30 h | CW_75 h | CW_100 h | CW_150 h | CW_300 h |
|---|---|---|---|---|---|---|---|---|
| SDQGLYTCAASSG LMTK (SEQ ID NO.: 67) | +4 | W58 | 0.016% | 0.063% | 0.124% | 0.161% | 0.228% | 0.526% |
| | +16 | | 0.047% | 0.129% | 0.227% | 0.283% | 0.377% | 0.795% |
| | +32 | | 0.200% | 1.601% | 2.706% | 3.139% | 3.925% | 6.974% |
| | +48 | | 0.000% | 0.001% | 0.002% | 0.002% | 0.003% | 0.005% |
| TELNVGIDFNWEY PSSK (SEQ ID NO.: 29) | +4 | W138 | 0.435% | 0.555% | 0.481% | 0.490% | 0.429% | 0.522% |
| | +16 | | 0.083% | 0.109% | 0.364% | 0.251% | 0.399% | 0.753% |
| | +32 | | 0.009% | 0.019% | 0.027% | 0.033% | 0.048% | 0.135% |
| | +48 | | 0.284% | 0.284% | 0.330% | 0.308% | 0.347% | 0.316% |
| GFIISNATYK (SEQ ID NO.: 69) | +16 | Y64 | 0.032% | 0.043% | 0.057% | 0.063% | 0.078% | 0.127% |
| KFPLDTLIPDGK (SEQ ID NO.: 70) | +16 | F44 | 0.068% | 0.087% | 0.07%2 | 0.088% | 0.079% | 0.144% |
| FLSTLTIDGVTR (SEQ ID NO.: 71) | +16 | F166 | 0.066% | 0.091% | 0.088% | 0.101% | 0.112% | 0.168% |

Figure 20:
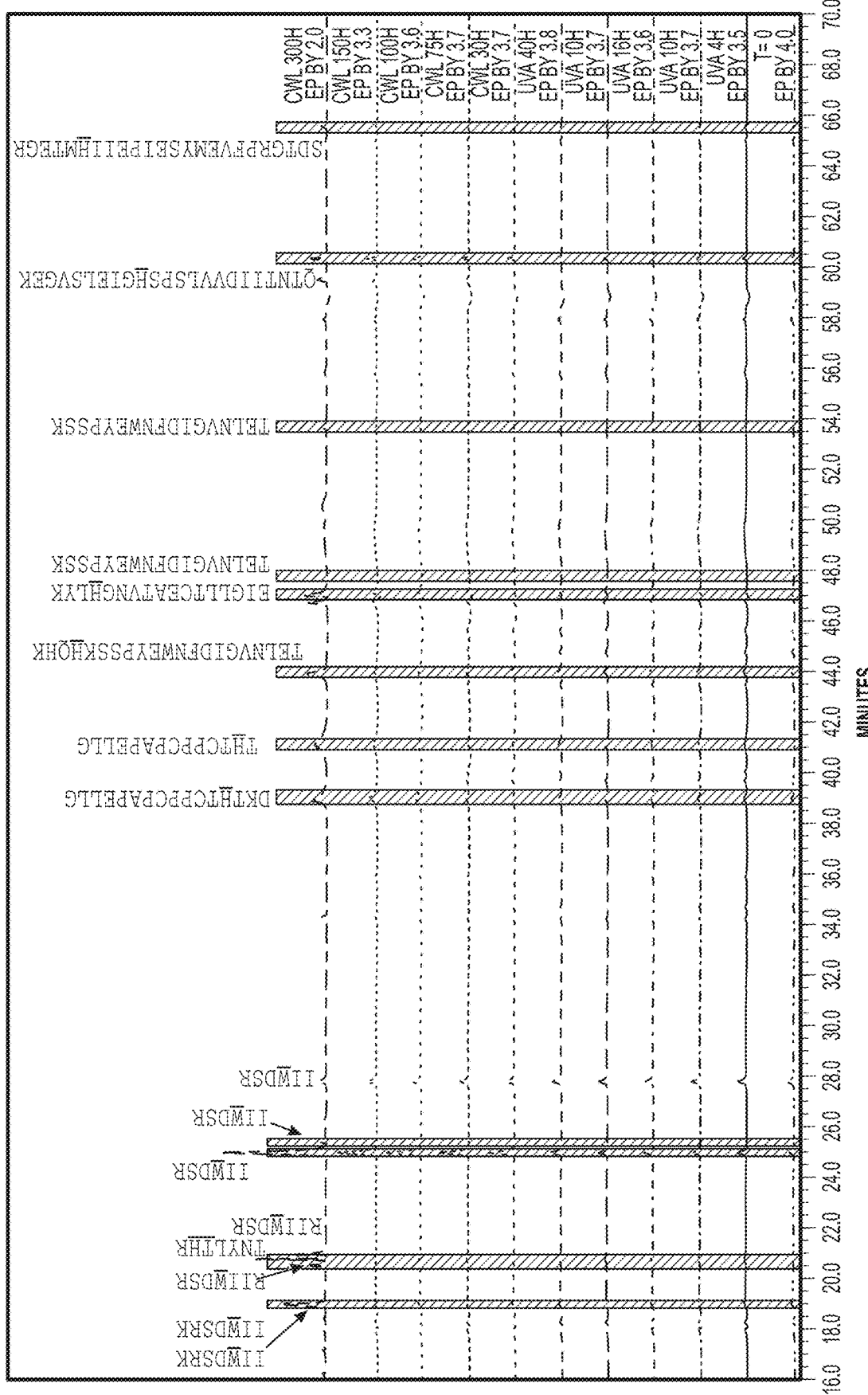
FIG. 20 depicts results of a study correlating the exposure of MT1 cool white light or UVA light with the appearance of oxidized amino acid residues, including SEQ ID NOS 114, 114-115, 21, 115, 28, 28, 28, 17, 83, 20, 18, 29, 29, 19, and 22, respectively, in order of appearance.

Thus, exposure of MT to cool white light or UVA light tracked with the appearance of oxidized residues (such as histidines/tryptophans (oxo-Trp)). Four species of oxo-trp were observed: +4 Da, +16 Da, +32 Da and +48 Da. The +4 Da species is explained by formation of kynurenine (FIG. 4), whereas the +16 Da, +32 Da and +48 Da are the mono-oxidation, di-oxidation and tri-oxidation of tryptophan residues. Peptide mapping of tryptic digests of MT samples monitored at 320 nm is shown in FIG. 20. The relative presence of oxidized residues comprising peptides can be compared in FIG. 20. For example, for the peptide IIW(+4)DSRK (SEQ ID NO.: 114), a significant difference in its presence can be seen for MT sample at t=0, and MT1 sample exposed to UVA for 40 hour and MT sample exposed to CWL for 300 hours.

Exposure of MT to cool white light or UVA light was also evaluated for the presence of HMW/low molecular weight (LMW) species (Table 4-6).

TABLE 4-6

HMW/LMW Species Were Generated After Extended UVA and CWL Stress Sample: MT1, 80 mg/mL, pH 5.8

| | Light exposed Samples % HMW | Dark control samples % HMW | Light exposed Samples % Native | Dark control samples % Native | Light exposed Samples % LMW | Dark control samples % LMW |
|---|---|---|---|---|---|---|
| Cumulative UVA exposure (×ICH) | | | | | | |
| t = 0 | 2.1 | NA | 96.7 | NA | 1.2 | NA |
| 0.2 × ICH (40 W*h/m2) | 2.1 | 2.1 | 96.7 | 96.7 | 1.2 | 1.3 |
| 0.5 × ICH (100 W*h/m2) | 11.6 | 2.2 | 86.5 | 96.6 | 1.9 | 1.2 |
| 0.8 × ICH (160 W*h/m2) | 14.5 | 2.2 | 83.4 | 96.6 | 2.1 | 1.2 |
| 1.0 × ICH (200 W*h/m2) | 15.8 | 2.2 | 81.9 | 96.6 | 2.3 | 1.3 |
| 2.0 × ICH (400 W*h/m2) | 22.7 | 2.3 | 74.5 | 96.7 | 2.8 | 1.0 |

TABLE 4-6-continued

HMW/LMW Species Were Generated
After Extended UVA and CWL Stress
Sample: MT1, 80 mg/mL, pH 5.8

| | Light exposed Samples % HMW | Dark control samples % HMW | Light exposed Samples % Native | Dark control samples % Native | Light exposed Samples % LMW | Dark control samples % LMW |
|---|---|---|---|---|---|---|
| Cumulative CWL exposure (×ICH) | | | | | | |
| 0.2 × ICH (0.24 million lux* h) | 12.1 | 2.2 | 86.6 | 96.6 | 1.4 | 1.2 |
| 0.5 × ICH (0.6 million lux*hr) | 20.4 | 2.3 | 77.9 | 96.4 | 1.6 | 1.3 |
| 0.8 × ICH (0.96 million lux*hr) | 23.2 | 2.4 | 75.1 | 96.2 | 1.7 | 1.4 |
| 1.0 × ICH (1.2 million lux*hr) | 30.1 | 2.6 | 68.1 | 96.2 | 1.9 | 1.3 |
| 2.0 × ICH (2.4 million lux*hr) | 45.0 | 2.9 | 52.6 | 95.8 | 2.4 | 1.4 |

Figure 22:
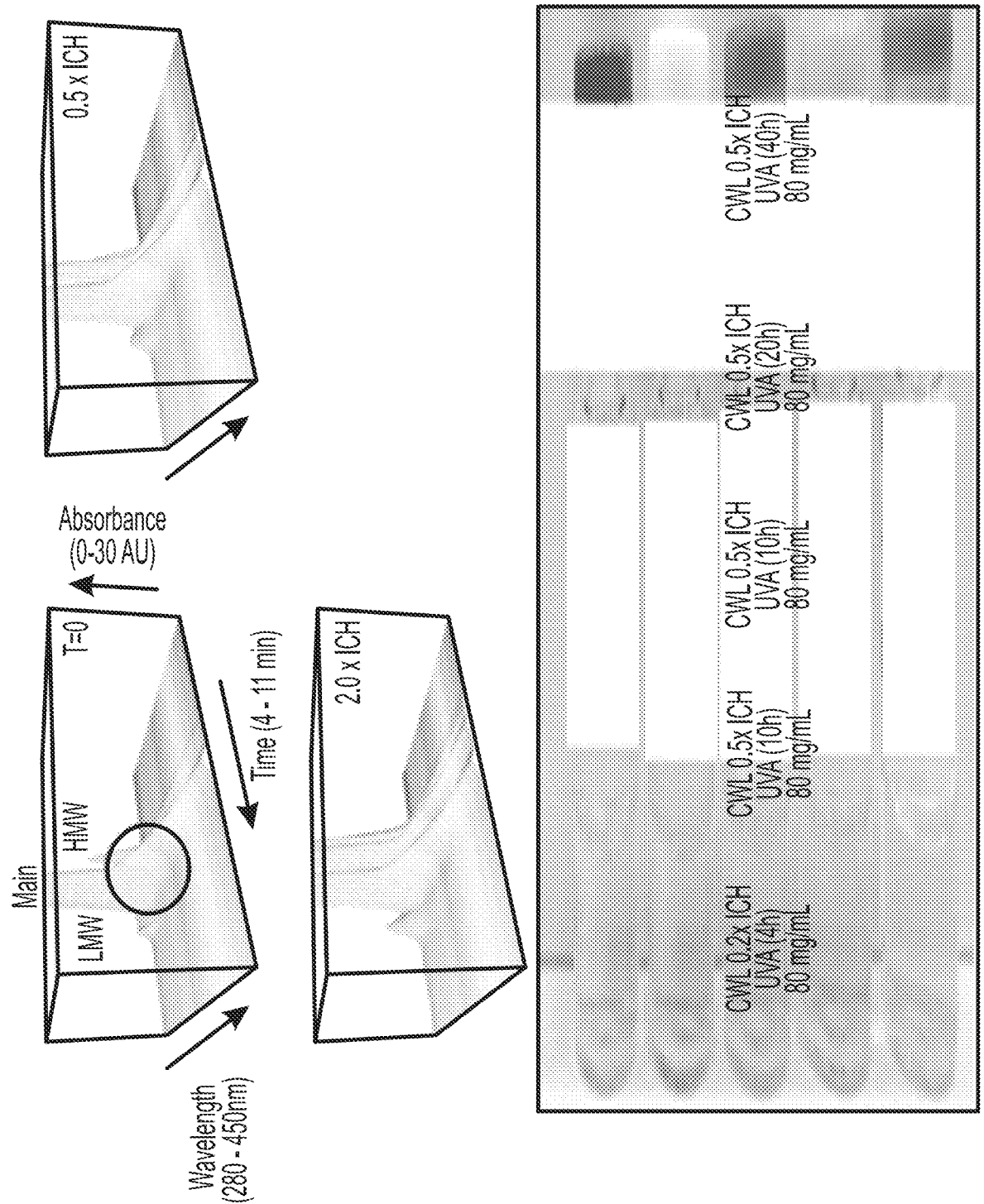
FIG. 22 depicts the 3D SEC-PDA chromatograms on UVA-stressed MT1 with absorbance at ~350 nm (see, e.g., circle highlighting ~350 nm) according to an exemplary embodiment where A shows the chromatogram at T=0, B shows the chromatogram at 0.5×ICH, C shows the chromatogram at 2.0×ICH, and D shows images of MT1 in vials (normalized to 80 mg/mL) stressed by UVA for different time intervals.

To track the coloration with respect to HMW/LMW species for each sample, analytical size-exclusion chromatography with full-spectrum PDA detection (SEC-PDA) was performed as shown above on all the stressed samples (CWL and UVA). SEC-PDA analysis of CWL-stressed MT reveals significant increases in absorbance at ~350 nm for all size variants except the LMW species (FIG. 21), whereas SEC-PDA on UVA-stressed MT reveals no increases in absorbance at ~350 nm (FIG. 22). Unlike CWL-treated stress samples, UVA-treated stress samples did not produce any significantly quantifiable yellow-brown color.

Figure 23A:
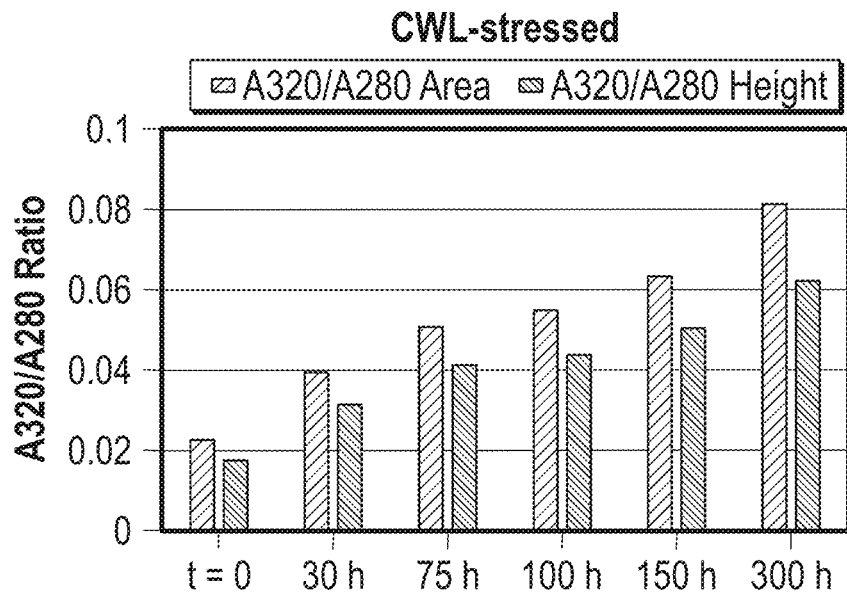
FIG. 23A depicts A320/280 absorbance ratios quantitated from SEC-PDA chromatograms for the samples stressed using CWL (top panel) and FIG. 23B depicts a chart of A320/280 absorbance ratios for size variants in the samples stressed using CWL (bottom panel), wherein the samples are stressed according to an exemplary embodiment.
Figure 23B:
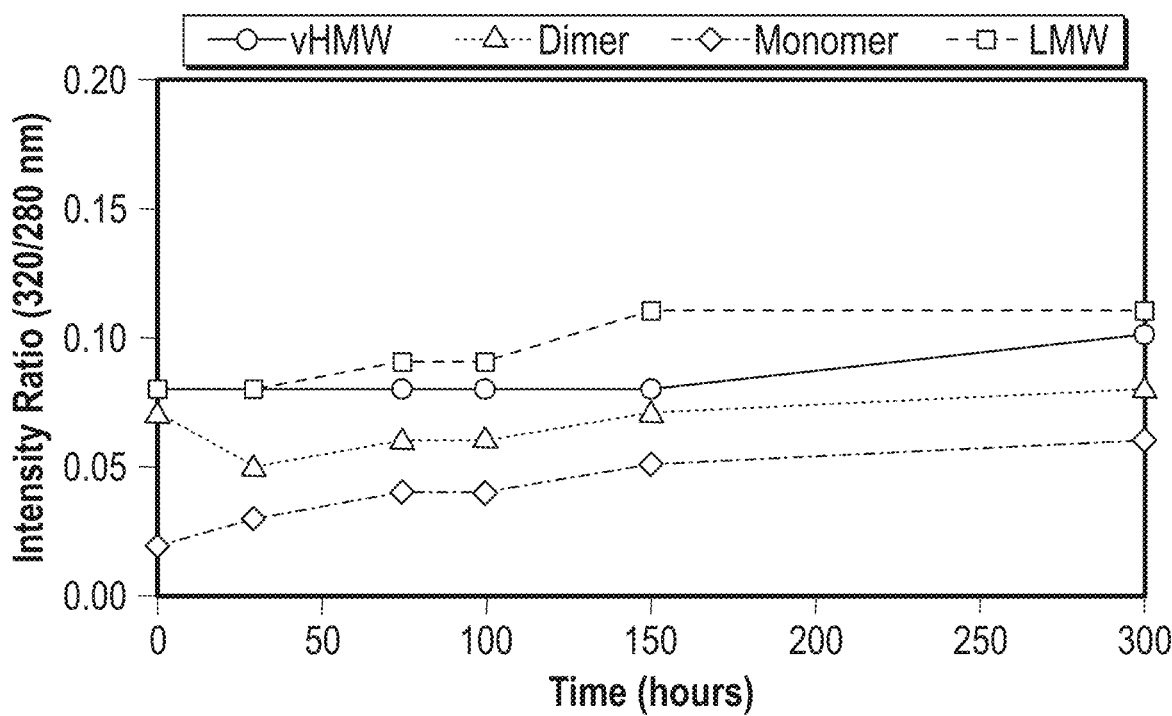
Figure 24A:
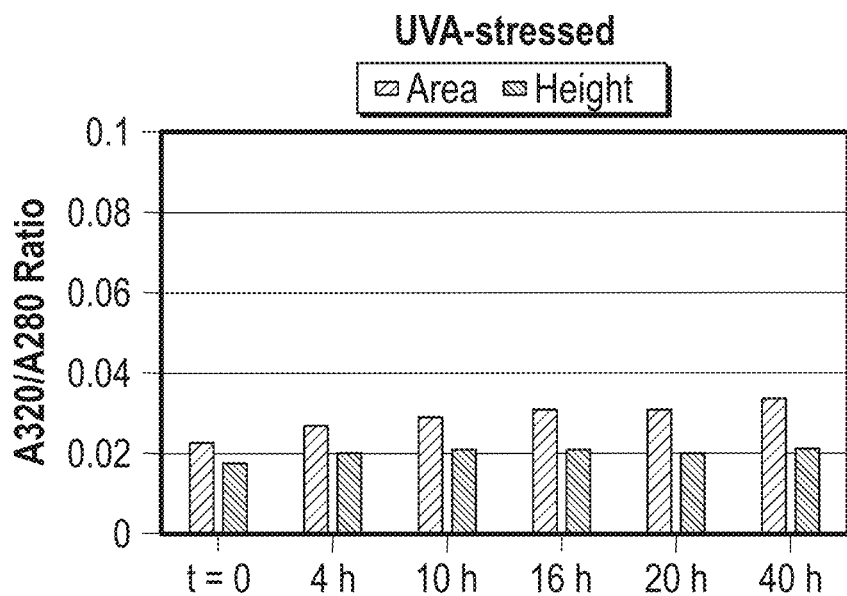
FIG. 24A depicts A320/280 absorbance ratios quantitated from SEC-PDA chromatograms for the samples stressed using UVA (top panel) and FIG. 24B depicts a chart of A320/280 absorbance ratios for size variants in the samples stressed using UVA (bottom panel), wherein the samples are stressed according to an exemplary embodiment.
Figure 24B:
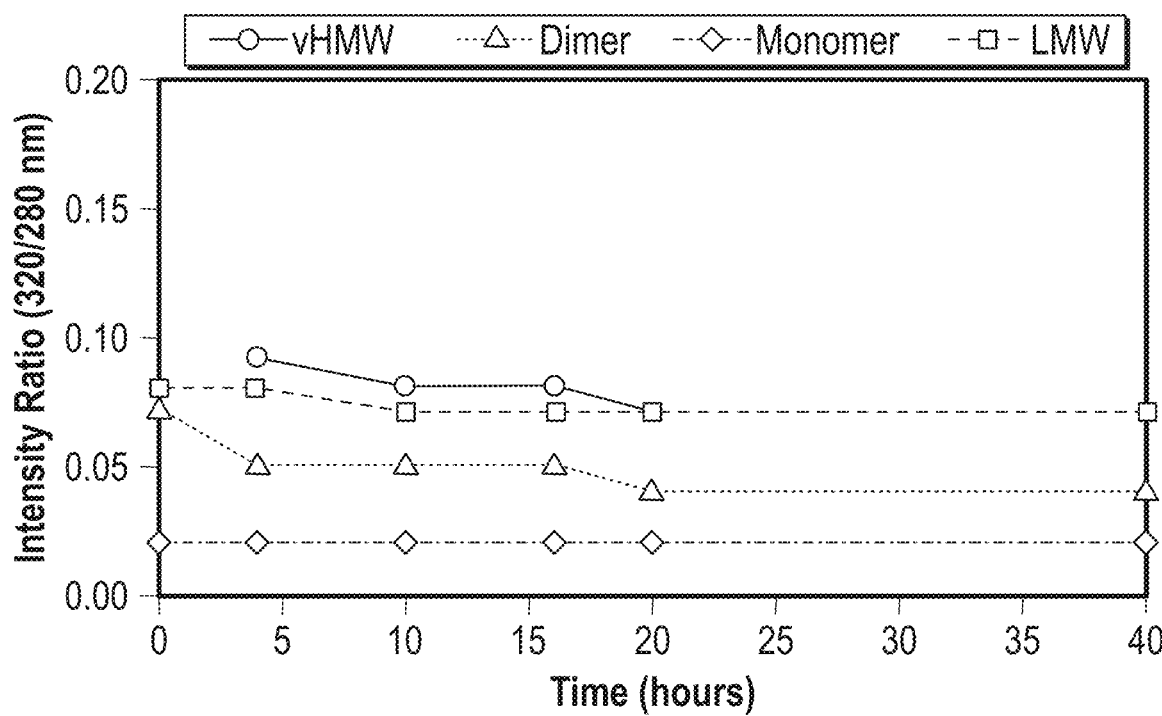

A similar result was obtained after studying absorbance ratios at 320 nm and 280 nm for the samples stressed by UVA and CWL. The A320/A280 ratios, analyzed by either raw intensity or total peak area, tracked with increasing intensity of yellow color in CWL-stressed samples (FIG. 23), whereas the A320/A280 ratios did not track with increasing intensity of yellow color in UVA-stressed samples (FIG. 24). This corroborates the previous observation that MT1 samples subjected to UVA stress does not result in the same yellow-brown color observed following CWL stress.

Example 5. Upstream Methods for Reducing Coloration 5.1 Chemically Defined Medium Incubation Study The effect of various constituents spiked into fresh chemically defined media (CDM) comprising aflibercept with respect to coloration was examined.

One or more 50 mL vent-capped shaker tubes with 10 mL working volume (fresh CDM1) were incubated for 7 days, taking samples on day 0 and day 7. Aflibercept samples (aflibercept recombinant protein in an aqueous buffered solution, pH 6.2, comprising 5 mM sodium phosphate, 5 mM sodium citrate and 100 mM sodium chloride) were spiked into shaker tubes at a concentration of 6 g/L.

Components added to reach a cumulative concentration:
Cysteine: 16.6 mM
Iron: 0.23 mM
Copper: 0.0071 mM
Zinc: 0.54 mM The scaled effect of each constituent added on the b* value (CIE L*, a*, b* color space) is set forth in FIG. 25A and plot of actual b* value against predicted b* value is set forth in FIG. 25B. Addition of cysteine resulted in the largest yellow-brown color increase. Iron and zinc also generated color. Folic acid and B vitamin group (including thiamine, niacinamide, D-pantothenic acid, D-biotin, and pyridoxine) increased the yellow-brown color. Riboflavin and Vitamin B12 did not statistically impact color.

5.2 Effect of Decreasing Cysteine and Metals on b* Value

Bioreactors (e.g., 2 L) were inoculated from a seed culture of an aflibercept producing cell line. The inoculated cultures were grown at a temperature of 35.5° C., pH of 7.1±0.25, and air sparge set point of 22 ccm. Glucose, antifoam, and basal feeds were supplemented to the bioreactors as needed. The effect of lowering the concentration of cysteine and of metals on color when aflibercept is expressed was evaluated in CDM1.

Medium at day 0=CDM1, including 1.48 mM of cysteine
Nutrient Feeds:
 Day 2=Chemically defined feed (CDF)+1.3-2.1 mM cysteine
 Day 4=CDF+1.6-1.7 mM cysteine
 Day 6=CDF+1.6-1.7 mM cysteine
 Day 8=CDF+1.6-1.7 mM cysteine
The bioreactor conditions were as follows:
Cysteine was added at a cumulative concentration of about 6-7 millimoles per L of culture, 8-9 millimoles per L of culture, or 10-11 millimoles per L of culture.
Metals in CDM1 (0.5×, 1×, or 1.5×CDM1 levels) at 1× levels are listed below (where the concentrations are prior to inoculum addition):
 Fe=68-83 micromoles per liter of culture
 Zn=6-7 micromoles per liter of culture
 Cu=0.1-0.2 micromoles per liter of culture
 Ni=0.5-1 micromoles per liter of culture
Decreasing cumulative cysteine levels to 6-7 millimoles/L reduced yellow-brown color with no significant impact to titer. Decreasing metal concentrations to 0.5× in the medium reduced color with significant increase in titer. There was a minimal impact to titer, VCC (viable cell concentration), viability, ammonia or osmolality (See FIG. 26A-E). The predicted scale effect of metal content and cysteine on b* value and titer is set forth in FIG. 27.

5.3 Evaluation of the Effect of Antioxidants on b* Value

The effect of the antioxidants taurine, hypotaurine, thioctic acid, glutathione, glycine and vitamin C on color when spiked into spent CDM comprising aflibercept was evaluated. One or more 50 mL vent-capped shaker tubes with 10 mL working volume (CDM1) were incubated for 7 days, taking samples on day 0 and day 7.

The conditions for component additions to spent CDM1 were as follows:
Aflibercept sample (aflibercept recombinant protein in an aqueous buffered solution, pH 6.2, comprising 5 mM sodium phosphate, 5 mM sodium citrate and 100 mM sodium chloride) spiked into shaker tubes at 6 g/L concentration
Antioxidants added to spent CDM1 at the following concentrations:
 Taurine=10 mM of culture
 Hypotaurine=10 mM of culture
 Glycine=10 mM of culture
 Thioctic Acid=0.0024 mM of culture
 Glutathione, reduced=2 mM of culture
 Hydrocortisone=0.0014 mM of culture
 Vitamin C (ascorbic acid)=0.028 mM of culture Multiple antioxidants decreased color formation in spent medium: a combination of hypotaurine, taurine and glycine; thioctic acid; and vitamin C. Glutathione increased b* value.

TABLE 5-1

Summary of Antioxidant Effect on Color Formation of MiniTrap

| Condition | b* value |
|---|---|
| Spent Medium Day 0 | 0.37 |
| Spent Medium Day 7 Control | 1.47 |
| Spent Medium Day 7 + Antioxidants* | 1.02 |

*Antioxidants that significantly decreased b* value: Hypotaurine/Taurine/Glycine, Thioctic Acid, Vitamin C.

A summary of the predicted effect of various antioxidants on b* value (CIE L*, a*, b* color space) is set forth in FIG. 28(A-C).

The effect of the further addition to the antioxidants on color, when spiked into spent CDM comprising aflibercept, was evaluated. One or more 50 mL vent-capped shaker tubes with 10 mL working volume (CDM1) were incubated for 7 days, taking samples on day 0 and day 7.

Figures 28A, 28B:
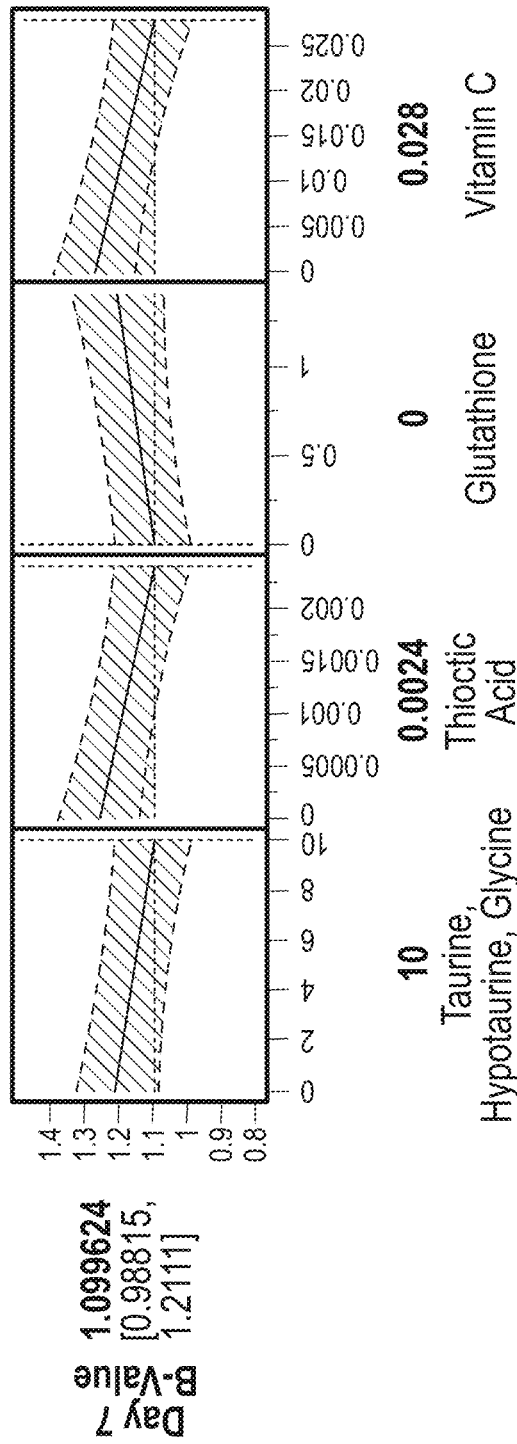
FIGS. 28A and 28B depicts the effect of incubation of various components with aflibercept in spent CDM on the generation of color (CIE L*, a*, b* predicted b value) (A); and by a plot of scaled predicted impacts on b value.
Figure 28D:
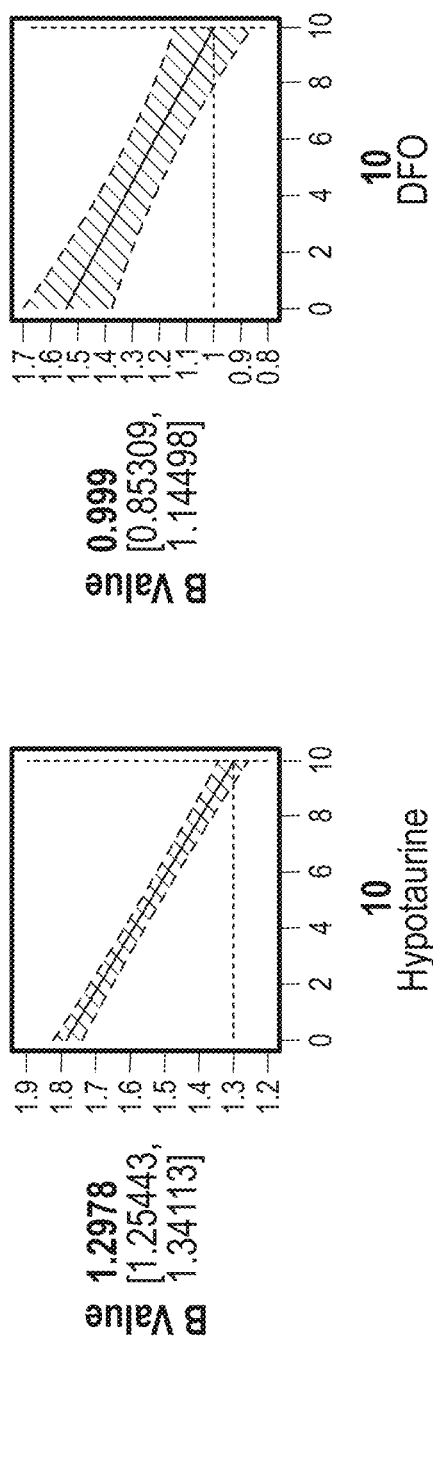
FIG. 28D depicts the effect of incubation of hypotaurine and deferoxamine mesylate salt (DFO) with aflibercept in spent CDM on the generation of color (CIE L*, a*, b* predicted "b" value).

The conditions for component additions to spent CDM1 were as follows:
  Aflibercept sample (aflibercept recombinant protein in an aqueous buffered solution, pH 6.2, comprising 5 mM sodium phosphate, 5 mM sodium citrate and 100 mM sodium chloride) spiked into shaker tubes at 6 g/L concentration
  Two DOE experiments were run:
  (i) Antioxidants added to spent CDM1 at the following concentrations:
    Taurine=10 mM of culture
    Hypotaurine=10 mM of culture
    Glycine=10 mM of culture
    Thioctic Acid=0.0024 mM of culture
    Vitamin C (ascorbic acid)=0.028 mM of culture
  (ii) Antioxidants added to reach the following cumulative concentrations:
    ATA=2.5 µM-5 µM
    Deferoxamine mesylate (DFO)=5 µM-10 µM
    Catalase=101.5 mg/L
    S-carboxymethyl-L-Cysteine=10 mM Hypotaurine was found to decrease the color formation in spent medium (FIG. 28D). DFO also significantly decreased the color formation in spent medium (FIG. 28D). The other antioxidants did not have a statistical impact on the color formation.

TABLE 5-2

Summary of Antioxidant Effect on Color Formation of MiniTrap

| Condition | b* value |
|---|---|
| Spent Medium Day 0 | 0.44 |
| Spent Medium Day 7 Control | 1.73 |
| Spent Medium Day 7 + Hypotaurine | 1.32 |
| Spent Medium Day 7 + DFO | 0.92 |

Shake-Flask Antioxidant Study:

Taurine, hypotaurine, glycine, thioctic acid and vitamin C were evaluated individually and in combination for their ability to decrease the color formation in cell culture (Table 5-3).

250 mL shake flasks were inoculated from a seed culture of an aflibercept producing cell line. The inoculated cells were grown at 35.5° C. in incubators with 5% $CO_2$ control. Glucose and basal feeds were supplemented to the shake flasks as needed. The process described above was used wherein metals were present at 0.5× concentration in CDM1 and cysteine was added at a cumulative concentration of 6-7 mM.

TABLE 5-3

| Antioxidant | Level 1 0× | Level 1 0.5× | Level 1 1× |
|---|---|---|---|
| Taurine | 0 | 3.75 mM | 7.5 mM |
| Hypotaurine | 0 | 3.75 mM | 7.5 mM |
| Glycine | 2.0 mM | 5.75 mM | 9.5 mM |
| Thioctic acid | 1.0 µM | 1.9 µM | 2.8 µM |
| Vitamin C | 0 | 11.0 µM | 21.0 µM |

Figure 28E:
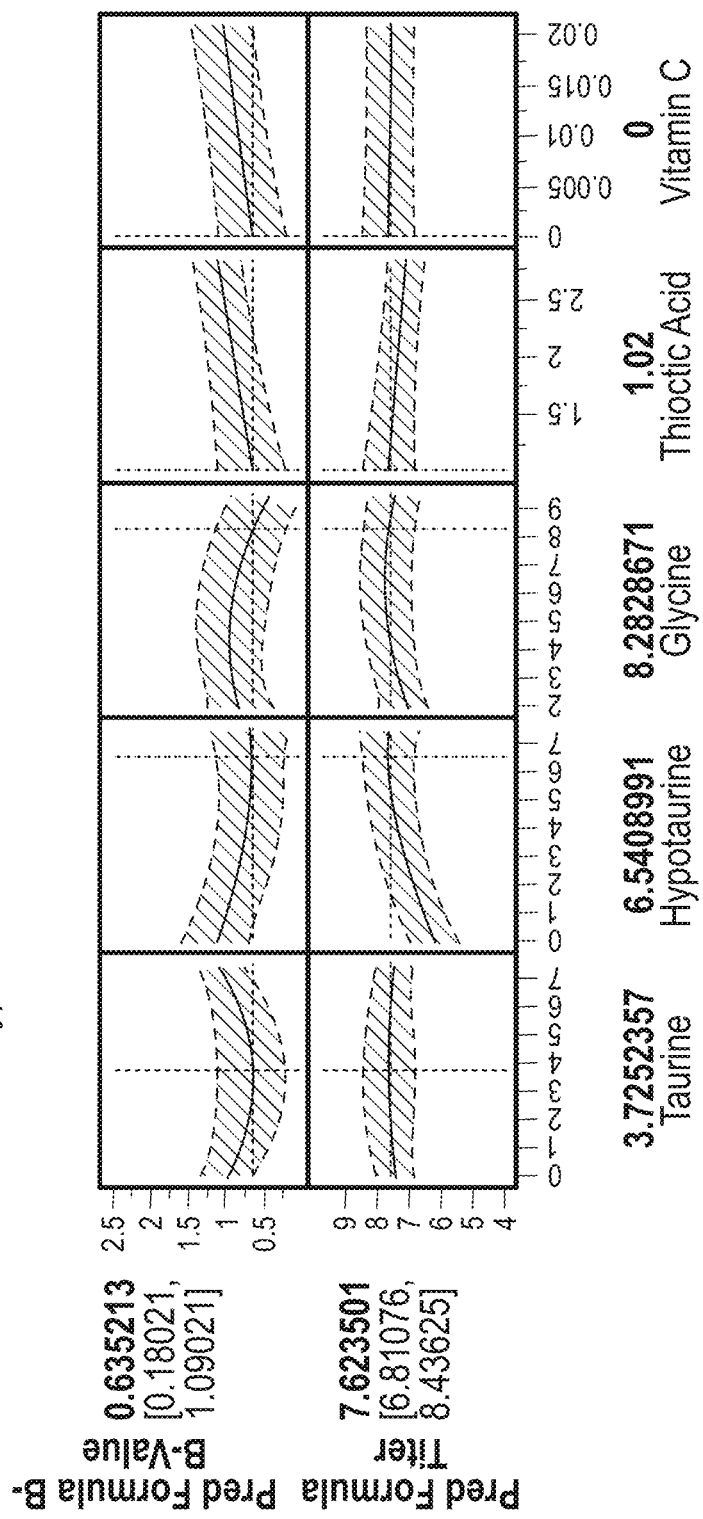
FIG. 28E depicts the effect of incubation of various components individually with aflibercept from shake flask culture on the generation of color (CIE L*, a*, b* predicted "b" value).

FIG. 28E shows the predicted effect of the antioxidants in Table 5-3 on b* value (CIE L*, a*, b* color space) and final titer. Taurine, hypotaurine, and glycine significantly reduced b* value without negatively impacting titer.

Example 6. Glycosylation and Viability Studies for Aflibercept Production Using CDM Bioreactors (e.g., 2 L) were inoculated from a seed culture of an aflibercept producing cell line. The inoculated cultures were grown at a temperature of 35.5° C., pH of 7.1±0.25, and air sparge set point of 22 ccm. Glucose, antifoam, and basal feeds were supplemented to the bioreactors as needed. Production of aflibercept protein was carried out using CDM1 (proprietary). Production of a host cell line expressing aflibercept fusion protein was carried out using CDM1 (proprietary), CDM2 (commercially obtained), and CDM3 (commercially obtained). A set of experiments was carried out using CDM 1, 2, and 3 with no additional media components. Another set of experiments was performed using CDMs 1-3 to which manganese (manganese chloride tetrahydrate, Sigma, 3.2 mg/L), galactose (Sigma, 8 g/L), and uridine (Sigma, 6 g/L) were added to the feeds to modify the galactosylation profile. Lastly, a set of experiments was performed using CDMs 1-3 to which manganese (manganese chloride tetrahydrate, Sigma, 3.2 mg/L), galactose (Sigma, 8 g/L), and uridine (Sigma, 6 g/L) were added to the feeds to modify the galactosylation profile and dexamethasone (Sigma, 12 mg/L) was added to the feeds to modify the sialyation profile of the composition. A clarified harvest using each of the CDM was prepared by centrifugation followed by 0.45 µm filtration.

Samples were processed by Protein A prior to N-glycan analysis.

Titer Measurements

Throughout these examples, unless stated otherwise, aflibercept titers were measured daily using an Agilent (Santa Clara, CA) 1200 Series HPLC, or equivalent, operating with a low pH, and step elution gradient with detection at 280 nm. Concentrations were assigned with respect to a reference standard calibration curve.

Viable Cell Density (VCD) and Cell Viability Values

Throughout these examples, unless stated otherwise, viable cell density (VCD) and cell viability values were measured through trypan blue exclusion via Nova BioProfile Flex automated cell counters (Nova Biomedical, Waltham, MA). Glucose, lactate, offline pH, dissolved oxygen (DO), pCO2 measurements, and osmolality were measured with the Nova BioProfile Flex (Nova Biomedical, Waltham, MA).

N-Glycan Oligosaccharide Profiling

Approximately 15 μg of Protein A processed samples from CDM 1-3 harvests were prepared for N-glycan analysis in accordance with the Waters GlycoWorks protocol using the GlycoWorks Rapid Deglycosylation and GlycoWorks RapiFluor-MS Label kits (Waters part numbers 186008939 and 186008091, respectively). N-glycans were removed from the aflibercept protein by treating the samples with PNGase-F at 50.5° C. for 5 minutes, followed by a cool down at 25° C. for 5 minutes. The released glycans were labeled with RapiFluor-MS fluorescent dye through reaction at room temperature for 5 minutes. The protein was precipitated by adding acetonitrile to the reaction mixture and pelletized to the bottom of the well through centrifugation at 2,204×g for 10 minutes. The supernatant comprising the labeled glycans was collected and analyzed on an UPLC using hydrophilic interaction liquid chromatography (Waters BEH Amide column) with post-column fluorescence detection. After binding to the column, the labeled glycans were separated and eluted using a binary mobile phase gradient comprised of acetonitrile and aqueous 50 mM ammonium formate (pH 4.4). The labeled glycans were detected using a fluorescence detector with an excitation wavelength of 265 nm and an emission wavelength of 425 nm. Using the relative area percentages of the N-glycan peaks in the resultant chromatograms, the N-glycan distribution is reported as the total percentage of N-glycans (1) containing a core fucose residue (Total Fucosylation, Table 6-1), (2) containing at least one sialic acid residue (Total Sialylation, Table 6-2), (3) identified as Mannose-5 (Mannose-5, Table 6-3), (4) containing at least one galactose residue (Total Galactosylation, Table 6-4), and (5) of known identity (Total Identified Peaks, Table 6-5).

Results

Figure 29:
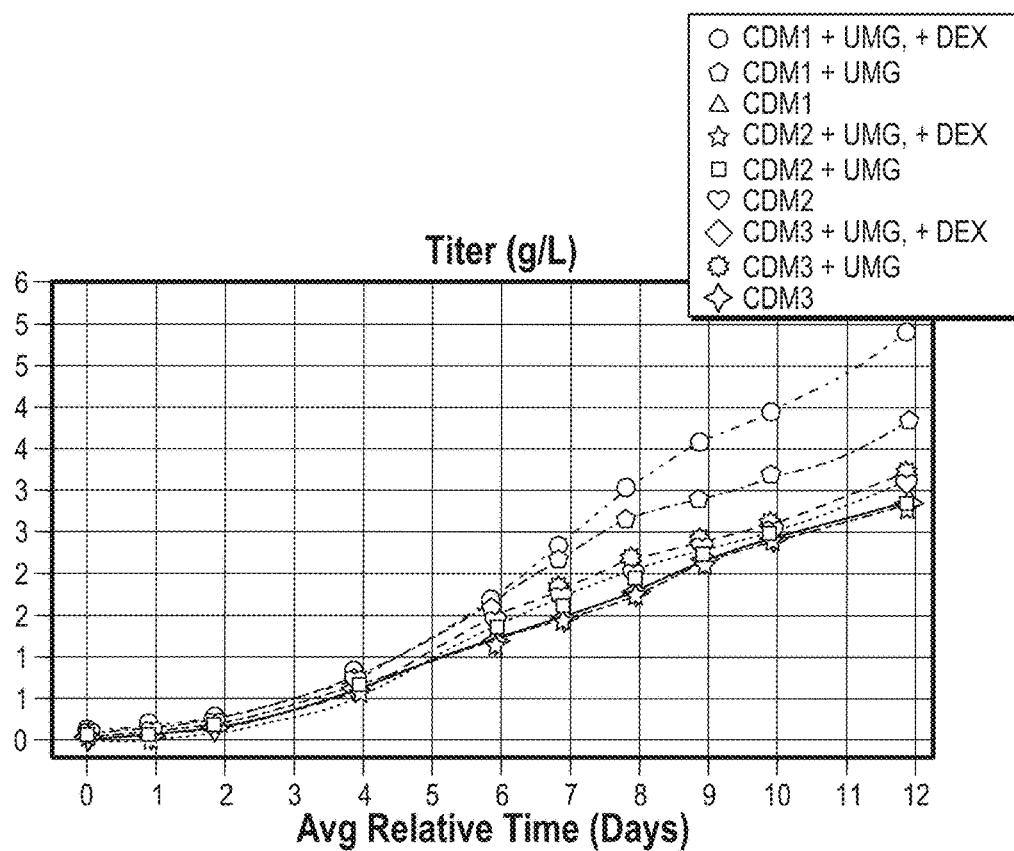
FIG. 29 is a chart showing the effect of addition of uridine, manganese, galactose and dexamethasone in CDMs on the titer of the aflibercept produced.
Figure 30:
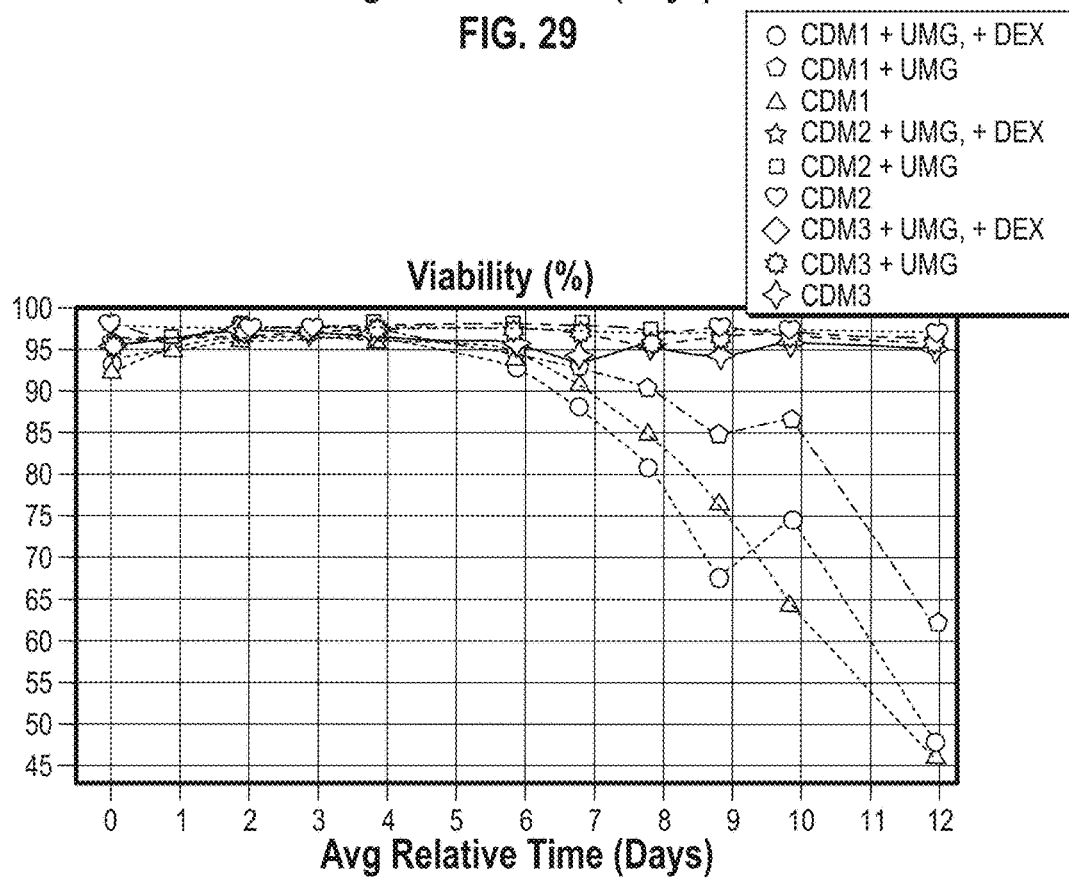
FIG. 30 is a chart showing the effect of addition of uridine, manganese, galactose and dexamethasone in CDMs on the viability of cells expressing aflibercept, wherein the aflibercept is produced.
Figure 31:
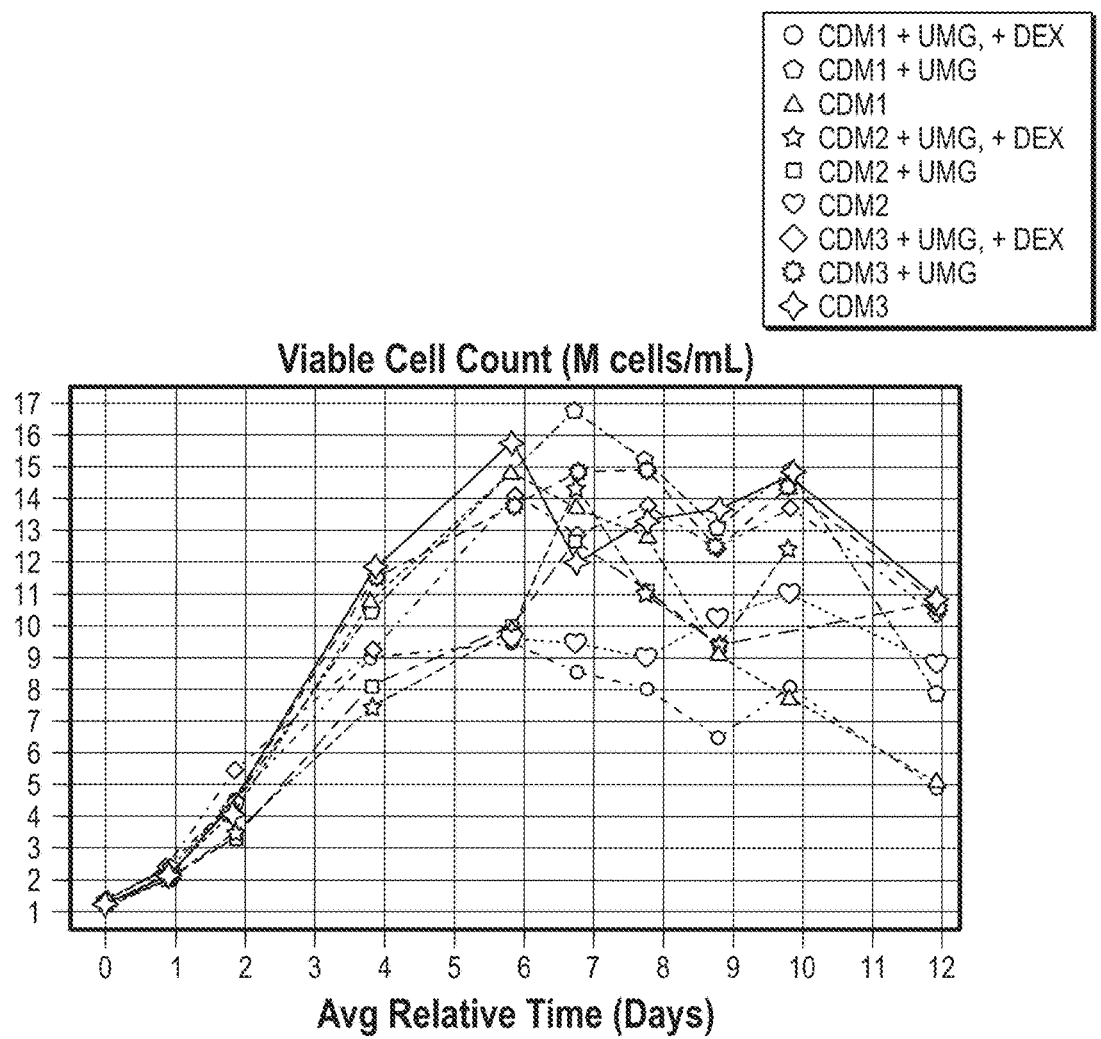
FIG. 31 is a chart showing the effect of addition of uridine, manganese, galactose and dexamethasone in CDMs on the viable cell count of cells expressing aflibercept, wherein the aflibercept is produced.

The viable cell count (VCC), viability, and harvest titer results are shown in FIGS. 29-31 for CDMs 1-3 with and without additional components.

Amongst the nine cultures, the CDM1 culture comprising uridine, manganese, and galactose showed the highest titer at 12 days (5.5 g/L). CDM1 without additional components also showed a high titer at 12 days (about 4.25 g/L) compared to the other seven cultures (FIG. 29).

Cell viability results were similar across the various conditions up to process day 6. After process day 7, the CDM2 and CDM3 cultures with or without additional media components showed more than about 90% viability (FIG. 30).

CDM1 culture with uridine, manganese and galactose showed the highest VCC around day 6 (FIG. 31).

The influence of cultures and supplements had a significant impact on the overall N-glycan distribution (Tables 6-1 to 6-5). The glycan levels were compared using Protein A processed aflibercept (two samples were evaluated) made using soy hydrolysate. The total identified peaks are listed in Table 6-5.

TABLE 6-1

Total Fucosylation (%)

| Condition | Day 6 | Day 10 | Day 12 |
|---|---|---|---|
| CDM1 | 48.75 | — | 46.26 |
| CDM1 + UMG | 49.21 | — | 44.38 |
| CDM1 + UMG + Dex | 48.88 | — | 46.23 |
| CDM2 | — | 45.68 | 45.14 |
| CDM2 + UMG | — | 46.36 | 45.27 |
| CDM2 + UMG + Dex | — | 46.92 | — |
| CDM3 | 49.24 | — | 45.59 |
| CDM3 + UMG | 48.71 | — | 42.61 |
| CDM3 + UMG + Dex | 49.36 | — | 44.56 |
| Soy hydrolysate 1 | | 51.37 | |
| Soy hydrolysate 2 | | 52.43 | |

U is uridine,
M is manganese,
G is galactose,
Dex is dexamethasone

TABLE 6-2

Total Sialylation (%)

| Condition | Day 6 | Day 10 | Day 12 |
|---|---|---|---|
| CDM1 | 44.06 | — | 39.14 |
| CDM1 + UMG | 43.72 | — | 35.8 |
| CDM1 + UMG + Dex | 43.2 | — | 36.72 |
| CDM2 | — | 37.62 | 36.67 |
| CDM2 + UMG | — | 37.57 | 36.29 |
| CDM2 + UMG + Dex | — | 38.06 | — |
| CDM3 | 44 | — | 31.21 |
| CDM3 + UMG | 42.48 | — | 30.84 |
| CDM3 + UMG + Dex | 43.82 | — | 32.74 |
| Soy hydrolysate 1 | | 58.24 | |
| Soy hydrolysate 2 | | 59.23 | |

U is uridine,
M is manganese,
G is galactose,
Dex is dexamethasone

TABLE 6-3

Mannose-5 (%)

| Condition | Day 6 | Day 10 | Day 12 |
|---|---|---|---|
| CDM1 | 6.76 | — | 10.1 |
| CDM1 + UMG | 6.9 | — | 13.17 |
| CDM1 + UMG + Dex | 6.23 | — | 8.86 |
| CDM2 | — | 9.71 | 11.96 |
| CDM2 + UMG | — | 9.44 | 10.93 |
| CDM2 + UMG + Dex | — | 8.21 | — |
| CDM3 | 2.31 | — | 12.63 |
| CDM3 + UMG | 2.71 | — | 13.38 |
| CDM3 + UMG + Dex | 2.05 | — | 11.98 |
| Soy hydrolysate 1 | | 5.19 | |
| Soy hydrolysate 2 | | 5.24 | |

U is uridine,
M is manganese,
G is galactose,
Dex is dexamethasone

TABLE 6-4

Total Galactosylation (%)

| Condition | Day 6 | Day 10 | Day 12 |
|---|---|---|---|
| CDM1 | 68.44 | — | 62.9 |
| CDM1 + UMG | 69.25 | — | 59.02 |
| CDM1 + UMG + Dex | 69.05 | — | 63.26 |
| CDM2 | — | 65.33 | 63.68 |
| CDM2 + UMG | — | 68.13 | 66 |
| CDM2 + UMG + Dex | — | 69.35 | — |
| CDM3 | 74.57 | — | 62.28 |
| CDM3 + UMG | 74.82 | — | 62.2 |
| CDM3 + UMG + Dex | 76.48 | — | 65.18 |

TABLE 6-4-continued

Total Galactosylation (%)

| Condition | Day 6 | Day 10 | Day 12 |
|---|---|---|---|
| Soy hydrolysate 1 | | 79.64 | |
| Soy hydrolysate 2 | | 80.55 | |

U is uridine,
M is manganese,
G is galactose, Dex is dexamethasone

TABLE 6-5

Total Identified Peaks (%)

| Condition | Day 6 | Day 10 | Day 12 |
|---|---|---|---|
| CDM1 | 87.28 | — | 84.67 |
| CDM1 + UMG | 88.43 | — | 83.82 |
| CDM1 + UMG + Dex | 87.36 | — | 83.44 |
| CDM2 | — | 86.23 | 86.67 |
| CDM2 + UMG | — | 87.81 | 86.87 |
| CDM2 + UMG + Dex | — | 87.53 | — |
| CDM3 | 86.38 | — | 86.31 |
| CDM3 +UMG | 87.07 | — | 86.13 |
| CDM3 + UMG + Dex | 87.18 | — | 87.43 |
| Soy hydrolysate 1 | | 93.93 | |
| Soy hydrolysate 2 | | 94.74 | |

U is uridine,
M is manganese,
G is galactose,
Dex is dexamethasone

The total fucosylation, total sialylation, total galactosylation and mannose-5 observed on day 12 of the cultures of the various CDMs was 42.61% to 46.26%, 30.84% to 39.14%, 59.02 to 66% and 8.86% to 13.38%, respectively. These values for glycosylation differ from the glycosylation values obtained using soy hydrolysate.

Lastly, color measurements were carried out for the clarified harvests obtained from cells expressing aflibercept in CDM1, CDM2, and CDM3 supplemented with uridine, manganese, and galactose. The operating parameters for the bioreactor study steps will be known to one of ordinary skill in the art.

Example 7. Affinity Production of Anti-VEGF Proteins 7.1 Expression of VEGF MiniTrap The coding regions of recombinant VEGF MiniTrap (e.g., MT5, SEQ ID NO.: 46) were operably linked to a signal sequence, cloned into a mammalian expression vector and transfected into Chinese hamster ovary (CHO-K1) cells; the stably transfected pools were isolated after selection with 400 µg/mL hygromycin for 12 days. The stable CHO cell pools, grown in chemically defined protein-free medium, were used to produce proteins for testing. The recombinant polypeptides were secreted from the cells into the growth medium.

Sequences of constituent domains of the VEGF MiniTrap
Human Flt1 (accession #NP_001153392.1)
Human Flk1 (accession #NP_002244.1)
Human Fc (IGHG1, accession #P01857-1)

The recombinant VEGF MiniTrap (MT5) was obtained from this process and was further processed.

7.2 Preparation of Affinity Chromatography Columns

Five distinct proteins capable of binding to the VEGF MiniTrap (MT5) were evaluated. The proteins used include VEGF$_{165}$ (SEQ ID NO.: 72), mAb1 (a mouse anti-VEGFR1 mAb human IgG1 where SEQ ID NO.: 73 is a heavy chain and SEQ ID NO.: 74 is a light chain); mAb2 (a mouse anti-VEGFR1 mAb human IgG1 where SEQ ID NO.: 75 is a heavy chain and SEQ ID NO.: 76 is a light chain); mAb3 (a mouse anti-VEGFR1 mAb mouse IgG1 where SEQ ID NO.: 77 is a heavy chain and SEQ ID NO.: 78 is a light chain) and mAb4 (a mouse anti-VEGFR 1 mAb mouse IgG1 where SEQ ID NO.: 79 is a heavy chain and SEQ ID NO.: 80 is a light chain).

The column was activated by washing the columns with 6 column volumes (CV) of 1 mM ice-cold hydrochloric acid at a flow rate not exceeding 1 mL/min. Ten mg of each of the proteins were loaded onto three HiTrap NHS-Activated HP affinity columns (1 mL, GE Healthcare, Cat #17-0716-01) and the columns were closed to allow coupling to take place for 30 minutes at room temperature. The columns were washed with 18 column volumes of 0.5 M sodium acetate, 0.5 M NaCl, pH 4.0 and the open sites were blocked with 18 column volumes of 0.5 M Tris-HCl, 0.5 M NaCl pH 8.3 (the wash was carried out in the following order: 6 column volumes of 0.5 M Tris-HCl, 0.5 M NaCl, pH 8.3; 6 column volumes of 0.5 M sodium acetate (sodium acetate: JT Baker, Cat #3470-01), 0.5 M NaCl, pH 4.0; 6 column volumes of 0.5 M Tris, pH 8.3; incubate the column for 30 minutes at room temperature; 6 column volumes of 0.5 M sodium acetate buffer, 0.5 M NaCl pH 4.0; 6 column volumes of 0.5 M Tris-HCl, 0.5 NaCl, pH 8.3 and 6 column volumes of 0.5 M sodium acetate buffer, 0.5 M NaCl pH 4.0). The columns were stored in DPBS, pH 7.5. The five columns evaluated are designated as column 1 (comprising VEGF$_{165}$), column 2 (comprising mAb1), column 3 (comprising mAb2), column 4 (comprising mAb3) and column 5 (comprising mAb4).

7.3 Production of MiniTrap Using Affinity Chromatography

Sample Preparation. Two different production processes for the MiniTrap were performed. In one case, material comprising a MiniTrap sample was produced using each of the affinity columns where the parent material (MiniTrap) was diluted in 1×DPBS buffer to 20 mg/mL and was applied to the column and included at RT for 30 minutes. Using the affinity column, the MiniTrap was isolated from ~7000 ppm of HCP.

Alternatively, harvested culture supernatant was used which comprised 0.4 mg/mL of protein in the supernatant and loaded onto the different affinity columns (1-5) separately. No further dilution was performed. The affinity columns were then washed with 9 CV of 1×DPBS buffer followed by eluting the proteins with IgG elution buffer, pH 2.8 (Thermo, Cat #21009).

MiniTrap material obtained as described above was then filtered through a 0.45 µm filter or centrifuged before loading onto the columns prepared as described in Section 7.2 above. Twenty-five mL of loading solution comprising approximately 0.4 mg/mL protein was loaded onto each of the columns and incubated for 20 minutes. Each column was washed with 9 CV of DPBS (Invitrogen, Cat #14190-144) before elution for equilibration. The amount of MT5 in the wash fractions is shown in Table 7-1. The washes were followed by elution using 6 CV of pH 2.8 (Commercial Elution Buffer, (Thermo, Cat #21009)) and 100 mM glycine buffer pH 2.5 and fractions were quickly neutralized with the addition of 1 M Tris, pH 7.5 (Invitrogen, Cat #15567-027). The amount of MiniTrap in the eluted fractions is also shown in Table 7-1.

The MiniTrap (MT5) was successfully produced from all five affinity columns. The yield from the column with VEGF$_{165}$ was higher than compared to mAb1 and mAb2 columns. The mAb3 and mAb4 comprising humanized anti-VEGFR1 mAb also showed successful production of MT5 with similar yield to mAb1 and mAb2. In Table 7-1, the expected yield was calculated based on 100% conjugation efficiency and 1:1 molar ratio of affinity-captured protein to MT5.

TABLE 7-1

| Affinity Column | Column 1 VEGF$_{165}$ | Column 2 mAb1 | Column 3 mAb2 | Column 4 mAb3 | Column 5 mAb4 |
|---|---|---|---|---|---|
| Conjugation Amount (mg) | 10 | 10 | 10 | 10 | 10 |
| Load (mg) | 21.2 | 21.2 | 21.2 | 20.1 | 20.1 |
| Expected (mg) | ~12 | ~3.2 | ~3.2 | ~3.2 | ~3.2 |
| Wash (mg) | 14.9 | 13.2 | 12.6 | 15.2 | 14.7 |
| Eluate (mg) | 4.8 | 1.6 | 1.8 | 1.5 | 1.6 |

7.4 Column Stability Study

Multiple runs were carried out using columns 1 and 2 following the method discussed in Section 7.3 (Table 7-2 for column 1 and Table 7-3 for column 2).

TABLE 7-2

| | Production Yield | | | | | | |
|---|---|---|---|---|---|---|---|
| Run # | 1 | 2 | 3 | 4 | 5 | 6 | 7 |
| Load (mg) | 21.2 | 19.7 | 19.7 | 19.7 | 19.6 | 19.6 | 19.6 |
| Wash (mg) | 14.9 | 13.5 | 15.0 | 15.0 | 14.6 | 14.6 | 14.3 |
| Eluate (mg) | 4.8 | 5.4 | 5.2 | 4.8 | 5.2 | 4.6 | 4.8 |

TABLE 7-3

| | Production Yield | | | | | | |
|---|---|---|---|---|---|---|---|
| Run # | 1 | 2 | 3 | 4 | 5 | 6 | 7 |
| Load (mg) | 21.2 | 19.7 | 19.7 | 19.7 | 19.6 | 19.6 | 19.6 |
| Wash (mg) | 13.2 | 16.0 | 16.4 | 16.4 | 17.1 | 17.2 | 17.2 |
| Eluate (mg) | 1.6 | 1.8 | 1.8 | 1.8 | 2.0 | 2.0 | 2.0 |

The columns were stored at 4° C. for about 5 weeks. A similar amount of MT5 was eluted from each production demonstrating good column stability.

7.5 Stability Study of the Produced VEGF MiniTrap

SDS-PAGE analysis of the eluted fractions from the three columns (column 1, column 2, and column 3) was performed. The samples were prepared in non-reducing and reducing SDS-PAGE sample buffer and run on a 4-12% gradient NuPage bis-Tris gel using 1×MES (Cat. No. NP0322, Invitrogen, Carlsbad, CA).

Figure 33:
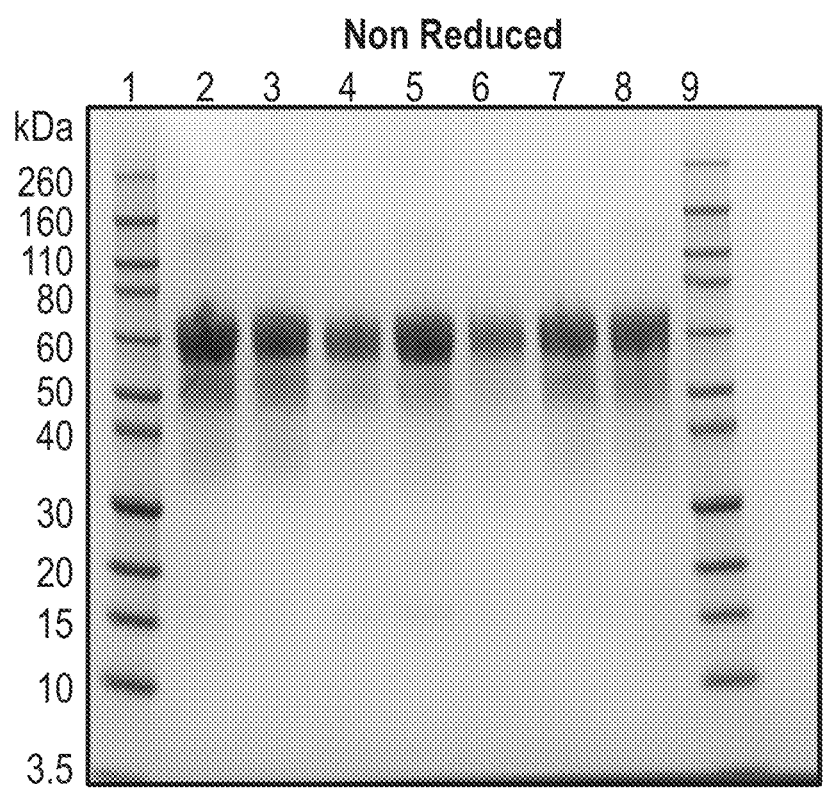
FIG. 33 is an image of SDS-PAGE analysis performed using non-reducing SDS-PAGE sample buffer.
Figure 34:
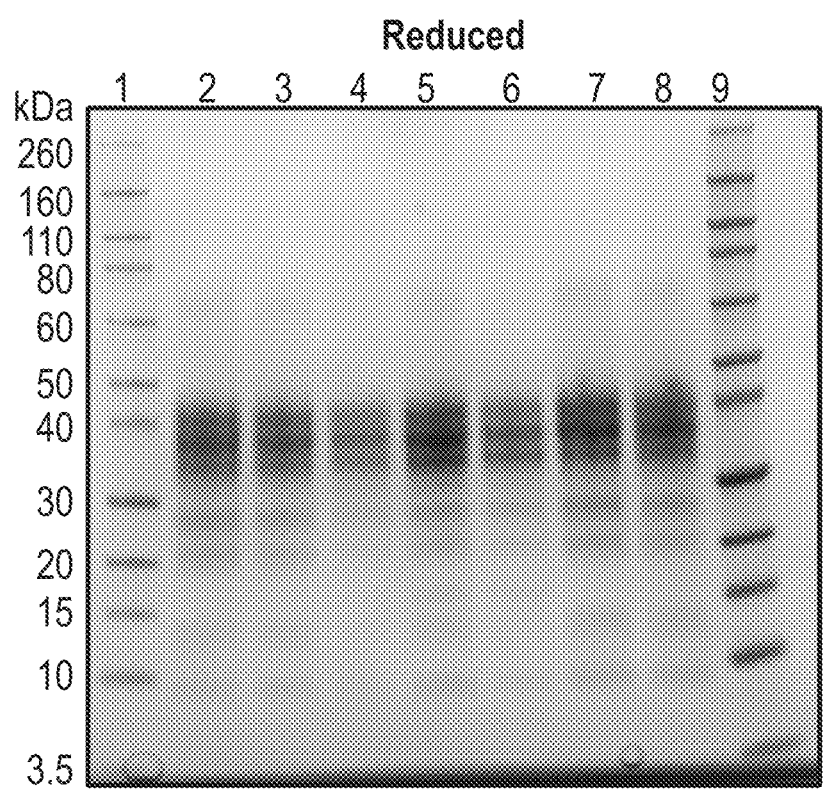
FIG. 34 is an image of SDS-PAGE analysis performed using reducing SDS-PAGE sample buffer.

The wells were loaded with (1) molecular weight standard, (2) loading solution, (3) column wash from column 1, (4) eluted fraction from column 2, (5) eluted fraction from column 1, (6) eluted fraction from column 3, (7) MT5 stored at pH 2.8 for 1 min, (8) MT5 stored at pH 2.8 for 30 min, and (9) molecular weight standard (FIG. 33 and FIG. 34). The analysis demonstrated that fractions obtained from the eluted fractions from all the three affinity columns (columns 1-3) showed similar size profiles and the use of the affinity columns did not destabilize the MiniTrap.

7.6 Host Cell Protein Level Calculations

Figure 32:
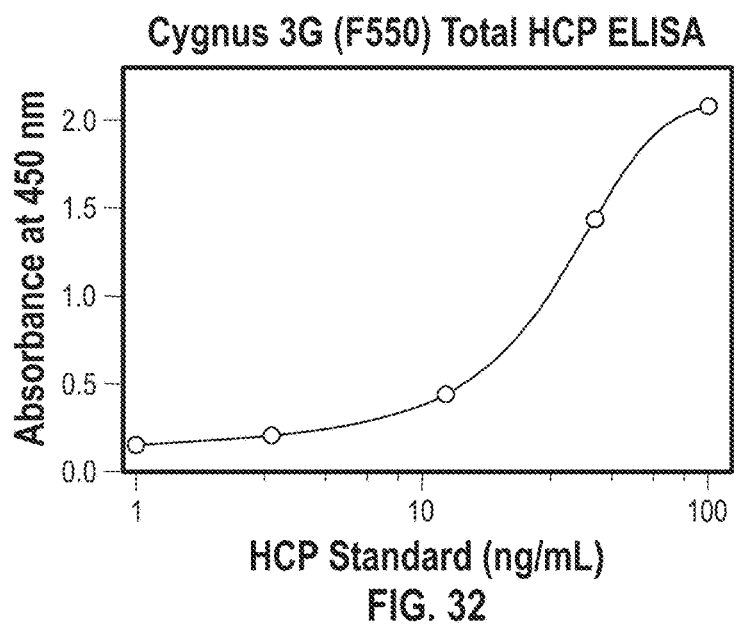
FIG. 32 is a chart showing a standard curve of absorbance versus host cell protein concentrations (ng/mL) prepared using standard host cell protein solutions from *Cygnus* 3G (F550).

A standard curve of concentration of host cell proteins was obtained using CHO HCP ELISA Kit, 3G (F550) (Cygus Technologies) (FIG. 32 and Table 7-4). The amount of HCPs in the loading solutions and the eluted fractions was calculated using the standard curve as depicted in FIG. 32 and curve formula listed in Table 7-4.

TABLE 7-4

| Curve Formula | Low Asymptote | Slope | EC$_{50}$ (ng/mL) | High Asymptote | R$^2$ |
|---|---|---|---|---|---|
| Y = (A − D)/ (1 + (X/C)^B) + D | 0.2 | 1.9 | 32.9 | 2.3 | 1 |

Figure 35A:
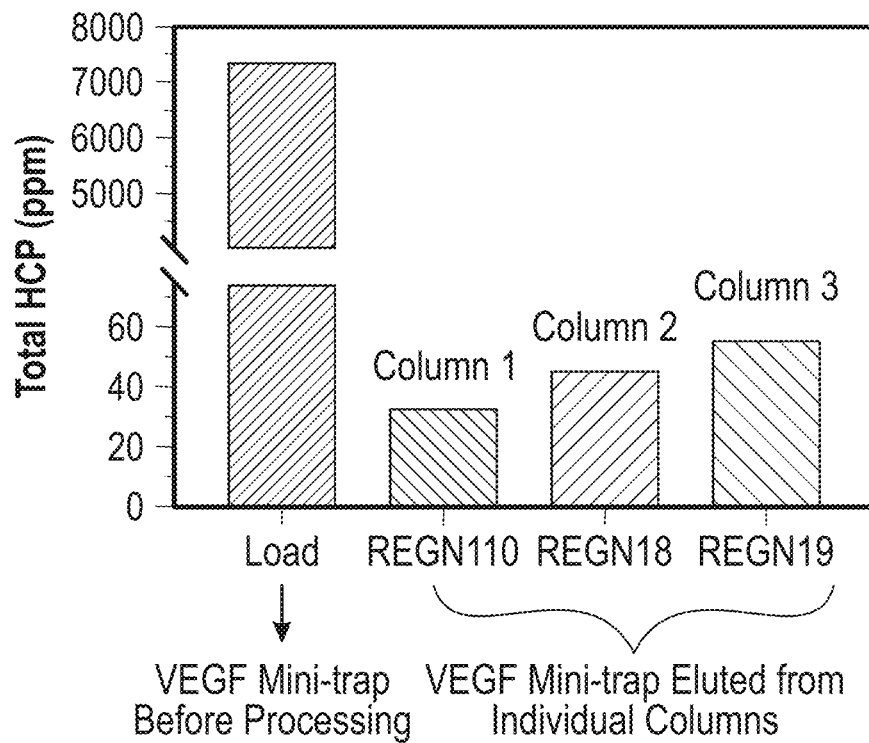
FIG. 35A is a chart of total host cell protein detected in loading solution, eluted fractions from affinity chromatography columns 1-3 comprising $VEGF_{165}$, mAb1 and mAb2, respectively.
Figure 35B:
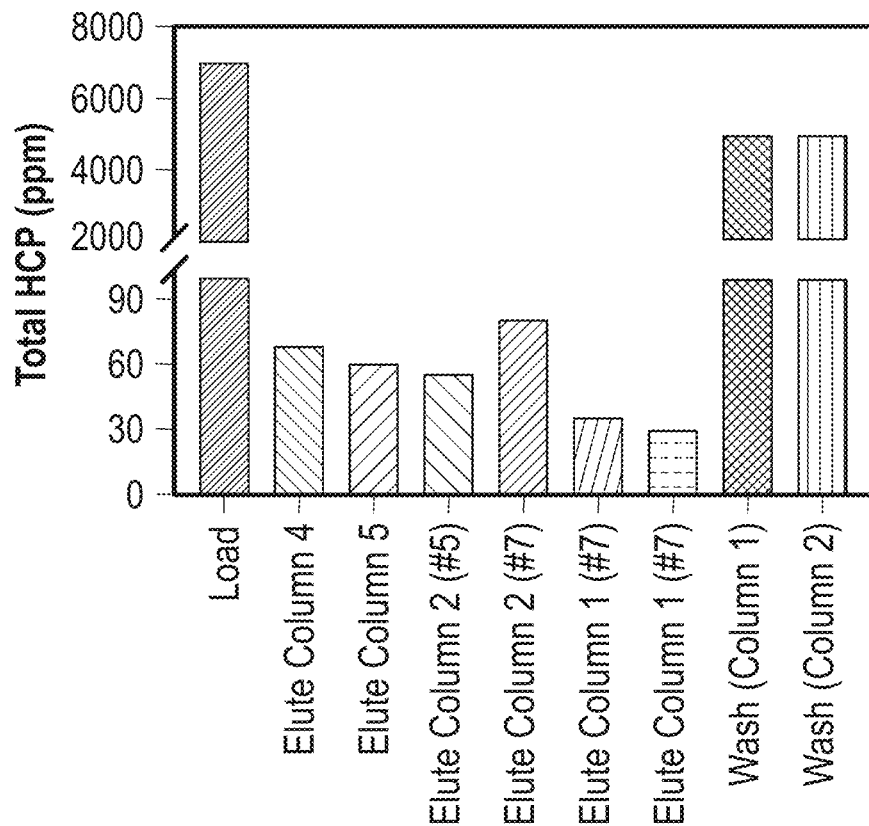
FIG. 35B is a chart of total host cell proteins detected in loading solution, eluted fractions from affinity chromatography columns 1, 2, 4 and 5 comprising $VEGF_{165}$, mAb1, mAb3 and mAb4, respectively.

The total HCPs were calculated using the standard curve and the chart with the total amount of host cell proteins is shown in FIG. 35A. FIG. 35B also shows total amount of host cell proteins in the load compared to the washes and eluted fractions from columns 1, 2, 4 and 5. Multiple runs were carried out using the columns and the (#) in FIG. 35B represent the run from which the fraction was evaluated.

The use of affinity capture using proteins capable of binding to MiniTrap showed an efficient reduction of HCPs from about 7000 ppm to about 25-50 ppm. As observed for the yield, the column with VEGF$_{165}$ showed higher purity of MiniTrap from HCPs than shown by mAb1 and mAb2 columns.

7.7 SEC Profiles of VEGF MiniTrap Before and After Affinity Production

Figure 36A:
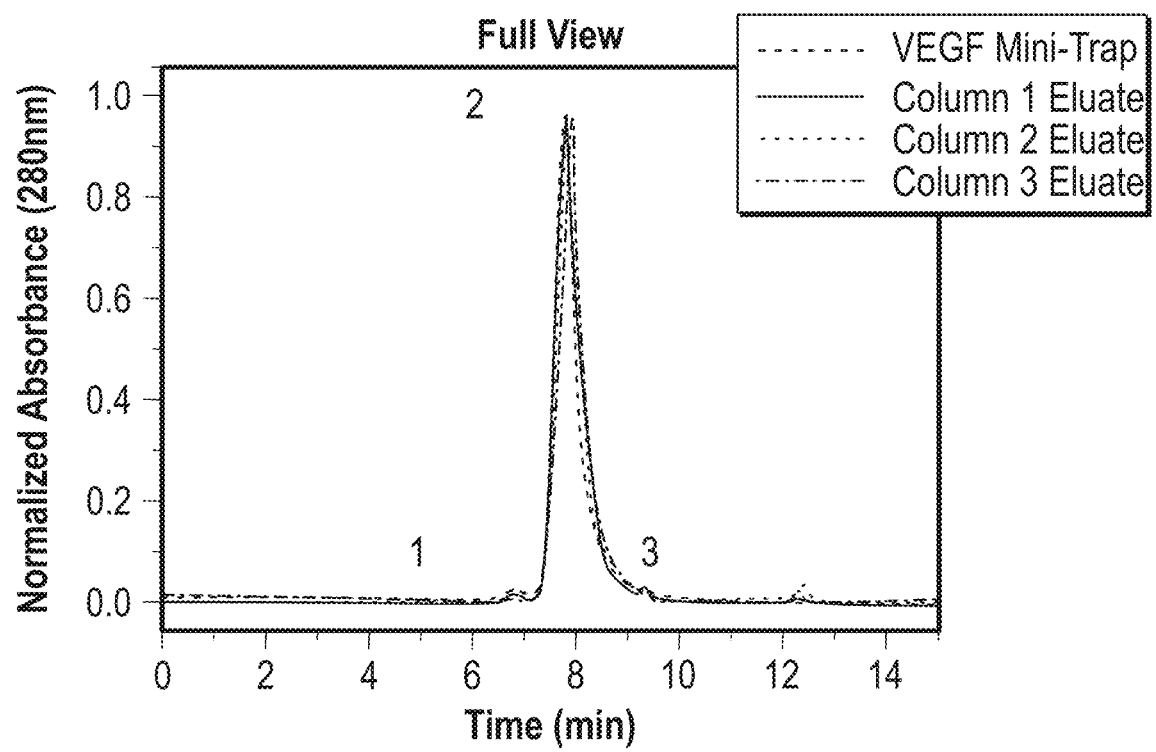
FIGS. 36A and 36B depicts the SEC profiles of VEGF MiniTrap A before and B after performing affinity chromatography production, respectively.
Figure 36B:
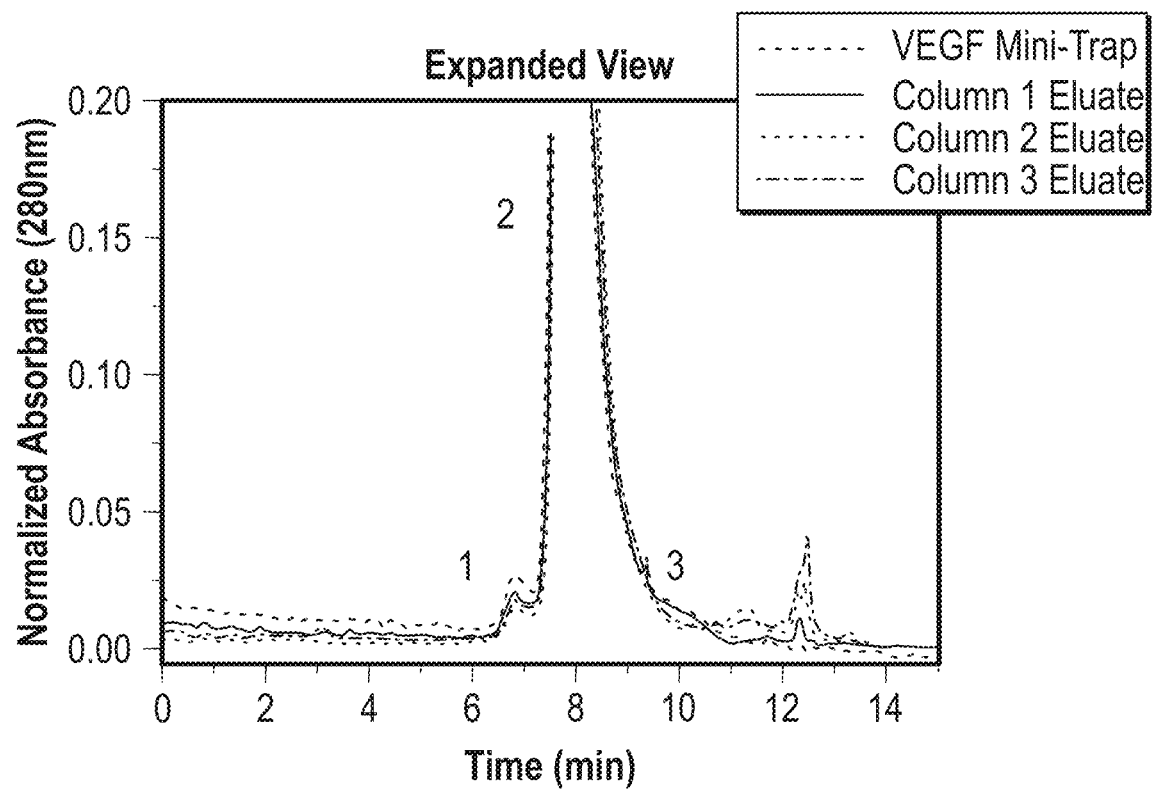

SEC profiles of the eluted fractions from three columns (columns 1-3) were compared to the SEC profile of MiniTrap in the loading solution. As seen in FIG. 36 and Table 7-5, the SEC profiles of the MT5 before or after affinity production were highly similar.

TABLE 7-5

| Peak No. as in FIG. 36 | Loading solution | | Column 1 Eluate | | Column 2 Eluate | | Column 3 Eluate | |
|---|---|---|---|---|---|---|---|---|
| | Retention Time | % Peak Area | Retention Time | % Peak Area | Retention Time | % Peak Area | Retention Time | % Peak Area |
| 1 | 6.8 | 1.8 | 6.8 | 1.2 | 6.9 | 1.1 | 7.0 | 1.2 |
| 2 | 7.8 | 94.6 | 7.9 | 97.2 | 7.9 | 97.3 | 7.9 | 98.3 |
| 3 | 9.4 | 3.6 | 10.2 | 1.7 | 11.4 | 1.6 | 11.3 | 0.5 |

7.8 Kinetics of VEGF MiniTrap Pre and Post Column Samples Binding to mAb1, mAb2 and VEGF$_{165}$ Kinetic studies were performed using a Biacore T200 instrument.

Equilibrium dissociation constants ($K_D$ values) for VEGF165 binding to MiniTrap in the eluates from columns 1 and 2 and loading solution were determined using a real-time surface plasmon resonance biosensor using a Biacore T200 instrument. All binding studies were performed in 10 mM HEPES, 150 mM NaCl, 3 mM EDTA, and 0.05% v/v Surfactant Tween-20, pH 7.4 (HBS-ET) running buffer at 25° C. The Biacore sensor surface was first derivitized by amine coupling with a mAb1 to capture MT5. A cartoon representation of the binding study is shown in FIG. 37.

Briefly, the eluates from the columns and loading solution were diluted into an HBS-EP (Biacore) buffer and injected across the immobilized protein matrices at a capture level of ~70 RUs. The VEGF$_{165}$ was then injected at a flow rate of 50 µL/min. Equivalent concentration of analyte was simultaneously injected over an untreated reference surface to serve as blank sensorgrams for subtraction of bulk refractive index background. The sensor chip surface was regenerated between cycles with two 5-min injections of 10 mM Glycine, at 25 µL/min. The resultant experimental binding sensorgrams were then evaluated using the BIA evaluation 4.0.1 software to determine kinetic rate parameters. Datasets for each sample were fit to the 1:1 Langmuir model. For these studies, binding and dissociation data were analyzed under the Global Fit Analysis protocol while selecting fit locally for maximum analyte binding capacity (RU) or Rmax attribute. In this case, the software calculated a single dissociation constant (kd), association constant (ka), and affinity constant (Kd). The equilibrium dissociation constant is $K_D$=kd/ka. The kinetic on-rate, the kinetic off rate, and the overall affinities were determined by using different VEGF$_{165}$ concentrations in the range of 0.03-2 nM (Table 7-6). The dissociative half-lives ($t_{1/2}$) were calculated from the kinetic rate constants as: $t_{1/2}$=ln(2)/60*Kd. Binding kinetic parameters for MT5 to VEGF$_{165}$ obtained from before and after the affinity chromatography production at 25° C. are shown in Table 7-6.

Figure 38:
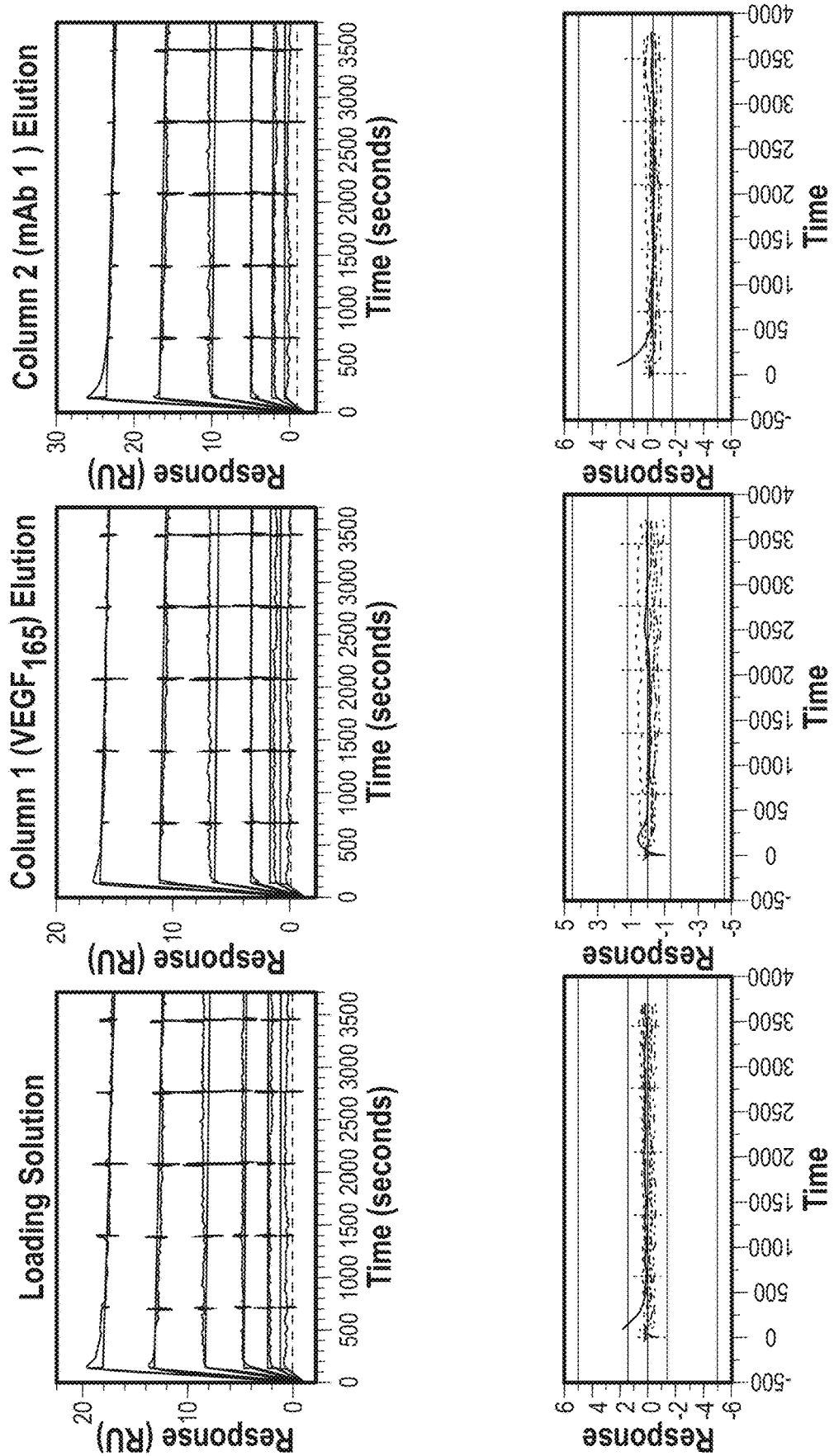
FIG. 38 depicts SPR sensorgrams from the kinetic study of VEGF MiniTrap to $VEGF_{165}$, wherein the VEGF Mini-Trap constructs studied were from before and after performing affinity chromatography production according to some exemplary embodiments.

The affinity (KD), on rate (ka, M-1 s−1) and off rate (kd) for MT5 produced by affinity chromatography compared with loading solution to assess the effect(s) of affinity chromatography step showed no change in the kinetics of MT5 from different samples. The SPR sensorgrams of the VEGF MiniTrap constructs are shown in FIG. 38.

Figure 39:
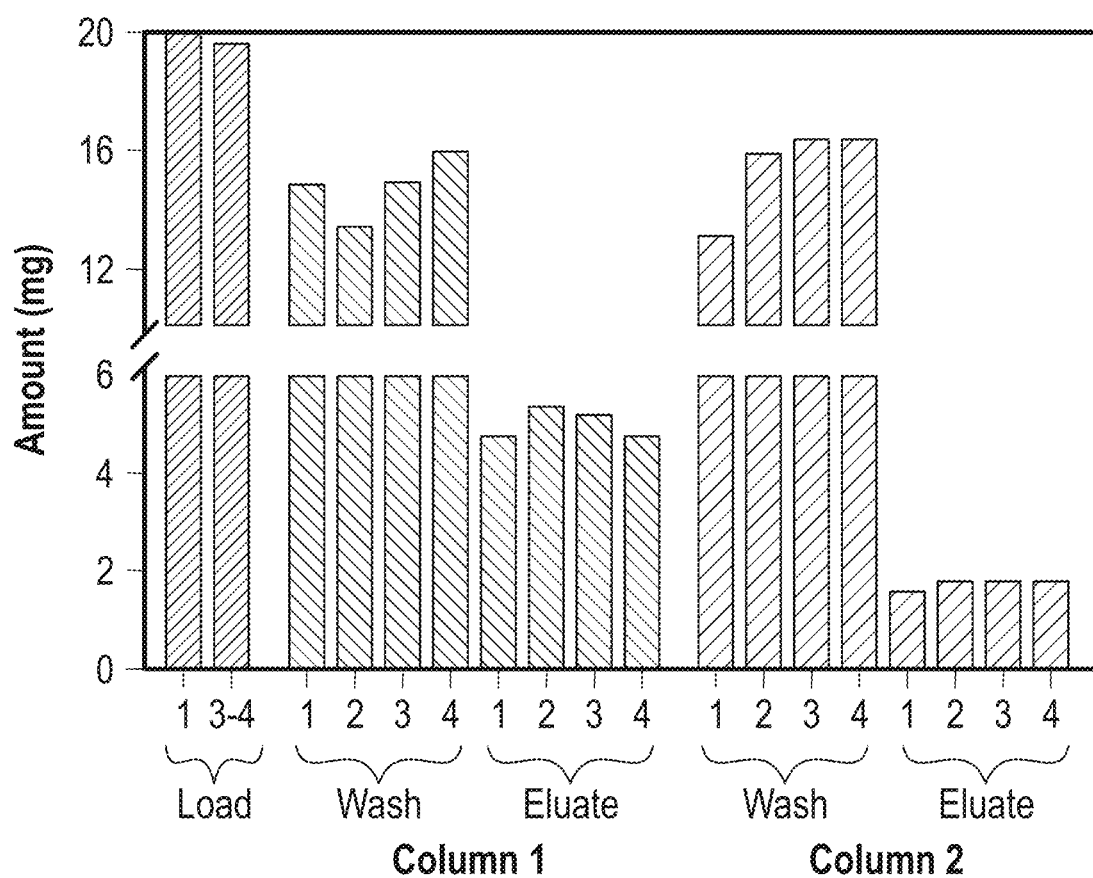
FIG. 39 is a chart of total host cell protein detected in loading solution, eluted fractions from affinity chromatography columns used repeatedly for columns comprising $VEGF_{165}$, mAb1 and mAb2.
Figure 40:
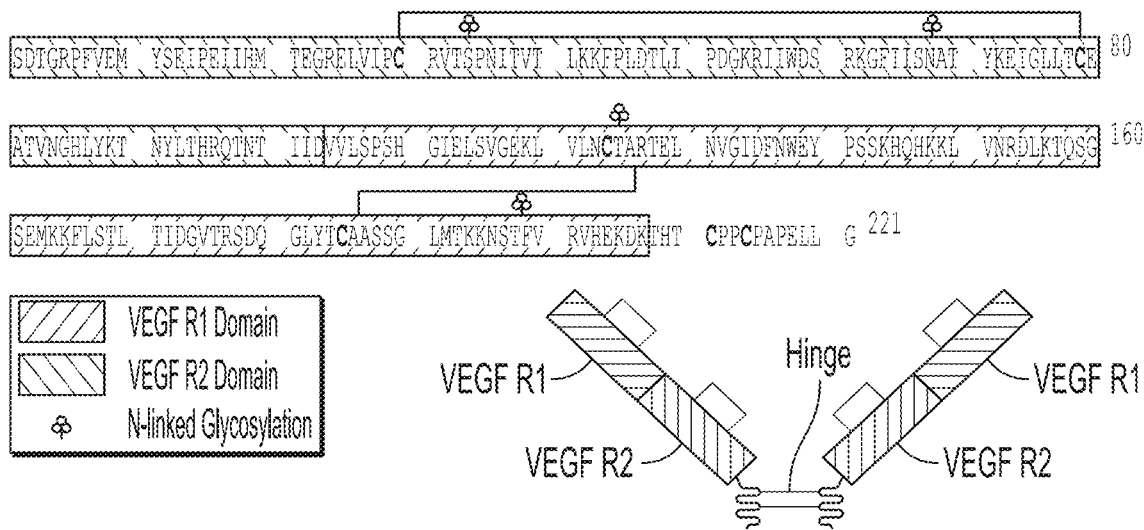
FIG. 40 depicts the structure of VEGF MiniTrap MT1 (SEQ ID NO.: 46) according to an exemplary embodiment.
Figure 41:
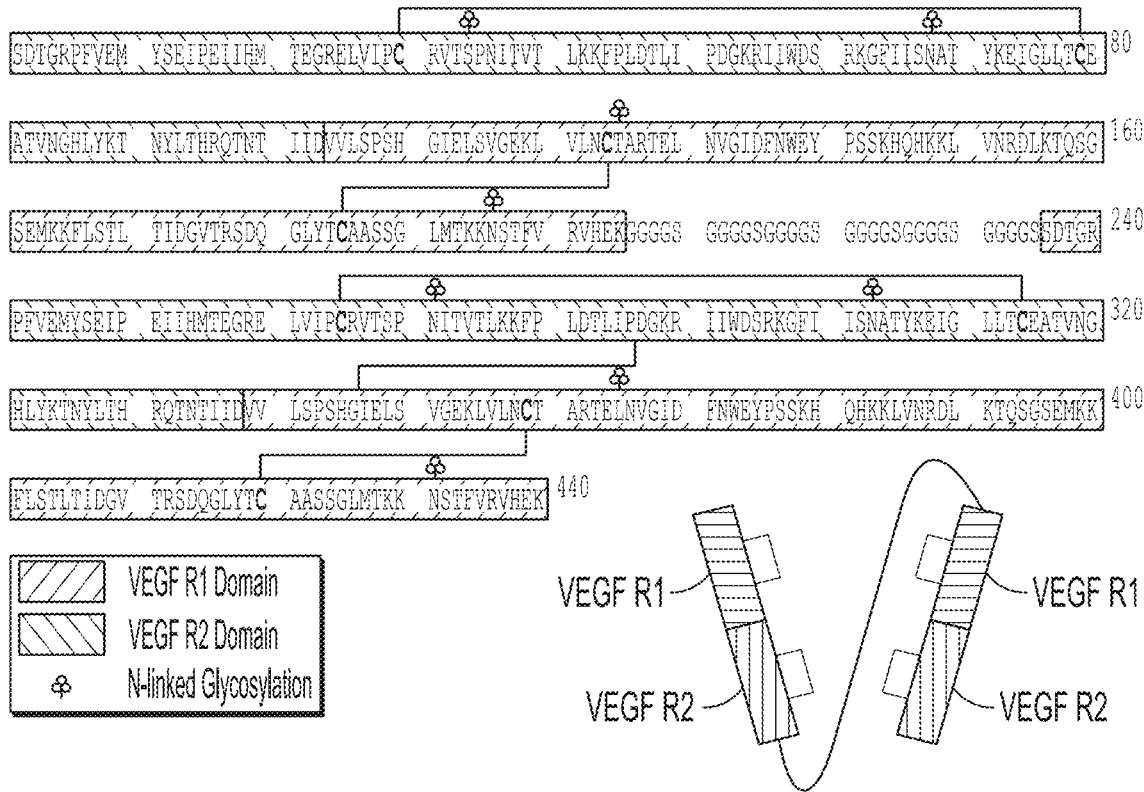
FIG. 41 depicts the structure of VEGF MiniTrap MT6 (SEQ ID NO.: 51) according to an exemplary embodiment.

HCP calculations in the loading solutions, wash fractions and eluted fractions for columns 1 and 2 were obtained using the method described in 7.4 (FIG. 39). The total HCPs calculated showed that repeated use of the columns did not reduce the ability of the columns to bind to MiniTrap.

7.10 Optimizing the Affinity Chromatographic Columns

The chromatographic production of harvest material as obtained in Section 7.1 was performed using column 1 (VEGF$_{165}$) and column 2 (mAb1). For the optimization studies, 14 mg or 45 mg instead of 10 mg of the VEGF165 or the anti-VEGFR1 mAb were loaded onto two HiTrap NHS-Activated HP affinity columns (1 mL, GE Healthcare) and the columns were closed to allow coupling to take place for 30 minutes at room temperature. The column preparation and production of the harvest including the MiniTrap was carried out as discussed in 7.2 and 7.3 above. The amount of MT5 in the wash and eluted fractions is shown in Table 7-8. The comparison of affinity column with 14 mg or 45 mg (VEGF$_{165}$ or anti-VEGFR1 mAb (mAb1)) conjugation amount instead of 10 mg shows an increased yield of MiniTrap from both columns. Thus, the column yield using the outlined method can be improved by optimizing the protein to column ratio or by increasing the conjugation efficiency by changing the pH, incubation time, incubation temperature, etc.

TABLE 7-8

| Affinity Column MW (kDa) | (hVEGF$_{165}$) ~40 (Dimer) | | (mouse anti-VEGFR1 mAb) 145 | |
|---|---|---|---|---|
| Conjugation Amount (mg) | 10 | 14 | 10 | 45 |
| Load (mg) | 21.2 | 45.5 | 21.2 | 45.5 |
| Wash (mg) | 14.9 | 36.8 | 13.2 | 29.2 |
| Eluate (mg) | ~5.0 | 7.6 | ~1.8 | 5.5 |

TABLE 7-6

| VEGF MiniTrap samples | $k_a$ ($10^6$ M$^{-1}$s$^{-1}$) | $k_d$ ($10^{-5}$ s$^{-1}$) | $K_D$ ($10^{-12}$ M) | t$^{1/2}$ (min) | Chi$^2$ (RU$^2$) | $R_{max}$ (RU) |
|---|---|---|---|---|---|---|
| Loading solution | 9.44 | 1.74 | 1.84 | 664 | 0.10 | 20 |
| column 2 eluate | 8.83 | 1.49 | 1.69 | 775 | 0.17 | 28 |
| column 1 eluate | 12.18 | 1.80 | 1.48 | 641 | 0.18 | 19 |

7.9 Multiple Production Cycles

Chromatographic production of harvest as obtained by step 7.1 was carried out using column 1 (hVEGF$_{165}$) and column 2 (mAb1) as shown in 7.3. The columns were used for multiple chromatographic cycles. The yields in the columns did not vary significantly due to additional runs, suggesting that the columns retained binding capacity (Table 7-7).

TABLE 7-7

Production Yield

| | Affinity Column | | | | | | | |
|---|---|---|---|---|---|---|---|---|
| | Column 1 | | | | Column 2 | | | |
| Run # | 1 | 2 | 3 | 4 | 1 | 2 | 3 | 4 |
| Load (mg) | 21.2 | 19.7 | 19.7 | 19.7 | 21.2 | 19.7 | 19.7 | 19.7 |
| Wash (mg) | 14.9 | 13.5 | 15.0 | 15.0 | 13.2 | 16.0 | 16.4 | 16.4 |
| Eluate (mg) | 4.8 | 5.4 | 5.2 | 4.8 | 1.6 | 1.8 | 1.8 | 1.8 |

7.11 Use of CEX with the Affinity Chromatography

A cell culture sample from MT5 expression was produced using column 1 as discussed in Section 7.3 above. The eluate obtained was subjected to cation exchange chromatography (CEX) column (HiTrap Capto S, 1 mL). The operating conditions of the column are shown in Table 7-9.

TABLE 7-9

| Steps | Affinity | Cation Exchange (CEX) |
|---|---|---|
| Column | Affinity Column, 1 mL | HiTrap Capto S, 1 mL |
| Load | MT5 CM2926 | 20 mM Acetate, pH 5.0 (Load/Wash1) |
| Wash | 1 × DPBS pH 7.2 | 10 mM Phosphate, pH 7.0 |
| Elution | Pierce ™ IgG Elution Buffer | 50 mM Tris, 62.5 mM (NH$_4$)$_2$SO$_4$, pH 8.5 |
| Regeneration/ Strip | 10 mM Glycine pH 2.5 | 50 mM Tris, 1M (NH$_4$)$_2$SO$_4$, pH 8.5 |

The total HCP in the original/starting cell culture sample, the affinity chromatography column 1 eluate and CEX eluate was about 230,000 ng/ml, about 9,000 ng/ml and about 850 ng/mL, respectively. The HCP amounts were quantitated determined using the *Cygnus* CHO HCP ELISA Kit, 3G, as mentioned above.

7.12 Use of Affinity Chromatography to Produce Other Anti-VEGF Proteins

Column 1 was evaluated to study its ability to produce other anti-VEGF proteins. Aflibercept and a scFv fragment with VEGF binding potential were used for this study. The production processes were carried out as discussed in Section 7.3. Table 7-10 demonstrates that column 1 was successful in binding and eluting other anti-VEGF proteins.

TABLE 7-10

| Affinity Column 1 | scFv | Aflibercept |
|---|---|---|
| Load (mg) | 10 | 20 |
| Wash (mg) | 4.5 | 10.6 |
| Eluate (mg) | 3.6 | 10.2 |

Example 8. Mass Spectrometry-Based Characterization of VEGF MiniTrap Constructs

Materials. VEGF MiniTrap (MT1) was produced from aflibercept as described in Example 1. VEGF MiniTrap 5 (MT5) was produced as described in Example 7. VEGF MiniTrap (MT6) was produced by the following method: the coding regions of recombinant VEGF MiniTrap (MT5) were operably linked to a signal sequence and cloned into a mammalian expression vector, transfected into Chinese hamster ovary (CHO-K1) cells and stably transfected pools were isolated after selection with 400 µg/mL hygromycin for 12 days. The stable CHO cell pools, grown in CDM, were used to produce proteins for analysis.

8.1 Deglycosylation of Glycoproteins.

Samples from clarified harvest of MT1, MT5 and MT6 were diluted or reconstituted to a concentration of 0.52 mg/mL into a 28.8 µL solution of 1% (w/v) RG surfactant (RapiGest SF, Waters, Milford, MA) and 50 mM HEPES (pH 7.9). These solutions were heated to approximately 95° C. over 2 min, allowed to cool to 50° C., and mixed with 1.2 µL of PNGase F solution (GlycoWorks Rapid PNGase F, Waters, Milford, MA). Deglycosylation was completed by incubating the samples at 50° C. for 5 min.

8.2 HILIC-Fluorescence-ESI-MS (MS/MS) Analysis.

MT1 was analyzed via HILIC separation combined with fluorescence and mass spectrometric detection. MT5 and MT6 were analyzed using only HILIC. Chromatography was performed using a Waters 2D Acquity UPLC equipped with photodiode array and fluorescence (FLR) detectors and interfaced with a Waters Synapt G2-S mass spectrometer (MS conditions). A hydrophilic interaction chromatography (HILIC) mode of separation was used with a Waters UPLC Glycan BEH Amide column, 150×2.1 mm, 1.7 µm. The column temperature was set to 60° C. and the autosampler temperature was set to 5° C. The injection volume was 50 µL. The photodiode array scan range was 190-700 nm. The FLR was set to excitation 265 nm, emission 425 nm for RapiFluor-labeled glycans and excitation 274 nm, and emission 303 nm for tyrosine present in the glycopeptides. The initial flow rate was 0.4 mL/min with mobile phase A comprising of 100 mM ammonium formate (pH 4.4) and mobile phase B being acetonitrile.

8.3 MS Conditions

Liquid chromatography/mass spectrometry (LC/MS) experiments were conducted using a Waters Synapt G2-S mass spectrometer. The scan range was mass-to-charge ratio 100-2400 for positive and negative ion mode analyses. Scan time was 1 s, and glu-fibrinopeptide B was constantly infused (2 µL/min) as a calibrant ("lock mass"). The capillary voltage was set to 2.5 kV, with a source temperature of 120° C. and desolvation temperature of 500° C. The nitrogen nebulizer gas flow was set to 700 l/h.

8.4 Native SEC-MS

ACQUITY UPLC I class system (Waters, Milford, MA) was coupled to Q Exactive HF hybrid quadrupole-Orbitrap mass spectrometer (Thermo Scientific, Bremen, Germany) for all online SEC-MS analyses. ACQUITY UPLC Protein BEH SEC Column (200 Å, 1.7 µm, 4.6×300 mm) was set at 30° C. and used for protein separation. The mobile phase was 100 mM ammonium acetate at pH 6.8. Each separation was 30 minutes with a flow rate of 0.3 mL/min, and the injection amount was set to 40 µg. The following MS parameters were used for online SEC-nano-ESI-MS data acquisition. Each acquisition was 25 minutes beginning immediately after sample injection. The deglycosylated samples were ionized in positive mode with 3 kV spray voltage, 200° C. capillary temperature, and 70 S-lens RF level. In-source CID was set at 75 eV. Full MS scans were acquired at 15 K resolving power with mass range between m/z 2000-8000. A maximum injection time of 100 ms, automatic gain control target value of 3e6, and 10 microscans were used for full MS scans.

8.5 Peptide Mapping

Sample preparation for peptide mapping. Reduction was achieved by the addition of 500 mmol/L dithiothreitol (DTT) to a final concentration of 5 mmol/L followed by incubation at 4° C. for 60 min. Alkylation was performed by adding 500 mmol/L iodoacetamide (IAM) to a final concentration of 10 mmol/L and incubating at 4° C. for 60 min in the dark. The denaturing buffer was exchanged for digestion buffer (1 mol/L urea in 0.1 mol/L Tris, pH 7.8) using Zeba™ Spin 7 K MWCO size-exclusion desalting columns (P/N 89882) (Thermo Scientific, Waltham, MA) according to the manufacturer's instructions. Recombinant porcine trypsin (purchased from Sigma, Cat #03708985001) was added at a 1:18 (enzyme: sample) mass ratio (based on VEGF MiniTrap protein concentration as measured by UV-Vis spectrophotometry after buffer exchange), the concentration of VEGF MiniTrap proteins was adjusted to 0.5 µg/µL and digestion allowed to proceed during a 4 h incubation at room temperature. When the digestion was complete, 0.1% formic acid in LC-MS grade water was added at a 1:1 volume ratio. Digests were stored at −80° C. until analysis.

LC-MS/MS analysis of tryptic digests. One or more 2.5 µg (10 µL) of peptide digests were loaded via autosampler onto a C18 column enclosed in a thermostated column oven set to 40° C. Samples were held at 7° C. while queued for injection. The chromatographic method was initiated with 98% Mobile Phase A (0.1% volume fraction of formic acid in water) and 2% Mobile Phase B (0.1% volume fraction of formic acid in acetonitrile) with the flow rate set at a constant 0.200 mL/min. After a 10 min wash, peptides were eluted over a 110 min gradient in which Mobile Phase B content rose at a rate of 0.39% per min to reach a final composition comprising 45% Mobile Phase B. Prior to the next sample injection, the column was washed for 15 min with 97% Mobile Phase B, then equilibrated at 98% Mobile Phase A for 25 min. The eluate was diverted to waste for the first 1.5 minutes and final 5 minutes of the run. Peptides eluting from the chromatography column were analyzed by UV absorption at 214 nm followed by mass spectrometry on the LTQ Orbitrap Elite or Discovery XL. Replicate peptide mapping data were collected for PS 8670 and RM 8671 samples to include three tandem MS (MS/MS) analyses and one MS-only analysis each. The MS/MS analyses were performed for peptide identification in data-dependent mode in which one cycle of experiments consisted of one full MS scan of 300 m/z to 2000 m/z followed by five sequential MS/MS events performed on the first through fifth most intense ions detected at a minimum threshold count of 500 in the MS scan initiating that cycle. The sequential mass spectrometry (MS") AGC target was set to 1 E4 with microscans=3. The ion trap was used in centroid mode at normal scan rate to analyze MS/MS fragments. Full MS scans were collected in profile mode using the high resolution FTMS analyzer (R=30,000) with a full scan AGC target of 1 E6 and microscans=1. Ions were selected for MS/MS using an isolation width of 2 Da, then fragmented by collision induced dissociation (CID) with helium gas using a normalized CID energy of 35, an activation Q of 0.25 and an activation time of 10 msec. A default charge state was set at z=2. Data dependent masses were placed on the exclusion list for 45 s if the precursor ion triggered an event twice within 30 s; the exclusion mass width was set at ±1 Da. Charge state rejection was enabled for unassigned charge states. A rejection mass list included common contaminants at 122.08 m/z, 185.94 m/z, 355.00 m/z, 371.00 m/z, 391.00 m/z, 413.30 m/z, 803.10 m/z, 1222.10 m/z, 1322.10 m/z, 1422.10 m/z, 1522.10 m/z, 1622.10 m/z, 1722.10 m/z, 1822.10 m/z, and 1922.10 m/z. MS-only analyses were performed for the generation of the TIC non-reduced peptide map and reduced maps.

8.6 Results

Structure of VEGF MiniTrap constructs. Structure of VEGF MiniTraps MT1, MT5 and MT6 are depicted in FIG. 40, FIG. 41, FIG. 43 and FIG. 44.

Figure 42:
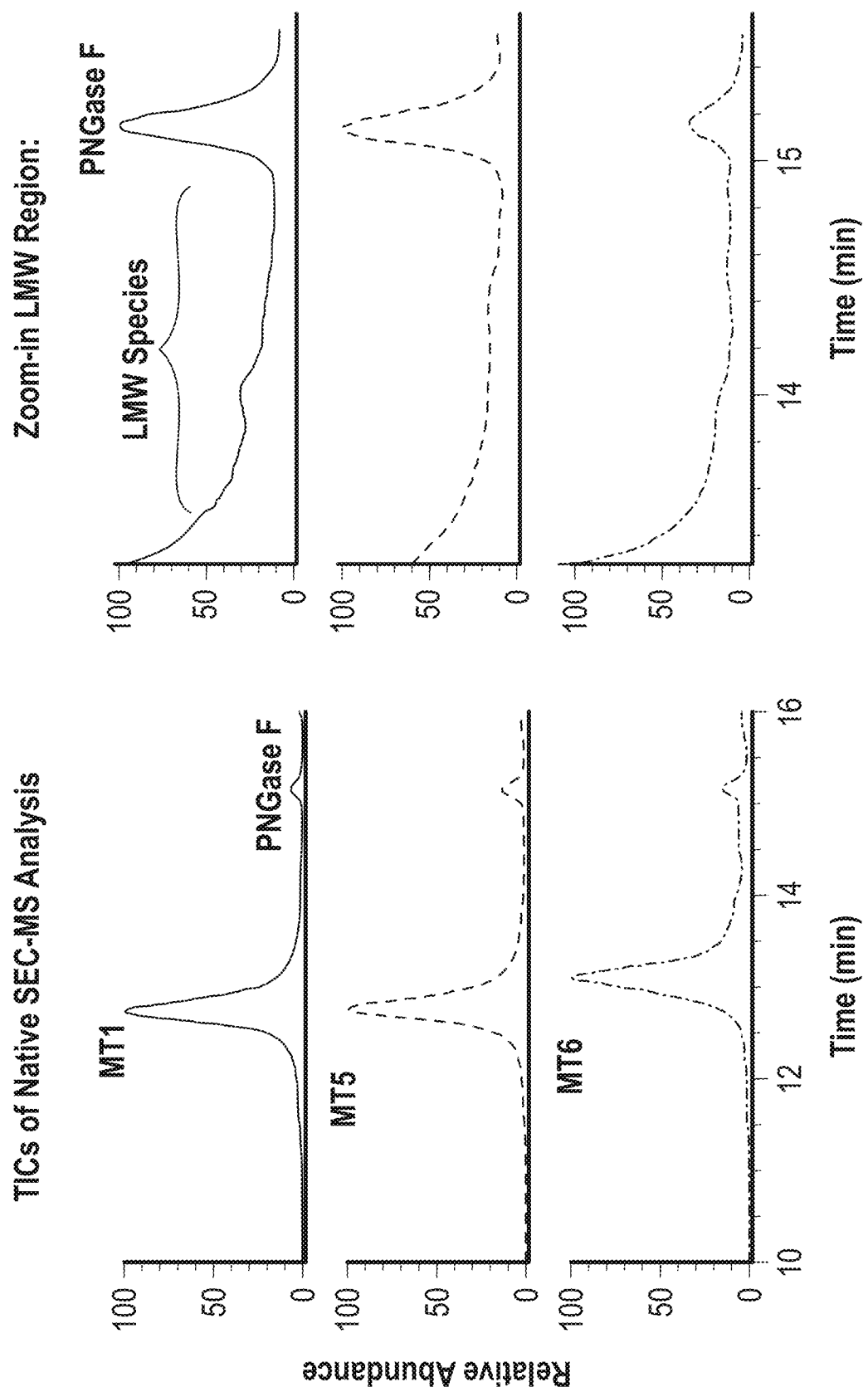
FIG. 42 depicts Total Ion Chromatograms (TIC) of relative absorbance versus time (minutes) for native SEC-MS analysis of MT1, MT5 and MT6 and a zoomed view of the low molecular weight region from the TICs.
Figure 43:
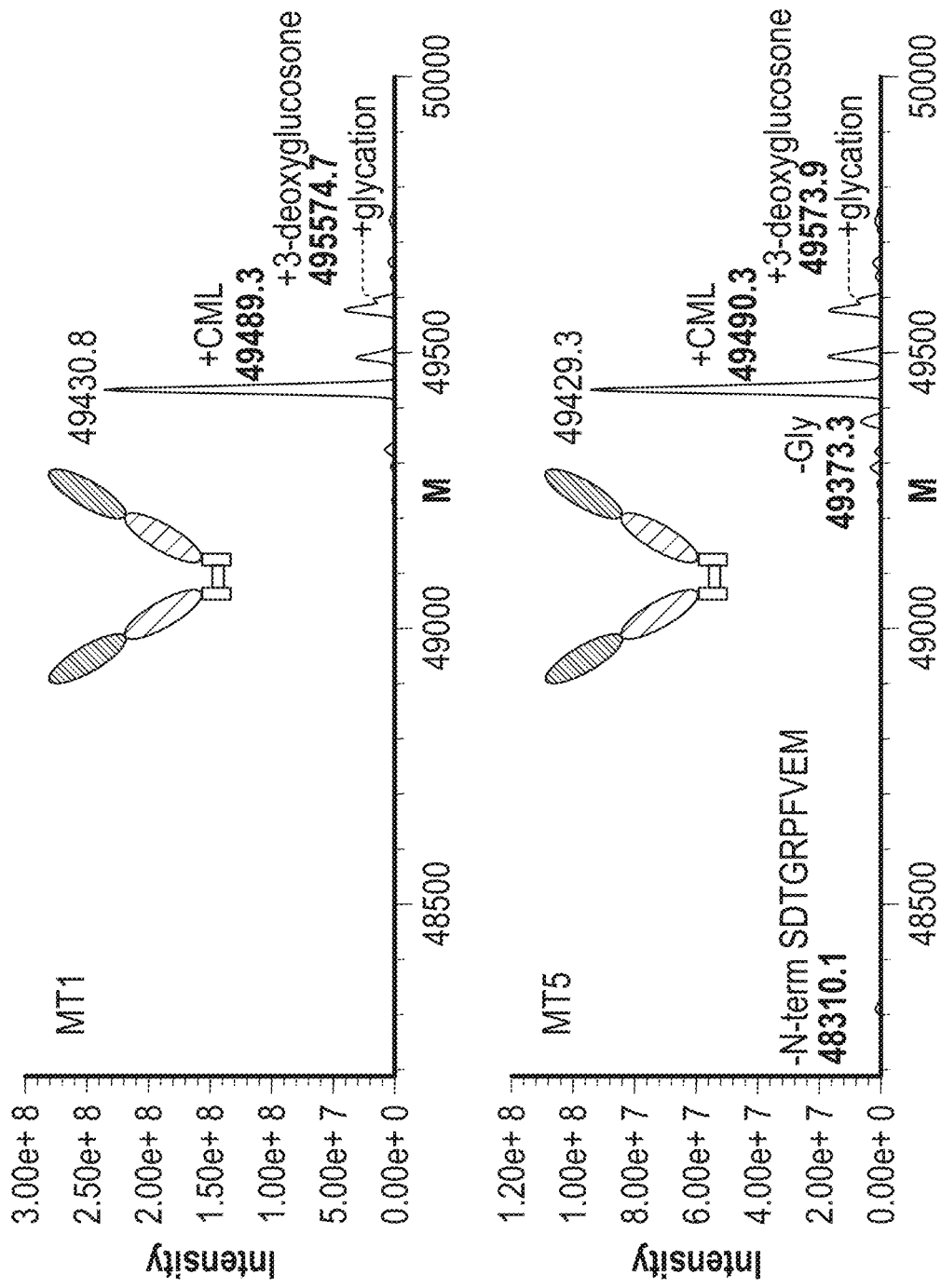
FIG. 43 depicts deconvoluted mass spectra of the main peak for MT1 and MT5 to confirm the MiniTrap dimer identity with elucidation for some PTMs, with the N-terminal amino acids indicated (SEQ ID NO.: 120).
Figure 44:
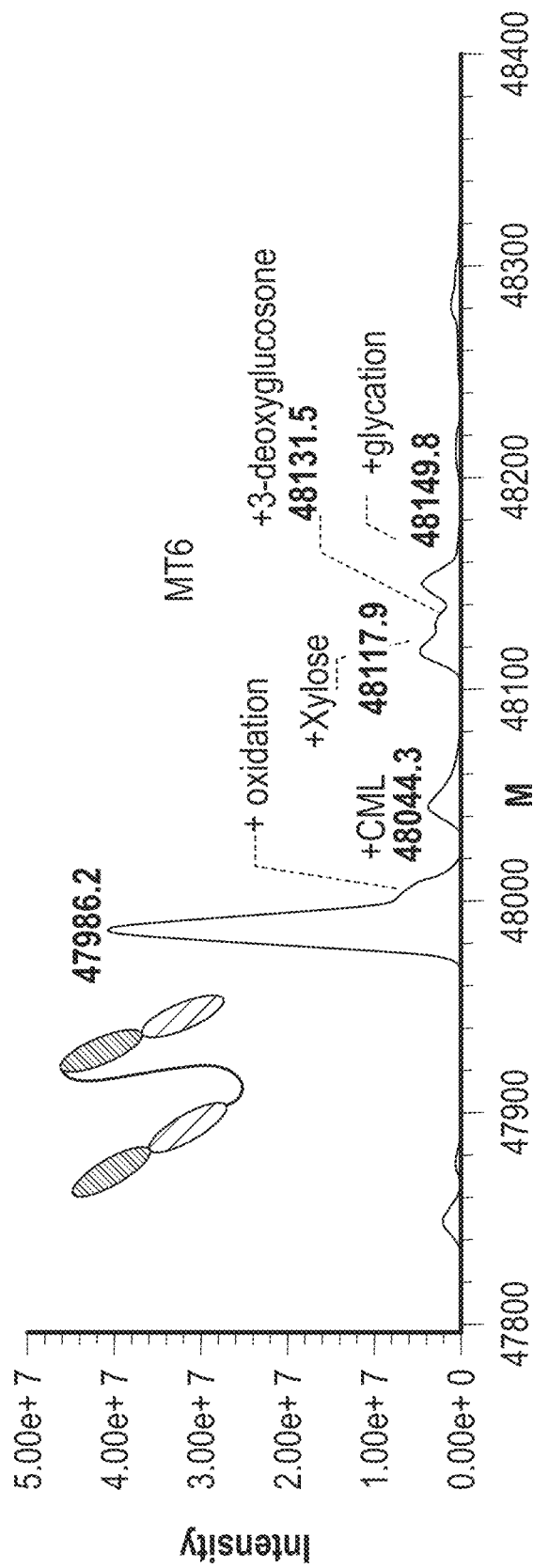
FIG. 44 depicts a deconvoluted mass spectrum of the main peak for MT6 to confirm the single chain MiniTrap identity with elucidation for some PTMs.

Initial mass analysis using SEC-MS confirmed the identities of all three molecules at intact protein level after deglycosylation (FIG. 42). The Total Ion Chromatogram (TIC) of the native SEC-MS analysis demonstrates detection of an intact VEGF MiniTrap molecules at around 12-13 minutes. The expansion of the low molecular weight (LMW) region of the TIC showed presence of LMW impurities in all the three protein samples.

The deconvoluted mass spectra for the VEGF MiniTraps further confirmed their identity and provided data for elucidation of the major PTMs present in the samples comprising MT1 and MT5 (FIG. 43), which are dimers and MT6 (FIG. 44) which is a single chain protein.

Figure 45A:
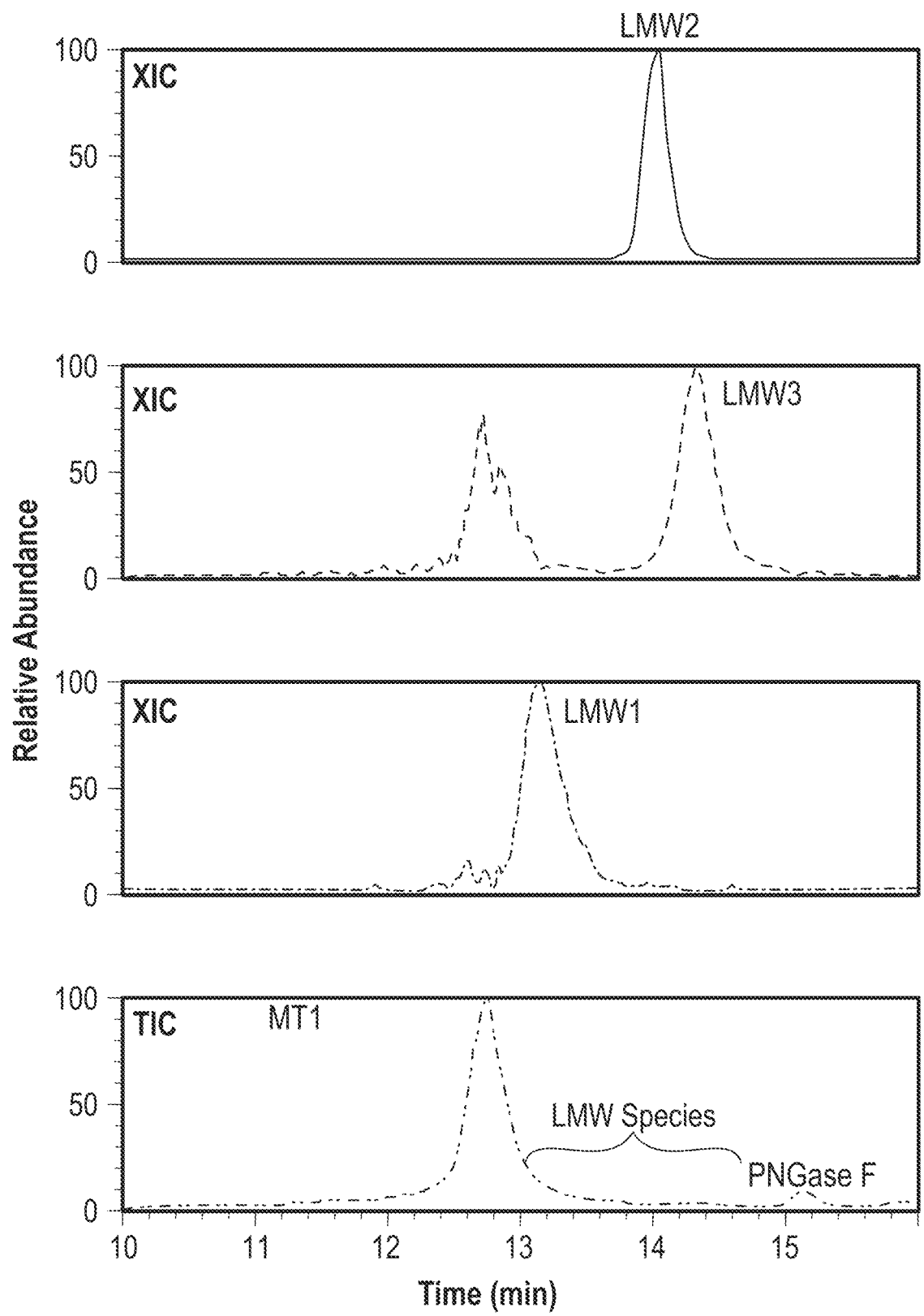
FIG. 45A depicts a chart of relative absorbance versus time (minutes) for low molecular weight impurities in MT1.
Figure 45B:
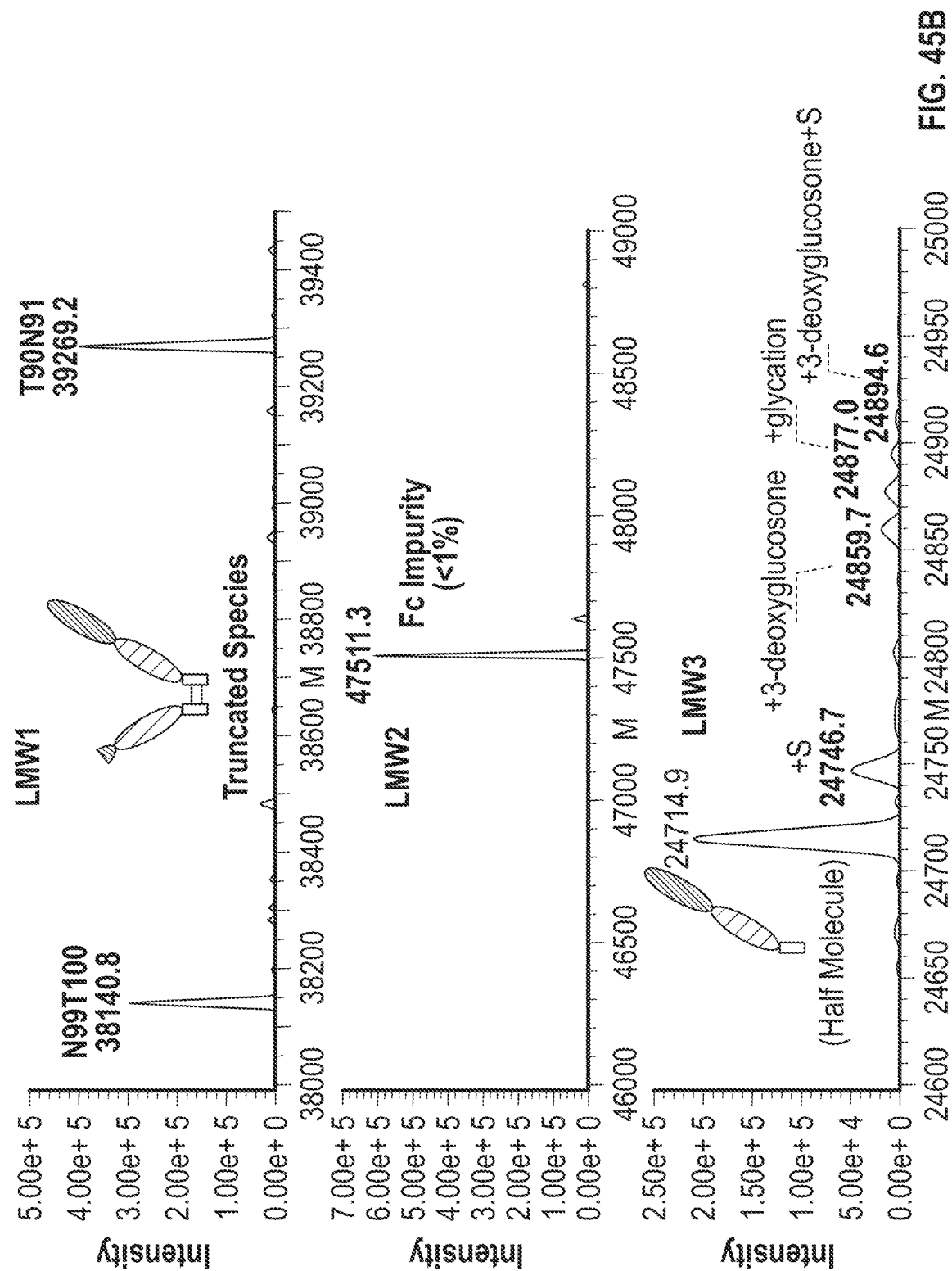
FIG. 45B depicts mass spectra for the low molecular weight impurities in MT1.

Analysis of MT1 sample. The LMW species identified from the TIC of the SEC-MS analysis of the samples comprising MT1 was extracted to examine three distinct LMW impurities—LMW1, LMW2, and LMW3 (FIG. 45A and FIG. 45B). LMW1 species comprised a truncated species of aflibercept. LMW2 species comprised the Fc impurity present in the sample form the cleavage of aflibercept which was performed to produce MiniTrap. LMW3 species comprised a monomer possibly cleaved from the MT1 (dimer) molecule.

Figure 46:
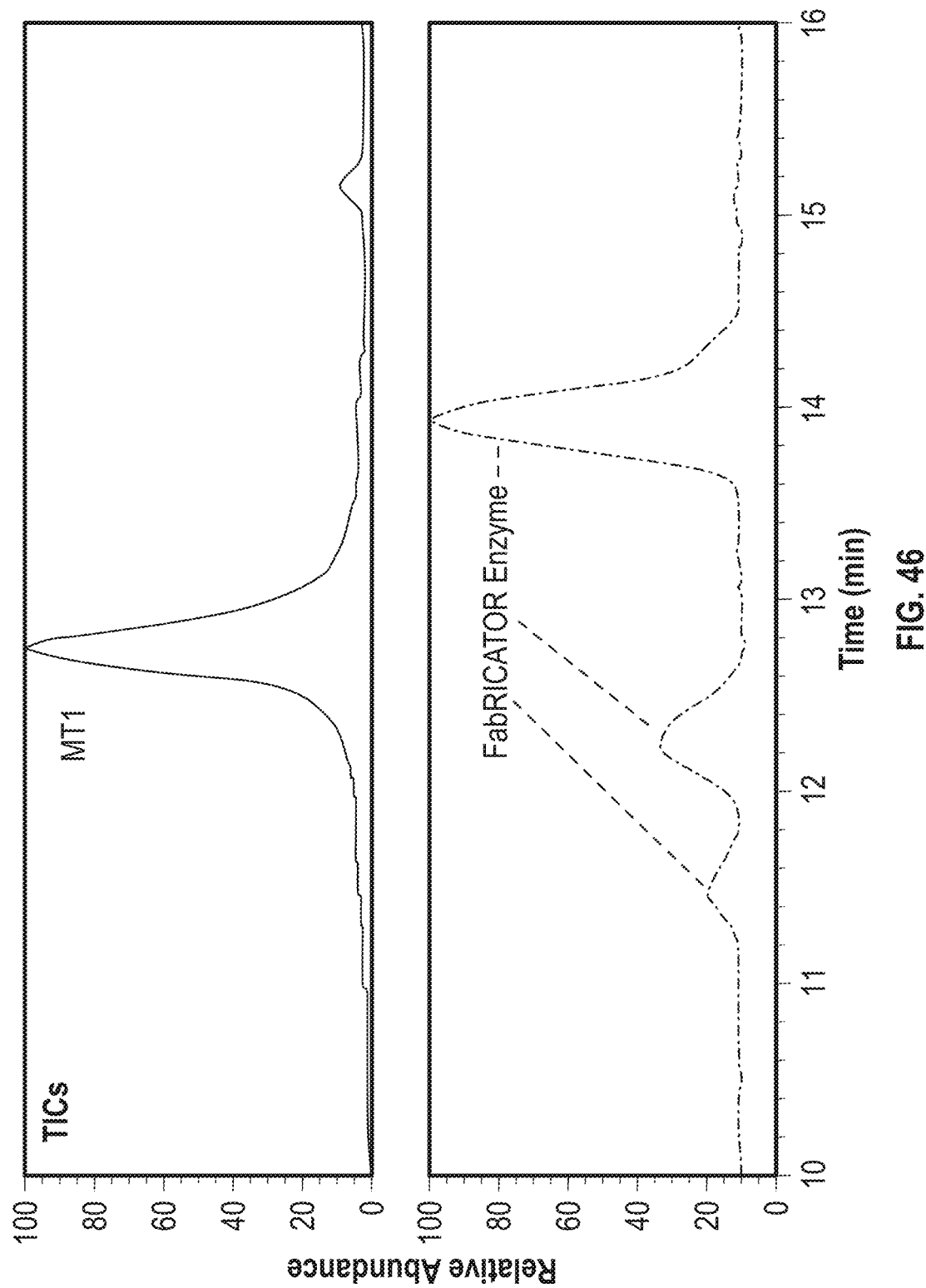
FIG. 46 depicts relative absorbance versus time (minutes) for MT1 which shows absence of the FabRICATOR enzyme which was used to cleave aflibercept into MT1.

MT1 sample did not show presence of FabRICATOR enzyme, which had been used to cleave aflibercept to form a MiniTrap protein. The enzyme, if present, is detected at about 11.5 and 12.5 minutes. No such peak was detected during the SEC-MS analysis of the MT1 sample (FIG. 46).

Figure 47:
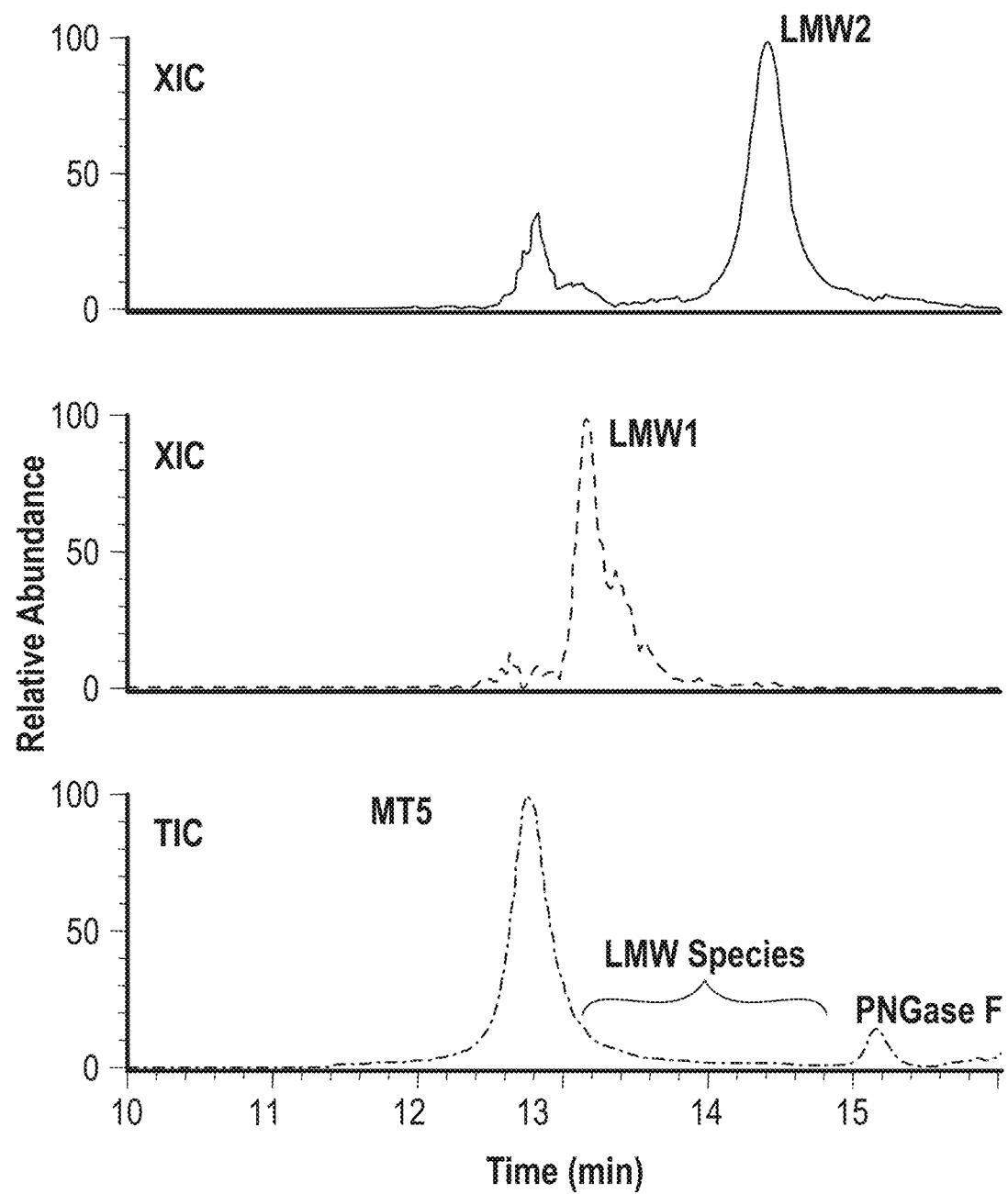
FIG. 47 depicts relative absorbance versus time (minutes) for low molecular weight impurities in MT5.

Analysis of MT5 sample. The LMW species identified from the TIC of the SEC-MS analysis of the samples comprising MT5 was extracted to examine the presence of two distinct LMW impurities—LMW1 and LMW2 (FIG. 47).

Figure 48:
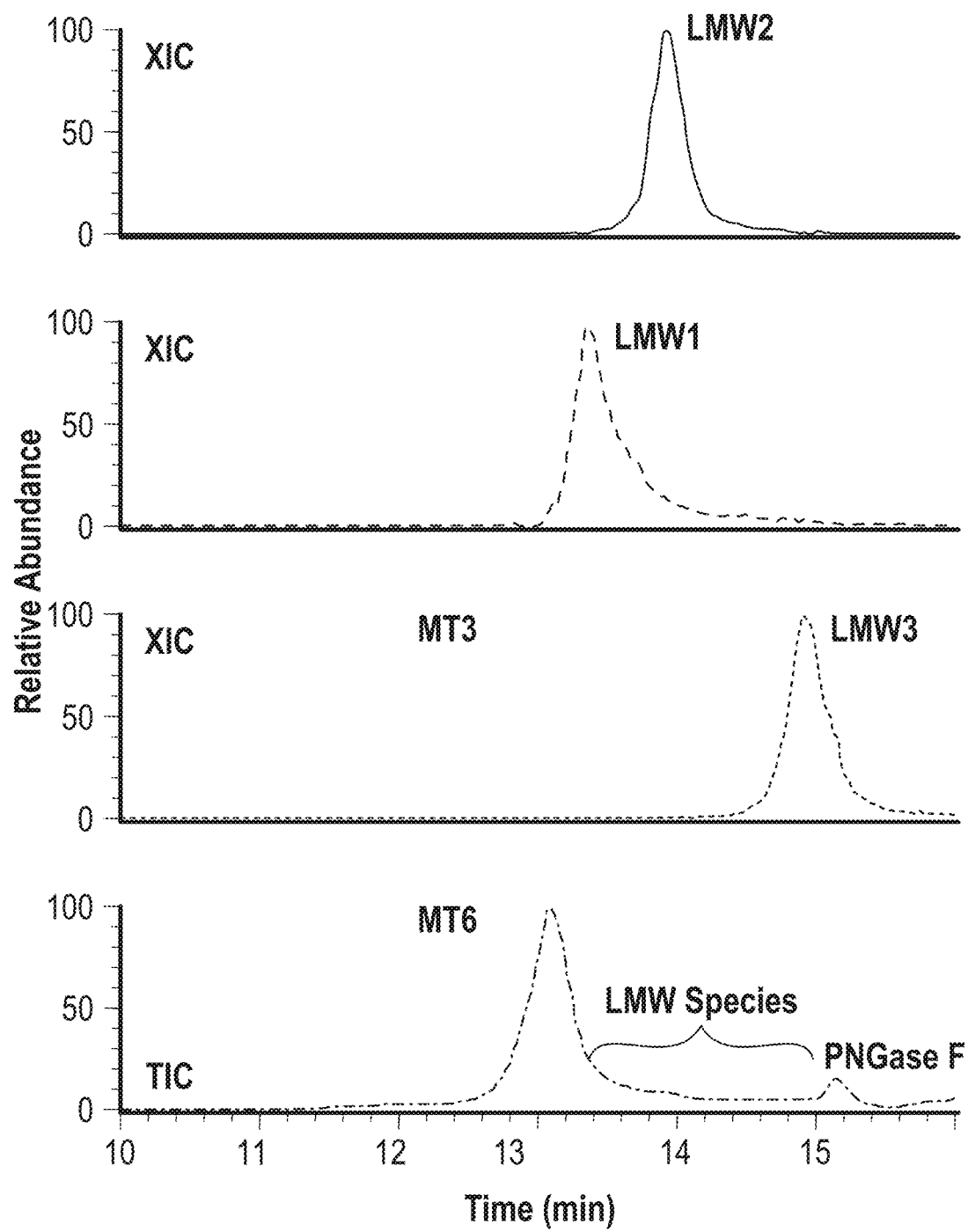
FIG. 48 depicts relative absorbance versus time (minutes) for low molecular weight impurities in MT6.

Analysis of MT6 sample. The LMW species identified from the TIC of the SEC-MS analysis of the samples comprising MT1 was extracted to examine the presence of three distinct LMW impurities—LMW1, LMW2, and LMW3 (FIG. 48). LMW2 species comprised a fragment of the MT6 wherein the cleavage produced the fragment of VEGF MiniTrap with the G4S linker (SEQ ID NO.: 111). LMW5 species comprised a fragment of the MT6 wherein the cleavage occurred right before or after the G4S linker (SEQ ID NO.: 111).

Figure 49A:
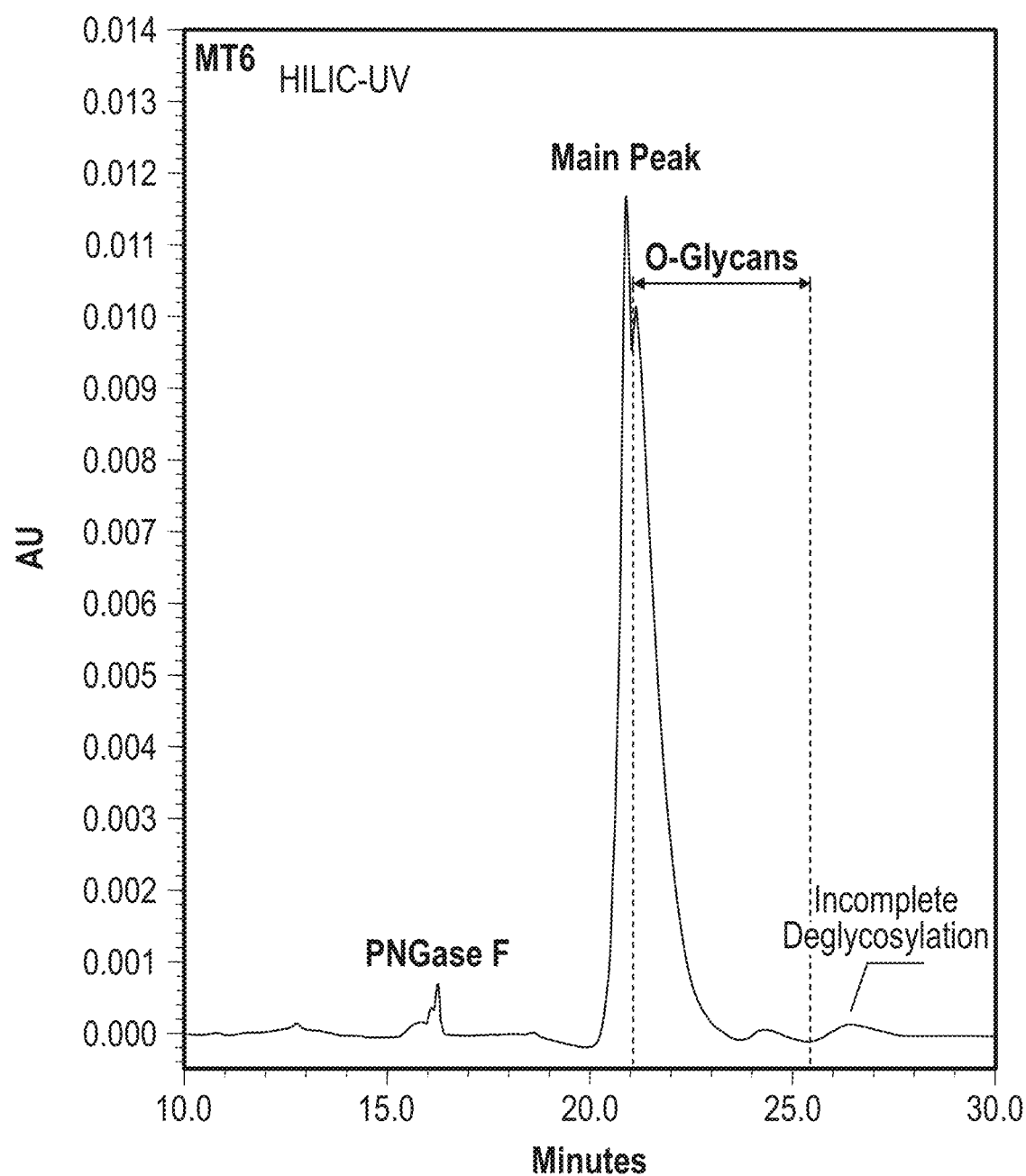
FIG. 49A depicts a chart of absorbance versus time (minutes) obtained on performing HILIC-UV/MS for VEGF MiniTrap MT6, wherein the chart shows the elution of main peak at 21 minutes and O-glycans at around 21.5 minutes.

The glycans in the MT6 sample were identified by their mass and elution order in the HILIC chromatography method using the glucose unit value pioneered by Waters and the National Institute for Bioprocessing Research and Training (Dublin, Ireland) (FIG. 49A and FIG. 49B).

Free thiol Quantification. Cysteine residues of the VEGF MiniTrap constructs may be involved in the formation of intra- and inter-molecular disulfide bond(s) or they may exist as free thiols. The presence of sulfide bonds in peptides and proteins has been shown to impose conformational rigidity on a protein. Thiols can be detected by a variety of reagents and separation techniques. The analysis of the three VEGF MiniTrap constructs for a very low level of free thiols is shown in Table 8-1.

TABLE 8-1

| Location | Peptide (site of free cysteine) | MT1 | MT5 | MT6 |
|---|---|---|---|---|
| VEGFR1 | ELVIPCR (SEQ ID NO.: 81) | <0.1% | <0.1% | <0.1% |
| VEGFR2 | LVLNCTAR (SEQ ID NO.: 82) | 0.3% | 0.3% | 0.3% |
| Fc Hinge | THTCPPCPAPELLG (SEQ ID NO.: 83) | 0.0% | 0.0% | N/A |

Trisulfide Quantification. Similar to free thiols in Cys residues of the VEGF MiniTrap constructs, trisulfide bonds can influence the structure of the protein. The analysis of the three VEGF MiniTrap constructs under conditions with very low level of free thiols is shown in Table 8-2.

TABLE 8-2

| Location | Peptide | MT1 | MT5 | MT6 |
|---|---|---|---|---|
| VEGFR1 | ELVIPCR - EIGLLTCEATVN GHLYK (SEQ ID NO.: 84) | 0.1% | <0.1% | 0.1% |
| VEGFR2 | LVLNCTAR - SDQGLYTCAAS SGLMTK(K) (SEQ ID NO.: 85) | <0.1% | <0.1% | <0.1% |
| Fc Hinge | THTCPPCPAPELLG - THTCP APCPPELL(G) (SEQ ID NO.: 86) | 1.5% | 3.7% | N/A |

Intra-chain disulfide in the Hinge region. Mispaired disulfide bonds in the hinge region can have implications on the structure, function and stability of the VEGF MiniTrap constructs. The analysis of the three VEGF MiniTrap constructs for a very low or no intra-chain disulfide binds in the hinge region of the VEGF MiniTrap constructs [THTC*PPC*PAPELLG, C* shows where intra-chain sulfide bond can be formed] (SEQ ID NO.: 83) is shown in Table 8-3.

TABLE 8-3

| Peptide | MT1 | MT5 | MT6 |
|---|---|---|---|
| Disulfide | <0.1% | <0.1% | N/A |
| Trisulfide | <0.1% | <0.1% | N/A |

Figure 50:
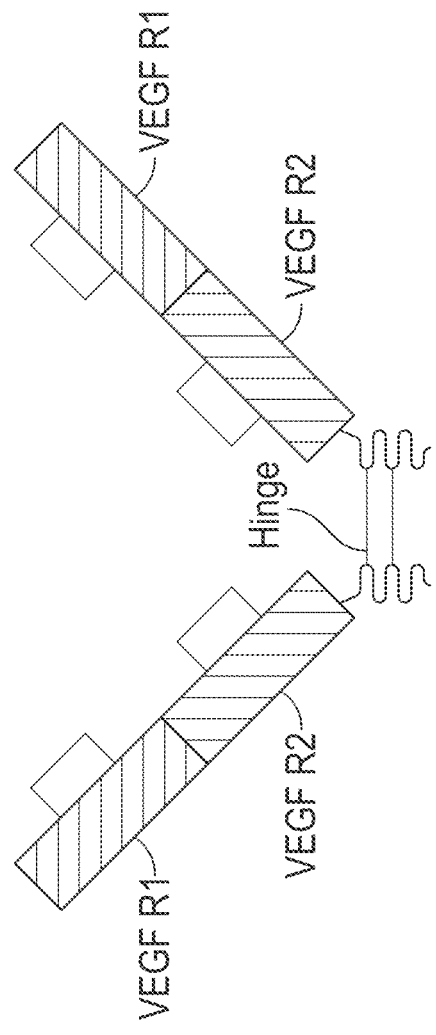
FIG. 50 is an image of VEGF MiniTrap dimer wherein the disulfide bridge in the hinge region (SEQ ID NO.: 83, 123, 83, and 123) of the VEGF MiniTrap can be parallel or crossed.

Cross and parallel disulfide linkage isomer quantification. For MT1 and MT5, which are dimers connected by parallel disulfide bonds in the hinge regions, there is a possibility of isomers wherein the disulfide bonds in the hinge region can be crossed (FIG. 50).

The quantification of types of disulfide bond, parallel versus cross, showed that MT5 recombinantly expressed protein had a slightly higher level of cross disulfide bridge in the Fc hinge region compared to the MT1-which is a FabRICATOR digested molecule (Table 8-4).

TABLE 8-4

| Disulfide | MT1 | MT5 | MT6 |
|---|---|---|---|
| Cross | 0.2% | 3.9% | N/A |
| Parallel | 99.8% | 96.1% | N/A |

Post-Translational Modifications (PTMs).

TABLE 8-5

| PTM | Site | Modified Peptide | | MT1 | MT5 | MT6 |
|---|---|---|---|---|---|---|
| Deamidation | Asn84 (Asn319) | EIGLLTCEATVNGHLYK (SEQ ID NO.: 87) | Succinimide | 3.1% | 3.2% | 3.2% |
| | | | Asp/iso Asp | 21.9% | 18.9% | 20.9% |
| | Asn99 (Asn334) | QTNTIIDVVLSPSHGIELSVGEK (SEQ ID NO.: 88) | Succinimide | 4.6% | 4.6% | 4.0% |
| | | | Asp/iso Asp | 0.7% | 0.5% | 0.6% |
| Oxidation | Met10 | SDTGRPFVEMYSEIPEIIHMTEGR (SEQ ID NO.: 89) | | 1.8% | 2.1% | 2.1% |
| | Met20 | SDTGRPFVEMYSEIPEIIHMTEGR (SEQ ID NO.: 90) | | 2.9% | 3.0% | 2.7% |
| | Met245 | GGGGSGGGGSGGGGSGGGGSGGGGSGGGGSS DTGRPFVEMYSEIPEIIHMTEGR (SEQ ID NO.: 91) | | — | — | 1.4% |
| | Met255 | GGGGSGGGGSGGGGSGGGGSGGGGSGGGGSS DTGRPFVEMYSEIPEIIHMTEGR (SEQ ID NO.: 92) | | — | — | 2.7% |
| | Met163 (Met398) | TQSGSEMK (SEQ ID NO.: 93) | | 4.3% | 4.3% | 3.8% |
| | Met192 (Met427) | SDQGLYTCAASSGLMTK (SEQ ID NO.: 94) | | 5.0% | 5.0% | 4.2% |
| C-term Glycine loss | Gly211 | THTCPPCPAPELLG (SEQ ID NO.: 95) | | 0.1% | 2.0% | — |

Evaluation of PTMs in all the three VEGF MiniTrap constructs showed comparable levels of PTMs (Table 8-5). The deamidation observed at Asn84 to form succinimide was in the range of about 3.1-3.2% and to form aspartic acid/iso aspartic acid was 18.9-21.9%. Oxidation of several methionine residues (e.g., Met10, Met20 m Met163 and Met192) was observed in the range of about 0.7-6.8% for all the three VEGF MiniTrap constructs. MT6, which, in contrast to MT1 and MT5, comprises a linker, showed additional oxidation of methionine residues on the linker (e.g., Met245 and Met255). About 0.1% and 2.0% of the C-terminal glycine (Gly211) in MT1 and MT5 showed a glycine loss. This was not observed for MT6, which lacks a C-terminal glycine.

Advanced glycation end-product modifications related to lysine and arginine glycation. Glycation of the VEGF MiniTrap constructs can alter their structure and function, leading to impaired anti-VEGF activity.

TABLE 8-6

| Site | PTM | MT1 | MT5 | MT6 |
|---|---|---|---|---|
| Arg5 | 3-Deoxyglucosone | 8.0% | 8.1% | 9.2% |
| | Glycation | 0.1% | 0.1% | 0.1% |
| | Carboxymethylation | 1.5% | 1.4% | 1.4% |
| Arg153 | 3-Deoxyglucosone | <0.1% | <0.1% | <0.1% |
| Arg96 | 3-Deoxyglucosone | <0.1% | <0.1% | <0.1% |
| Lys62 | Glycation | 1.1% | 1.1% | 1.3% |
| | Carboxymethylation | <0.1% | <0.1% | <0.1% |
| Lys68 | Glycation | 0.4% | 0.3% | 0.5% |
| Lys149 | Glycation | 0.6% | 0.5% | 0.6% |
| | Carboxymethylation | <0.1% | <0.1% | <0.1% |
| Lys185 | Glycation | <0.1% | <0.1% | <0.1% |

Evaluation of modifications in all three VEGF MiniTrap constructs showed comparable levels (Table 8-6).

Modified sites. The modified sites on the VEGF MiniTrap constructs, as elucidated by the intact mass analysis as per Section 8.4, were confirmed and quantified using reduced peptide mapping as illustrated in Section 8.5 (Table 8-7). The site T90N91 for peptide sequence TNYLTHR (SEQ ID NO.: 21), the ** represents that asparagine was converted to aspartic acid after truncation, whereas for site N99T100 the peptide sequence QTNTIIDVVLSPSHGIELSVGEK (SEQ ID NO.: 19), the * represents a high level of no-specific cleavage by trypsin. These two truncation sites were found to form LMW species impurities during evaluation of MT1 and MT5. The truncation at M245Y246 was found only on MT6 which had the unique linker and was responsible for the LMW2 species impurity during the MT6 preparation.

TABLE 8-7

| Site | Peptide Sequence | MT1 | MT5 | MT6 |
|---|---|---|---|---|
| N99T100 | QTNTIIDVVLSPSHGIE LSVGEK* (SEQ ID NO.: 96) | 12.6% | 13.2% | 13.6% |
| T90N91 | TNYLTHR** (SEQ ID NO.: 97) | 0.5% | 0.1% | 0.3% |
| M245Y246 | GGGGSGGGGSGGGGSGG GGSGGGGSGGGGSSDTG RPFVEMYSEIPEIIHMT | — | — | 1.8% |

TABLE 8-7-continued

| Site | Peptide Sequence | MT1 | MT5 | MT6 |
|---|---|---|---|---|
| | EGR (SEQ ID NO.: 98) | | | |
| M10Y11 | SDTGRPFVEMYSEIPEI IHMTEGR (SEQ ID NO.: 99) | 0.2% | 1.5% | 1.7% |

Figure 51:
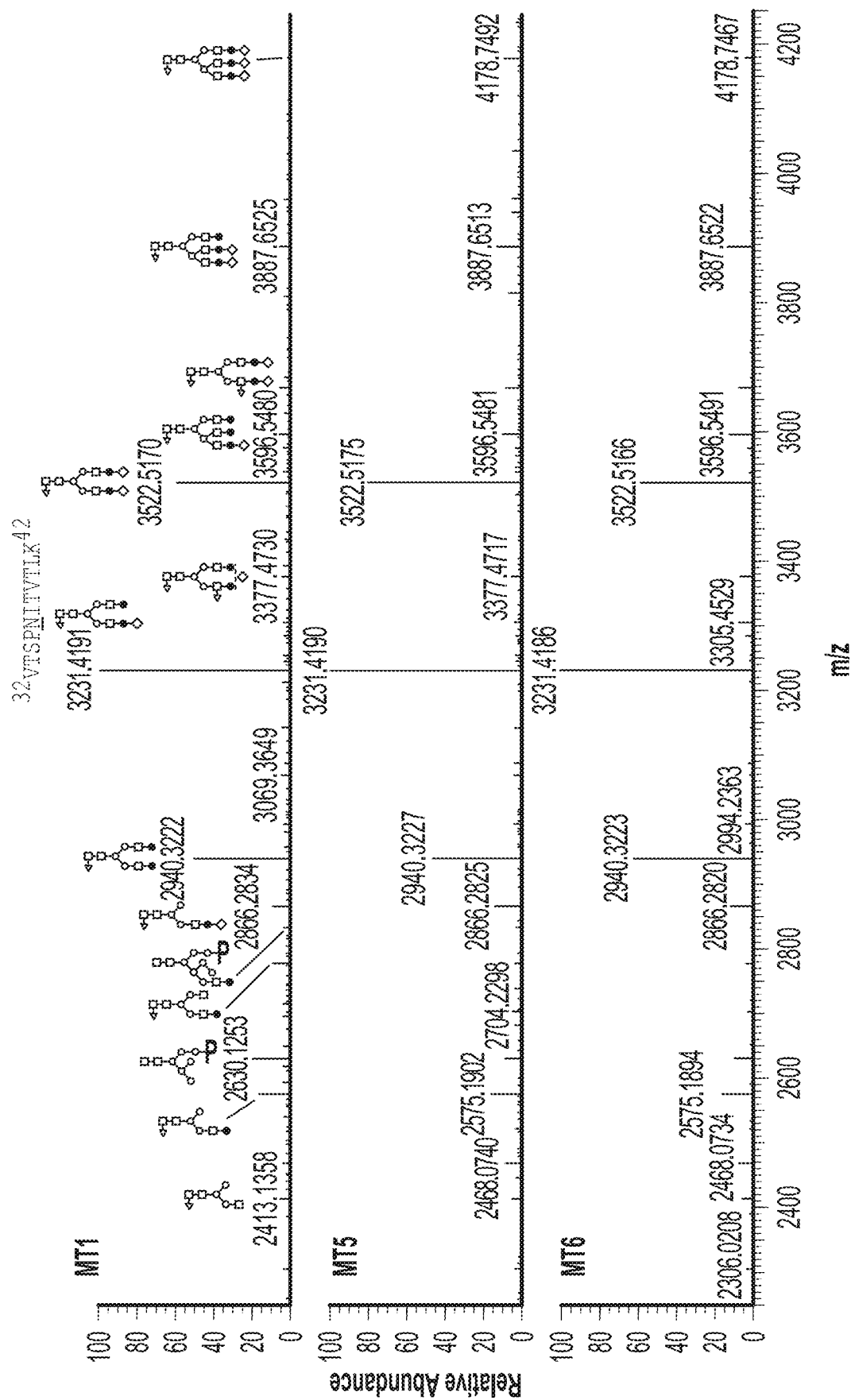
FIG. 51 depicts relative abundance of distribution of glycans observed at Asn36 among MT1, MT5 and MT6. Figure discloses SEQ ID NO.: 121.
Figure 52:
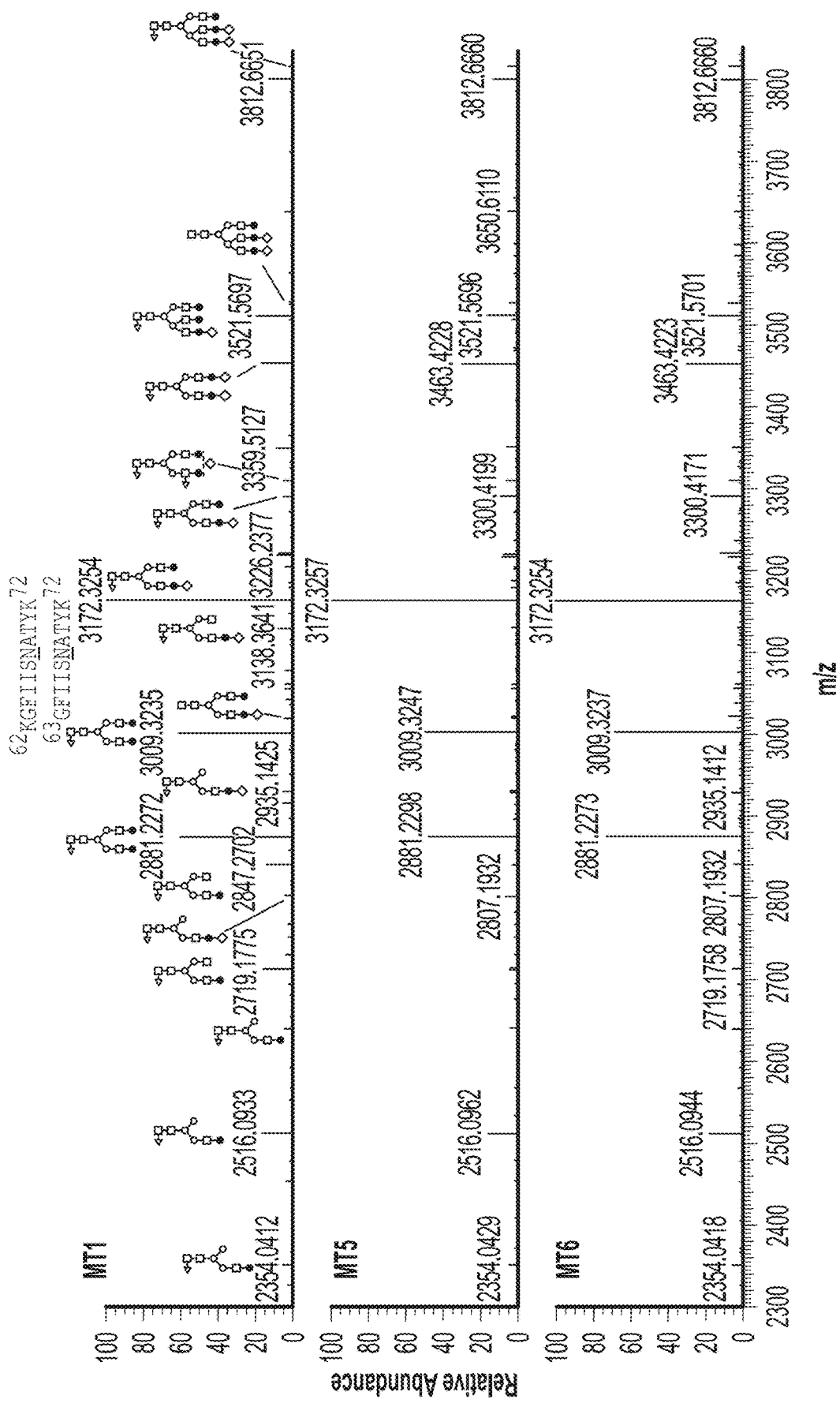
FIG. 52 depicts relative abundance of distribution of glycans observed at Asn68 among MT1, MT5 and MT6. Figure discloses SEQ ID NOS 101 and 30, respectively, in order of appearance.
Figure 53:
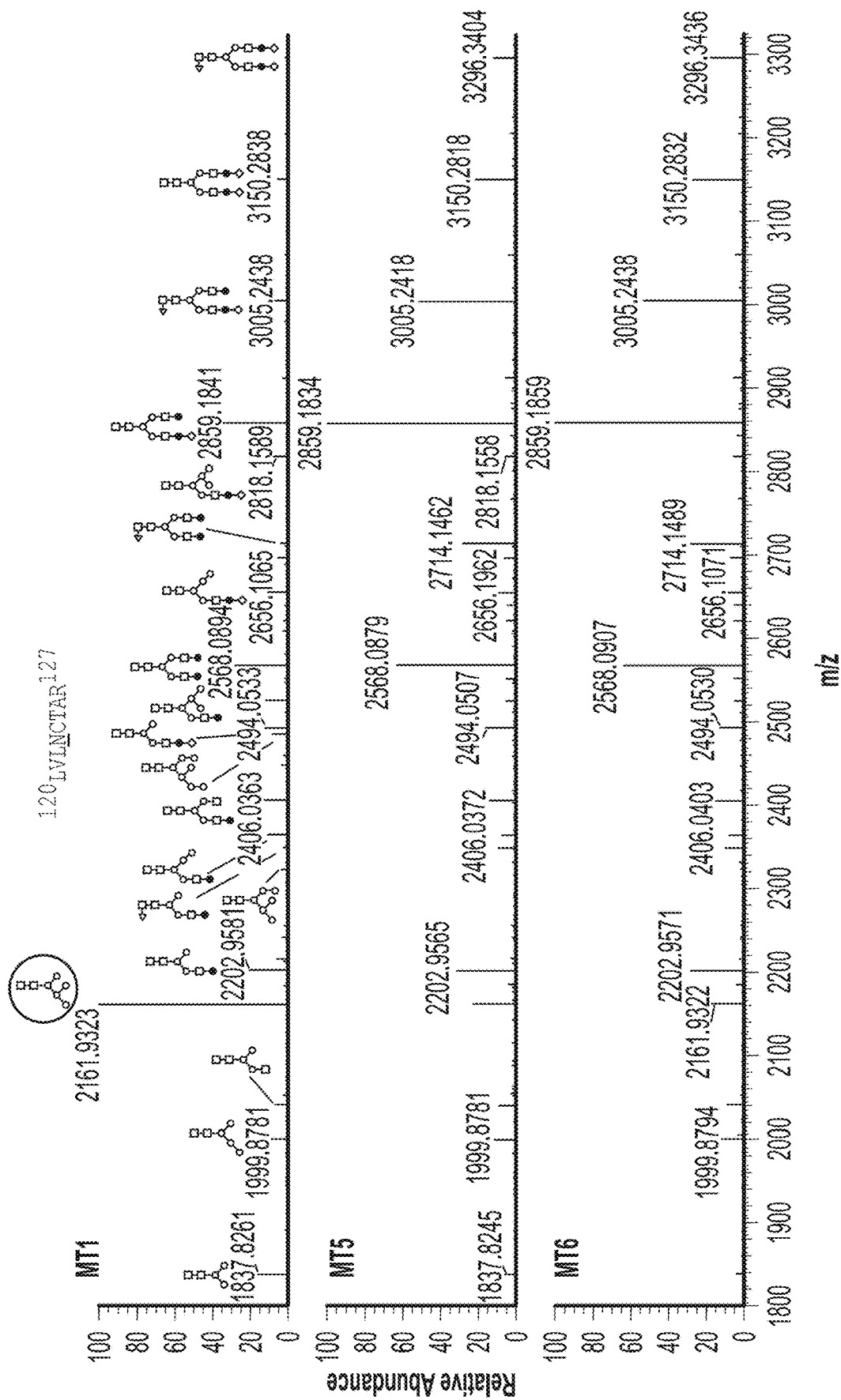
FIG. 53 depicts relative abundance of distribution of glycans observed at Asn123 among MT1, MT5 and MT6. Figure discloses SEQ ID NO.: 82.
Figure 54:
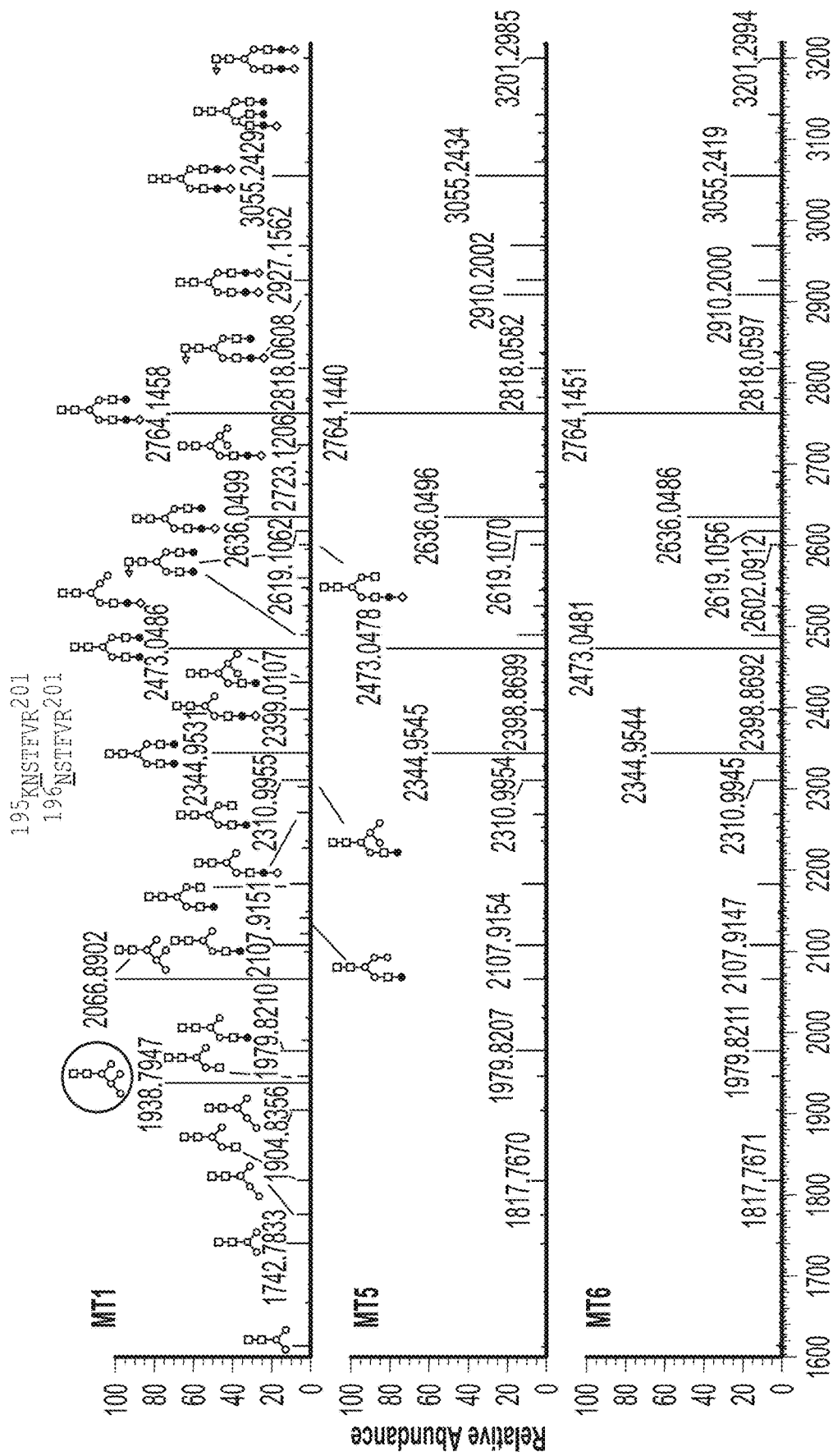
FIG. 54 depicts relative abundance of distribution of glycans observed at Asn196 among MT1, MT5 and MT6. Figure discloses SEQ ID NOS 103 and 122, respectively, in order of appearance.

Glycosites occupancy quantification. N-glycosylation is a common PTM. Characterizing the site-specific N-glycosylation including N-glycan macroheterogeneity (glycosylation site occupancy) and microheterogeneity (site-specific glycan structure) is important for the understanding of glycoprotein biosynthesis and function. The extent of glycosylation can change depending on how the protein is expressed. The levels of glycosylation at N36 were similar for all the three VEGF MiniTraps (Table 8-8 and FIG. 51). Similarly, the levels of glycosylation at N68 were also similar for all the three VEGF MiniTraps (Table 8-8 and FIG. 52). The levels of glycosylation at N123 were also similar for all the three VEGF MiniTraps (Table 8-8 and FIG. 53), but mannose-5 was found to be elevated in the MT1 preparation. For the VEGF MiniTrap constructs, glycosylation at Asn196 was lower for MT5 and MT6, compared to MT1 (Table 8-8 and FIG. 54). Additionally, the mannose-5 was also elevated for the MT1 preparation than MT5 and MT6 preparations.

TABLE 8-8

| Site | Peptide | MT1 | MT5 | MT6 |
|---|---|---|---|---|
| N36 | (R)VTSPNITVTLK (SEQ ID NO.: 100) | 98.3% | 98.1% | 99.4% |
| N68 | (K)GFIISNATYK (SEQ ID NO.: 101) | 51.9% | 55.4% | 64.9% |
| N123 | (K)LVLNCTAR (SEQ ID NO.: 102) | 99.9% | 99.4% | 98.4% |
| N196 | (K)NSTFVR (SEQ ID NO.: 103) | 98.6% | 44.5% | 55.1% |

Analysis of N-glycans. The glycosylation at N36 is shown in Table 8-9. G2F, G2FS, G2FS2 were the major N-glycans found in all the three VEGF MiniTraps. For glycosylation at N68 shown in Table 8-10, G2F and G2FS were the major N-glycans found in all the three VEGF MiniTraps. For glycosylation at N123 is shown in Table 8-11, G2F and G2S were the major N-glycans found in all the three VEGF MiniTraps and Mannose-5 was detected at high levels in MT1 compared to MT5 and MT6. For glycosylation at N196 shown in Table 8-12, G2, G2S, G2S2 were the major N-glycans found in all the three VEGF MiniTraps and Mannose-5 was detected at high levels in MT1 compared to MT5 and MT6.

TABLE 8-9

| Glycans at N36 | MT1 | MT5 | MT6 |
|---|---|---|---|
| G0F-GlcNAc | 2.0% | 1.8% | 1.8% |
| G1F | 3.2% | 1.0% | 1.4% |
| G1F-GlcNAc | 4.8% | 4.6% | 4.9% |
| G1FS-GlcNAc | 3.1% | 3.8% | 3.1% |
| G2F | 17.4% | 15.1% | 19.8% |
| G2F2S | 1.7% | 2.0% | 2.2% |

TABLE 8-9-continued

| Glycans at N36 | MT1 | MT5 | MT6 |
|---|---|---|---|
| G2FS | 34.2% | 31.5% | 31.9% |
| G2FS2 | 20.4% | 25.8% | 19.0% |
| G3FS | 2.3% | 4.0% | 5.5% |
| G3FS2 | 2.6% | 4.7% | 5.0% |
| G3FS3 | 1.1% | 2.4% | 1.9% |
| G1_Man5 + Phos | 1.2% | 0.3% | 0.2% |
| Man6 + Phos | 5.7% | 2.5% | 2.8% |

TABLE 8-10

| Glycans at N68 | MT1 | MT5 | MT6 |
|---|---|---|---|
| G0F-GlcNAc | 1.2% | 1.1% | 1.1% |
| G1F | 5.1% | 1.4% | 1.7% |
| G1F-GlcNAc | 3.9% | 3.9% | 4.0% |
| G1FS | 1.2% | 0.4% | 0.4% |
| G1FS1-GlcNAc | 1.2% | 1.6% | 1.4% |
| G2F | 27.4% | 23.6% | 28.6% |
| G2F2S | 2.2% | 3.0% | 3.4% |
| G2FS | 52.4% | 55.2% | 50.2% |
| G2FS2 | 3.9% | 6.9% | 5.8% |
| G3FS | 0.5% | 1.2% | 1.6% |
| G3FS2 | 0.4% | 1.1% | 1.2% |

TABLE 8-11

| Glycans at N123 | MT1 | MT5 | MT6 |
|---|---|---|---|
| G0-GlcNAc | 3.5% | 3.7% | 3.5% |
| G1-GlcNAc | 6.2% | 6.8% | 6.4% |
| G1S-GlcNAc | 4.1% | 3.5% | 2.8% |
| G2 | 10.6% | 16.7% | 17.1% |
| G2F | 1.5% | 7.2% | 7.0% |
| G2FS | 2.1% | 13.6% | 14.2% |
| G2S | 12.7% | 26.1% | 25.5% |
| G2S2 | 1.3% | 5.0% | 6.6% |
| G1_Man4 | 3.8% | 1.3% | 1.4% |
| G1S_Man4 | 3.9% | 2.1% | 1.8% |
| G1_Man5 | 4.0% | 1.2% | 1.1% |
| G1S_Man5 | 3.2% | 1.4% | 1.4% |
| Man4 | 2.6% | 1.9% | 1.8% |
| Man5 | 35.5% | 4.3% | 3.1% |
| Man6 | 1.1% | 0.1% | 0.1% |
| Man7 | 2.8% | 0.1% | 0.1% |

TABLE 8-12

| Glycans at N196 | MT1 | MT5 | MT6 |
|---|---|---|---|
| G0-GlcNAc | 1.9% | 1.8% | 1.9% |
| G1 | 4.1% | 3.6% | 4.2% |
| G1-GlcNAc | 1.9% | 2.5% | 2.4% |
| G1S-GlcNAc | 2.9% | 2.6% | 1.8% |
| G2 | 20.7% | 28.2% | 32.1% |
| G2F | 2.0% | 5.1% | 6.0% |
| G2FS | 2.0% | 6.1% | 6.2% |
| G2FS2 | 0.5% | 1.6% | 1.3% |
| G2S | 17.7% | 31.2% | 29.9% |
| G2S2 | 4.4% | 9.7% | 6.7% |
| G3S | 0.1% | 0.7% | 1.0% |
| G1S_Man4 | 1.0% | 0.3% | 0.3% |
| G1_Man5 | 2.3% | 0.5% | 0.5% |
| Man3 | 3.1% | 0.7% | 0.6% |
| Man4 | 2.7% | 0.8% | 0.6% |
| Man5 | 30.4% | 3.6% | 3.4% |

O-glycans at the linker for MT6. The GS linker for MT6 was evaluated to study O-glycans on MT6. O-xylosylation was found to on serine residues located on the GS linker of MT6

(GGGGSGGGGSGGGGSGGGGSGGGGGGGGSSDT-GRPFVEMYSEIPEIIHMTEGR, underlined serine residues were glycosylated) (SEQ ID NO.: 98). The composition of the O-glycans is shown in Table 8-13.

TABLE 8-13

| Composition | Mass | Annotation | Number | Level |
|---|---|---|---|---|
| Xylosylation | +132.0 | ✳ | Tri | <0.1% |
|  |  |  | di | 1.5% |
|  |  |  | mono | 15% |
| Xylose + Galactose | +294.1 | ✳—○ | mono | 0.9% |
| Xylose + Galactose + Sialic Acid | +585.2 | ✳—○—◆ | mono | 0.7% |

Figure 55:
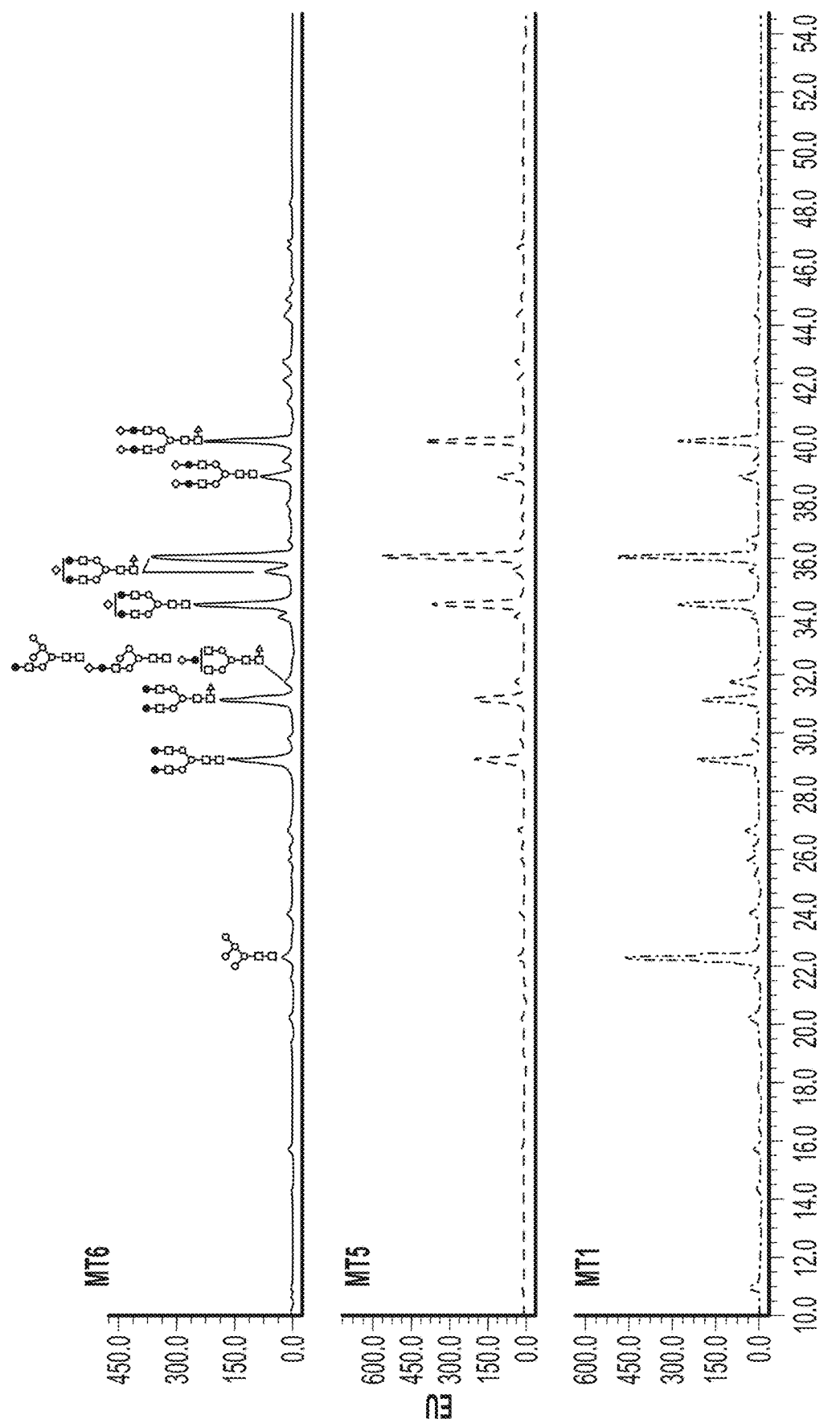
FIG. 55 depicts the released N-linked glycan analysis by hydrophilic interaction chromatography (HILIC) coupled to fluorescence detection and mass spectrometry analysis (full scale and stacked).
Figure 56:
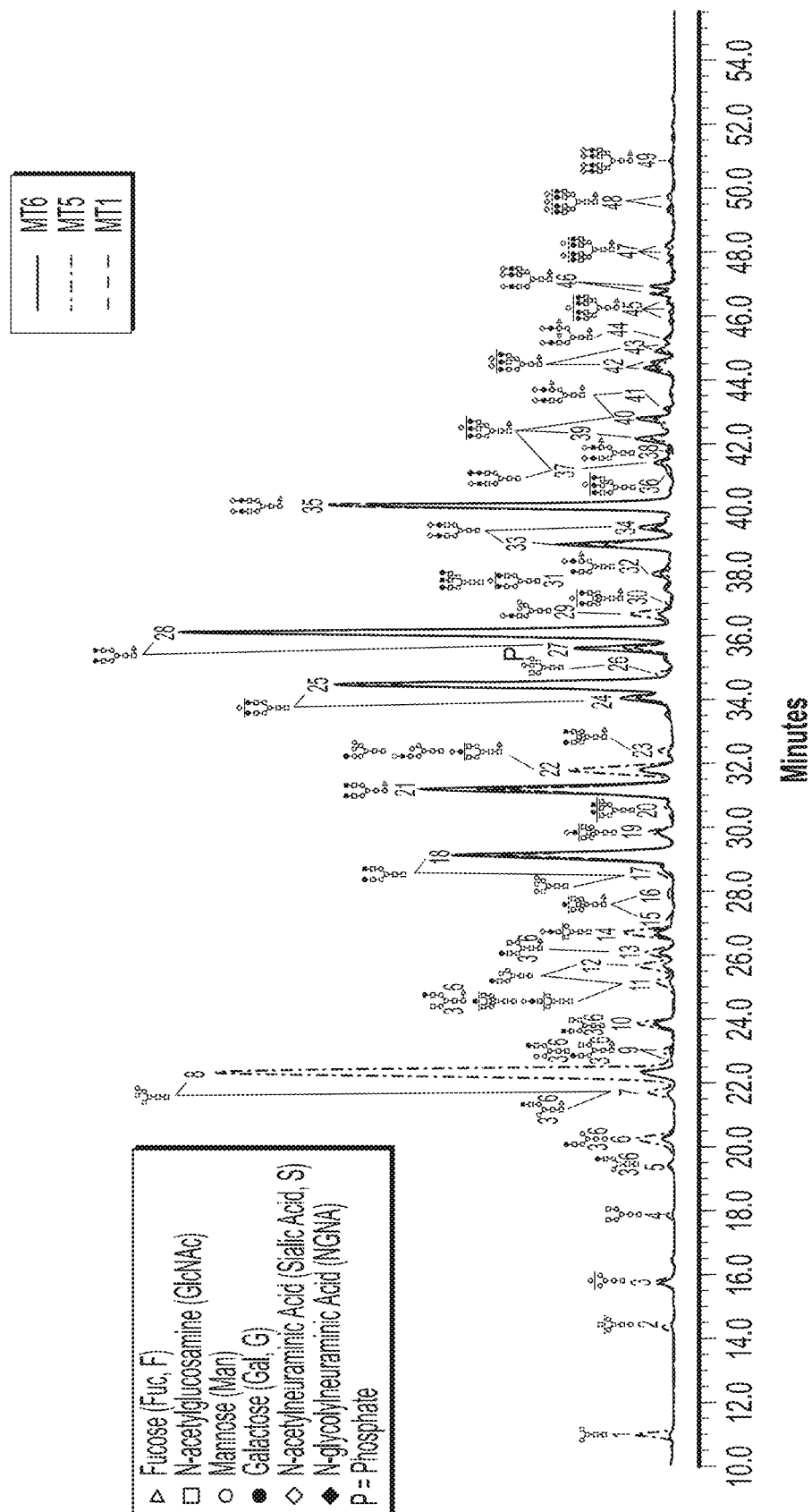
FIG. 56 depicts HILIC-FLR chromatograms for MT1, MT5 and MT6.
Figure 57:
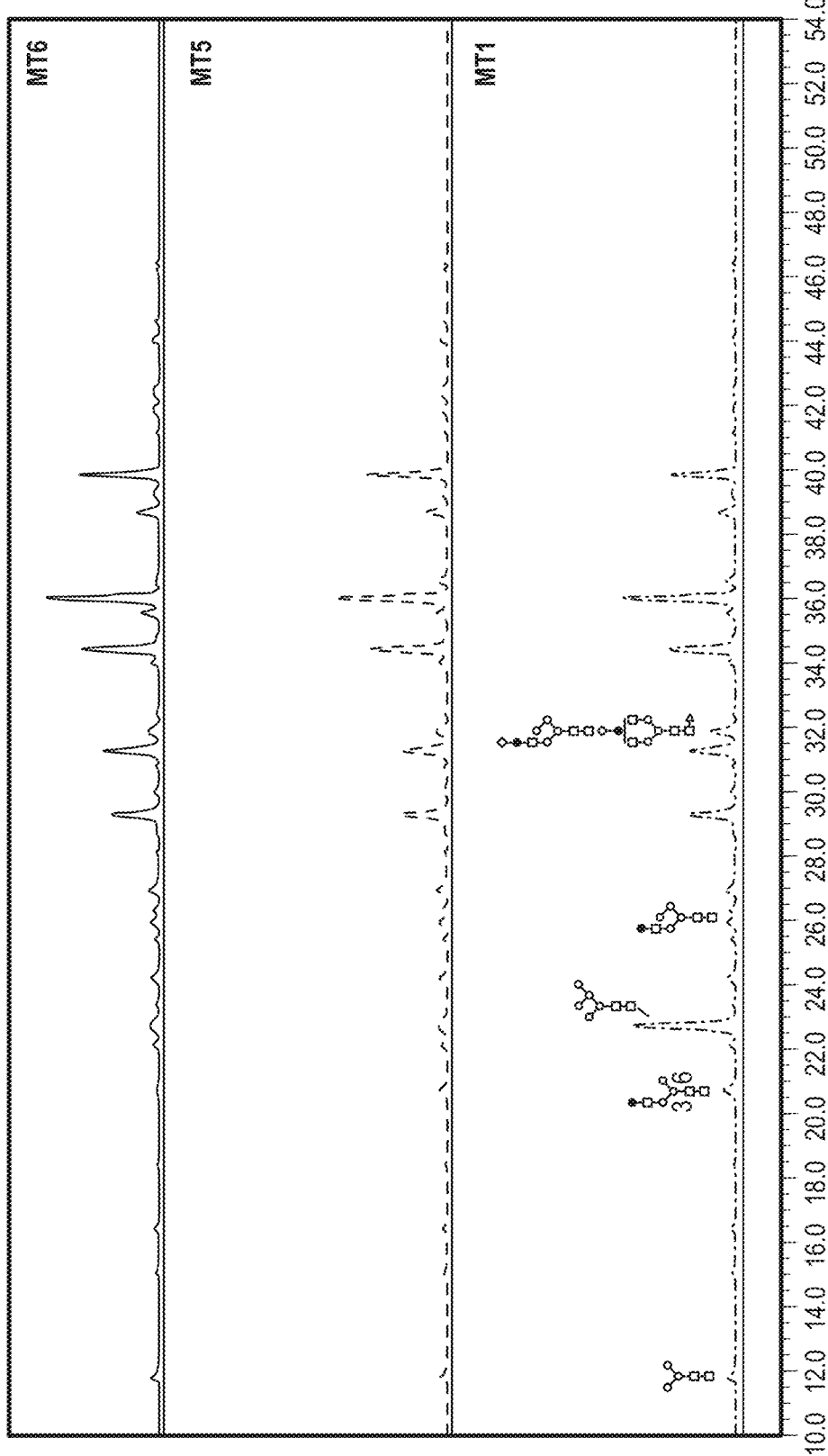
FIG. 57 depicts the released N-linked glycan analysis by HILIC coupled to fluorescence detection and mass spectrometry analysis (full scale, stacked and normalized).

HILIC-FLR-MS analysis. HILIC-FLR-MS analysis was performed for all the VEGF MiniTrap proteins as described in Section 8.2. The analysis showed that the N-linked glycans for MT5 and MT6 were similar but were different than the ones obtained for MT1 (FIG. 55 shows the full scale and stacked chromatograms, FIG. 56 shows full scale and overlaid chromatograms and FIG. 57 shows the full scale, stacked and normalized chromatograms).

Finally, the percent glycosylation and detailed glycan identification and quantification for all three VEGF Mini-Trap proteins is listed in Table 8-14 and FIG. 58A-C, respectively. As observed in all the glycan analysis, the glycosylation profile and mannose levels for MT5 and MT6 are similar, but different from MT1.

TABLE 8-14

|  | MT1 | MT5 | MT6 |
|---|---|---|---|
| % Fucosylation | 42.9% | 57.8% | 57.2% |
| % Galactosylation | 71.6% | 92.9% | 93.7% |
| % Sialylation | 33.1% | 47.6% | 44.8% |
| % High Mannose | 17.6% | 2.6% | 2.3% |
| % Bisecting | 1.9% | 0.4% | 0.4% |

Example 9. Production and Color Quantification Using Upstream Medium and Feed Process Optimization (A) Un-Optimized CDM (Control Bioreactor)

The manufacture of MiniTrap described in Example 5 was employed.

The operating parameters for the study steps are as known to one of ordinary skill in the art.

Medium at day 0=CDM1 and included the following nutrients, antioxidants and metals:

Cysteine was added at a cumulative concentration of 8-9 mM

Figure 59:
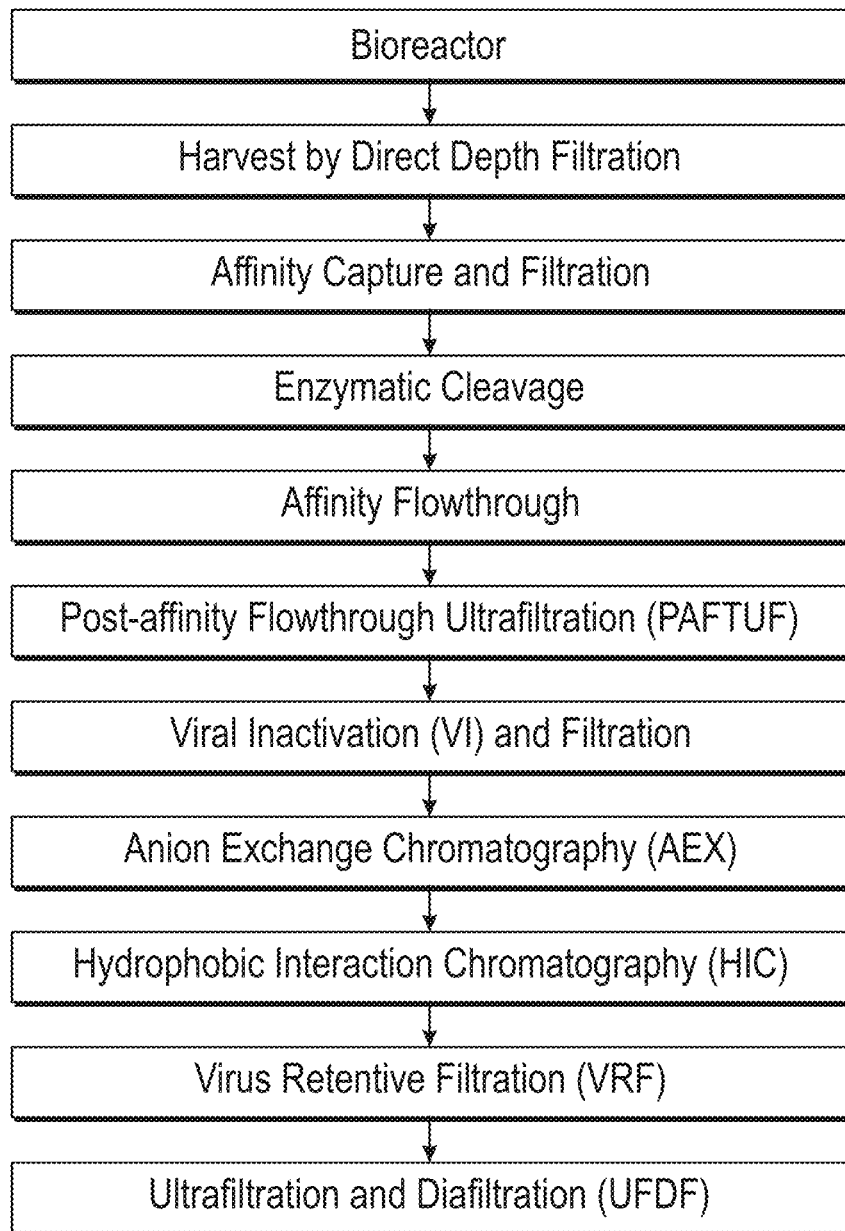
FIG. 59 depicts an exemplary production procedure for manufacturing MiniTrap according to an exemplary embodiment.

Metals in Starting Medium are listed below at 1× concentration (where the concentrations are prior to inoculum addition):

Fe=68-83 micromoles per liter of culture
Zn=6-7 micromoles per liter of culture
Cu=0.1-0.2 micromoles per liter of culture
Ni=0.5-1 micromoles per liter of culture On harvesting MT1, the production procedure as shown in FIG. 59 was followed. The operating parameters for the chromatography are known to one of ordinary skill in the art. The operating parameters for the affinity capture (step 3 of FIG. 59), affinity Flowthrough (step 5 of FIG. 59), AEX (step 8 of FIG. 59), and HIC (step 9 of FIG. 59) are outlined in Table 9-1. The proteolytic cleavage of aflibercept following affinity capture and filtration step was carried out using the procedure as outlined in Example 1.2.

TABLE 9-1

| Steps | Affinity Capture | Affinity flowthrough | AEX | HIC |
|---|---|---|---|---|
| Resin | MabSelect SuRe | MabSelect SuRe | POROS 50 HQ | Capto Phenyl HS |
| Load | 30 g/L resin | 30 g/L resin pH 6.80-7.20 | 40 g/L resin pH 8.30-8.50, 1.90-2.10 mS/cm | 100 g/L resin pH 4.40-4.60 7.50-10.50 mS/cm |
| Equilibration | 20 mM Sodium Phosphate pH 7.10-7.30, 2.60-3.20 mS/cm | 26 mM Tris, 16 mM Sodium Phosphate, 18 mM Acetate pH 6.90-7.10, 2.00-4.00 mS/cm | 50 mM Tris pH 8.30-8.50, 1.90-2.10 mS/cm | 40 mM Tris, 30 mM Sodium Citrate, 74 mM Acetate pH 4.40-4.60, 7.50-10.50 mS/cm |
| Wash 1 | 10 mM Sodium Phosphate, 500 mM NaCl pH 7.10-7.30, 40-50 mS/cm | 26 mM Tris, 16 mM Sodium Phosphate, 18 mM Acetate pH 6.90-7.10, 2.00-4.00 mS/cm | 50 mM Tris pH 8.30-8.50, 1.90-2.10 mS/cm | 40 mM Tris, 30 mM Sodium Citrate, 74 mM Acetate pH 4.40-4.60, 7.50-10.50 mS/cm |
| Wash 2 | 20 mM Sodium Phosphate pH 7.10-7.30, 2.60-3.20 mS/cm | N/A | N/A | N/A |
| Elution | 40 mM Acetic Acid pH 2.80-3.20, 0.28-0.36 mS/cm | 40 mM Acetic Acid pH 2.80-3.20, 0.28-0.36 mS/cm | N/A | N/A |
| Regeneration/Strip 1 | 500 mM Acetic Acid, pH 2.25- | 500 mM Acetic Acid, pH 2.25- | 2M Sodium Chloride (NaCl) | Proprietary buffer |

TABLE 9-1-continued

| Steps | Affinity Capture | Affinity flowthrough | AEX | HIC |
|---|---|---|---|---|
| | 2.65, 0.90-1.25 mS/cm | 2.65, 0.90-1.25 mS/cm | | |
| Regeneration/Strip 2 | N/A | N/A | 1N Sodium Hydroxide (NaOH) | N/A |

Table 9-2 shows the color quantification of the pools obtained on performing various chromatographic steps. The color quantification was carried using samples from the pool having a protein concentration of 5 g/L.

Affinity Capture Pool refers to the eluate collected on performing the affinity capture step (step 3 of FIG. 59). Enzymatic Pool refers to the flowthrough collected on performing the enzymatic cleavage step (step 4 of FIG. 59). Affinity flowthrough Pool refers to the flowthrough collected on performing the affinity flowthrough step (step 5 of FIG. 59) and Affinity flowthrough Eluate refers to the eluate collected on performing the affinity flowthrough step (step 5 of FIG. 59). AEX Pool and AEX Strip refer to the flowthrough and stripped fractions obtained on performing anion exchange chromatography step (step 8 of FIG. 59). HIC Pool refers to the flowthrough collected on performing the hydrophobic interaction chromatography step (step 9 of FIG. 59).

Each step as seen in Table 9-2 shows a reduction in coloration (as observed from the reduction in b* values of the pools). For example, on performing affinity flowthrough chromatography, the flowthrough fraction has a b* value of 2.16 (reduced from a b* value of 2.52 for the flowthrough collected from the affinity capture step). The flowthrough and wash following the AEX separation further reduced the coloration, as observed by reduction in the b* value from 2.16 to 0.74. As expected, stripping the AEX column led to a sample with a yellow-brown color which was significantly more intense than the coloration from the flowthrough and wash following the AEX separation as seen from the b* values (8.10 versus 0.74). Lastly, a HIC step afforded a further reduction in color (the b* value can be normalized for 5 g/L protein concentration from the b* value obtained for HIC pool at 28.5 g/L protein concentration).

TABLE 9-2

Color Quantification of Samples at Various Production Steps

| Sample | Conc. (g/L) | L* | a* | b* |
|---|---|---|---|---|
| Affinity Capture Pool | 5.0 ± 0.1 | 98.75 | −0.12 | 2.52 |
| Enzymatic Cleavage Pool | 5.0 ± 0.1 | 99.03 | −0.07 | 1.61 |
| Affinity flowthrough Pool | 5.0 ± 0.1 | 98.95 | −0.08 | 2.16 |
| Affinity flowthrough Eluate | 5.0 ± 0.1 | 98.92 | −0.01 | 0.83 |
| AEX Pool | 5.0 ± 0.1 | 99.72 | −0.03 | 0.74 |
| AEX 2M NaCl Strip | 5.0 ± 0.1 | 96.25 | −0.42 | 8.10 |
| HIC Pool | 28.5 | 98.78 | −0.28 | 3.11 |

(B) Optimized CDM (Low Cysteine, Low Metals and Increased Antioxidants Bioreactor)

The effect of lowering the concentration of cysteine, lowering the concentration of metals, and increasing antioxidants on coloration was evaluated using the following protocols:

Medium at day 0=CDM1

Cysteine was added at a cumulative concentration of 5-6 mM

Antioxidants were added to CDM1 to reach the following cumulative concentrations (where the concentrations are prior to inoculum addition):

Taurine=10 mM of culture
Glycine=10 mM of culture
Thioctic Acid=0.0024 mM of culture
Vitamin C (ascorbic acid)=0.028 mM of culture
Metals in Starting Medium are listed below for the 1× level.
Fe=68-83 micromoles per liter of culture
Zn=6-7 micromoles per liter of culture
Cu=0.1-0.2 micromoles per liter of culture
Ni=0.5-1 micromoles per liter of culture.
The reduction of all the metals included using 0.25× the concentrations noted above for the medium.

Upon harvesting of the MT1 sample, the production procedure as shown in FIG. 59 was followed. The operating parameters for the chromatography are known to one of ordinary skill in the art. The operating parameters for the affinity capture, affinity flowthrough, and HIC are outlined in Table 9-1. The proteolytic cleavage of aflibercept following affinity capture and filtration step was carried out using the procedure as outlined in Example 1.2.

Table 9-3 shows the color quantification of the pools obtained on performing the various chromatographic steps. The color quantification was carried using samples from the pool having a protein concentration of 5 g/L. The steps as seen in Table 9-3 afforded a similar production as seen for steps in Table 9-2.

TABLE 9-3

Color Quantification of Samples at Various Production Steps of MiniTrap

| Sample | Conc. (g/L) | L* | a* | b* |
|---|---|---|---|---|
| Affinity Capture Pool | 5.0 ± 0.1 | 99.18 | −0.09 | 1.77 |
| Enzymatic Cleavage Pool | 5.0 ± 0.1 | 99.44 | −0.06 | 1.17 |
| Affinity flowthrough Pool | 5.0 ± 0.1 | 99.32 | −0.10 | 1.58 |
| Affinity flowthrough Eluate | 5.0 ± 0.1 | 99.74 | −0.05 | 0.60 |
| AEX Pool | 5.0 ± 0.1 | 99.63 | −0.07 | 0.50 |
| AEX 2M NaCl Strip | 5.0 ± 0.1 | 97.63 | −0.49 | 6.10 |
| HIC Pool | 27.6 | 99.07 | −0.29 | 2.32 |

Comparing Table 9-2 and Table 9-3, it is evident that the "Low Cysteine, Low Metals, and Increased Antioxidants Bioreactor Condition" had lower color in affinity capture pool (b* value of 1.77) compared to the "Control Bioreactor Condition" (b* value 2.52).

An MT sample with a concentration of 160 g/L, where the MT is formed using the steps listed in Table 9-2 and Table 9-3, is predicted to have a b* value of 13.45 for the "Low Cysteine, Low Metals, and Increased Antioxidants Bioreactor Condition" and a b* value of 17.45 for the "Control Bioreactor Condition." A 23% reduction in color is achieved through optimization of the upstream media and feeds. Similarly, an MT sample with a concentration of 110 g/L, where the MT is formed using the steps listed in Table 9-2 and Table 9-3, is predicted to have a b* value of 9.25 for the "Low Cysteine, Low Metals, and Increased Antioxidants Bioreactor Condition" and a b* value of 12 for the "Control Bioreactor Condition."

To understand how each production unit operation contributes to color reduction, the b* value for each production process intermediate as a percentage of the color of affinity capture pool was calculated (Table 9-4).

TABLE 9-4

| Sample | | Conc. (g/L) | b* | Δb* | b* as % of Affinity Capture Pool |
|---|---|---|---|---|---|
| Control Bioreactor | Affinity Capture Pool | 5.0 ± 0.1 | 2.52 | N/A | 100.0 |
| | Enzymatic Cleavage Pool | 5.0 ± 0.1 | 1.61 | −0.91 | 63.8 |
| | Affinity flowthrough Pool | 5.0 ± 0.1 | 2.16 | 0.55 | 85.7 |
| | AEX Pool | 5.0 ± 0.1 | 0.74 | −1.42 | 29.4 |
| | HIC Pool | 5.0 ± 0.1 | 0.55 | −0.19 | 21.8 |
| Low Cysteine, Low Metals, and Increased Antioxidants Bioreactor | Affinity Capture Pool | 5.0 ± 0.1 | 1.77 | N/A | 100.0 |
| | Enzymatic Cleavage Pool | 5.0 ± 0.1 | 1.17 | −0.60 | 66.1 |
| | Affinity flowthrough Pool | 5.0 ± 0.1 | 1.58 | 0.41 | 89.2 |
| | AEX Pool | 5.0 ± 0.1 | 0.50 | −1.08 | 28.2 |
| | HIC Pool | 5.0 ± 0.1 | 0.42 | −0.08 | 23.7 |

The AEX unit operation provides the most color reduction (1.08 to 1.42 change in b*) while the HIC unit operation provides some additional color reduction (0.08 to 0.19 change in b*). The unit operations evaluated overall remove 76.3%-78.2% of the color present in affinity capture pool.

The color of various production process intermediates for "Control Bioreactor Condition" and "Low Cysteine, Low Metals, and Increased Antioxidants Bioreactor Condition" were also studied for the percentage of 2-oxo-histidines and percentage of oxo-tryptophans in the oligopeptides that were generated by protease digestion, as measured by mass spectrometry as shown in Table 9-5 and Table 9-6, respectively. The peptide mapping was performed as discussed in Example 3.

Referring to Table 9-5, on comparing the histidine oxidation levels in the pools in different production steps, it is evident that relative abundance of the percentage of histidine oxidation levels for MT formed reduces in the pool as the production process progresses. For example, for H209 in the "Control Bioreactor Condition", the percent histidine oxidation level was 0.062 for the enzymatic cleavage pool and this was reduced to 0.029 for AEX flowthrough and further reduced to 0.020 for the HIC pool. Similarly, for H209 in the "Low Cysteine, Low Metals, and Increased Antioxidants Bioreactor Condition", the percent histidine oxidation level was 0.039 for the enzymatic cleavage pool and this was reduced to 0.023 for AEX flowthrough and further reduced to 0.016 for the HIC pool. Thus, the production strategy led to a reduction in percentage of histidine oxidation levels in MT. As the coloration reduced, presence of some of the oxidized residues in the sample also reduced. Similar to histidine oxidation, tryptophan oxidation levels were also tracked for the pools in different production steps for both the "Control Bioreactor Condition" and "Low Cysteine, Low Metals, and Increased Antioxidants Bioreactor Condition" (Table 9-6).

TABLE 9-5

| | | | Histidine Oxidation Levels (%) | | | | | |
|---|---|---|---|---|---|---|---|---|
| | Fraction | Color (b*) | H19 (+14) | H86 (+14) | H95 (+14) | H110 (+14) | H145 (+14) | H209 (+14) |
| Control Bioreactor Condition | Enzymatic Cleavage Pool | 1.61 | 0.023 | 0.018 | 0.011 | 0.014 | 0.007 | 0.062 |
| | Affinity flowthrough Pool (AEX Load) | 2.16 | 0.030 | 0.027 | 0.018 | 0.015 | 0.011 | 0.067 |
| | Affinity flowthrough Eluate | 0.83 | 0.030 | 0.022 | 0.000 | 0.018 | 0.004 | 0.046 |
| | AEX flowthrough | 0.74 | 0.026 | 0.025 | 0.013 | 0.016 | 0.010 | 0.029 |
| | AEX 2 M NaCl Strip | 8.10 | 0.024 | 0.063 | 0.033 | 0.019 | 0.012 | 0.063 |
| | HIC Pool | 0.55 | 0.018 | 0.009 | 0.002 | 0.021 | 0.005 | 0.020 |
| Low Cysteine, Low Metals, and Increased Antioxidants Bioreactor Condition | Enzymatic Cleavage Pool | 1.17 | 0.019 | 0.017 | 0.009 | 0.014 | 0.008 | 0.039 |
| | Affinity flowthrough Pool (AEX Load) | 1.58 | 0.026 | 0.025 | 0.013 | 0.014 | 0.010 | 0.043 |
| | Affinity flowthrough Eluate | 0.60 | 0.031 | 0.017 | 0.007 | 0.020 | 0.003 | 0.016 |
| | AEX flowthrough | 0.50 | 0.020 | 0.022 | 0.009 | 0.014 | 0.010 | 0.023 |
| | AEX 2 M NaCl Strip | 6.10 | 0.020 | 0.055 | 0.025 | 0.016 | 0.011 | 0.042 |
| | HIC Pool | 0.42 | 0.013 | 0.009 | 0.002 | 0.017 | 0.003 | 0.016 |

TABLE 9-6

| | | | Tryptophan Oxidation Levels (%) | | | | | | |
|---|---|---|---|---|---|---|---|---|---|
| | Fraction | Color (b*) | W58 (+4) | W58 (+16) | W58 (+32) | W58 (+48) | W138 (+4) | W138 (+16) | W138 (+32) |
| Control Bioreactor Condition | Enzymatic Cleavage Pool | 1.61 | 0.006 | 0.032 | 0.289 | 0.000 | 0.020 | 1.093 | 0.106 |
| | Affinity flowthrough Pool (AEX Load) | 2.16 | 0.016 | 0.055 | 0.327 | 0.000 | 0.017 | 0.771 | 0.111 |
| | Affinity flowthrough Eluate | 0.83 | 0.009 | 0.031 | 0.453 | 0.000 | 0.025 | 1.039 | 0.132 |
| | AEX flowthrough | 0.74 | 0.014 | 0.038 | 0.283 | 0.000 | 0.023 | 0.720 | 0.120 |
| | AEX 2 M NaCl Strip | 8.10 | 0.043 | 0.089 | 0.462 | 0.000 | 0.031 | 0.620 | 0.175 |
| | HIC Pool | 0.55 | 0.037 | 0.126 | 0.413 | 0.000 | 0.020 | 0.656 | 0.274 |
| Low Cysteine, Low Metals, and Increased Antioxidants Bioreactor Condition | Enzymatic Cleavage Pool | 1.17 | 0.009 | 0.027 | 0.239 | 0.001 | 0.027 | 1.026 | 0.136 |
| | Affinity flowthrough Pool (AEX Load) | 1.58 | 0.013 | 0.045 | 0.284 | 0.000 | 0.021 | 0.628 | 0.107 |
| | Affinity flowthrough Eluate | 0.60 | 0.003 | 0.026 | 0.421 | 0.021 | 0.025 | 1.032 | 0.132 |
| | AEX flowthrough | 0.50 | 0.011 | 0.031 | 0.235 | 0.000 | 0.022 | 0.676 | 0.102 |
| | AEX 2 M NaCl Strip | 6.10 | 0.034 | 0.073 | 0.478 | 0.000 | 0.032 | 0.635 | 0.169 |
| | HIC Pool | 0.42 | 0.029 | 0.122 | 0.355 | 0.000 | 0.022 | 0.800 | 0.236 |

SEQUENCE LISTING

```
Sequence total quantity: 124
SEQ ID NO: 1            moltype = AA  length = 339
FEATURE                 Location/Qualifiers
source                  1..339
                        mol_type = protein
                        organism = synthetic construct
                        note = Description of Artificial Sequence: Synthetic
                         polypeptide
SEQUENCE: 1
MRKRCYSTSA AVLAAVTLFV LSVDRGVIAD SFSANQEIRY SEVTPYHVTS VWTKGVTPPA  60
NFTQGEDVFH APYVANQGWY DITKTFNGKD DLLCGAATAG NMLHWWFDQN KDQIKRYLEE 120
HPEKQKINFN GEQMFDVKEA IDTKNHQLDS KLFEYFKEKA FPYLSTKHLG VFPPDHVIDMF 180
INGYRLSLTN HGPTPVKEGS KDPRGGIFDA VFTRGDQSKL LTSRHDFKEK NLKEISDLIK 240
KELTEGKALG LSHTYANVRI NHVINLWGAD FDSNGNLKAI YVTDSDSNAS IGMKKYFVGV 300
NSAGKVAISA KEIKEDNIGA QVLGLFTLST GQDSWNQTN                       339

SEQ ID NO: 2            moltype = AA  length = 339
FEATURE                 Location/Qualifiers
source                  1..339
                        mol_type = protein
                        organism = synthetic construct
                        note = Description of Artificial Sequence: Synthetic
                         polypeptide
SEQUENCE: 2
MRKRCYSTSA AVLAAVTLFV LSVDRGVIAD SFSANQEIRY SEVTPYHVTS VWTKGVTPPA  60
NFTQGEDVFH APYVANQGWY DITKTFDGKD DLLCGAATAG NMLHWWFDQN KDQIKRYLEE 120
HPEKQKINFN GEQMFDVKEA IDTKNHQLDS KLFEYFKEKA FPYLSTKHLG VFPPDHVIDMF 180
INGYRLSLTN HGPTPVKEGS KDPRGGIFDA VFTRGDQSKL LTSRHDFKEK NLKEISDLIK 240
KELTEGKALG LSHTYANVRI NHVINLWGAD FDSNGNLKAI YVTDSDSNAS IGMKKYFVGV 300
NSAGKVAISA KEIKEDNIGA QVLGLFTLST GQDSWNQTN                       339

SEQ ID NO: 3            moltype = AA  length = 339
FEATURE                 Location/Qualifiers
source                  1..339
                        mol_type = protein
                        organism = synthetic construct
                        note = Description of Artificial Sequence: Synthetic
```

```
                                    polypeptide
SEQUENCE: 3
MRKRCYSTSA AVLAAVTLFV LSVDRGVIAD SFSANQEIRY SEVTPYHVTS VWTKGVTPPA    60
NFTQGEDVFH APYVANQGWY DITKTFNGKD DLLCGAATAG NMLHWWFDQN KDQIKRYLEE   120
HPEKQKINFR GEQMFDVKEA IDTKNHQLDS KLFEYFKEKA FPYLSTKHLG VFPDHVIDMF   180
INGYRLSLTN HGPTPVKEGS KDPRGGIFDA VFTRGDQSKL LTSRHDFKEK NLKEISDLIK   240
KELTEGKALG LSHTYANVRI NHVINLWGAD FDSNGNLKAI YVTDSDSNAS IGMKKYFVGV   300
NSAGKVAISA KEIKEDNIGA QVLGLFTLST GQDSWNQTN                          339

SEQ ID NO: 4           moltype = AA    length = 339
FEATURE                Location/Qualifiers
source                 1..339
                       mol_type = protein
                       organism = synthetic construct
                       note = Description of Artificial Sequence: Synthetic
                                    polypeptide
SEQUENCE: 4
MRKRCYSTSA AVLAAVTLFV LSVDRGVIAD SFSANQEIRY SEVTPYHVTS VWTKGVTPPA    60
NFTQGEDVFH APYVANQGWY DITKTFNGKD DLLCGAATAG NMLHWWFDQN KDQIKRYLEE   120
HPEKQKINFN GEQMFDVKEA IDTKNHQLDS KLFEYFKEKA FPYLSTKHLG VFPDHVIDMF   180
ILGYRLSLTN HGPTPVKEGS KDPRGGIFDA VFTRGDQSKL LTSRHDFKEK NLKEISDLIK   240
KELTEGKALG LSHTYANVRI NHVINLWGAD FDSNGNLKAI YVTDSDSNAS IGMKKYFVGV   300
NSAGKVAISA KEIKEDNIGA QVLGLFTLST GQDSWNQTN                          339

SEQ ID NO: 5           moltype = AA    length = 339
FEATURE                Location/Qualifiers
source                 1..339
                       mol_type = protein
                       organism = synthetic construct
                       note = Description of Artificial Sequence: Synthetic
                                    polypeptide
SEQUENCE: 5
MRKRCYSTSA AVLAAVTLFV LSVDRGVIAD SFSANQEIRY SEVTPYHVTS VWTKGVTPPA    60
NFTQGEDVFH APYVANQGWY DITKTFNGKD DLLCGAATAG NMLHWWFDQN KDQIKRYLEE   120
HPEKQKINFN GEQMFDVKEA IDTKNHQLDS KLFEYFKEKA FPYLSTKHLG VFPDHVIDMF   180
INGYRLSLTN HGPTPVKEGS KDPRGGIFDA VFTRGDQSKL LTSRHDFKEK NLKEISDLIK   240
KELTEGKALG LSHTYANVRI NHVINLWGAD FDSDGNLKAI YVTDSDSNAS IGMKKYFVGV   300
NSAGKVAISA KEIKEDNIGA QVLGLFTLST GQDSWNQTN                          339

SEQ ID NO: 6           moltype = AA    length = 339
FEATURE                Location/Qualifiers
source                 1..339
                       mol_type = protein
                       organism = synthetic construct
                       note = Description of Artificial Sequence: Synthetic
                                    polypeptide
SEQUENCE: 6
MRKRCYSTSA AVLAAVTLFV LSVDRGVIAD SFSANQEIRY SEVTPYHVTS VWTKGVTPPA    60
NFTQGEDVFH APYVANQGWY DITKTFDGKD DLLCGAATAG NMLHWWFDQN KDQIKRYLEE   120
HPEKQKINFR GEQMFDVKEA IDTKNHQLDS KLFEYFKEKA FPYLSTKHLG VFPDHVIDMF   180
INGYRLSLTN HGPTPVKEGS KDPRGGIFDA VFTRGDQSKL LTSRHDFKEK NLKEISDLIK   240
KELTEGKALG LSHTYANVRI NHVINLWGAD FDSNGNLKAI YVTDSDSNAS IGMKKYFVGV   300
NSAGKVAISA KEIKEDNIGA QVLGLFTLST GQDSWNQTN                          339

SEQ ID NO: 7           moltype = AA    length = 339
FEATURE                Location/Qualifiers
source                 1..339
                       mol_type = protein
                       organism = synthetic construct
                       note = Description of Artificial Sequence: Synthetic
                                    polypeptide
SEQUENCE: 7
MRKRCYSTSA AVLAAVTLFV LSVDRGVIAD SFSANQEIRY SEVTPYHVTS VWTKGVTPPA    60
NFTQGEDVFH APYVANQGWY DITKTFDGKD DLLCGAATAG NMLHWWFDQN KDQIKRYLEE   120
HPEKQKINFN GEQMFDVKEA IDTKNHQLDS KLFEYFKEKA FPYLSTKHLG VFPDHVIDMF   180
ILGYRLSLTN HGPTPVKEGS KDPRGGIFDA VFTRGDQSKL LTSRHDFKEK NLKEISDLIK   240
KELTEGKALG LSHTYANVRI NHVINLWGAD FDSNGNLKAI YVTDSDSNAS IGMKKYFVGV   300
NSAGKVAISA KEIKEDNIGA QVLGLFTLST GQDSWNQTN                          339

SEQ ID NO: 8           moltype = AA    length = 339
FEATURE                Location/Qualifiers
source                 1..339
                       mol_type = protein
                       organism = synthetic construct
                       note = Description of Artificial Sequence: Synthetic
                                    polypeptide
SEQUENCE: 8
MRKRCYSTSA AVLAAVTLFV LSVDRGVIAD SFSANQEIRY SEVTPYHVTS VWTKGVTPPA    60
NFTQGEDVFH APYVANQGWY DITKTFDGKD DLLCGAATAG NMLHWWFDQN KDQIKRYLEE   120
```

```
HPEKQKINFN GEQMFDVKEA IDTKNHQLDS KLFEYFKEKA FPYLSTKHLG VFPDHVIDMF    180
INGYRLSLTN HGPTPVKEGS KDPRGGIFDA VFTRGDQSKL LTSRHDFKEK NLKEISDLIK    240
KELTEGKALG LSHTYANVRI NHVINLWGAD FDSDGNLKAI YVTDSDSNAS IGMKKYFVGV    300
NSAGKVAISA KEIKEDNIGA QVLGLFTLST GQDSWNQTN                          339

SEQ ID NO: 9             moltype = AA   length = 339
FEATURE                  Location/Qualifiers
source                   1..339
                         mol_type = protein
                         organism = synthetic construct
                         note = Description of Artificial Sequence: Synthetic
                         polypeptide
SEQUENCE: 9
MRKRCYSTSA AVLAAVTLFV LSVDRGVIAD SFSANQEIRY SEVTPYHVTS VWTKGVTPPA    60
NFTQGEDVFH APYVANQGWY DITKTFNGKD DLLCGAATAG NMLHWWFDQN KDQIKRYLEE    120
HPEKQKINFR GEQMFDVKEA IDTKNHQLDS KLFEYFKEKA FPYLSTKHLG VFPDHVIDMF    180
ILGYRLSLTN HGPTPVKEGS KDPRGGIFDA VFTRGDQSKL LTSRHDFKEK NLKEISDLIK    240
KELTEGKALG LSHTYANVRI NHVINLWGAD FDSNGNLKAI YVTDSDSNAS IGMKKYFVGV    300
NSAGKVAISA KEIKEDNIGA QVLGLFTLST GQDSWNQTN                          339

SEQ ID NO: 10            moltype = AA   length = 339
FEATURE                  Location/Qualifiers
source                   1..339
                         mol_type = protein
                         organism = synthetic construct
                         note = Description of Artificial Sequence: Synthetic
                         polypeptide
SEQUENCE: 10
MRKRCYSTSA AVLAAVTLFV LSVDRGVIAD SFSANQEIRY SEVTPYHVTS VWTKGVTPPA    60
NFTQGEDVFH APYVANQGWY DITKTFNGKD DLLCGAATAG NMLHWWFDQN KDQIKRYLEE    120
HPEKQKINFR GEQMFDVKEA IDTKNHQLDS KLFEYFKEKA FPYLSTKHLG VFPDHVIDMF    180
INGYRLSLTN HGPTPVKEGS KDPRGGIFDA VFTRGDQSKL LTSRHDFKEK NLKEISDLIK    240
KELTEGKALG LSHTYANVRI NHVINLWGAD FDSDGNLKAI YVTDSDSNAS IGMKKYFVGV    300
NSAGKVAISA KEIKEDNIGA QVLGLFTLST GQDSWNQTN                          339

SEQ ID NO: 11            moltype = AA   length = 339
FEATURE                  Location/Qualifiers
source                   1..339
                         mol_type = protein
                         organism = synthetic construct
                         note = Description of Artificial Sequence: Synthetic
                         polypeptide
SEQUENCE: 11
MRKRCYSTSA AVLAAVTLFV LSVDRGVIAD SFSANQEIRY SEVTPYHVTS VWTKGVTPPA    60
NFTQGEDVFH APYVANQGWY DITKTFNGKD DLLCGAATAG NMLHWWFDQN KDQIKRYLEE    120
HPEKQKINFN GEQMFDVKEA IDTKNHQLDS KLFEYFKEKA FPYLSTKHLG VFPDHVIDMF    180
ILGYRLSLTN HGPTPVKEGS KDPRGGIFDA VFTRGDQSKL LTSRHDFKEK NLKEISDLIK    240
KELTEGKALG LSHTYANVRI NHVINLWGAD FDSDGNLKAI YVTDSDSNAS IGMKKYFVGV    300
NSAGKVAISA KEIKEDNIGA QVLGLFTLST GQDSWNQTN                          339

SEQ ID NO: 12            moltype = AA   length = 339
FEATURE                  Location/Qualifiers
source                   1..339
                         mol_type = protein
                         organism = synthetic construct
                         note = Description of Artificial Sequence: Synthetic
                         polypeptide
SEQUENCE: 12
MRKRCYSTSA AVLAAVTLFV LSVDRGVIAD SFSANQEIRY SEVTPYHVTS VWTKGVTPPA    60
NFTQGEDVFH APYVANQGWY DITKTFDGKD DLLCGAATAG NMLHWWFDQN KDQIKRYLEE    120
HPEKQKINFR GEQMFDVKEA IDTKNHQLDS KLFEYFKEKA FPYLSTKHLG VFPDHVIDMF    180
ILGYRLSLTN HGPTPVKEGS KDPRGGIFDA VFTRGDQSKL LTSRHDFKEK NLKEISDLIK    240
KELTEGKALG LSHTYANVRI NHVINLWGAD FDSNGNLKAI YVTDSDSNAS IGMKKYFVGV    300
NSAGKVAISA KEIKEDNIGA QVLGLFTLST GQDSWNQTN                          339

SEQ ID NO: 13            moltype = AA   length = 339
FEATURE                  Location/Qualifiers
source                   1..339
                         mol_type = protein
                         organism = synthetic construct
                         note = Description of Artificial Sequence: Synthetic
                         polypeptide
SEQUENCE: 13
MRKRCYSTSA AVLAAVTLFV LSVDRGVIAD SFSANQEIRY SEVTPYHVTS VWTKGVTPPA    60
NFTQGEDVFH APYVANQGWY DITKTFDGKD DLLCGAATAG NMLHWWFDQN KDQIKRYLEE    120
HPEKQKINFR GEQMFDVKEA IDTKNHQLDS KLFEYFKEKA FPYLSTKHLG VFPDHVIDMF    180
INGYRLSLTN HGPTPVKEGS KDPRGGIFDA VFTRGDQSKL LTSRHDFKEK NLKEISDLIK    240
KELTEGKALG LSHTYANVRI NHVINLWGAD FDSDGNLKAI YVTDSDSNAS IGMKKYFVGV    300
NSAGKVAISA KEIKEDNIGA QVLGLFTLST GQDSWNQTN                          339
```

```
SEQ ID NO: 14            moltype = AA  length = 339
FEATURE                  Location/Qualifiers
source                   1..339
                         mol_type = protein
                         organism = synthetic construct
                         note = Description of Artificial Sequence: Synthetic
                         polypeptide
SEQUENCE: 14
MRKRCYSTSA AVLAAVTLFV LSVDRGVIAD SFSANQEIRY SEVTPYHVTS VWTKGVTPPA   60
NFTQGEDVFH APYVANQGWY DITKTFDGKD DLLCGAATAG NMLHWWFDQN KDQIKRYLEE  120
HPEKQKINFN GEQMFDVKEA IDTKNHQLDS KLFEYFKEKA FPYLSTKHLG VFPDHVIDMF  180
ILGYRLSLTN HGPTPVKEGS KDPRGGIFDA VFTRGDQSKL LTSRHDFKEK NLKEISDLIK  240
KELTEGKALG LSHTYANVRI NHVINLWGAD FDSDGNLKAI YVTDSDSNAS IGMKKYFVGV  300
NSAGKVAISA KEIKEDNIGA QVLGLFTLST GQDSWNQTN                         339

SEQ ID NO: 15            moltype = AA  length = 339
FEATURE                  Location/Qualifiers
source                   1..339
                         mol_type = protein
                         organism = synthetic construct
                         note = Description of Artificial Sequence: Synthetic
                         polypeptide
SEQUENCE: 15
MRKRCYSTSA AVLAAVTLFV LSVDRGVIAD SFSANQEIRY SEVTPYHVTS VWTKGVTPPA   60
NFTQGEDVFH APYVANQGWY DITKTFNGKD DLLCGAATAG NMLHWWFDQN KDQIKRYLEE  120
HPEKQKINFR GEQMFDVKEA IDTKNHQLDS KLFEYFKEKA FPYLSTKHLG VFPDHVIDMF  180
ILGYRLSLTN HGPTPVKEGS KDPRGGIFDA VFTRGDQSKL LTSRHDFKEK NLKEISDLIK  240
KELTEGKALG LSHTYANVRI NHVINLWGAD FDSDGNLKAI YVTDSDSNAS IGMKKYFVGV  300
NSAGKVAISA KEIKEDNIGA QVLGLFTLST GQDSWNQTN                         339

SEQ ID NO: 16            moltype = AA  length = 339
FEATURE                  Location/Qualifiers
source                   1..339
                         mol_type = protein
                         organism = synthetic construct
                         note = Description of Artificial Sequence: Synthetic
                         polypeptide
SEQUENCE: 16
MRKRCYSTSA AVLAAVTLFV LSVDRGVIAD SFSANQEIRY SEVTPYHVTS VWTKGVTPPA   60
NFTQGEDVFH APYVANQGWY DITKTFDGKD DLLCGAATAG NMLHWWFDQN KDQIKRYLEE  120
HPEKQKINFR GEQMFDVKEA IDTKNHQLDS KLFEYFKEKA FPYLSTKHLG VFPDHVIDMF  180
ILGYRLSLTN HGPTPVKEGS KDPRGGIFDA VFTRGDQSKL LTSRHDFKEK NLKEISDLIK  240
KELTEGKALG LSHTYANVRI NHVINLWGAD FDSDGNLKAI YVTDSDSNAS IGMKKYFVGV  300
NSAGKVAISA KEIKEDNIGA QVLGLFTLST GQDSWNQTN                         339

SEQ ID NO: 17            moltype = AA  length = 16
FEATURE                  Location/Qualifiers
source                   1..16
                         mol_type = protein
                         organism = synthetic construct
                         note = Description of Artificial Sequence: Synthetic peptide
VARIANT                  4
                         note = MISC_FEATURE - May be oxidized
VARIANT                  6
                         note = MISC_FEATURE - May be carboxymethylated
VARIANT                  9
                         note = MISC_FEATURE - May be carboxymethylated
SEQUENCE: 17
DKTHTCPPCP APELLG                                                   16

SEQ ID NO: 18            moltype = AA  length = 17
FEATURE                  Location/Qualifiers
source                   1..17
                         mol_type = protein
                         organism = synthetic construct
                         note = Description of Artificial Sequence: Synthetic peptide
VARIANT                  7
                         note = MISC_FEATURE - May be carboxymethylated
VARIANT                  14
                         note = MISC_FEATURE - May be oxidized
SEQUENCE: 18
EIGLLTCEAT VNGHLYK                                                  17

SEQ ID NO: 19            moltype = AA  length = 23
FEATURE                  Location/Qualifiers
source                   1..23
                         mol_type = protein
                         organism = synthetic construct
```

-continued

```
                              note = Description of Artificial Sequence: Synthetic peptide
VARIANT                       14
                              note = MISC_FEATURE - May be oxidized
SEQUENCE: 19
QTNTIIDVVL SPSHGIELSV GEK                                                     23

SEQ ID NO: 20                 moltype = AA  length = 21
FEATURE                       Location/Qualifiers
source                        1..21
                              mol_type = protein
                              organism = synthetic construct
                              note = Description of Artificial Sequence: Synthetic peptide
VARIANT                       18
                              note = MISC_FEATURE - May be oxidized
SEQUENCE: 20
TELNVGIDFN WEYPSSKHQH K                                                       21

SEQ ID NO: 21                 moltype = AA  length = 7
FEATURE                       Location/Qualifiers
source                        1..7
                              mol_type = protein
                              organism = synthetic construct
                              note = Description of Artificial Sequence: Synthetic peptide
VARIANT                       6
                              note = MISC_FEATURE - May be oxidized
SEQUENCE: 21
TNYLTHR                                                                        7

SEQ ID NO: 22                 moltype = AA  length = 24
FEATURE                       Location/Qualifiers
source                        1..24
                              mol_type = protein
                              organism = synthetic construct
                              note = Description of Artificial Sequence: Synthetic peptide
VARIANT                       19
                              note = MISC_FEATURE - May be oxidized
SEQUENCE: 22
SDTGRPFVEM YSEIPEIIHM TEGR                                                    24

SEQ ID NO: 23                 moltype = AA  length = 6
FEATURE                       Location/Qualifiers
source                        1..6
                              mol_type = protein
                              organism = synthetic construct
                              note = Description of Artificial Sequence: Synthetic peptide
VARIANT                       2
                              note = MISC_FEATURE - May be oxidized
SEQUENCE: 23
VHEKDK                                                                         6

SEQ ID NO: 24                 moltype = AA  length = 24
FEATURE                       Location/Qualifiers
source                        1..24
                              mol_type = protein
                              organism = synthetic construct
                              note = Description of Artificial Sequence: Synthetic peptide
VARIANT                       10
                              note = MISC_FEATURE - May be oxidized
SEQUENCE: 24
SDTGRPFVEM YSEIPEIIHM TEGR                                                    24

SEQ ID NO: 25                 moltype = AA  length = 24
FEATURE                       Location/Qualifiers
source                        1..24
                              mol_type = protein
                              organism = synthetic construct
                              note = Description of Artificial Sequence: Synthetic peptide
VARIANT                       20
                              note = MISC_FEATURE - May be oxidized
SEQUENCE: 25
SDTGRPFVEM YSEIPEIIHM TEGR                                                    24

SEQ ID NO: 26                 moltype = AA  length = 8
FEATURE                       Location/Qualifiers
source                        1..8
                              mol_type = protein
                              organism = synthetic construct
                              note = Description of Artificial Sequence: Synthetic peptide
VARIANT                       7
```

```
                        note = MISC_FEATURE - May be oxidized
SEQUENCE: 26
TQSGSEMK                                                                    8

SEQ ID NO: 27           moltype = AA   length = 17
FEATURE                 Location/Qualifiers
source                  1..17
                        mol_type = protein
                        organism = synthetic construct
                        note = Description of Artificial Sequence: Synthetic peptide
VARIANT                 8
                        note = MISC_FEATURE - May be carboxymethylated
SEQUENCE: 27
SDQGLYTCAA SSGLMTK                                                         17

SEQ ID NO: 28           moltype = AA   length = 6
FEATURE                 Location/Qualifiers
source                  1..6
                        mol_type = protein
                        organism = synthetic construct
                        note = Description of Artificial Sequence: Synthetic peptide
VARIANT                 3
                        note = MISC_FEATURE - May be oxidized
SEQUENCE: 28
IIWDSR                                                                      6

SEQ ID NO: 29           moltype = AA   length = 17
FEATURE                 Location/Qualifiers
source                  1..17
                        mol_type = protein
                        organism = synthetic construct
                        note = Description of Artificial Sequence: Synthetic peptide
VARIANT                 11
                        note = MISC_FEATURE - May be oxidized
SEQUENCE: 29
TELNVGIDFN WEYPSSK                                                         17

SEQ ID NO: 30           moltype = AA   length = 10
FEATURE                 Location/Qualifiers
source                  1..10
                        mol_type = protein
                        organism = synthetic construct
                        note = Description of Artificial Sequence: Synthetic peptide
VARIANT                 9
                        note = MISC_FEATURE - May be oxidized
SEQUENCE: 30
GFIISNATYK                                                                 10

SEQ ID NO: 31           moltype = AA   length = 12
FEATURE                 Location/Qualifiers
source                  1..12
                        mol_type = protein
                        organism = synthetic construct
                        note = Description of Artificial Sequence: Synthetic peptide
VARIANT                 2
                        note = MISC_FEATURE - May be oxidized
SEQUENCE: 31
KFPLDTLIPD GK                                                              12

SEQ ID NO: 32           moltype = AA   length = 12
FEATURE                 Location/Qualifiers
source                  1..12
                        mol_type = protein
                        organism = synthetic construct
                        note = Description of Artificial Sequence: Synthetic peptide
VARIANT                 1
                        note = MISC_FEATURE - May be oxidized
SEQUENCE: 32
FLSTLTIDGV TR                                                              12

SEQ ID NO: 33           moltype = AA   length = 227
FEATURE                 Location/Qualifiers
source                  1..227
                        mol_type = protein
                        organism = synthetic construct
                        note = Description of Artificial Sequence: Synthetic
                         polypeptide
VARIANT                 8
                        note = MOD_RES - Leu or Pro
```

```
VARIANT                  173
                         note = MOD_RES - Ala or Thr
SEQUENCE: 33
DKTHTCPXCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKXTPPVLDS   180
DGSFFLYSKL TVDKSRWQQG NVFSCSVMHE ALHNHYTQKS LSLSPGK                 227

SEQ ID NO: 34            moltype = AA  length = 103
FEATURE                  Location/Qualifiers
source                   1..103
                         mol_type = protein
                         organism = synthetic construct
                         note = Description of Artificial Sequence: Synthetic
                          polypeptide
SEQUENCE: 34
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IID                     103

SEQ ID NO: 35            moltype = AA  length = 93
FEATURE                  Location/Qualifiers
source                   1..93
                         mol_type = protein
                         organism = synthetic construct
                         note = Description of Artificial Sequence: Synthetic
                          polypeptide
SEQUENCE: 35
PFVEMYSEIP EIIHMTEGRE LVIPCRVTSP NITVTLKKFP LDTLIPDGKR IIWDSRKGFI    60
ISNATYKEIG LLTCEATVNG HLYKTNYLTH RQT                                93

SEQ ID NO: 36            moltype = AA  length = 102
FEATURE                  Location/Qualifiers
source                   1..102
                         mol_type = protein
                         organism = synthetic construct
                         note = Description of Artificial Sequence: Synthetic
                          polypeptide
SEQUENCE: 36
VVLSPSHGIE LSVGEKLVLN CTARTELNVG IDFNWEYPSS KHQHKKLVNR DLKTQSGSEM    60
KKFLSTLTID GVTRSDQGLY TCAASSGLMT KKNSTFVRVH EK                      102

SEQ ID NO: 37            moltype = AA  length = 97
FEATURE                  Location/Qualifiers
source                   1..97
                         mol_type = protein
                         organism = synthetic construct
                         note = Description of Artificial Sequence: Synthetic
                          polypeptide
SEQUENCE: 37
PFVAFGSGME SLVEATVGER VRIPAKYLGY PPPEIKWYKN GIPLESNHTI KAGHVLTIME    60
VSERDTGNYT VILTNPISKE KQSHVVSLVV YVPPGPG                            97

SEQ ID NO: 38            moltype = AA  length = 92
FEATURE                  Location/Qualifiers
source                   1..92
                         mol_type = protein
                         organism = synthetic construct
                         note = Description of Artificial Sequence: Synthetic
                          polypeptide
SEQUENCE: 38
FVAFGSGMES LVEATVGERV RIPAKYLGYP PPEIKWYKNG IPLESNHTIK AGHVLTIMEV    60
SERDTGNYTV ILTNPIKSEK QSHVVSLVVY VP                                 92

SEQ ID NO: 39            moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 39
DKTHTCPPC                                                           9

SEQ ID NO: 40            moltype = AA  length = 12
FEATURE                  Location/Qualifiers
source                   1..12
                         mol_type = protein
                         organism = synthetic construct
                         note = Description of Artificial Sequence: Synthetic peptide
SEQUENCE: 40
```

```
DKTHTCPPCP PC                                                        12

SEQ ID NO: 41         moltype = AA  length = 15
FEATURE               Location/Qualifiers
source                1..15
                      mol_type = protein
                      organism = synthetic construct
                      note = Description of Artificial Sequence: Synthetic peptide
SEQUENCE: 41
DKTHTCPPCP PCPPC                                                     15

SEQ ID NO: 42         moltype = AA  length = 16
FEATURE               Location/Qualifiers
source                1..16
                      mol_type = protein
                      organism = synthetic construct
                      note = Description of Artificial Sequence: Synthetic peptide
SEQUENCE: 42
DKTHTCPPCP APELLG                                                    16

SEQ ID NO: 43         moltype = AA  length = 16
FEATURE               Location/Qualifiers
source                1..16
                      mol_type = protein
                      organism = synthetic construct
                      note = Description of Artificial Sequence: Synthetic peptide
SEQUENCE: 43
DKTHTCPLCP APELLG                                                    16

SEQ ID NO: 44         moltype = AA  length = 6
FEATURE               Location/Qualifiers
source                1..6
                      mol_type = protein
                      organism = synthetic construct
                      note = Description of Artificial Sequence: Synthetic peptide
SEQUENCE: 44
DKTHTC                                                               6

SEQ ID NO: 45         moltype = AA  length = 12
FEATURE               Location/Qualifiers
source                1..12
                      mol_type = protein
                      organism = synthetic construct
                      note = Description of Artificial Sequence: Synthetic peptide
SEQUENCE: 45
DKTHTCPLCP AP                                                        12

SEQ ID NO: 46         moltype = AA  length = 221
FEATURE               Location/Qualifiers
source                1..221
                      mol_type = protein
                      organism = synthetic construct
                      note = Description of Artificial Sequence: Synthetic
                        polypeptide
SEQUENCE: 46
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKDKTHT CPPCPAPELL G                       221

SEQ ID NO: 47         moltype = AA  length = 315
FEATURE               Location/Qualifiers
source                1..315
                      mol_type = protein
                      organism = synthetic construct
                      note = Description of Artificial Sequence: Synthetic
                        polypeptide
SEQUENCE: 47
GRPFVEMYSE IPEIIHMTEG RELVIPCRVT SPNITVTLKK FPLDTLIPDG KRIIWDSRKG    60
FIISNATYKE IGLLTCEATV NGHLYKTNYL THRQTNTIID VVLSPSHGIE LSVGEKLVLN   120
CTARTELNVG IDFNWEYPSS KHQHKKLVNR DLKTQSGSEM KKFLSTLTID GVTRSDQGLY   180
TCAASSGLMT KKNSTFVRVH ENLSVAFGSG MESLVEATVG ERVRIPAKYL GYPPPEIKWY   240
KNGIPLESNH TIKAGHVLTI MEVSERDTGN YTVILTNPIS KEKQSHVVSL VVYVPPGPGD   300
KTHTCPLCPA PELLG                                                   315

SEQ ID NO: 48         moltype = AA  length = 214
FEATURE               Location/Qualifiers
source                1..214
                      mol_type = protein
```

```
                          organism = synthetic construct
                          note = Description of Artificial Sequence: Synthetic
                              polypeptide
SEQUENCE: 48
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKDKTHT CPPC                               214

SEQ ID NO: 49             moltype = AA   length = 217
FEATURE                   Location/Qualifiers
source                    1..217
                          mol_type = protein
                          organism = synthetic construct
                          note = Description of Artificial Sequence: Synthetic
                              polypeptide
SEQUENCE: 49
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKDKTHT CPPCPPC                            217

SEQ ID NO: 50             moltype = AA   length = 220
FEATURE                   Location/Qualifiers
source                    1..220
                          mol_type = protein
                          organism = synthetic construct
                          note = Description of Artificial Sequence: Synthetic
                              polypeptide
SEQUENCE: 50
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKDKTHT CPPCPPCPPC                         220

SEQ ID NO: 51             moltype = AA   length = 440
FEATURE                   Location/Qualifiers
source                    1..440
                          mol_type = protein
                          organism = synthetic construct
                          note = Description of Artificial Sequence: Synthetic
                              polypeptide
SEQUENCE: 51
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKGGGGS GGGGSGGGGS GGGGSGGGGS GGGGSSDTGR   240
PFVEMYSEIP EIIHMTEGRE LVIPCRVTSP NITVTLKKFP LDTLIPDGKR IIWDSRKGFI   300
ISNATYKEIG LLTCEATVNG HLYKTNYLTH RQTNTIIDVV LSPSHGIELS VGEKLVLNCT   360
ARTELNVGID FNWEYPSSKH QHKKLVNRDL KTQSGSEMKK FLSTLTIDGV TRSDQGLYTC   420
AASSGLMTKK NSTFVRVHEK                                               440

SEQ ID NO: 52             moltype = AA   length = 425
FEATURE                   Location/Qualifiers
source                    1..425
                          mol_type = protein
                          organism = synthetic construct
                          note = Description of Artificial Sequence: Synthetic
                              polypeptide
SEQUENCE: 52
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKGGGGS GGGGSGGGGS SDTGRPFVEM YSEIPEIIHM   240
TEGRELVIPC RVTSPNITVT LKKFPLDTLI PDGKRIIWDS RKGFIISNAT YKEIGLLTCE   300
ATVNGHLYKT NYLTHRQTNT IIDVVLSPSH GIELSVGEKL VLNCTARTEL NVGIDFNWEY   360
PSSKHQHKKL VNRDLKTQSG SEMKKFLSTL TIDGVTRSDQ GLYTCAASSG LMTKKNSTFV   420
RVHEK                                                               425

SEQ ID NO: 53             moltype = AA   length = 455
FEATURE                   Location/Qualifiers
source                    1..455
                          mol_type = protein
                          organism = synthetic construct
                          note = Description of Artificial Sequence: Synthetic
                              polypeptide
SEQUENCE: 53
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
```

```
VLNCTARTEL NVGIDFNWEY PSSKHQHKKL VNRDLKTQSG SEMKKFLSTL TIDGVTRSDQ   180
GLYTCAASSG LMTKKNSTFV RVHEKGGGGS GGGGSGGGGS GGGGSGGGGS GGGGSGGGGS   240
GGGGSGGGGS SDTGRPFVEM YSEIPEIIHM TEGRELVIPC RVTSPNITVT LKKFPLDTLI   300
PDGKRIIWDS RKGFIISNAT YKEIGLLTCE ATVNGHLYKT NYLTHRQTNT IIDVVLSPSH   360
GIELSVGEKL VLNCTARTEL NVGIDFNWEY PSSKHQHKKL VNRDLKTQSG SEMKKFLSTL   420
TIDGVTRSDQ GLYTCAASSG LMTKKNSTFV RVHEK                             455

SEQ ID NO: 54           moltype = AA  length = 470
FEATURE                 Location/Qualifiers
source                  1..470
                        mol_type = protein
                        organism = synthetic construct
                        note = Description of Artificial Sequence: Synthetic
                            polypeptide
SEQUENCE: 54
SDTGRPFVEM YSEIPEIIHM TEGRELVIPC RVTSPNITVT LKKFPLDTLI PDGKRIIWDS   60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKGGGGS GGGGSGGGGS GGGGSGGGGS GGGGSGGGGS   240
GGGGSGGGGS GGGGSGGGGS GGGGSSDTGR PFVEMYSEIP EIIHMTEGRE LVIPCRVTSP   300
NITVTLKKFP LDTLIPDGKR IIWDSRKGFI ISNATYKEIG LLTCEATVNG HLYKTNYLTH   360
RQTNTIIDVV LSPSHGIELS VGEKLVLNCT ARTELNVGID FNWEYPSSKH QHKKLVNRDL   420
KTQSGSEMKK FLSTLTIDGV TRSDQGLYTC AASSGLMTKK NSTFVRVHEK             470

SEQ ID NO: 55           moltype = AA  length = 432
FEATURE                 Location/Qualifiers
source                  1..432
                        mol_type = protein
                        organism = synthetic construct
                        note = Description of Artificial Sequence: Synthetic
                            polypeptide
SEQUENCE: 55
SDTGRPFVEM YSEIPEIIHM TEGRELVIPC RVTSPNITVT LKKFPLDTLI PDGKRIIWDS   60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKDKTHT CPPCPAPELL GGPSVFLFPP KPKDTLMISR   240
TPEVTCVVVD VSHEDPEVKF NWYVDGVEVH NAKTKPREEQ YNSTYRVVSV LTVLHQDWLN   300
GKEYKCKVSN KALPAPIEKT ISKAKGQPRE PQVYTLPPSR DELTKNQVSL TCLVKGFYPS   360
DIAVEWESNG QPENNYKTTP PVLDSDGSFF LYSKLTVDKS RWQQGNVFSC SVMHEALHNH   420
YTQKSLSLSP GK                                                      432

SEQ ID NO: 56           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 56
IIWDSR                                                             6

SEQ ID NO: 57           moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 57
EIGLLTCEAT VNGHLYK                                                 17

SEQ ID NO: 58           moltype = AA  length = 23
FEATURE                 Location/Qualifiers
source                  1..23
                        mol_type = protein
                        organism = synthetic construct
                        note = Description of Artificial Sequence: Synthetic peptide
SEQUENCE: 58
QTNTIIDVVL SPSHGIELSV GEK                                          23

SEQ ID NO: 59           moltype = AA  length = 21
FEATURE                 Location/Qualifiers
source                  1..21
                        mol_type = protein
                        organism = synthetic construct
                        note = Description of Artificial Sequence: Synthetic peptide
SEQUENCE: 59
TELNVGIDFN WEYPSSKHQH K                                            21

SEQ ID NO: 60           moltype = AA  length = 16
FEATURE                 Location/Qualifiers
```

| | | |
|---|---|---|
| source | 1..16<br>mol_type = protein<br>organism = synthetic construct<br>note = Description of Artificial Sequence: Synthetic peptide | |
| SEQUENCE: 60<br>DKTHTCPPCP APELLG | | 16 |
| SEQ ID NO: 61<br>FEATURE<br>source | moltype = AA  length = 7<br>Location/Qualifiers<br>1..7<br>mol_type = protein<br>organism = synthetic construct<br>note = Description of Artificial Sequence: Synthetic peptide | |
| SEQUENCE: 61<br>TNYLTHR | | 7 |
| SEQ ID NO: 62<br>FEATURE<br>source | moltype = AA  length = 17<br>Location/Qualifiers<br>1..17<br>mol_type = protein<br>organism = synthetic construct<br>note = Description of Artificial Sequence: Synthetic peptide | |
| VARIANT | 7<br>note = MISC_FEATURE - May be carboxymethylated | |
| SITE | 12<br>note = deamidation of asparagine | |
| SEQUENCE: 62<br>EIGLLTCEAT VNGHLYK | | 17 |
| SEQ ID NO: 63<br>FEATURE<br>source | moltype = AA  length = 23<br>Location/Qualifiers<br>1..23<br>mol_type = protein<br>organism = synthetic construct<br>note = Description of Artificial Sequence: Synthetic peptide | |
| SITE | 3<br>note = deamidation of asparagine | |
| SEQUENCE: 63<br>QTNTIIDVVL SPSHGIELSV GEK | | 23 |
| SEQ ID NO: 64<br>FEATURE<br>source | moltype = AA  length = 24<br>Location/Qualifiers<br>1..24<br>mol_type = protein<br>organism = synthetic construct<br>note = Description of Artificial Sequence: Synthetic peptide | |
| VARIANT | 10<br>note = MISC_FEATURE - May be oxidized | |
| SEQUENCE: 64<br>SDTGRPFVEM YSEIPEIIHM TEGR | | 24 |
| SEQ ID NO: 65<br>FEATURE<br>source | moltype = AA  length = 24<br>Location/Qualifiers<br>1..24<br>mol_type = protein<br>organism = synthetic construct<br>note = Description of Artificial Sequence: Synthetic peptide | |
| VARIANT | 20<br>note = MISC_FEATURE - May be oxidized | |
| SEQUENCE: 65<br>SDTGRPFVEM YSEIPEIIHM TEGR | | 24 |
| SEQ ID NO: 66<br>FEATURE<br>source | moltype = AA  length = 8<br>Location/Qualifiers<br>1..8<br>mol_type = protein<br>organism = synthetic construct<br>note = Description of Artificial Sequence: Synthetic peptide | |
| VARIANT | 7<br>note = MISC_FEATURE - May be oxidized | |
| SEQUENCE: 66<br>TQSGSEMK | | 8 |
| SEQ ID NO: 67<br>FEATURE<br>source | moltype = AA  length = 17<br>Location/Qualifiers<br>1..17<br>mol_type = protein<br>organism = synthetic construct<br>note = Description of Artificial Sequence: Synthetic peptide | |

```
VARIANT                      8
                             note = MISC_FEATURE - May be carboxymethylated
VARIANT                      15
                             note = MISC_FEATURE - May be oxidized
SEQUENCE: 67
SDQGLYTCAA SSGLMTK                                                              17

SEQ ID NO: 68                moltype = AA  length = 24
FEATURE                      Location/Qualifiers
source                       1..24
                             mol_type = protein
                             organism = synthetic construct
                             note = Description of Artificial Sequence: Synthetic peptide
SITE                         5
                             note = arginine 3-deoxygluconasone
SEQUENCE: 68
SDTGRPFVEM YSEIPEIIHM TEGR                                                      24

SEQ ID NO: 69                moltype = AA  length = 10
FEATURE                      Location/Qualifiers
source                       1..10
                             mol_type = protein
                             organism = synthetic construct
                             note = Description of Artificial Sequence: Synthetic peptide
VARIANT                      9
                             note = MISC_FEATURE - May be oxidized
SEQUENCE: 69
GFIISNATYK                                                                      10

SEQ ID NO: 70                moltype = AA  length = 12
FEATURE                      Location/Qualifiers
source                       1..12
                             mol_type = protein
                             organism = synthetic construct
                             note = Description of Artificial Sequence: Synthetic peptide
VARIANT                      2
                             note = MISC_FEATURE - May be oxidized
SEQUENCE: 70
KFPLDTLIPD GK                                                                   12

SEQ ID NO: 71                moltype = AA  length = 12
FEATURE                      Location/Qualifiers
source                       1..12
                             mol_type = protein
                             organism = synthetic construct
                             note = Description of Artificial Sequence: Synthetic peptide
VARIANT                      1
                             note = MISC_FEATURE - May be oxidized
SEQUENCE: 71
FLSTLTIDGV TR                                                                   12

SEQ ID NO: 72                moltype = AA  length = 165
FEATURE                      Location/Qualifiers
source                       1..165
                             mol_type = protein
                             organism = synthetic construct
                             note = Description of Artificial Sequence: Synthetic
                             polypeptide
SEQUENCE: 72
APMAEGGGQN HHEVVKFMDV YQRSYCHPIE TLVDIFQEYP DEIEYIFKPS CVPLMRCGGC   60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRC DKPRR                 165

SEQ ID NO: 73                moltype = AA  length = 451
FEATURE                      Location/Qualifiers
source                       1..451
                             mol_type = protein
                             organism = synthetic construct
                             note = Description of Artificial Sequence: Synthetic
                             polypeptide
SEQUENCE: 73
EVQLVESGGD LVKPGGSLKL SCAASGFTFS SSGMSWVRQT PDKRLEWVAT ITSGGSYTYY   60
PDSVKGRFTI SRDNAKNTLY LQMSSLKSED TAMFYCARLG NYGGYYAMDY WGQGTSVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451
```

```
SEQ ID NO: 74            moltype = AA   length = 213
FEATURE                  Location/Qualifiers
source                   1..213
                         mol_type = protein
                         organism = synthetic construct
                         note = Description of Artificial Sequence: Synthetic
                             polypeptide
SEQUENCE: 74
DIQMTQSPSS LSASLGGKVT ITCTTSQDSN NYIAWYQHKP GKGPRLLIHY ASTLQPGIPS    60
RFSGSGSGRD YSFSISNLEP EDIATYFCLQ YDYLWTFGGG TKLELKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 75            moltype = AA   length = 451
FEATURE                  Location/Qualifiers
source                   1..451
                         mol_type = protein
                         organism = synthetic construct
                         note = Description of Artificial Sequence: Synthetic
                             polypeptide
SEQUENCE: 75
EVQLVESGGD LVKPGGSLKL SCAASGFTFS DSGMSWVRQT PDKRLEWVAT ISSGGGYTYY    60
SDSVEGRFTI SRDNANNTLF LQMSSLKSED TAMFYCARLG NYGGYYGMDY WGQGTSVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 76            moltype = AA   length = 213
FEATURE                  Location/Qualifiers
source                   1..213
                         mol_type = protein
                         organism = synthetic construct
                         note = Description of Artificial Sequence: Synthetic
                             polypeptide
SEQUENCE: 76
DIQMTQSPSS LSASLGGKVT ITCKTSQDSN KYIAWYQHKP GKGPRLLIHY TSTLQPGIPS    60
RFSGSGSGRD YSFSISNLEP EDIATYYCLQ YDNLWTFGGG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 77            moltype = AA   length = 445
FEATURE                  Location/Qualifiers
source                   1..445
                         mol_type = protein
                         organism = synthetic construct
                         note = Description of Artificial Sequence: Synthetic
                             polypeptide
SEQUENCE: 77
EVQLVESGGD LVKPGGSLKL SCAASGFTFS SSGMSWVRQT PDKRLEWVAT ITSGGSYTYY    60
PDSVKGRFTI SRDNAKNTLY LQMSSLKSED TAMFYCARLG NYGGYYAMDY WGQGTSVTVS   120
SAKTTPPSVY PLAPGSAAQT NSMVTLGCLV KGYFPEPVTV TWNSGSLSSG VHTFPAVLQS   180
DLYTLSSSVT VPSSTWPSET VTCNVAHPAS STKVDKKIVP RDCGCKPCIC TVPEVSSVFI   240
FPPKPKDVLT ITLTPKVTCV VVDISKDDPE VQFSWFVDDV EVHTAQTQPR EEQFNSTFRS   300
VSELPIMHQD WLNGKEFKCR VNSAAFPAPI EKTISKTKGR PKAPQVYTIP PPKEQMAKDK   360
VSLTCMITDF FPEDITVEWQ WNGQPAENYK NTQPIMDTDG SYFVYSKLNV QKSNWEAGNT   420
FTCSVLHEGL HNHHTEKSLS HSPGK                                        445

SEQ ID NO: 78            moltype = AA   length = 213
FEATURE                  Location/Qualifiers
source                   1..213
                         mol_type = protein
                         organism = synthetic construct
                         note = Description of Artificial Sequence: Synthetic
                             polypeptide
SEQUENCE: 78
DIQMTQSPSS LSASLGGKVT ITCTTSQDSN NYIAWYQHKP GKGPRLLIHY ASTLQPGIPS    60
RFSGSGSGRD YSFSISNLEP EDIATYFCLQ YDYLWTFGGG TKLELKRADA APTVSIFPPS   120
SEQLTSGGAS VVCFLNNFYP KDINVKWKID GSERQNGVLN SWTDQDSKDS TYSMSSTLTL   180
TKDEYERHNS YTCEATHKTS TSPIVKSFNR GEC                                213

SEQ ID NO: 79            moltype = AA   length = 445
FEATURE                  Location/Qualifiers
source                   1..445
                         mol_type = protein
                         organism = synthetic construct
```

```
                           note = Description of Artificial Sequence: Synthetic
                             polypeptide
SEQUENCE: 79
EVQLVESGGD LVKPGGSLKL SCAASGFTFS DSGMSWVRQT PDKRLEWVAT ISSGGGYTYY    60
SDSVEGRFTI SRDNANNTLF LQMSSLKSED TAMFYCARLG NYGGYYGMDY WGQGTSVTVS   120
SAKTTPPSVY PLAPGSAAQT NSMVTLGCLV KGYFPEPVTV TWNSGSLSSG VHTFPAVLQS   180
DLYTLSSSVT VPSSTWPSET VTCNVAHPAS STKVDKKIVP RDCGCKPCIC TVPEVSSVFI   240
FPPKPKDVLT ITLTPKVTCV VVDISKDDPE VQFSWFVDDV EVHTAQTQPR EEQFNSTFRS   300
VSELPIMHQD WLNGKEFKCR VNSAAFPAPI EKTISKTKGR PKAPQVYTIP PPKEQMAKDK   360
VSLTCMITDF FPEDITVEWQ WNGQPAENYK NTQPIMDTDG SYFVYSKLNV QKSNWEAGNT   420
FTCSVLHEGL HNHHTEKSLS HSPGK                                        445

SEQ ID NO: 80          moltype = AA  length = 200
FEATURE                Location/Qualifiers
source                 1..200
                       mol_type = protein
                       organism = synthetic construct
                       note = Description of Artificial Sequence: Synthetic
                         polypeptide
SEQUENCE: 80
DIQMTQSPSS LSASLGGKVT ITCKTSQDSN KYIAWYQHKP GKGPRLLIHY TSTLQPGIPS    60
RFSGSGSGRD YSFSISNLEP EDIATYYCLQ YDNLWTFGGG TKLEIKRADA APTVSIFPPS   120
SEQLTSGGAS VVCFLNNFYP KDINVKWKID GSERQNGVLN SWTDQDSKDS TYSMSSTLTL   180
TKDEYERHNS YTCEATHKTS                                              200

SEQ ID NO: 81          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 81
ELVIPCR                                                              7

SEQ ID NO: 82          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 82
LVLNCTAR                                                             8

SEQ ID NO: 83          moltype = AA  length = 14
FEATURE                Location/Qualifiers
source                 1..14
                       mol_type = protein
                       organism = synthetic construct
                       note = Description of Artificial Sequence: Synthetic peptide
VARIANT                2
                       note = MISC_FEATURE - May be oxidized
DISULFID               4..7
                       note = intra-chain sulfide bond formed between cysteines
SEQUENCE: 83
THTCPPCPAP ELLG                                                     14

SEQ ID NO: 84          moltype = AA  length = 24
FEATURE                Location/Qualifiers
source                 1..24
                       mol_type = protein
                       organism = synthetic construct
                       note = Description of Artificial Sequence: Synthetic peptide
SEQUENCE: 84
ELVIPCREIG LLTCEATVNG HLYK                                          24

SEQ ID NO: 85          moltype = AA  length = 26
FEATURE                Location/Qualifiers
source                 1..26
                       mol_type = protein
                       organism = synthetic construct
                       note = Description of Artificial Sequence: Synthetic peptide
VARIANT                26
                       note = MISC_FEATURE - Lysine may or may not be present
SEQUENCE: 85
LVLNCTARSD QGLYTCAASS GLMTKX                                        26

SEQ ID NO: 86          moltype = AA  length = 28
FEATURE                Location/Qualifiers
source                 1..28
```

```
                        mol_type = protein
                        organism = synthetic construct
                        note = Description of Artificial Sequence: Synthetic peptide
VARIANT                 28
                        note = MISC_FEATURE - Glycine may or may not be present
SEQUENCE: 86
THTCPPCPAP ELLGTHTCPP CPAPELLX                                              28

SEQ ID NO: 87           moltype = AA   length = 17
FEATURE                 Location/Qualifiers
source                  1..17
                        mol_type = protein
                        organism = synthetic construct
                        note = Description of Artificial Sequence: Synthetic peptide
SITE                    12
                        note = deamidation of asparagine
SEQUENCE: 87
EIGLLTCEAT VNGHLYK                                                          17

SEQ ID NO: 88           moltype = AA   length = 23
FEATURE                 Location/Qualifiers
source                  1..23
                        mol_type = protein
                        organism = synthetic construct
                        note = Description of Artificial Sequence: Synthetic peptide
SITE                    3
                        note = deamidation of asparagine
SEQUENCE: 88
QTNTIIDVVL SPSHGIELSV GEK                                                   23

SEQ ID NO: 89           moltype = AA   length = 24
FEATURE                 Location/Qualifiers
source                  1..24
                        mol_type = protein
                        organism = synthetic construct
                        note = Description of Artificial Sequence: Synthetic peptide
VARIANT                 10
                        note = MISC_FEATURE - May be oxidized
SEQUENCE: 89
SDTGRPFVEM YSEIPEIIHM TEGR                                                  24

SEQ ID NO: 90           moltype = AA   length = 24
FEATURE                 Location/Qualifiers
source                  1..24
                        mol_type = protein
                        organism = synthetic construct
                        note = Description of Artificial Sequence: Synthetic peptide
VARIANT                 20
                        note = MISC_FEATURE - May be oxidized
SEQUENCE: 90
SDTGRPFVEM YSEIPEIIHM TEGR                                                  24

SEQ ID NO: 91           moltype = AA   length = 54
FEATURE                 Location/Qualifiers
source                  1..54
                        mol_type = protein
                        organism = synthetic construct
                        note = Description of Artificial Sequence: Synthetic
                         polypeptide
VARIANT                 40
                        note = MISC_FEATURE - May be oxidized
SEQUENCE: 91
GGGGSGGGGS GGGGSGGGGS GGGGSGGGGS SDTGRPFVEM YSEIPEIIHM TEGR                 54

SEQ ID NO: 92           moltype = AA   length = 54
FEATURE                 Location/Qualifiers
source                  1..54
                        mol_type = protein
                        organism = synthetic construct
                        note = Description of Artificial Sequence: Synthetic
                         polypeptide
VARIANT                 50
                        note = MISC_FEATURE - May be oxidized
SEQUENCE: 92
GGGGSGGGGS GGGGSGGGGS GGGGSGGGGS SDTGRPFVEM YSEIPEIIHM TEGR                 54

SEQ ID NO: 93           moltype = AA   length = 8
FEATURE                 Location/Qualifiers
source                  1..8
```

```
                        mol_type = protein
                        organism = synthetic construct
                        note = Description of Artificial Sequence: Synthetic peptide
VARIANT                 7
                        note = MISC_FEATURE - May be oxidized
SEQUENCE: 93
TQSGSEMK                                                                  8

SEQ ID NO: 94           moltype = AA  length = 17
FEATURE                 Location/Qualifiers
source                  1..17
                        mol_type = protein
                        organism = synthetic construct
                        note = Description of Artificial Sequence: Synthetic peptide
VARIANT                 15
                        note = MISC_FEATURE - May be oxidized
SEQUENCE: 94
SDQGLYTCAA SSGLMTK                                                       17

SEQ ID NO: 95           moltype = AA  length = 14
FEATURE                 Location/Qualifiers
source                  1..14
                        mol_type = protein
                        organism = synthetic construct
                        note = Description of Artificial Sequence: Synthetic peptide
VARIANT                 14
                        note = Glycine or absent
SEQUENCE: 95
THTCPPCPAP ELLX                                                          14

SEQ ID NO: 96           moltype = AA  length = 23
FEATURE                 Location/Qualifiers
source                  1..23
                        mol_type = protein
                        organism = synthetic construct
                        note = Description of Artificial Sequence: Synthetic peptide
SEQUENCE: 96
QTNTIIDVVL SPSHGIELSV GEK                                                23

SEQ ID NO: 97           moltype = AA  length = 7
FEATURE                 Location/Qualifiers
source                  1..7
                        mol_type = protein
                        organism = synthetic construct
                        note = Description of Artificial Sequence: Synthetic peptide
REGION                  1..7
                        note = See specification as filed for detailed description
                         of substitutions and preferred embodiments
SEQUENCE: 97
TNYLTHR                                                                   7

SEQ ID NO: 98           moltype = AA  length = 54
FEATURE                 Location/Qualifiers
source                  1..54
                        mol_type = protein
                        organism = synthetic construct
                        note = Description of Artificial Sequence: Synthetic
                         polypeptide
SITE                    5
                        note = glycosylated serine
SITE                    10
                        note = glycosylated serine
SITE                    15
                        note = glycosylated serine
SITE                    20
                        note = glycosylated serine
SITE                    25
                        note = glycosylated serine
SITE                    30
                        note = glycosylated serine
SEQUENCE: 98
GGGGSGGGGS GGGGSGGGGS GGGGSGGGGS SDTGRPFVEM YSEIPEIIHM TEGR               54

SEQ ID NO: 99           moltype = AA  length = 24
FEATURE                 Location/Qualifiers
source                  1..24
                        mol_type = protein
                        organism = synthetic construct
                        note = Description of Artificial Sequence: Synthetic peptide
```

```
SEQUENCE: 99
SDTGRPFVEM YSEIPEIIHM TEGR                                                    24

SEQ ID NO: 100            moltype = AA  length = 12
FEATURE                   Location/Qualifiers
source                    1..12
                          mol_type = protein
                          organism = synthetic construct
                          note = Description of Artificial Sequence: Synthetic peptide
VARIANT                   1
                          note = MISC_FEATURE - Arginine may or may not be present
SITE                      6
                          note = glycosylated asparagine
SEQUENCE: 100
XVTSPNITVT LK                                                                 12

SEQ ID NO: 101            moltype = AA  length = 11
FEATURE                   Location/Qualifiers
source                    1..11
                          mol_type = protein
                          organism = synthetic construct
                          note = Description of Artificial Sequence: Synthetic peptide
VARIANT                   1
                          note = MISC_FEATURE - Lysine may or may not be present
SITE                      7
                          note = glycosylated asparagine
SEQUENCE: 101
XGFIISNATY K                                                                  11

SEQ ID NO: 102            moltype = AA  length = 9
FEATURE                   Location/Qualifiers
source                    1..9
                          mol_type = protein
                          organism = synthetic construct
                          note = Description of Artificial Sequence: Synthetic peptide
VARIANT                   1
                          note = MISC_FEATURE - Lysine may or may not be present
SITE                      5
                          note = glycosylated asparagine
SEQUENCE: 102
XLVLNCTAR                                                                      9

SEQ ID NO: 103            moltype = AA  length = 7
FEATURE                   Location/Qualifiers
source                    1..7
                          mol_type = protein
                          organism = synthetic construct
                          note = Description of Artificial Sequence: Synthetic peptide
VARIANT                   1
                          note = MISC_FEATURE - Lysine may or may not be present
SITE                      2
                          note = glycosylated asparagine
SEQUENCE: 103
XNSTFVR                                                                        7

SEQ ID NO: 104            moltype = AA  length = 60
FEATURE                   Location/Qualifiers
source                    1..60
                          mol_type = protein
                          organism = synthetic construct
                          note = Description of Artificial Sequence: Synthetic
                           polypeptide
VARIANT                   1..60
                          note = MISC_FEATURE - This sequence may encompass 1-15 Gly
                           Gly Gly Ser repeating units
SEQUENCE: 104
GGGSGGGSGG GSGGGSGGGS GGGSGGGSGG GSGGGSGGGS GGGSGGGSGG GSGGGSGGGS              60

SEQ ID NO: 105            moltype = AA  length = 21
FEATURE                   Location/Qualifiers
source                    1..21
                          mol_type = protein
                          organism = synthetic construct
                          note = Description of Artificial Sequence: Synthetic peptide
VARIANT                   7..21
                          note = MISC_FEATURE - This region may encompass 1-5 Pro Pro
                           Cys repeating units
SEQUENCE: 105
DKTHTCPPCP PCPPCPPCPP C                                                       21
```

```
SEQ ID NO: 106          moltype = AA   length = 226
FEATURE                 Location/Qualifiers
source                  1..226
                        mol_type = protein
                        organism = synthetic construct
                        note = Description of Artificial Sequence: Synthetic
                         polypeptide
VARIANT                 212..226
                        note = MISC_FEATURE - This region may encompass 1-5 Pro Pro
                         Cys repeating units
SEQUENCE: 106
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKDKTHT CPPCPPCPPC PPCPPC                 226

SEQ ID NO: 107          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 107
GGGGSGGGGS GGGGS                                                    15

SEQ ID NO: 108          moltype = AA   length = 30
FEATURE                 Location/Qualifiers
source                  1..30
                        mol_type = protein
                        organism = synthetic construct
                        note = Description of Artificial Sequence: Synthetic
                         polypeptide
SEQUENCE: 108
GGGGSGGGGS GGGGSGGGGS GGGGSGGGGS                                    30

SEQ ID NO: 109          moltype = AA   length = 45
FEATURE                 Location/Qualifiers
source                  1..45
                        mol_type = protein
                        organism = synthetic construct
                        note = Description of Artificial Sequence: Synthetic
                         polypeptide
SEQUENCE: 109
GGGGSGGGGS GGGGSGGGGS GGGGSGGGGS GGGGSGGGGS GGGGS                   45

SEQ ID NO: 110          moltype = AA   length = 60
FEATURE                 Location/Qualifiers
source                  1..60
                        mol_type = protein
                        organism = synthetic construct
                        note = Description of Artificial Sequence: Synthetic
                         polypeptide
SEQUENCE: 110
GGGGSGGGGS GGGGSGGGGS GGGGSGGGGS GGGGSGGGGS GGGGSGGGGS GGGGSGGGGS   60

SEQ ID NO: 111          moltype = AA   length = 5
FEATURE                 Location/Qualifiers
source                  1..5
                        mol_type = protein
                        organism = synthetic construct
                        note = Description of Artificial Sequence: Synthetic peptide
SEQUENCE: 111
GGGGS                                                                5

SEQ ID NO: 112          moltype = AA   length = 485
FEATURE                 Location/Qualifiers
source                  1..485
                        mol_type = protein
                        organism = synthetic construct
                        note = Description of Artificial Sequence: Synthetic
                         polypeptide
VARIANT                 206..280
                        note = MISC_FEATURE - This region may encompass 1-15 Gly
                         Gly Gly Gly Ser repeating units
SEQUENCE: 112
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
```

```
GLYTCAASSG LMTKKNSTFV RVHEKGGGGS GGGGSGGGGS GGGGSGGGGS GGGGSGGGGS    240
GGGGSGGGGS GGGGSGGGGS GGGGSGGGGS GGGGSGGGGS SDTGRPFVEM YSEIPEIIHM    300
TEGRELVIPC RVTSPNITVT LKKFPLDTLI PDGKRIIWDS RKGFIISNAT YKEIGLLTCE    360
ATVNGHLYKT NYLTHRQTNT IIDVVLSPSH GIELSVGEKL VLNCTARTEL NVGIDFNWEY    420
PSSKHQHKKL VNRDLKTQSG SEMKKFLSTL TIDGVTRSDQ GLYTCAASSG LMTKKNSTFV    480
RVHEK                                                                485

SEQ ID NO: 113         moltype = AA  length = 211
FEATURE                Location/Qualifiers
source                 1..211
                       mol_type = protein
                       organism = synthetic construct
                       note = Description of Artificial Sequence: Synthetic
                        polypeptide
SEQUENCE: 113
GPSVFLFPPK PKDTLMISRT PEVTCVVVDV SHEDPEVKFN WYVDGVEVHN AKTKPREEQY     60
NSTYRVVSVL TVLHQDWLNG KEYKCKVSNK ALPAPIEKTI SKAKGQPREP QVYTLPPSRD    120
ELTKNQVSLT CLVKGFYPSD IAVEWESNGQ PENNYKTTPP VLDSDGSFFL YSKLTVDKSR    180
WQQGNVFSCS VMHEALHNHY TQKSLSLSPG K                                   211

SEQ ID NO: 114         moltype = AA  length = 7
FEATURE                Location/Qualifiers
source                 1..7
                       mol_type = protein
                       organism = synthetic construct
                       note = Description of Artificial Sequence: Synthetic peptide
VARIANT                3
                       note = MISC_FEATURE - May be oxidized
SEQUENCE: 114
IIWDSRK                                                                7

SEQ ID NO: 115         moltype = AA  length = 7
FEATURE                Location/Qualifiers
source                 1..7
                       mol_type = protein
                       organism = synthetic construct
                       note = Description of Artificial Sequence: Synthetic peptide
VARIANT                4
                       note = MISC_FEATURE - May be oxidized
SEQUENCE: 115
RIIWDSR                                                                7

SEQ ID NO: 116         moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 116
GPSVFLFPPK PK                                                         12

SEQ ID NO: 117         moltype = AA  length = 16
FEATURE                Location/Qualifiers
source                 1..16
                       mol_type = protein
                       organism = synthetic construct
                       note = Description of Artificial Sequence: Synthetic peptide
VARIANT                9
                       note = MISC_FEATURE - May be oxidized
SEQUENCE: 117
VVSVLTVLHQ DWLNGK                                                     16

SEQ ID NO: 118         moltype = AA  length = 26
FEATURE                Location/Qualifiers
source                 1..26
                       mol_type = protein
                       organism = synthetic construct
                       note = Description of Artificial Sequence: Synthetic peptide
VARIANT                2
                       note = MISC_FEATURE - May be oxidized
VARIANT                4
                       note = MISC_FEATURE - May be carboxymethylated
VARIANT                7
                       note = MISC_FEATURE - May be carboxymethylated
SEQUENCE: 118
THTCPPCPAP ELLGGPSVFL FPPKPK                                          26

SEQ ID NO: 119         moltype = AA  length = 16
FEATURE                Location/Qualifiers
```

```
source                  1..16
                        mol_type = protein
                        organism = synthetic construct
                        note = Description of Artificial Sequence: Synthetic peptide
VARIANT                 9
                        note = MISC_FEATURE - May be oxidized
SEQUENCE: 119
VVSVLTVLHQ DWLNGK                                                          16

SEQ ID NO: 120          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 120
SDTGRPFVEM                                                                 10

SEQ ID NO: 121          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 121
VTSPNITVTL K                                                               11

SEQ ID NO: 122          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 122
NSTFVR                                                                      6

SEQ ID NO: 123          moltype = AA  length = 14
FEATURE                 Location/Qualifiers
source                  1..14
                        mol_type = protein
                        organism = synthetic construct
                        note = Description of Artificial Sequence: Synthetic peptide
VARIANT                 14
                        note = MISC_FEATURE - Glycine may or may not be present
SEQUENCE: 123
THTCPPCPAP ELLX                                                            14

SEQ ID NO: 124          moltype = AA  length = 7
FEATURE                 Location/Qualifiers
source                  1..7
                        mol_type = protein
                        organism = synthetic construct
                        note = Description of Artificial Sequence: Synthetic peptide
VARIANT                 4
                        note = MISC_FEATURE - May be oxidized
SEQUENCE: 124
IIIWDSR                                                                     7
```

What is claimed is:

1. A composition comprising oxo-aflibercept, wherein one or more amino acid residues of aflibercept is oxidized and wherein said one or more amino acid residues is phenylalanine and/or tyrosine.

2. The composition of claim 1, wherein said oxo-aflibercept has a glycosylation profile based on molar percentage selected from the group consisting of about 40% to about 50% total fucosylated glycans, about 30% to about 55% total sialylated glycans, about 2% to about 15% mannose-5, and about 60% to about 79% galactosylated glycans.

3. The composition of claim 1, further comprising a pharmaceutically acceptable carrier.

4. The composition of claim 3, wherein said oxo-aflibercept is freeze-dried.

5. The composition of claim 4, wherein said composition is sterile.

6. The composition of claim 1, wherein said oxo-aflibercept is enzymatically digested resulting in one or more oligopeptides, and wherein said one or more oligopeptides is selected from the group consisting of: SEQ ID NO. 69, SEQ ID NO. 70, SEQ ID NO. 32, and combinations thereof.

7. The composition of claim 6, wherein said enzymatic digestion is performed using trypsin.

8. An oxo-aflibercept composition produced in a cell culture media, wherein CDM is added to said cell culture media, wherein one or more amino acid residues of aflibercept is oxidized and wherein said one or more amino acid residues is phenylalanine and/or tyrosine.

9. The oxo-aflibercept composition of claim 8, wherein said oxo-aflibercept composition has a glycosylation profile based on molar percentage selected from the group consisting of about 40% to about 50% total fucosylated glycans, about 30% to about 55% total sialylated glycans, about 2% to about 15% mannose-5, and about 60% to about 79% galactosylated glycans.

10. The oxo-aflibercept composition of claim 9, wherein soy hydrolysate media is added to said cell culture media.

11. The oxo-aflibercept composition of claim 8, wherein components derived from soy hydrolysate are added to said cell culture media.

12. The oxo-aflibercept composition of claim 8, wherein plant or animal-derived components are added to said cell culture media.

13. The composition of claim 8, wherein said oxo-aflibercept is enzymatically digested resulting in one or more oligopeptides, and wherein said one or more oligopeptides is selected from the group consisting of: SEQ ID NO. 69, SEQ ID NO. 70, SEQ ID NO. 32, and combinations thereof.

14. The composition of claim 13, wherein said enzymatic digestion is performed using trypsin.

15. An oxo-aflibercept composition produced in a cell culture media, wherein CDM is a majority component of said cell culture media, wherein one or more amino acid residues of aflibercept is oxidized and wherein said one or more amino acid residues is histidine and/or tryptophan.

16. The oxo-aflibercept composition of claim 15, wherein said oxo-aflibercept composition has a glycosylation profile based on molar percentage selected from the group consisting of about 40% to about 50% total fucosylated glycans, about 30% to about 55% total sialylated glycans, about 2% to about 15% mannose-5, and about 60% to about 79% galactosylated glycans.

17. The oxo-aflibercept composition of claim 16, wherein said cell culture media is supplemented with soy hydrolysate media.

18. The oxo-aflibercept composition of claim 15, wherein components derived from soy hydrolysate are added to said cell culture media.

19. The oxo-aflibercept composition of claim 15, wherein plant or animal-derived components are added to cell culture media.

20. The composition of claim 15, wherein said oxo-aflibercept is enzymatically digested resulting in one or more oligopeptides, and wherein said one or more oligopeptides is selected from the group consisting of: SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 28, SEQ ID NO. 29, SEQ ID NO. 30, SEQ ID NO. 31, SEQ ID NO. 32 and combinations thereof.

21. The composition of claim 20, wherein said enzymatic digestion is performed using trypsin.

22. The composition of claim 15, further comprising a pharmaceutically acceptable carrier.

23. An oxo-aflibercept composition produced in a cell culture media, wherein CDM is a majority component of said cell culture media, wherein one or more amino acid residues of aflibercept is oxidized and wherein said one or more amino acid residues is phenylalanine and/or tyrosine.

24. The oxo-aflibercept composition of claim 23, wherein said oxo-aflibercept composition has a glycosylation profile based on molar percentage selected from the group consisting of about 40% to about 50% total fucosylated glycans, about 30% to about 55% total sialylated glycans, about 2% to about 15% mannose-5, and about 60% to about 79% galactosylated glycans.

25. The oxo-aflibercept composition of claim 23, wherein said cell culture media is supplemented with soy hydrolysate media.

26. The oxo-aflibercept composition of claim 23, wherein components derived from soy hydrolysate are added to said cell culture media.

27. The oxo-aflibercept composition of claim 23, wherein plant or animal-derived components are added to cell culture media.

28. The composition of claim 23, wherein said oxo-aflibercept is enzymatically digested resulting in one or more oligopeptides, and wherein said one or more oligopeptides is selected from the group consisting of: SEQ ID NO. 69, SEQ ID NO. 70, SEQ ID NO. 32 and combinations thereof.

29. The composition of claim 28, wherein said enzymatic digestion is performed using trypsin.

30. The composition of claim 23, further comprising a pharmaceutically acceptable carrier.

* * * * *